(12) United States Patent
Slusher et al.

(10) Patent No.: US 10,842,763 B2
(45) Date of Patent: *Nov. 24, 2020

(54) METHODS FOR CANCER AND IMMUNOTHERAPY USING PRODRUGS OF GLUTAMINE ANALOGS

(71) Applicant: The Johns Hopkins University, Baltimore, MD (US)

(72) Inventors: Barbara Slusher, Kingsville, MD (US); Jonathan Powell, Baltimore, MD (US); Lukas Tenora, Prague (CZ); Pavel Majer, Sykesville, MD (US); Andrei Jancarik, Kopřivnice (CZ); Robert Leone, Lutherville, MD (US); Judson Englert, Baltimore, MD (US)

(73) Assignees: The Johns Hopkins University, Baltimore, MD (US); Ústav organické chemie a biochemie AV Čr, v.v.i., Prague (CZ)

( * ) Notice: Subject to any disclaimer, the term of this patent is extended or adjusted under 35 U.S.C. 154(b) by 0 days.

This patent is subject to a terminal disclaimer.

(21) Appl. No.: 16/262,476

(22) Filed: Jan. 30, 2019

(65) Prior Publication Data

US 2019/0216757 A1    Jul. 18, 2019

Related U.S. Application Data

(63) Continuation-in-part of application No. 15/885,275, filed on Jan. 31, 2018, now abandoned, which is a
(Continued)

(51) Int. Cl.
*A61K 31/24* (2006.01)
*A61K 38/00* (2006.01)
(Continued)

(52) U.S. Cl.
CPC ............ *A61K 31/198* (2013.01); *A61K 35/17* (2013.01); *A61K 39/0011* (2013.01);
(Continued)

(58) Field of Classification Search
CPC ..... A61K 31/223; A61K 38/06; A61K 39/395
(Continued)

(56) References Cited

U.S. PATENT DOCUMENTS 3,773,919 A    11/1973   Boswell et al.
4,485,045 A    11/1984   Regen
(Continued)

FOREIGN PATENT DOCUMENTS

EP    0058481 A1    8/1982
EP    0102324 A2    3/1984
(Continued)

OTHER PUBLICATIONS

Liwschitz et al. "Diazo-ketone with potential tumor-inhibitory properties derived from L-aspartic and L-glutamic acids," J. Chem. Soc. C, 1971, pp. 223-225. (Year: 1971).*
(Continued)

*Primary Examiner* — Shengjun Wang
(74) *Attorney, Agent, or Firm* — Sterne, Kessler, Goldstein & Fox P.L.L.C.

(57) ABSTRACT

The disclosure provides methods of treating cancer in a subject or preventing a relapse or reducing the incidence of relapse of cancer in a subject in remission, comprising administering to the subject: (a) a therapeutically effective amount of an immunotherapeutic agent, e.g., an immune checkpoint blockade therapy, an adoptive cellular therapy, a marrow-infiltrating lymphocytes, an adenosine A2aR inhibitor, or an antibody; and (b) a compound having formula (I):
(Continued)

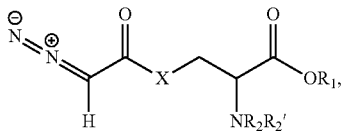

(I)

and the pharmaceutically acceptable salts thereof, wherein $R_1$, $R_2$, $R_2'$, and X are as defined as set forth in the specification. Compounds having formula (I) are prodrugs that release glutamine analogs, e.g., 6-diazo-5-oxo-L-norleucine (DON).

16 Claims, 84 Drawing Sheets

Related U.S. Application Data continuation-in-part of application No. PCT/US2016/044829, filed on Jul. 29, 2016.

(60) Provisional application No. 62/199,381, filed on Jul. 31, 2015, provisional application No. 62/199,566, filed on Jul. 31, 2015.

(51) Int. Cl.

| | | |
|---|---|---|
| *A61K 38/17* | (2006.01) | |
| *A61K 39/395* | (2006.01) | |
| *A61K 31/198* | (2006.01) | |
| *A61K 35/17* | (2015.01) | |
| *A61P 35/00* | (2006.01) | |
| *A61K 39/00* | (2006.01) | |
| *C07K 16/28* | (2006.01) | |
| *A61K 39/39* | (2006.01) | |

(52) U.S. Cl.
CPC .......... *A61K 39/39* (2013.01); *A61K 39/3955* (2013.01); *A61K 39/39558* (2013.01); *A61P 35/00* (2018.01); *C07K 16/2818* (2013.01); *A61K 2039/505* (2013.01); *A61K 2039/507* (2013.01)

(58) Field of Classification Search
USPC .................. 514/538, 19.3, 21.92; 424/141.1
See application file for complete search history.

(56) References Cited

U.S. PATENT DOCUMENTS

| | | | |
|---|---|---|---|
| 4,544,545 | A | 10/1985 | Ryan et al. |
| 5,328,470 | A | 7/1994 | Nabel et al. |
| 6,362,226 | B2 | 3/2002 | Phillips, III et al. |
| 10,336,778 | B2 | 7/2019 | Slusher et al. |
| 2004/0029801 | A1 | 2/2004 | Zhong et al. |
| 2006/0035838 | A1* | 2/2006 | Khosla .................. A61K 31/198 514/160 |
| 2006/0276438 | A1 | 12/2006 | Sethuraman et al. |
| 2008/0107624 | A1 | 5/2008 | D'Andrea et al. |
| 2008/0146526 | A1 | 6/2008 | Gallop et al. |
| 2008/0160024 | A1 | 7/2008 | Ware |
| 2009/0042806 | A1* | 2/2009 | Khosla .................... A61K 31/42 514/1.1 |
| 2009/0062223 | A1 | 3/2009 | Keicher et al. |
| 2009/0169537 | A1 | 7/2009 | Bausch et al. |
| 2014/0004081 | A1* | 1/2014 | Cobbold ................ A61K 39/12 424/85.2 |
| 2014/0065100 | A1* | 3/2014 | Rossignol .......... A61K 39/0011 424/85.2 |
| 2015/0202291 | A1 | 7/2015 | Bosch et al. |
| 2015/0258082 | A1 | 9/2015 | Parlati et al. |
| 2016/0022674 | A1 | 1/2016 | Steggerda et al. |
| 2016/0193239 | A1 | 7/2016 | Baylin et al. |
| 2016/0310453 | A1 | 10/2016 | Mathios et al. |
| 2017/0190657 | A1 | 7/2017 | Gallop et al. |
| 2018/0193362 | A1 | 7/2018 | Slusher et al. |
| 2018/0221337 | A1 | 8/2018 | Slusher et al. |
| 2018/0221395 | A1 | 8/2018 | Slusher et al. |

FOREIGN PATENT DOCUMENTS

| | | |
|---|---|---|
| EP | 0123170 A2 | 10/1984 |
| EP | 0133988 A2 | 3/1985 |
| WO | WO-2004113363 A2 | 12/2004 |
| WO | WO-2005068455 A1 | 7/2005 |
| WO | WO-2005097108 A1 | 10/2005 |
| WO | WO-2013019058 A2 | 2/2013 |
| WO | WO-2014138391 A1 | 9/2014 |
| WO | WO-2014160071 A1 | 10/2014 |
| WO | WO-2015101957 A2 | 7/2015 |
| WO | WO-2017023774 A1 | 2/2017 |
| WO | WO-2017023787 A1 | 2/2017 |
| WO | WO-2017023791 A1 | 2/2017 |
| WO | WO-2017023793 A2 | 2/2017 |

OTHER PUBLICATIONS

Sznol et al. "Antagonist antibodies to PD-1 and B7-H1 (PD-L1) in the treatment of Advanced human cancer," Clinical Cancer Research, 2013, vol. 19, No. 5, pp. 1021-1034. (Year: 2013).*
Noonan et al. "Phase I/II study of marrow infiltrating lymphocytes (MILs) generates Measurable myeloma-specific immunity in the autologous stem cell transplant (SCT) setting," Blood, 2011, vol. 118, Issue 21, p. 997. (Year: 2011).*
Leone et al. "A2aR antagonists: next generation checkpoint blockade for cancer immunotherapy," Computational and Structural Biotechnology Journal, Apr. 8, 2015, vol. 13, pp. 265-272. (Year: 2015).*
Simplicio et al. "Prodrug for Amines," Molecules, 2008, vol. 13, pp. 519-547. (Year: 2008).*
Abdelmalek, M.F., et.al., "Sirolimus Conversion Regimen Versus Continued Calcineurin Inhibitors in Liver Allograft Recipients: a Randomized Trial.," American Journal of Transplantation : Official Journal of the American Society of Transplantation and the American Society of Transplant Surgeons 12(3):694-705, Wiley-blackwell on Behalf of the American Society of Transplant Surgeons and the American Society of Transplantation, United States (Jan. 2012).
Acevedo., et.al., "Synthesis and Analysis of the Sterically Constrained L-glutamine Analogues (3s,4r)-3,4-dimethyl-1-glutamine and (3s,4r)-3,4-dimethyl-l-pyroglutamic Acid," Tetrahedron 57 (30):6353-6359, Elsevier Science Ltd (Jul. 2001).
Ahluwalia.,G.S., et.al., "Metabolism and Action of Amino Acid Analog Anti-cancer Agents.," Pharmacology & Therapeutics 46(2):243-271, Pergamon Press, England (1990).
Alt,J., et.al., "Bioanalysis of 6-diazo-5-oxo-I-norleucine in Plasma and Brain by Ultra-performance Liquid Chromatography Mass Spectrometry.," Analytical Biochemistry 474:28-34, Elsevier, United States (Jan. 2010).
Altschul, S.F., et al., "Basic Local Alignment Search Tool," Journal of Molecular Biology 215(3):403-410, Elsevier, England (Oct. 1990).
Altschul, S.F., et al., "Gapped BLAST and PSI-BLAST: A New Generation of Protein Database Search Programs," Nucleic Acids Research 25(17):3389-3402, Oxford University Press, England (Sep. 1997).
Antinori, A., et.al., "Updated Research Nosology for HIV-associated Neurocognitive Disorders.," Neurology 69(18):1789-1799, Lippincott Williams & Wilkins, United States (Oct. 2007).
Arnold, R., et.al., "Association Between Calcineurin Inhibitor Treatment and Peripheral Nerve Dysfunction in Renal Transplant Recipients.," American Journal of Transplantation : Official Journal of the American Society of Transplantation and the American Society of Transplant Surgeons 13(9):2426-2432, Wiley-blackwell

(56) References Cited

OTHER PUBLICATIONS on Behalf of the American Society of Transplant Surgeons and the American Society of Transplantation, United States (Jul. 2010).
Barclay, R.K., et.al., "Effects of 6-diazo-5-oxol-norleucine and Other Tumor Inhibitors on the Biosynthesis of Nicotinamide Adenine Dinucleotide in Mice.," Cancer research 26(2):282-286, American Association for Cancer Research, United States (Feb. 1966).
Berge, S.M., et al., "Pharmaceutical Salts," Journal of Pharmaceutical Sciences 66(1):1-19, Wiley, United States (Jan. 1977).
Bestard, O., et.al., "Costimulatory Blockade With Mtor Inhibition Abrogates Effector T-cell Responses Allowing Regulatory T-cell Survival in Renal Transplantation.," Transplant International : Official Journal of the European Society for Organ Transplantation 24(5):451-460, Blackwell Pub, England (May 2011).
Borjabad, A., et.al., "Significant Effects of Antiretroviral Therapy on Global Gene Expression in Brain Tissues of Patients With Hiv-1-associated Neurocognitive Disorders.," Plos Pathogens 7(9):e1002213, Public Library of Science, United States (Sep. 2011).
Buzzai, M., et.al., "Systemic Treatment With the Antidiabetic Drug Metformin Selectively Impairs P53-deficient Tumor Cell Growth.," Cancer Research 67(14):6745-6752, American Association for Cancer Research, United States (Jul. 2007).
Cao, X., et.al., "Astrocyte-derived Atp Modulates Depressive-like Behaviors.," Nature Medicine 19(6):773-777, Nature Publishing Company, United States (Jun. 2013).
Carr, E.L., et.al., "Glutamine Uptake and Metabolism Are Coordinately Regulated by Erk/mapk During T Lymphocyte Activation.," Journal of Immunology (Baltimore, Md. : 1950) 185(2):1037-1044, American Association of Immunologists, United States (Jul. 2010).
Cervantes-Madrid, D., et al., "Reviving Lonidamine and 6-Diazo-5-oxo-L-norleucine to be used in Combination for Metabolic Cancer Therapy," BioMed Research International 2015:690492, Hindawi Pub. Co, United States (2015).
Cham, C.M and Gajewski, T.F, "Glucose Availability Regulates IFN-gamma Production and p70S6 Kinase Activation in CD8+ Effector T Cells," Journal of Immunology (Baltimore, Md. : 1950) 174(8):4670-4677, American Association of Immunologists, United States (Apr. 2005).
Cham, C.M., et.al., "Glucose Deprivation Inhibits Multiple Key Gene Expression Events and Effector Functions in Cd8+ T Cells.," European Journal of Immunology 38(9):2438-2450, Wiley-vch, Germany (Sep. 2008).
Chambers, J.W., et al., "Glutamine Metabolism is Essential for Human Cytomegalovirus Infection," Journal of Virology 84(4):1867-1873, American Society for Microbiology, United States (Feb. 2010).
Chang, L., et al., "Persistent Brain Abnormalities in Antiretroviral-naive HIV Patients 3 Months after HAART," Antiviral Therapy 8(1):17-26, International Medical Press, England (Feb. 2003).
Chapman, A.P., "PEGylated Antibodies and Antibody Fragments for Improved Therapy: a Review," Advanced Drug Delivery Reviews 54(4):531-545, Elsevier Science Publishers, Netherlands (Jun. 2002).
Chen, S.H., et al., "Gene Therapy for Brain Tumors: Regression of Experimental Gliomas by Adenovirus-mediated Gene Transfer in Vivo," Proceedings of the National Academy of Sciences 91(8):3054-3057, National Academy of Sciences, United States (Apr. 1994 ).
Cheng, G., et al., "Mitochondria-targeted Drugs Synergize with 2-deoxyglucose to Trigger Breast Cancer Cell Death," Cancer Research 72(10):2634-2644, American Association for Cancer Research, United States (May 2012).
Cheng, G., et al., "Profiling and Targeting of Cellular Bioenergetics: Inhibition of Pancreatic Cancer Cell Proliferation," British Journal of Cancer 111(1):85-93, Nature Publishing Group on behalf of Cancer Research UK, England (Jul. 2014).
Cheong, J.H., et al., "Dual inhibition of tumor energy pathway by 2-Deoxyglucose and Metformin is Effective against a Broad Spectrum of Preclinical Cancer Models," Molecular Cancer Therapeutics 10(12):2350-2362, American Association for Cancer Research, United States (Dec. 2011).

Cinatl, J., et al., "Antiviral Effects of 6-diazo-5-oxo-L-norleucin on Replication of Herpes Simplex Virus Type 1," Antiviral Research 33(3):165-175, Elsevier, Netherlands (Feb. 1997).
Coffey, G.L., et al., "6-diazo-5-oxo-L-norleucine, a New Tumor-inhibitory Substance, I. Biologic Studies," Antibiotics & Chemotherapy 6(8):487-497, Washington Institute of Medicine, United States (Aug. 1956).
Coggin, Jr., J.H. and Martin, W. R., "6-Diazo-5-Oxo-I-Norleucine Inhibition of *Escherichia coli*," Journal of Bacteriology 89(5):1348-1353, American Society for Microbiology, United States (May 1965).
Corry, R.J., et al., "Primarily Vascularized Allografts of Hearts in Mice. The Role of H-2D, H-2K, and Non-H-2 Antigens in Rejection," Transplantation 16(4):343-350, Lippincott Williams & Wilkins, United States (Oct. 1973).
Csibi, A., et al., "The mTORC1 Pathway Stimulates Glutamine Metabolism and Cell Proliferation by Repressing SIRT4," Cell 153(4):840-854, Cell Press, United States (May 2013).
Cui, F., et al., "Overexpression of Cathepsin L is Associated with Gefitinib Resistance in Non-small Cell Lung Cancer," Clinical & Translational Oncology 18(7):722-727, Springer Italia, Italy (Jul. 2016).
Cunningham-Rundles, C., et al., "Biological Activities of Polyethylene-glycol Immunoglobulin Conjugates. Resistance to Enzymatic Degradation," Journal of Immunological Methods 152(2):177-190, Elsevier, Netherlands (Aug. 1992).
Crutchlow, M.F. and Bloom, R.D., "Transplant-Associated Hyperglycemia: A New Look at an Old Problem," Clinical Journal of the American Society of Nephrology 2(2):343-355, American Society of Nephrology, United States (Mar. 2007).
Dickens, A.M., et al., "Cerebrospinal Fluid Metabolomics Implicate Bioenergetic Adaptation as a Neural Mechanism Regulating Shifts in Cognitive States of HIV-infected Patients," AIDS 29(5):559-569, Lippincott Williams & Wilkins, England (Mar. 2015).
Darmaun, D., et al., "Phenylbutyrate-induced Glutamine Depletion in Humans: Effect on Leucine Metabolism," The American Journal of Physiology 274(5pt1):E801-E807, American Physiological Society, United States (May 1998).
Deberardinis, R.J. and Cheng, T., "Q's Next: the Diverse Functions of Glutamine in Metabolism, Cell Biology and Cancer," Oncogene 29(3):313-324, Nature Publishing Group, England (Jan. 2010).
Delgoffe, G.M., et al., "The Kinase mTOR Regulates the Differentiation of Helper T Cells Through the Selective Activation of Signaling by mTORC1 and mTORC2," Nature Immunology 12(4):295-303, Nature America Inc, United States (Apr. 2011),.
Delgoffe, G.M., et al., "The mTOR Kinase Differentially Regulates Effector and Regulatory T Cell Lineage Commitment," Immunity 30(6):832-844, Cell Press, United States (Jun. 2009).
Dewald, H.A.and Alexander M.M., "6-diazo-5-oxo-L-norleucine, a New Tumor-inhibitory Substance. Preparation of L-, D- and DI-forms," Journal of the American Chemical Society 80(15):3941-3945, (Aug. 1958).
Dion, H.W., et al., "6-Diazo-5-oxo-L-norleucine, A New Tumor-inhibitory Substance. II. Isolation and Characterization," Journal of the American Chemical Society 78(13):3075-3077, (Jul. 1956).
Dolan, D.E. and Gupta, S., "PD-1 Pathway Inhibitors: Changing the Landscape of Cancer Immunotherapy," Cancer Control 21(3):231-237, SAGE Publishing, United States (Jul. 2014).
Dranoff, G., et al., "Combination Chemotherapy in Vitro Exploiting Glutamine Metabolism of Human Glioma and Medulloblastoma," Cancer Research 45(9):4082-4086, American Association for Cancer Research, United States (Sep. 1985).
Dranoff, G., et al., "Influence of Glutamine on the Growth of Human Glioma and Medulloblastoma in Culture," Cancer Research 45(9):4077-4081, American Association for Cancer Research, United States (Sep. 1985).
Eagan, R.T., et al., "Phase II Study on DON in Patients with Previously Treated Advanced Lung Cancer," Cancer Treatment Reports 66(8):1665-1666, National Cancer Institute, United States (Aug. 1982).

(56) References Cited

OTHER PUBLICATIONS

Earhart, R.N., et al., "Phase I Trial of 6-diazo-5-oxo-L-norleucine (DON) Administered by 5-day Courses," Cancer Treatment Reports 66(5):1215-1217, National Cancer Institute, United States (May 1982).

Earhart, R.H., et al., "Phase II Trial of 6-diazo-5-oxo-L-norleucine Versus Aclacinomycin-a in Advanced Sarcomas and Mesotheliomas," Investigational New Drugs 8(1):113-119, Springer, United States (Feb. 1990).

Ellis, R., et al., "HIV and Antiretroviral Therapy in the Brain: Neuronal Injury and Repair," Nature Reviews. Neuroscience 8(1):33-44, Nature Pub. Group, England (Jan. 2007).

El-Mir, M.Y., et al., "Dimethylbiguanide Inhibits Cell Respiration via an Indirect Effect Targeted on the Respiratory Chain Complex I," The Journal of Biological Chemistry 275(1):223-228, American Society for Biochemistry and Molecular Biology, United States (Jan. 2000).

Engels, E.A., et al., "Spectrum of Cancer Risk among U.S. Solid Organ Transplant Recipients: the Transplant Cancer Match Study," JAMA 306(17):1891-1901, American Medical Association, United States (Nov. 2011).

Eppstein, D.A., et al., "Biological activity of liposome-encapsulated murine interferon gamma is mediated by a cell membrane receptor," Proceedings of the National Academy of Sciences 82(11):3688-3692, National Academy of Sciences, United States (1985).

Erickson, J.W. and Cerione R.A., "Glutaminase: A Hot Spot for Regulation of Cancer Cell Metabolism?," Oncotarget 1(8):734-740, Impact Journals, United States (Dec. 2010).

Eshleman, J.S., et al., "Inhibition of the Mammalian Target of Rapamycin Sensitizes U87 Xenografts to Fractionated Radiation Therapy," Cancer Research 62(24):7291-7297, American Association for Cancer Research, United States (Dec. 2002).

Everall, I., et al., "Cliniconeuropathologic Correlates of Human Immunodeficiency Virus in the Era of Antiretroviral Therapy," Journal of Neurovirology 15(5-6):360-370, Springer, United States (Sep. 2009).

Franciosi, M., et al., "Metformin Therapy and Risk of Cancer in Patients with Type 2 Diabetes: Systematic Review," PloS one 8(8):e71583, Public Library of Science, United States (Aug. 2013).

Kull, F.C., et al., "Mixtures of Quaternary Ammonium Compounds and Long-chain Fatty Acids as Antifungal Agents," Applied Microbiology 9(6):538-541, American Society for Microbiology, United States (Nov. 1961).

Fogal, V., et al., "Mitochondrial p32 is Upregulated in Myc Expressing Brain Cancers and Mediates Glutamine Addiction," Oncotarget 6(2):1157-1170, Impact Journals, United States (Jan. 2015).

Gelman, B.B., et al., "The National NeuroAIDS Tissue Consortium Brain Gene Array: Two Types of HIV-associated Neurocognitive Impairment," PLoS One 7(9):e46178, Public Library of Science, United States (2012).

Grayzel, A.I., et al., "Suppression of Uric Acid Synthesis in the Gouty Human by the Use of 6-diazo-5-oxo-L-norleucine.," The Journal of Clinical Investigation 39:447-454, American Society for Clinical Investigation, United States (Mar. 1960).

Gross, M.I., et al., "Antitumor Activity of the Glutaminase Inhibitor CB-839 in Triple-Negative Breast Cancer," Molecular Cancer Therapeutics 13(4):890-901, American Association for Cancer Research, United States (Apr. 2014).

Grupp, S.A., et al., "Chimeric Antigen Receptor-Modified T Cells for Acute Lymphoid Leukemia," The New England Journal of Medicine 368(16):1509-1518, Massachusetts Medical Society, United States (Apr. 2013).

Guba, M., et al., "Pro- and Anti-cancer Effects of Immunosuppressive Agents used in Organ Transplantation," Transplantation 77(12):1777-1782, Lippincott Williams & Wilkins, United States (Jun. 2004).

Harding, J.J., et al., "Safety and Tolerability of Increasing Doses of CB-839, a First-in-class, Orally Administered Small Molecule Inhibitor of Glutaminase, in Solid Tumors," Journal of Clinical Oncology 33(15_suppl ):2512, (May 2015).

Harezlak, J., et al., "Persistence of HIV-associated Cognitive Impairment, Inflammation, and Neuronal Injury in Era of Highly Active Antiretroviral Treatment," AIDS 25(5):625-633, Lippincott Williams & Wilkins, England (Mar. 2011).

Hart, R.G., et al., "Neuroprotection Trials in Parkinson's Disease: Systematic Review," Movement Disorders 24(5):647-654, Wiley-Liss, United States (Apr. 2009).

Hausch, F., et al., "Design, Synthesis, and Evaluation of Gluten Peptide Analogs as Selective Inhibitors of Human Tissue Transglutaminase," Chemistry & Biology 10(3):225-231, Elsevier, United States (Mar. 2003).

Heaton, R.K., et al., "HIV-associated Neurocognitive Disorders Before and During the Era of Combination Antiretroviral Therapy: Differences in Rates, Nature, and Predictors," Journal of Neurovirology 17(1):3-16, Springer, United States (Feb. 2011).

Heaton, R.K., et al., "HIV-associated Neurocognitive Disorders Persist in the Era of Potent Antiretroviral Therapy: Charter Study," Neurology 75(23):2087-2096, Lippincott Williams & Wilkins, United States (Dec. 2010).

Henderson, J.M., et al., "Hepatocellular Carcinoma: Mouse Models and the Potential Roles of Proteases," Cancer Letters 387:106-113, Elsevier Science Ireland, Ireland (Feb. 2017).

Hensley, C.T., et al., "Glutamine and Cancer: Cell Biology, Physiology, and Clinical Opportunities," The Journal of Clinical Investigation 123(9):3678-3684, American Society for Clinical Investigation, United States (Sep. 2013).

Hodes, G.E., et al., "Individual Differences in the Peripheral Immune System Promote Resilience Versus Susceptibility to Social Stress," Proceedings of the National Academy of Sciences of the United States of America 111(45):16136-16141, National Academy of Sciences, United States (Nov. 2014).

Hofer, A., et al., "Trypanosoma Brucei CTP Synthetase: a Target for the Treatment of African Sleeping Sickness," Proceedings of the National Academy of Sciences of the United States of America 98(11):6412-6416, National Academy of Sciences, United States (May 2001).

Hollinger, K.R., et al., "Dose-dependent Inhibition of GCPII to Prevent and Treat Cognitive Impairment in the EAE Model of Multiple Sclerosis," Brain Research 1635:105-112, North-Holland Biomedical Press, Netherlands (Mar. 2016).

Hoorn, E.J., et al., "Pathogenesis of Calcineurin Inhibitor-induced Hypertension," Journal of Nephrology 25(3):269-275, Springer, Italy (May-Jun. 2012).

Hu, X., et al., "Genetic Alterations and Oncogenic Pathways Associated with Breast Cancer Subtypes," Molecular Cancer Research 7(4):511-522, American Association for Cancer Research, United States (Apr. 2009).

Hutchinson, J.A., et al., "Peptide Hormones and Lipopeptides: from Self-assembly to Therapeutic Applications," Journal of Peptide Science 23(2):82-94, John Wiley & Sons, England (Feb. 2017).

Hwang, K.J., et al., "Hepatic uptake and degradation of unilamellar sphingomyelin/cholesterol liposomes: a kinetic study," Proceedings of the National Academy of Sciences 77(7):4030-4034, National Academy of Sciences, United States (1980).

International Search Report and Written Opinion for International Application No. PCT/US2016/044767, European Patent Office, Netherlands, dated Oct. 31, 2016, 9 pages.

International Search Report and Written Opinion for International Application No. PCT/US2016/044810, European Patent Office, Netherlands, dated Dec. 5, 2016, 10 pages.

International Search Report and Written Opinion for International Application No. PCT/US2016/044825, European Patent Office, Netherlands, dated Dec. 5, 2016, 10 pages.

Jacobs, S.R., et al., "Glucose Uptake is Limiting in T Cell Activation and Requires CD28-Mediated Akt-Dependent and Independent Pathways," Journal of Immunology 180(7):4476-4486, American Association of Immunologists, United States (Apr. 2008).

Jones, R.G. and Thompson, C.B., "Revving the Engine: Signal Transduction Fuels T Cell Activation," Immunity 27(2):173-178, Cell Press, United States (Aug. 2007).

Karlin, S. and Altschul, S.E., "Methods for Assessing the Statistical Significance of Molecular Sequence Features by using General

(56) References Cited

OTHER PUBLICATIONS

Scoring Schemes," Proceedings of the National Academy of Sciences USA 87(6):2264-2268, National Academy of Sciences, United States (Mar. 1990).

Karlin, S, and Altschul, S.F., "Applications and Statistics for Multiple High-scoring Segments in Molecular Sequences," Proceedings of the National Academy of Sciences USA 90(12):5873-5877, National Academy of Sciences, United States (Jun. 1993).

Kaul, M., et al., "HIV-1 Infection and AIDS: Consequences for the Central Nervous System," Cell Death and Differentiation 12 Suppl 1:878-892, Nature Publishing Group, England (Aug. 2005).

Konopleva., et al., "Phase 1 study: Safety and tolerability of increasing doses of cb-839, an orally-administered small molecule inhibitor of glutaminase," In Acute Leukemia, Haematologica (2015).

Kovach, J.S., et al., "Phase I and Pharmacokinetic Studies of DON," Cancer Treatment Reports 65(11-12):1031-1036, National Cancer Institute, United States (Nov.-Dec. 1981).

Krishnan, V., et al., "Molecular Adaptations Underlying Susceptibility and Resistance to Social Defeat in Brain Reward Regions," Cell 131(2):391-404, Cell Press, United States (Oct. 2007).

Lagodzinski, Z., et al., "Effect of FK506 and Cyclosporine on Primary and Secondary Skin Allograft Survival in Mice," Immunology 71(1):148-150, Blackwell Scientific Publications, England (Sep. 1990).

Langer, R., et al., "Biocompatibility of Polymeric Delivery Systems for Macromolecules," Journal of Biomedical Materials Research 15(2):267-277, John Wiley & Sons, Inc., United States (1981).

Le, A., et al., "Glucose-independent Glutamine Metabolism via TCA Cycling for Proliferation and Survival in B Cells," Cell Metabolism 15(1):110-121, Cell Press, United States (Jan. 2012).

Le Maux, P., et al., "Chemical Reactivity of 6-diazo-5-oxo-L-norleucine (DON) Catalyzed by Metalloporphyrins (Fe,Ru)," Tetrahedron 66(25):4462-4468, Elsevier (Jun. 2010).

Lee, M.D., et al., "New Antitumor Antibiotic, LL-D05139 Beta. Fermentation, Isolation, Structure Determination and Biological Activities," The Journal of Antibiotics 40(12):1657-1663, Nature Publishing Group, Japan (Dec. 1987).

Lee, C.F., et al., "Preventing Allograft Rejection by Targeting Immune Metabolism," Cell Reports 13(4)760-770, Cell Press, United States (Oct. 2015).

Lee, Y.Z., et al., "Discovery of Selective Inhibitors of Glutaminase-2, which Inhibit mTORC1, Activate Autophagy and Inhibit Proliferation in Cancer Cells," Oncotarget 5(15):6087-6101, Impact Journals, United States (Aug. 2014).

Lentz, M.R., et al., "Changes in MRS Neuronal Markers and T Cell Phenotypes Observed During Early HIV Infection," Neurology 72(17):1465-1472, Lippincott Williams & Wilkins, United States (Apr. 2009).

Li, Q., et al., "A Central Role for mTOR Kinase in Homeostatic Proliferation Induced CD8+ T Cell Memory and Tumor Immunity," Immunity 34(4):541-553, Cell Press, United States (Apr. 2011).

Li, Y., et al., "Learning and Reconsolidation Implicate Different Synaptic Mechanisms," Proceedings of the National Academy of Sciences of the United States of America 110(12):4798-4803, National Academy of Sciences, United States (Mar. 2013).

Liddy, N., et al., "Monoclonal TCR-redirected Tumor Cell Killing," Nature Medicine 18(6):980-987, Nature Publishing Company, United States (Jun. 2012).

Lim, J.H., et al., "Targeting Mitochondrial Oxidative Metabolism in Melanoma Causes Metabolic Compensation through Glucose and Glutamine Utilization," Cancer Research 74(13):3535-3545, American Association for Cancer Research, United States (Jul. 2014).

Liu, W., et al., "Reprogramming of Proline and Glutamine Metabolism Contributes to the Proliferative and Metabolic Responses Regulated by Oncogenic Transcription Factor c-MYC," Proceedings of the National Academy of Sciences of the United States of America 109(23):8983-8988, National Academy of Sciences, United States (Jun. 2012).

Lo, Y.C., et al., "Insight into the Role of mTOR and Metabolism in T Cells Reveals New Potential Approaches to Preventing Graft Rejection," Current Opinion in Organ Transplantation 19(4):363-371, Lippincott Williams & Wilkins, United States (Aug. 2014).

Stupp, R., et al., "Effects of Radiotherapy with Concomitant and Adjuvant Temozolomide Versus Radiotherapy Alone on Survival in Glioblastoma in a Randomised Phase III Study: 5-year Analysis of the EORTC-NCIC Trial," The Lancet. Oncology 10(5):459-466, Lancet Pub. Group, England (May 2009).

Lynch, G., et al., "Phase II Evaluation of DON (6-diazo-5-oxo-L-norleucine) in Patients with Advanced Colorectal Carcinoma," American Journal of Clinical Oncology 5(5):541-543, Lippincott Williams & Wilkins, United States (Oct. 1982).

Macintyre, A.N., et al., "The Glucose Transporter Glut1 is Selectively Essential for CD4 T Cell Activation and Effector Function," Cell Metabolism 20(1):61-72, Cell Press, United States (Jul. 2014).

Maciver, N.J., et al., "Metabolic Regulation of T Lymphocytes," Annual Review of Immunology 31:259-283, Annual Reviews Inc, United States (2013).

Magill, G.B. and Myers, W.P., "Alterations in Calcium Metabolism in Cancer Patients Treated with 6-diazo-5-oxo-L-norleucine," Proceedings of the Society for Experimental Biology and Medicine 93(2):314-318, Blackwell Science, United States (Nov. 1956).

Magill, G.B., et al., "Pharmacological and Initial Therapeutic Observations on 6-diazo-5-oxo-1-norleucine (DON) in Human Neoplastic Disease," Cancer 10(6):1138-1150, Wiley, United States (Nov.-Dec. 1957).

Mcarthur, J.C., et al., "Human Immunodeficiency Virus-associated Neurocognitive Disorders: Mind the Gap," Annals of Neurology 67(6):699-714, Wiley-Liss, United States (Jun. 2010).

Mcdermott, L.A., et al., "Design and Evaluation of Novel Glutaminase Inhibitors," Bioorganic & Medicinal Chemistry 24(8):1819-1839, Elsevier Science, England (Apr. 2016).

Mcgaugh, J.L., "Memory—a Century of Consolidation," Science 287(5451):248-251, American Association for the Advancement of Science, United States (Jan. 2000).

Medina, M.A., et al., "Relevance of Glutamine Metabolism to Tumor Cell Growth," Molecular and Cellular Biochemistry 113(1):1-15, Springer, Netherlands (Jul. 1992).

Michalek, R.D., et al., "Cutting Edge: Distinct Glycolytic and Lipid Oxidative Metabolic Programs are Essential for Effector and Regulatory CD4+ T Cell Subsets," Journal of Immunology 186(6):3299-3303, American Association of Immunologists, United States (Mar. 2011).

Nakaya, M., et al., "Inflammatory T Cell Responses Rely on Amino Acid Transporter ASCT2 Facilitation of Glutamine Uptake and mTORC1 Kinase Activation," Immunity 40(5):692-705, Cell Press, United States (May 2014).

Nedelcovych, M.T., et al. "N-(Pivaloyloxy)alkoxy-carbonyl Prodrugs of the Glutamine Antagonist 6-Diazo-5-oxo-L-norleucine (DON) as a Potential Treatment for HIV Associated Neurocognitive Disorders," Journal of Medicinal Chemistry 60(16):7186-7198, American Chemical Society, United States (Aug. 2017).

Ngiow, S.F., et al., "Prospects for TIM3-Targeted Antitumor Immunotherapy," Cancer Research 71(21):6567-6571, American Association for Cancer Research, United States (Nov. 2011).

Nishio, M., et al., "Antiviral Effect of 6-diazo-5-oxo-L-norleucine, Antagonist of Gamma-glutamyl Transpeptidase, on Replication of Human Parainfluenza Virus Type 2," The Journal of General Virology 71( Pt 1):61-67, Microbiology Society, England (Jan. 1990).

Oberhuber, R., et al., "Murine Cervical Heart Transplantation Model using a Modified Cuff Technique," Journal of Visualized Experiments 92:e50753, MYJoVE Corporation, United States (Oct. 2014).

Oderup, C., et al., "Costimulation Blockade-Induced Cardiac Allograft Tolerance: Inhibition of T Cell Expansion and Accumulation of Intragraft cD4+Foxp3+ T Cells," Transplantation 82(11):1493-1500, Lippincott Williams & Wilkins, United States (Dec. 2006).

Online Mendelian Inheritance in Man, OMIM as of [retrieved on May 1, May 1, 2010]. World Wide Web Retrieved from the Internet: (URL: http://www.ncbi.nlm,nih.gov/omim/and m OnlineMendelianInheritance in Animals (OMIA) at http://omia.angis.org.au/contact.shtml).

Ostrom, Q.T., et al., "CBTRUS Statistical Report: Primary Brain and Central Nervous System Tumors Diagnosed in the United States

(56) References Cited

OTHER PUBLICATIONS in 2008-2012," Neuro-oncology 17(Suppl 4):iv1-iv62, Oxford University Press, England (Oct. 2015).
Ovejera, A.A., et al., "Efficacy of 6-diazo-5-oxo-L-norleucine and N-[N-gamma-glutamyl-6-diazo-5-oxo-norleucinyl]-6-diazo-5-oxo-norleucine against Experimental Tumors in Conventional and Nude Mice," Cancer Research 39(8):3220-3224, American Association for Cancer Research, United States (Aug. 1979).
Pawlik, T.M., et al., "Hepatic Glutamine Transporter Activation in Burn Injury: Role of Amino Acids and Phosphatidylinositol-3-kinase," American Journal of Physiology. Gastrointestinal and Liver Physiology 278(4):G532-G541, American Physiological Society, United States (Apr. 2000).
Pearce, E.L., et al., "Fueling Immunity: Insights into Metabolism and Lymphocyte Function," Science 342(6155):1242454, American Association for the Advancement of Science, United States (Oct. 2013).
Pilon, C.B., et al., "Administration of Low Doses of IL-2 Combined to Rapamycin Promotes Allogeneic Skin Graft Survival in Mice," American Journal of Transplantation 14(12):2874-2882, Wiley-Blackwell, United States (Dec. 2014).
Pollizzi, K.N. and Powell, J.D., "Integrating Canonical and Metabolic Signalling Programmes in the Regulation of T Cell Responses," Nature Reviews. Immunology 14(7):435-446, Nature Pub. Group, England (Jul. 2014).
Potter, M.C., et al., "Neurological Sequelae Induced by Alphavirus Infection of the CNS are Attenuated by Treatment with the Glutamine Antagonist 6-diazo-5-oxo-l-norleucine," Journal of Neurovirology 21(2):159-173, Stockton Press, United States (Apr. 2015).
Potter, M.C., et al., "Targeting the Glutamatergic System for the Treatment of HIV-associated Neurocognitive Disorders," Journal of Neuroimmune Pharmacology 8(3):594-607, Springer Science, United States (Jun. 2013).
Powell, J.D. and Zheng, Y. "Dissecting the Mechanism of T-cell Anergy with Immunophilin Ligands," Current Opinion in Investigational Drugs 7(11):1002-1007, Thomson Reuters, England (Nov. 2006).
Powell, J.D., et al., "A Modified Model of T-Cell Differentiation Based on mTOR Activity and Metabolism," Cold Spring Harbor Symposia on Quantitative Biology 78(1):125-130, Cold Spring Harbor Laboratory Press, United States (2013).
Powell, J.D., et al., "A2ar Antagonists: Next Generation Checkpoint Blockade for Cancer Immunotherapy," Computational and Structural Biotechnology Journal 13:265-272, Elsevier B.V, Netherlands (Apr. 2015).
Pugh, C.R., et al., "Selective Effects of Peripheral Lipopolysaccharide Administration on Contextual and Auditory-cue Fear Conditioning," Brain, Behavior, and Immunity 12(3):212-229, Elsevier, Netherlands (Sep. 1998).
Raez, L.E., et al., "A Phase I Dose-escalation Trial of 2-deoxy-d-glucose Alone or Combined with Docetaxel in Patients with Advanced Solid Tumors," Cancer Chemotherapy and Pharmacology 71(2):523-530, Springer Verlag, Germany (Feb. 2013).
Rahman, A., et al., "Phase I Study and Clinical Pharmacology of 6-diazo-5-oxo-L-norleucine (DON)," Investigational New Drugs 3(4):369-374, Springer, United States (1985).
Rahn, K.A., et al., "Inhibition of Glutamate Carboxypeptidase II (GCPII) Activity as a Treatment for Cognitive Impairment in Multiple Sclerosis," Proceedings of the National Academy of Sciences of the United States of America 109(49):20101-20106, National Academy of Sciences, United States (Dec. 2012).
Rais, R., et al., "Discovery of 6-diazo-5-oxo-L-norleucine (DON) Prodrugs with Enhanced CSF Delivery in Monkeys: a Potential Treatment for Glioblastoma," Journal of Medicinal Chemistry 59(18):8621-8633, American Chemical Society, United States (Sep. 2016).
Rautio, J., et al., "Prodrugs: Design and Clinical Applications," Nature Reviews, Drug Discovery 7(3):255-270, Nature Publishing Group, England (Mar. 2008).

Reitzer, L.J., et al., "Evidence that Glutamine, not Sugar, is the Major Energy Source for Cultured HeLa Cells," The Journal of Biological Chemistry 254(8):2669-2676, American Society for Biochemistry and Molecular Biology, United States (Apr. 1979).
Robertson, K.R., et al., "The Prevalence and Incidence of Neurocognitive Impairment in the HAART Era," AIDS 21(14):1915-1921, Lippincott Williams & Wilkins, England (Sep. 2007).
Roodnat, J.I., et al., "15-year Follow-up of a Multicenter, Randomized, Calcineurin Inhibitor withdrawal Study in Kidney Transplantation," Transplantation 98(1):47-53, Lippincott Williams & Wilkins, United States (Jul. 2014).
Rowe, I., et al., "Defective Glucose Metabolism in Polycystic Kidney Disease Identifies a New Therapeutic Strategy," Nature Medicine 19(4):488-493, Nature Publishing Company, United States (Apr. 2013).
Roybal, K., et al., "Mania-like Behavior Induced by Disruption of CLOCK," Proceedings of the National Academy of Sciences of the United States of America 104(15):6406-6411, National Academy of Sciences, United States (Apr. 2007).
Ru, P., et al., "Tumor Metabolism of Malignant Gliomas," Cancers 5(4):1469-1484, MDPI, Switzerland (Dec. 2013).
Rubin, J., et al., "A Phase II Study of 6-diazo-5-oxo-L-norleucine (DON, NSC-7365) in Advanced Large Bowel Carcinoma," American Journal of Clinical Oncology 6(3):325-326, Lippincott Williams & Wilkins, United States (Jun. 1983).
Sailasuta, N., et al., "Change in Brain Magnetic Resonance Spectroscopy After Treatment During Acute HIV Infection," PLoS One 7(11):e49272, Public Library of Science, United States (2012).
Satake, A., et al., "Inhibition of Calcineurin Abrogates while Inhibition of mTOR Promotes Regulatory T Cell Expansion and Graft-versus-host Disease Protection by IL-2 in Allogeneic Bone Marrow Transplantation," PLoS One 9(3):e92888, Public Library of Science, United States (Mar. 2014).
Sayegh, M.H., and Carpente, C.B., "Transplantation 50 Years Later—progress, Challenges, and Promises," The New England Journal of Medicine 351(26):2761-2766, Massachusetts Medical Society, United States (Dec. 2004).
Sengupta, S., et al., "Regulation of the mTOR Complex 1 Pathway by Nutrients, Growth Factors, and Stress," Molecular Cell 40(2):310-322, Cell Press, United States (Oct. 2010).
Shah, U., and Hodgson, R., "Recent Progress in the Discovery of Adenosine A(2A) Receptor Antagonists for the Treatment of Parkinson's Disease," Current Opinion in Drug Discovery & Development 13(4):466-480, Thomson Reuters, England (Jul. 2010).
Shi, L.Z., et al., "HIF1alpha-dependent Glycolytic Pathway Orchestrates a Metabolic Checkpoint for the Differentiation of TH17 and Treg Cells," The Journal of Experimental Medicine 208(7):1367-1376, Rockefeller University Press, United States (Jul. 2011).
Shijie, J., et al., "Blockade of Glutamate Release from Microglia Attenuates Experimental Autoimmune Encephalomyelitis in Mice," The Tohoku Journal of Experimental Medicine 217(2):87-92, Tohoku University Medical Library, Japan (Feb. 2009).
Schulze, A. and Harris, A.L., "How Cancer Metabolism is Tuned for Proliferation and Vulnerable to Disruption," Nature 491(7424):364-373, Nature Publishing Group, England (Nov. 2012).
Shelton, L.M., et al., "Glutamine Targeting Inhibits Systemic Metastasis in the VM-M3 Murine Tumor Model," International Journal of Cancer 127(10):2478-2485, International Union Against Cancer, United States (Nov. 2010).
Shukla, K., et al., "Design, Synthesis, and Pharmacological Evaluation of Bis-2-(5-phenylacetamido-1,2,4-thiadiazol-2-yl)ethyl Sulfide 3 (BPTES) Analogs as Glutaminase Inhibitors," Journal of Medicinal Chemistry 55(23)10551-10563, American Chemical Society, United States (Dec. 2012).
Sidman, et al., "Controlled Release of Macromolecules and Pharmaceuticals from Synthetic Polypeptides Based on Glutamic Acid," Biopolymers 22:547-556, John Wiley & Sons, Inc., United States (Jan. 1983).
Simioni, S., et al., "Cognitive Dysfunction in HIV Patients Despite Long-standing Suppression of Viremia," AIDS 24(9):1243-1250, Lippincott Williams & Wilkins, England (Jun. 2010).

(56) References Cited

OTHER PUBLICATIONS

Sklaroff, R.B., et al., "Phase I Study of 6-diazo-5-oxo-L-norleucine (DON)," Cancer Treatment Reports 64(12):1247-1251, National Cancer Institute, United States (1980).
Srikanth, K., et al., "Synthesis, Screening and Quantitative Structure-activity Relationship (QSAR) Studies of Some Glutamine Analogues for Possible Anticancer Activity," Bioorganic & Medicinal Chemistry 10(7):2119-2131, Elsevier Science, England (Jul. 2002).
Stupp, R., et al., "Radiotherapy Plus Concomitant and Adjuvant Temozolomide for Glioblastoma," The New England Journal of Medicine 352(10):987-996, Massachusetts Medical Society, United States (Mar. 2005).
Sullivan, M.P., et al., "A Comparison of the Effectiveness of Standard Dose 6-mercaptopurine, Combination 6-mercaptopurine and DON, and High-loading 6-mercaptopurine Therapies in Treatment of the Acute Leukemias of Childhood: Results of a Coperative Study," Cancer Chemotherapy Reports 18:83-95, National Cancer Institute, United States (May 1962).
Sullivan, M.P., et al., "Pharmacokinetic and Phase I Study of Intravenous DON (6-diazo-5-oxo-L-norleucine) in Children," Cancer Chemotherapy Reports 21(1):78-84, Springer Verlag, Germany (1988).
Suzuki, A., et al., "Memory Reconsolidation and Extinction have Distinct Temporal and Biochemical Signatures," The Journal of Neuroscience 24(20):4787-4795, Society for Neuroscience, United States (May 2004).
Tanaka, K., et al., "Compensatory Glutamine Metabolism Promotes Glioblastoma Resistance to mTOR Inhibitor Treatment," The Journal of Clinical Investigation 125(4):1591-1602, American Society for Clinical Investigation, United States (Apr. 2015).
Tarnowski, G.S., and Stock, C.C., "Effects of Combinations of Azaserine and of 6-diazo-5-oxo-L-norleucine with Purine Analogs and Other Antimetabolites on the Growth of Two Mouse Mammary Carcinomas," Cancer Research 17(10):1033-1039, American Association for Cancer Research, United States (Nov. 1957).
Thangavelu, K., et al., "Structural Basis for the Active Site Inhibition Mechanism of Human Kidney-type Glutaminase (KGA)," Scientific Reports 4:3827, Nature Publishing Group, England (Jan. 2014).
Thomas, A.G., et al., "Kinetic Characterization of Ebselen, Chelerythrine and Apomorphine as Glutaminase Inhibitors," Biochemical and Biophysical Research Communications 438(2):243-248, Elsevier, United States (Aug. 2013).
Thomas, A.G., et al., "Small Molecule Glutaminase Inhibitors Block Glutamate Release from Stimulated Microglia," Biochemical and Biophysical Research Communications 443(1):32-36, Elsevier, United States (Jan. 2014).
Thomson, L.M., and Sutherland, R.J., "Systemic Administration of Lipopolysaccharide and Interleukin-1 beta have Different Effects on Memory Consolidation," Brain Research Bulletin 67(1-2):24-29, Elsevier Science, United States (Sep. 2005).
Tran, T.Q., et al., "Glutamine Deficiency Induces DNA Alkylation Damage and Sensitizes Cancer Cells to Alkylating Agents through Inhibition of ALKBH Enzymes," PLoS Biology 15(11):e2002810, Public Library of Science, United States (Nov. 2017).
Tsilidis, K.K., et al., "Metformin does not Affect Cancer Risk: A Cohort Study in the U.K. Clinical Practice Research Datalink Analyzed like an Intention-to-Treat Trial," Diabetes Care 37(9)2522-2532, American Diabetes Association, United States (Sep. 2014).
Ueki, N., et al., "Synthesis and Preclinical Evaluation of a Highly Improved Anticancer Prodrug Activated by Histone Deacetylases and Cathepsin L," Theranostics 6(6):808-816, Ivyspring International Publisher, Australia (Mar. 2016).
Upadhyay, R.K., "Drug Delivery Systems, CNS Protection, and the Blood Brain Barrier," BioMed Research International 2014:869269, Hindawi Pub. Co, United States (2014).
Vander Heiden, M.G., et al., "Understanding the Warburg Effect: The Metabolic Requirements of Cell Proliferation," Science 324(5930):1029-1033, American Association for the Advancement of Science, United States (May 2009).

Varoqui, H., et al., "Cloning and Functional Identification of a Neuronal Glutamine Transporter," The Journal of Biological Chemistry 275(6):4049-4054, American Society for Biochemistry and Molecular Biology, United States (Feb. 2000).
Waickman, A.T., and Powell, J.D., "mTOR, Metabolism, and the Regulation of T-cell Differentiation and Function," Immunological Reviews 249(1)43-58, Blackwell, England (Sep. 2012).
Wang, R., et al., "The Transcription Factor Myc Controls Metabolic Reprogramming upon T Lymphocyte Activation," Immunity 35(6):871-882, Cell Press, United States (Dec. 2011).
Warburg, O., "On Respiratory Impairment in Cancer Cells," Science 124(3215):269-270, American Association for the Advancement of Science, United States (Aug. 1956).
Weller, M., et al., "EANO Guideline for the Diagnosis and Treatment of Anaplastic Gliomas and Glioblastoma.," The Lancet. Oncology 15(9):e395-403, Lancet Pub. Group, England (Aug. 2014).
Willems, L., et al., "Inhibiting Glutamine Uptake Represents an Attractive New Strategy for Treating Acute Myeloid Leukemia," Blood 122(20):3521-3532, American Society of Hematology, United States (Nov. 2013).
Willis, R.C. and Seegmiller, J.E., "The Inhibition by 6-diazo-5-oxo-L-norleucine of Glutamine Catabolism of the Cultured Human Lymphoblast," Journal of Cellular Physiology 93(3):375-382, Wiley-Liss, United States (Dec. 1977).
Windmueller, H.G. and Spaeth, A.E., "Uptake and Metabolism of Plasma Glutamine by the Small Intestine," The Journal of Biological Chemistry 249(16):5070-5079, American Society for Biochemistry and Molecular Biology, United States (Aug. 1974).
Wise, D.R. and Thompson, C.B., "Glutamine Addiction: A New Therapeutic Target in Cancer," Trends in Biochemical Sciences 35(8):427-433, Elsevier Trends Journals, England (Aug. 2010).
Wise, D.R., et al., "Myc Regulates a Transcriptional Program that Stimulates Mitochondrial Glutaminolysis and Leads to Glutamine Addiction," Proceedings of the National Academy of Sciences of the United States of America 105(48):18782-18787, National Academy of Sciences, United States (Dec. 2008).
Wook Koo, J., et al., "Essential Role of Mesolimbic Brain-Derived Neurotrophic Factor in Chronic Social Stress-InducedDepressive Behaviors," Biological Psychiatry 80(6):469-478, Elsevier, United States (Sep. 2016).
Wu, T., et al., "Immunosuppressive Drugs on Inducing Ag-specific CD4(+)CD25(+)Foxp3(+) Treg Cells During Immune Response in Vivo," Transplant Immunology 27(1):30-38, Elsevier, Netherlands (Aug. 2012).
Yamasaki, T., et al., "Exploring a Glycolytic Inhibitor for the Treatment of an FH-deficient Type-2 Papillary RCC," Nature Reviews. Urology 8(3):165-171, Nature Pub. Group, England (Mar. 2011).
Yang, K. and Chi. H., "mTOR and Metabolic Pathways in T Cell Quiescence and Functional Activation," Seminars in Immunology 24(6):421-428, Academic Press, England (Dec. 2012).
Zgodka, D., et al., "A Diffusible Analogue of N3-(4-methoxyfumaroyl)-I-2,3-diaminopropanoic Acid With Antifungal Activity," Microbiology 147(Pt 7):1955-1959, (Jul. 2001).
Zhang, W., et al., "Overexpression of Cysteine Cathepsin L Is a Marker of Invasion and Metastasis in Ovarian Cancer," Oncology Reports 31(3):1334-1342, D.A. Spandidos, Greece (Mar. 2014).
Zheng, Y., et al., "Anergic T Cells Are Metabolically Anergic," Journal of Immunology 183(10):6095-6101, American Association of Immunologists, United States (Nov. 2009).
Zimmermann, S.C., et al., "N-substituted Prodrugs of Mebendazole Provide Improved Aqueous Solubility and Oral Bioavailability in Mice and Dogs," Journal of Medicinal Chemistry 61(9):3918-3929, American Chemical Society, United States (May 2018).
Zink, M.C, "Translational Research Models and Novel Adjunctive Therapies for NeuroAIDS," Journal of Neuroimmune Pharmacology 2(1):14-19, Springer Science + Business Media, United States (Mar. 2007).
Office Action dated Dec. 14, 2018, for co-pending U.S. Appl. No. 15/885,147, filed Jan. 31, 2018, U.S. Patent and Trademark Office, Alexandria, Virginia.
Daye, D., et al., "Metabolic reprogramming in cancer: Unraveling the role of glutamine in tumorigenesis," Seminars in Cell & Developmental Biology 23:362-369, Elsevier Ltd., (2012).

(56) References Cited

OTHER PUBLICATIONS

Ostroukhova, M., et al., "Switching of Glucose Metabolism from Oxidative Phosphorylation to Aerobic Glycolysis (the Warburg Effect) in T-Cells from Patients with Asthma," J Allergy Clin Immunol 125 (Issue 2, Supplement 1) p. AB39, abstract 155 (2010).
Extended European Search Report, European Appl. No. 16833623.8, dated Feb. 12, 2019.
Abo-Ghalia, M, et al., "Synthesis of inhibitors of the meso-diaminopimelate-adding enzyme from *Escherichia coli*", Int. J. Peptide Protein Res. 32:208-222, Munksgaard International Publishers, Copenhagen (1988).
Jancarik, A. "Novel lymphoid targeted prodrugs of the glutamine antagonist DON for the treatment of hematological malignancies", The FASEB Journal, Abstract No. Ib472, Published Online: Apr. 1, 2016.
Englert, J. et al., "Abstract 1035: Targeting glutamine metabolism with the novel inhibitor JHU-083 inhibits tumor growth and alters the tumor immune microenvironment", Proceedings: AACR 107th Annual Meeting, New Orleans, LA, American Association for Cancer Research, Apr. 16-20, 2016.
Extended European Search Report, European Appl. No. 16833638.6, dated May 22, 2019.
Ramsay: "Immune checkpoint blockade immunotherapy to activate anti-tumour T-cell immunity", The British Journal of Haematology 162:313-325, John Wiley & Sons Ltd. (2013).
Renault: "Getting away with murder: how does the BCL-2 family of proteins kill with immunity? : The BCL-2 family as regulators of immunity", Annals of The New York Academy of Sciences 1285:59-79, The New York Academy of Sciences (2013).
Co-pending U.S. Appl. No. 16/454,853, inventors Slusher et al., filed Jun. 27, 2019.
Co-pending U.S. Appl. No. 16/454,880, inventors Slusher et al., filed Jun. 27, 2019.
Office Action dated Jan. 14, 2020, in U.S. Appl. No. 16/454,853, Slusher B. et al., filed Jun. 27, 2019, 8 pages.
Office Action dated Sep. 24, 2019, in U.S. Appl. No. 16/454,880, Slusher B. et al., filed Jun. 27, 2019, 8 pages.
Office Action dated Jan. 17, 2020, in U.S. Appl. No. 16/454,880, Slusher B. et al., filed Jun. 27, 2019, 10 pages.
Notice of Allowance dated May 5, 2020, in U.S. Appl. No. 16/454,880, Slusher, B. et al., filed Jun. 27, 2019, 8 pages.
Office Action dated Aug. 1, 2018, in U.S. Appl. No. 15/885,258, Slusher B. et al., filed Jan. 31, 2018 2019, 8 pages.
Office Action dated Nov. 13, 2018, in U.S. Appl. No. 15/885,258, Slusher B. et al., filed Jan. 31, 2018 2019, 9 pages.
Office Action dated Feb. 26, 2019, in U.S. Appl. No. 15/885,258, Slusher B. et al., filed Jan. 31, 2018 2019, 11 pages.
Notice of Allowance dated Apr. 2, 2019 in U.S. Appl. No. 15/885,258, Slusher B. et al., filed Jan. 31, 2018 2019, 5 pages.

\* cited by examiner

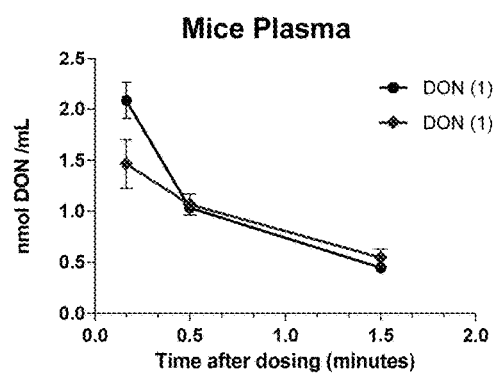
FIG. 6A
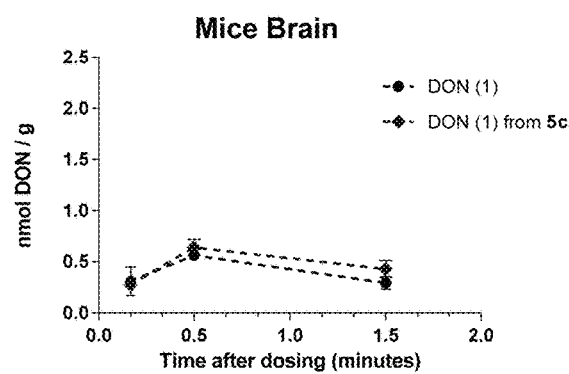
FIG. 6B
| Compound Dosed | Dose (mg/kg equiv) | Tissue | DON $C_{max}$ (nmol/mL or nmol/g) | DON $T_{max}$ (hr) | DON $AUC_{0-t}$ (hr*nmol/mL or hr*nmol/g) | Brain to plasma ratio |
|---|---|---|---|---|---|---|
| DON (1) | 0.8 | Plasma | 2.2 | 0.17 | 1.25 | 0.46 |
| | | Brain | 0.56 | 0.50 | 0.57 | |
| 5c | 0.8 | Plasma | 1.5 | 1.50 | 1.22 | 0.57 |
| | | Brain | 0.64 | 30 | 0.69 | |
FIG. 6C

FIG. 7A

Monkey Plasma — DON Concentrations (nmol/mL) vs hours; DON (1) and DON (1) from 5c

FIG. 7B

Monkey CSF — CSF to plasma ratio for DON (1) and DON (1) from 5c

FIG. 7C

| Compound Dosed | Dose (mg/kg equiv) | DON $C_{max}$ (nmol/mL) | DON $T_{max}$ (hr) | DON $AUC_{0-t}$ (hr*nmol/mL) |
|---|---|---|---|---|
| 1 | 1.6 | 12.6 | 0.25 | 42.7 |
| 5c | 1.6 | 2.23 | 0.25 | 5.71 |

FIG. 7D

DON (1)            Prodrug 5c

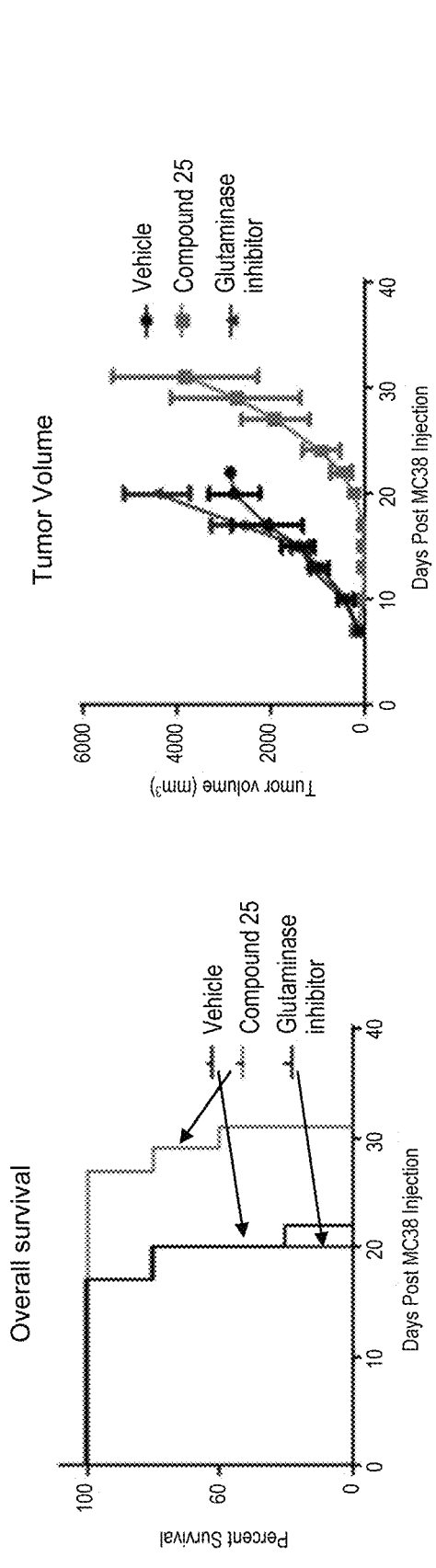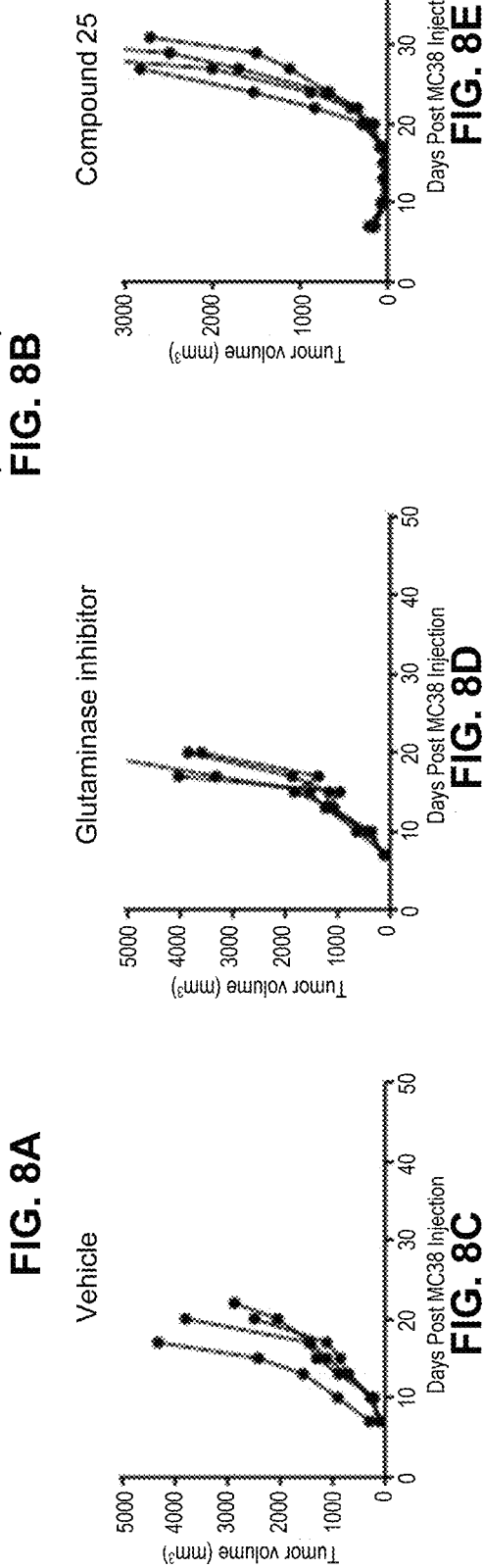

1.0 mg/kg x 5 then 0.3 mg/kg with anti-PD1

Compound 25 1.0 mg/kg BID with anti-PD1

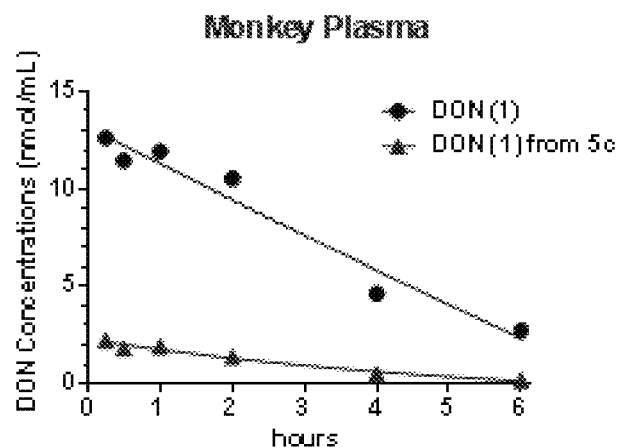
FIG. 22A
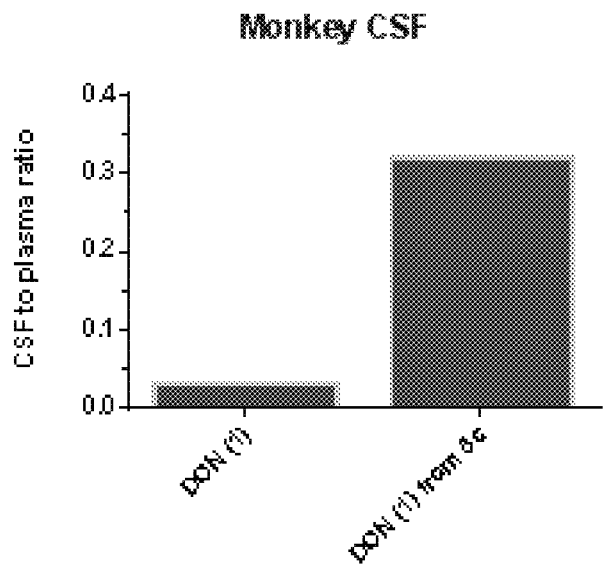
FIG. 22B
| Compound Dosed | Dose (mg/kg equiv) | DON $C_{max}$ (nmol/mL) | DON $T_{max}$ (hr) | DON $AUC_{0-t}$ (hr*nmol/mL) |
|---|---|---|---|---|
| 1 | 1.6 | 12.6 | 0.25 | 42.7 |
| 5c | 1.6 | 2.23 | 0.25 | 5.71 |
FIG. 22C

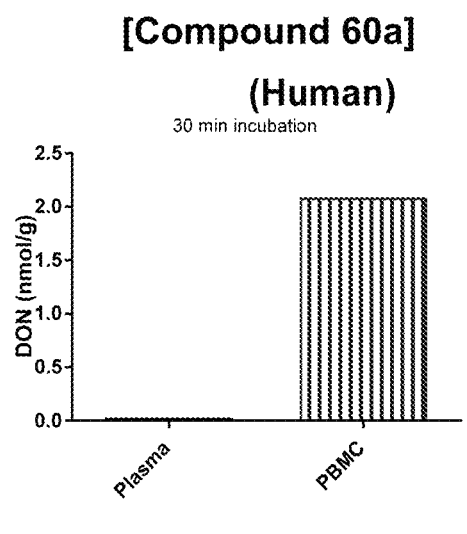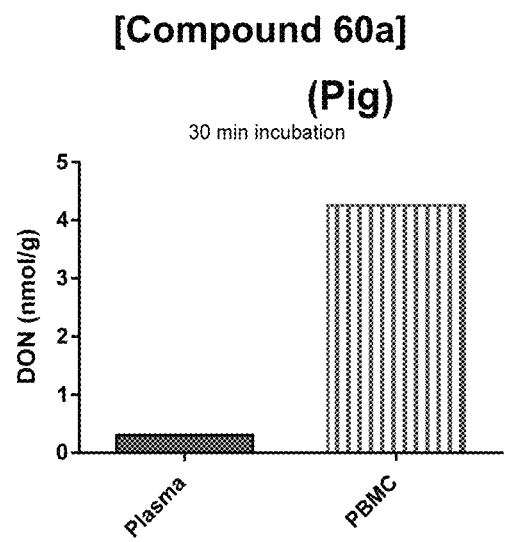
FIG. 27I          FIG. 27J

25: DON Plasma
25: DON PBMC

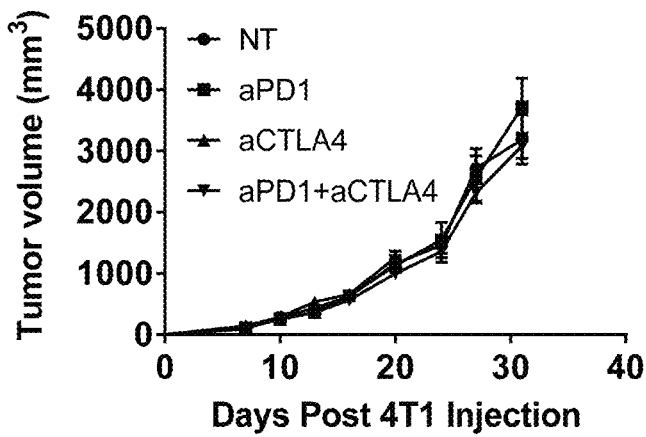
FIG. 41A
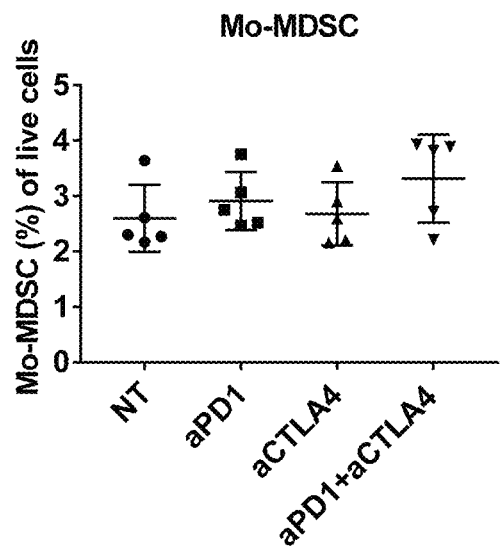 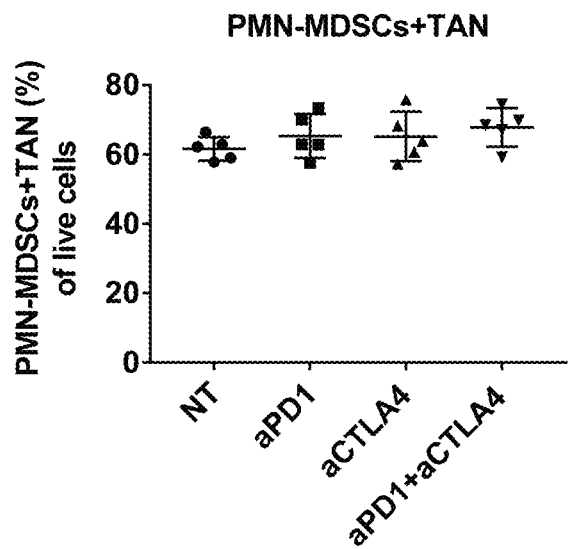
FIG. 41B  FIG. 41C

NT 4T1
D30 Lung

Compound 25 4T1
D30 Lung

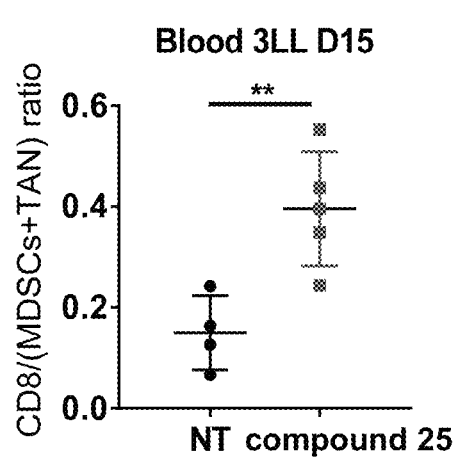
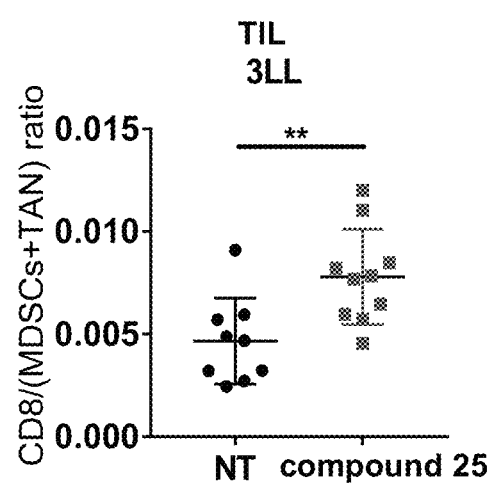
FIG. 51C
FIG. 51D

METHODS FOR CANCER AND IMMUNOTHERAPY USING PRODRUGS OF GLUTAMINE ANALOGS

CROSS-REFERENCE TO RELATED APPLICATIONS

This application is a continuation-in-part of U.S. patent application Ser. No. 15/885,275, filed on Jan. 31, 2018, which is a continuation in part of PCT/US2016/044829, filed Jul. 29, 2016, that claims the benefit of U.S. Provisional Application Nos. 62/199,381 and 62/199,566, both filed Jul. 31, 2015, the contents of each are incorporated herein by reference in their entirety.

BACKGROUND

Cells under certain conditions may undergo a metabolic switch from a metabolic profile that requires less activity of certain metabolic pathways to meet the cell's energy demands to a metabolic profile that requires greater activity of those metabolic pathways or increased activity of other metabolic pathways to meet its energy demands. For example, cells under certain conditions may undergo a switch toward increased glycolysis and away from oxidative phosphorylation (OXPHOS). While glycolysis provides less adenosine triphosphate (ATP) than oxidative phosphorylation, it has been proposed that aerobic glycolysis permits the generation of the substrates necessary for the generation of amino acids, nucleic acids and lipids, all of which are crucial for proliferation (Vander Heiden et al. (2009) *Science* 324(5930):1029-1033). This use of glycolysis in the presence of oxygen was first described by Otto Warburg in cancer cells (Warburg (1956) *Science* 124 (3215):269-270) and was subsequently found to be important in activated T cells (Warburg et al. (1958) [Metabolism of leukocytes]. *Zeitschrift fur Naturforschung. Teil B: Chemie, Biochemie, Biophysik, Biologie* 13B (8):515-516). These metabolically reprogrammed cells depend on the increased activity of certain metabolic pathways, such as pathways involved in glutamine metabolism, glycolysis, and fatty acid synthesis. However, specific inhibitors of individual enzymes in these metabolic pathways alone have not proven effective because multiple points within each metabolic pathway are modulated as a cell's metabolism is reprogrammed to meet the extraordinarily large energy demands of the abnormal, harmful, or unhealthy state.

SUMMARY

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., edition as of December 2008; Sambrook, Russell, and Sambrook, *Molecular Cloning. A Laboratory Manual.* 3$^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange 10$^{th}$ ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, World Wide Web URL: http://www.ncbi.nlm.nih.gov/omim/ and in Online Mendelian Inheritance in Animals (OMIA), a database of genes, inherited disorders and traits in animal species (other than human and mouse), at http://omia.angis.org.au/contact.shtml.

In some aspects, the presently disclosed subject matter provides a method for treating a cancer in a subject in need thereof, the method comprising: (a) administering a therapeutically effective amount of a first immunotherapy to the subject, wherein the first immunotherapy is a metabolic reprogramming agent that decreases glutamine metabolic activity; and (b) optionally administering a therapeutically effective amount of a second immunotherapy to the subject.

In particular embodiments, the metabolic reprogramming agent is a glutamine antagonist. In particular embodiments, the metabolic reprogramming agent is a glutamine analog that interferes with a glutamine metabolic pathway. In particular embodiments, the metabolic reprogramming agent is selected from the group consisting of acivicin (L-(alpha S, 5S)-alpha-amino-3-chloro-4,5-dihydro-5-isoxazoleacetic acid), azaserine, and 6-diazo-5-oxo-norleucine (DON), and 5-diazo-4-oxo-L-norvaline (L-DONV). In particular embodiments, the metabolic reprogramming agent is a prodrug of a glutamine analog that interferes with a glutamine metabolic pathway. In particular embodiments, at least one metabolic reprogramming agent is a prodrug of acivicin, azaserine, DON, and L-DONV. In particular embodiments, at least one metabolic reprogramming agent is a compound having any one of formula (I), formula (IIA), formula (IIB), or formula (III), below.

In particular embodiments, the method includes simultaneously or sequentially administering a therapeutically effective amount of the second immunotherapy, e.g., an immunotherapeutic agent, to the subject.

In particular embodiments, the method includes simultaneously or sequentially administering a therapeutically effective amount of the second immunotherapy to the subject, wherein the second immunotherapy is an immune checkpoint blockade therapy. In particular embodiments, the immune checkpoint blockade therapy is selected from the group consisting of PD-1 antagonists, PD-L1 antagonists, CTLA-4 antagonists, LAG3 antagonists, B7-H3 antagonists, and combinations thereof.

In particular embodiments, the method includes simultaneously or sequentially administering a therapeutically effective amount of the second immunotherapy to the subject, wherein the second immunotherapy is an adoptive cellular therapy.

In particular embodiments, the method includes simultaneously or sequentially administering a therapeutically effective amount of the second immunotherapy to the subject, wherein the second immunotherapy is marrow-infiltrating lymphocytes (MILs).

In particular embodiments, the method includes simultaneously or sequentially administering a therapeutically effective amount of the second immunotherapy to the subject, wherein the second immunotherapy is an adenosine A2aR blockade.

In particular embodiments, the method includes simultaneously or sequentially administering a therapeutically effective amount of the second immunotherapy to the subject, wherein the second immunotherapy is a tumor vaccine.

In particular embodiments, the method includes simultaneously or sequentially administering a therapeutically effective amount of the second immunotherapy to the subject, wherein the second immunotherapy is a passive immunotherapy antibody. In particular embodiments, the passive immunotherapy antibody is selected from the group consisting of bevacizumab, cetuximab, rituximab, trastuzumab, alemtuzumab, ibritumomab tiuxetan, panitumumab, and combinations thereof.

In particular embodiments, the method includes simultaneously or sequentially administering to the subject a therapeutically effective amount of a cancer therapy selected from the group consisting of: (i) chemotherapy; (ii) photodynamic therapy; (iii) proton therapy; (iv) radiotherapy; (v) surgery; and combinations thereof.

In particular embodiments, the first immunotherapy, and the second immunotherapy if administered, is/are administered to the subject in the absence of a cancer therapy selected from the group consisting of: (i) chemotherapy; (ii) photodynamic therapy; (iii) proton therapy; (iv) radiotherapy; (v) surgery; and combinations thereof.

In particular embodiments, the cancer is: (i) a cancer of the central nervous system; (ii) a cancer that is associated with transplant and/or immunosuppression; (iii) a cancer that is refractory to chemotherapy; (iv) a cancer that is refractory to photodynamic therapy; (v) a cancer that is refractory to proton therapy; (vi) a cancer that is refractory to radiotherapy; and (vii) a cancer that is refractory to surgery.

In particular embodiments, the cancer is a newly diagnosed, recurrent, and/or refractory cancer selected from the group consisting of celnasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, brain cancer, oligodendroglioma, neuroblastoma, meningioma, spinal cord tumor, bone cancer, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, colorectal cancer, rectal cancer, esophagus cancer, gall bladder cancer, head cancer, eye cancer, neck cancer, kidney cancer. Wilms' tumor, liver cancer, Kaposi's sarcoma, prostate cancer, lung cancer, testicular cancer, Hodgkin's disease, non-Hodgkin's lymphoma, oral cancer, skin cancer, mesothelioma, multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer and tonsil cancer.

In some aspects, the presently disclosed subject matter provides a method of preventing or reducing the incidence of a relapse in a cancer subject in remission, the method comprising administering to the subject a therapeutically effective amount of a metabolic reprogramming agent, wherein the metabolic reprogramming agent is selected from the group consisting of acivicin (L-(alpha S, 5S)-alpha-amino-3-chloro-4,5-dihydro-5-isoxazoleacetic acid), azaserine, and 6-diazo-5-oxo-norleucine (DON), and 5-diazo-4-oxo-L-norvaline (L-DONV), and prodrugs thereof. In particular embodiments, at least one metabolic reprogramming agent is a compound having any one of formula (I), formula (IIA), formula (IIB), or formula (III), below.

In particular embodiments, the metabolic reprogramming agent is: (i) administered to the subject post transplant; (ii) administered to the subject post chemotherapy; (iii) administered to the subject post immunotherapy; (iv) administered to the subject post photodynamic therapy; (v) administered to the subject post proton therapy; (vi) administered to the subject post radiotherapy; (vii) administered to the subject post surgery; and combinations thereof.

Applicant has found that compounds of the disclosure having formula (I), formula (IIA), formula (IIB), and formula (III) are stable in plasma, liver microsomes, liver tissue, and gastrointestinal tissue, yet these compounds are cleaved in tumor cells to liberate DON in tumor tissue. The unexpected tumor-targeted properties of compounds having formula (I), formula (IIA), formula (IIB), and formula (III) result in a surprising improvement in therapeutic index for treating cancer with DON and provide the maximum therapeutic benefit to a subject in need of such treatment.

Applicant has also found unexpectedly that compounds of the disclosure having formula (I), formula (IIA), formula (IIB), and formula (III) exhibit unexpected enhanced CSF to plasma partitioning after administration, making them uniquely useful for the treatment of CNS cancers such as glioblastoma, oligodendroglioma, neuroblastoma, meningioma, spinal cord tumor and metastatic cancer that has spread to the central nervous system (CNS).

Applicant has also found unexpectedly that compounds of the disclosure having formula (I), formula (IIA), formula (IIB), and formula (III) condition tumors to be eliminated by checkpoint inhibitor therapy, e.g. with anti PD-1 antibodies, in subjects with cancer.

Applicant has also found unexpectedly that compounds of the disclosure having formula (I), formula (IIA), formula (IIB), and formula (III) enhance the response to checkpoint inhibitor therapy, e.g., with anti PD-1 antibodies.

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWINGS

Figure 1:
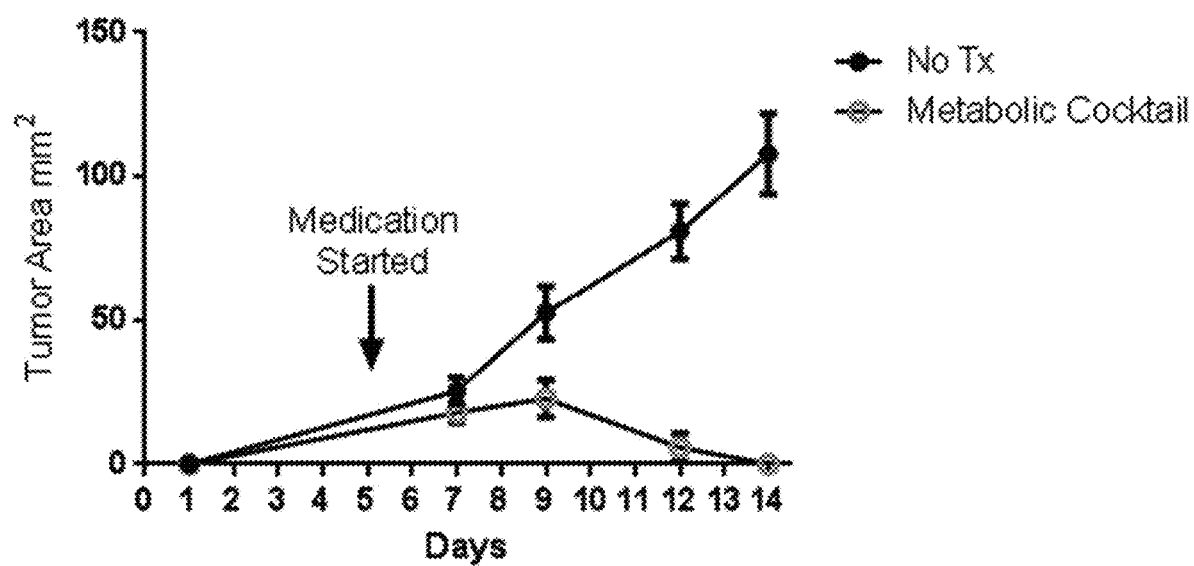
Figure 2:
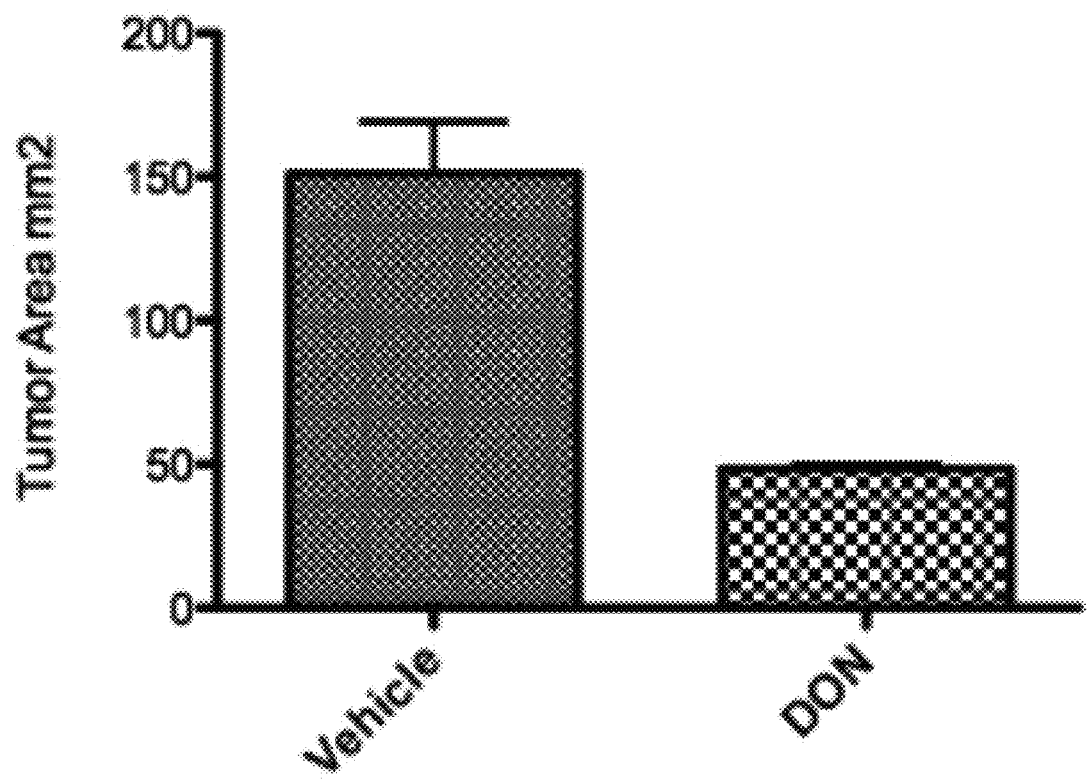
Figure 3:
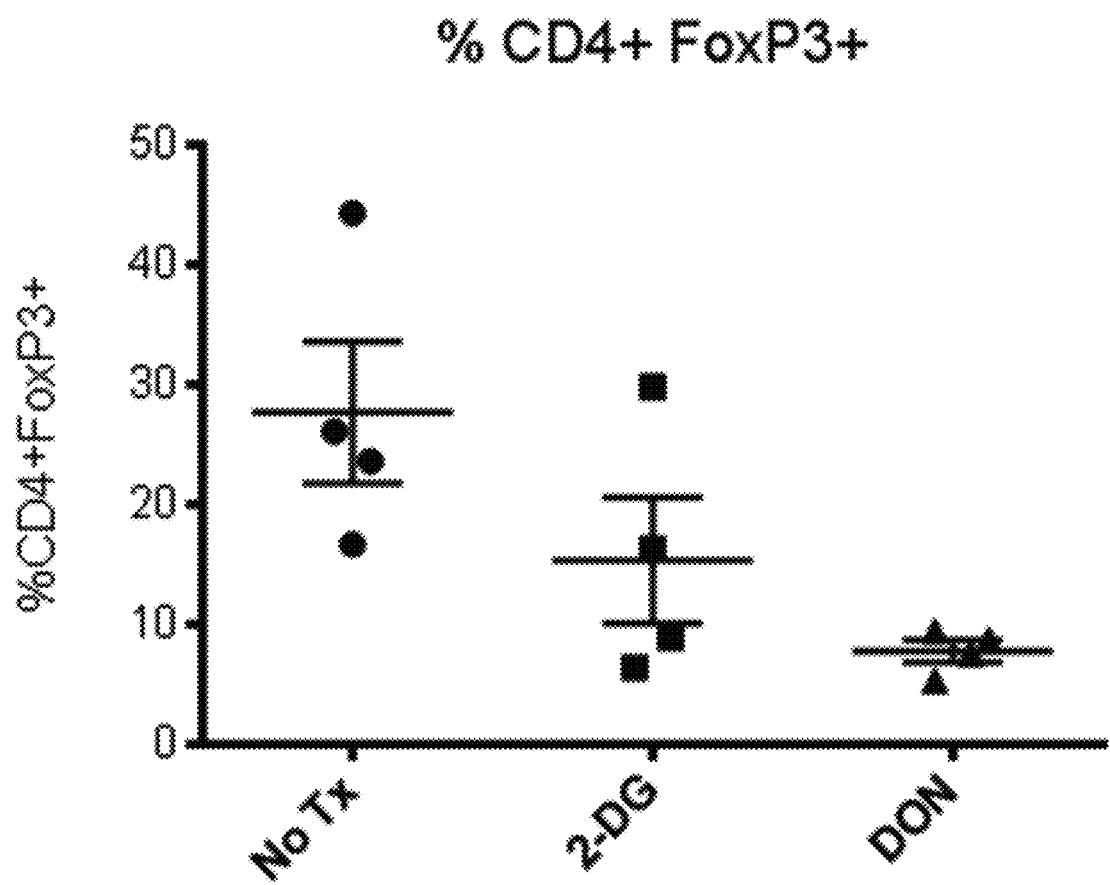
Figure 4:
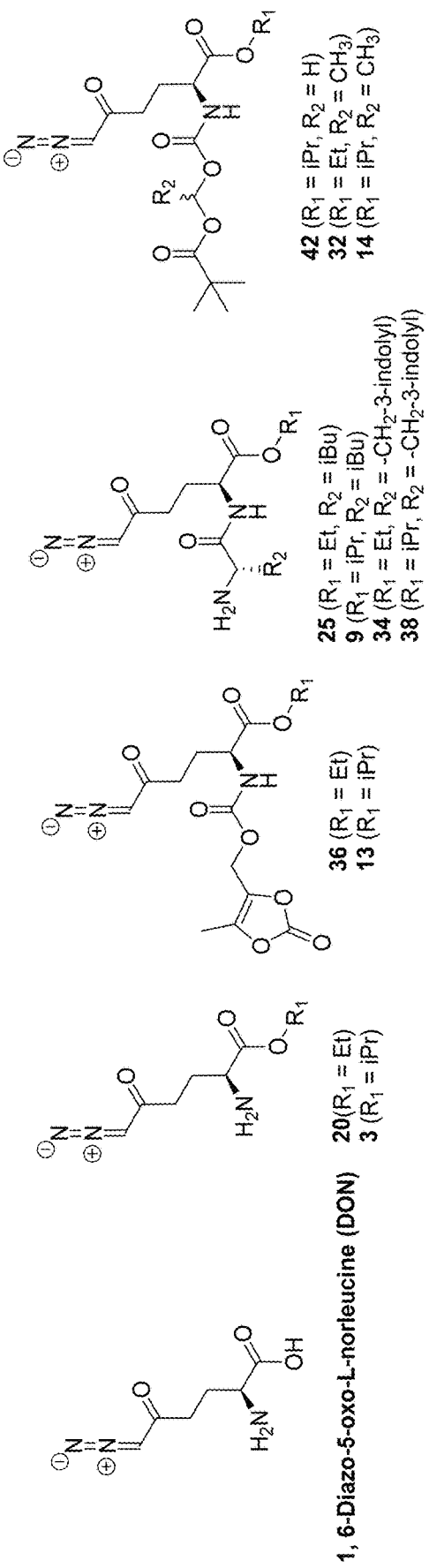
Figure 5A:
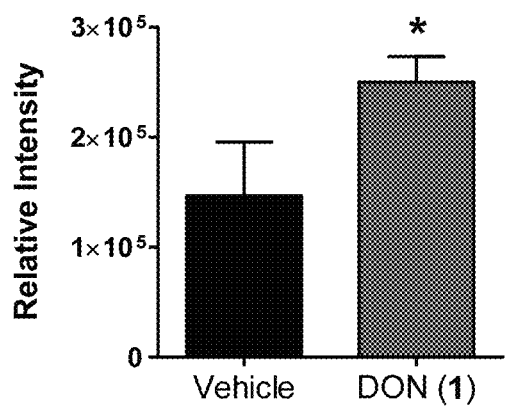
Figure 5B:
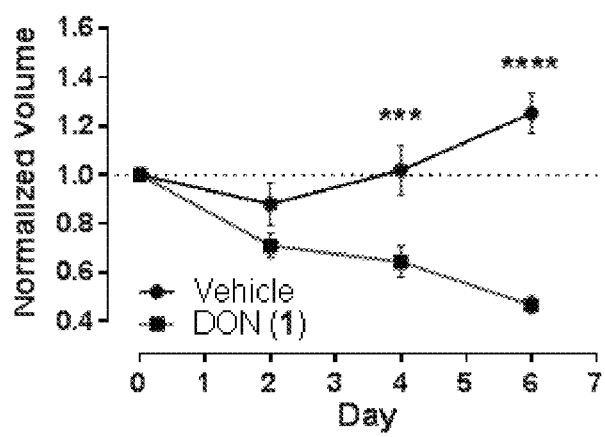

Having thus described the presently disclosed subject matter in general terms, reference will now be made to the accompanying Figures, which are not necessarily drawn to scale, and wherein:

FIG. 1 is a line graph showing that metabolic reprogramming therapy with at least one metabolic reprogramming agent (e.g., DON) markedly inhibits lymphoma growth in a EL4 mouse lymphoma model, suggesting that bone marrow derived tumors may be exquisitely susceptible to metabolic reprogramming therapy with at least one metabolic reprogramming agent (e.g., DON);

FIG. 2 is a bar graph showing that metabolic reprogramming therapy with at least one metabolic reprogramming agent (e.g., DON) has a modest effect on inhibiting melanoma growth, which is a not a bone marrow derived tumor;

FIG. 3 is a graph showing that metabolic reprogramming therapy with at least one metabolic reprogramming agent (e.g., DON) conditions B16 melanoma to be killed by immunotherapy by inhibiting tumor infiltrating Regulatory T cells (Foxp3+);

FIG. 4 is an illustration showing the structures of DON and DON-based prodrugs;

FIG. 5A is a bar graph and FIG. 5B is a line graph showing that DON (1) inhibits glutamine metabolism and GBM tumor growth in vivo. FIG. 5A shows compound 1 (0.8 mg/kg, i.p.) inhibited glutamine metabolism as evidenced by increased endogenous glutamine concentrations in flank GBM tumors 2 hours post-administration relative to vehicle-treated controls; *p<0.05. FIG. 5B shows in efficacy studies, compared to Day 0 baseline, vehicle-treated mice exhibited significant growth of flank GBM tumors during the course of the experiment. By contrast, systemic administration of 1 (0.8 mg/kg, i.p, q.d. days 1-6) caused a dramatic reduction in tumor size; *p<0.001, **p<0.0001. Note the bold numbers following the terms "DON", "DON prodrugs", "DON-based prodrugs", and the like, refer to particular compounds disclosed in Table 1 below.

Figure 9:
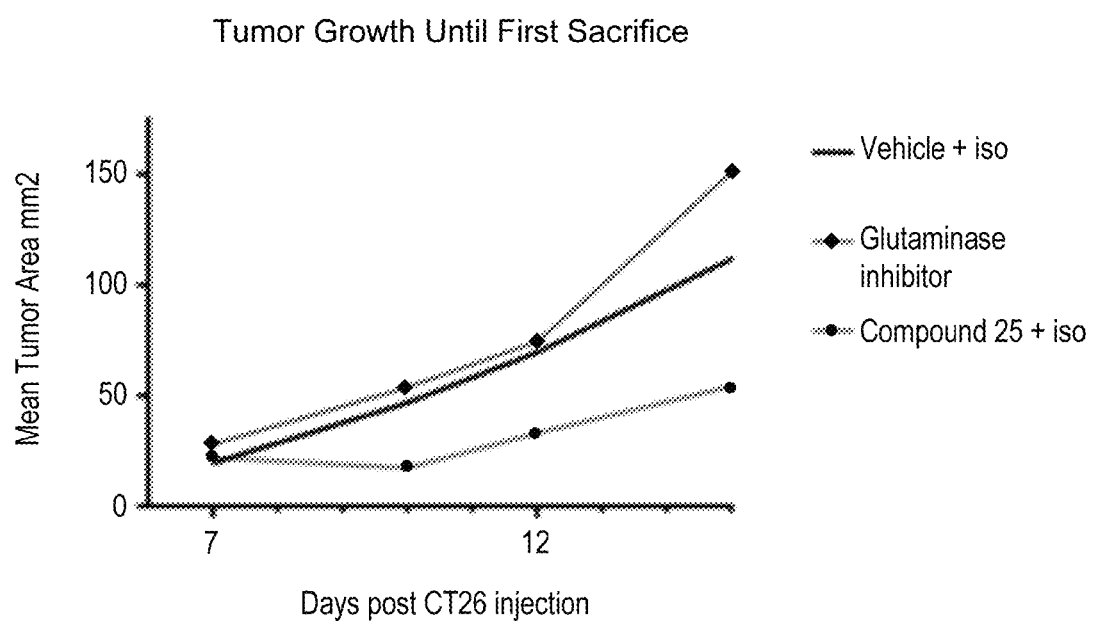
Figure 10:
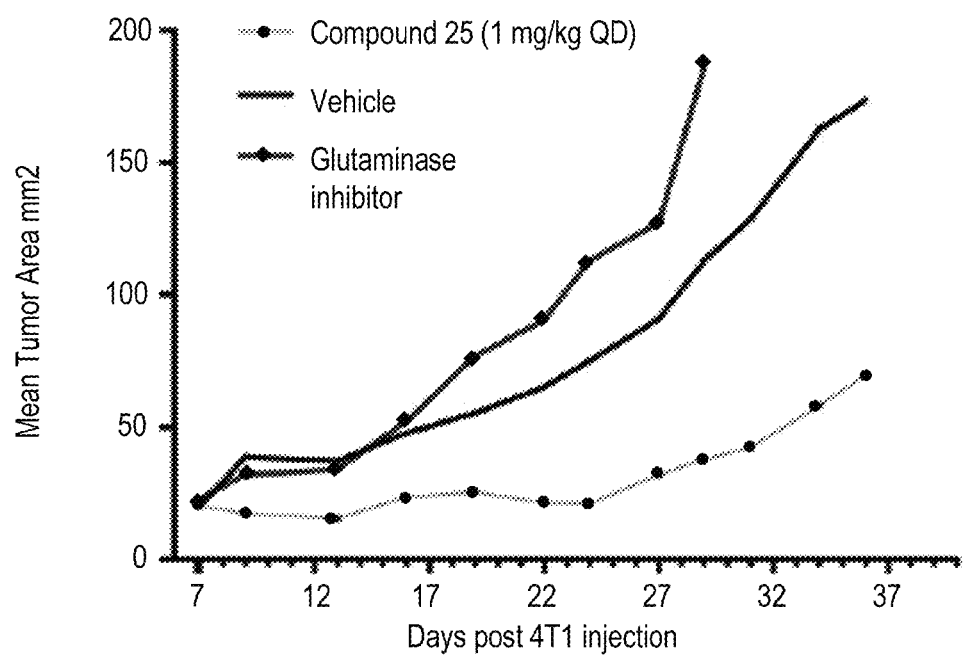
Figure 11A:
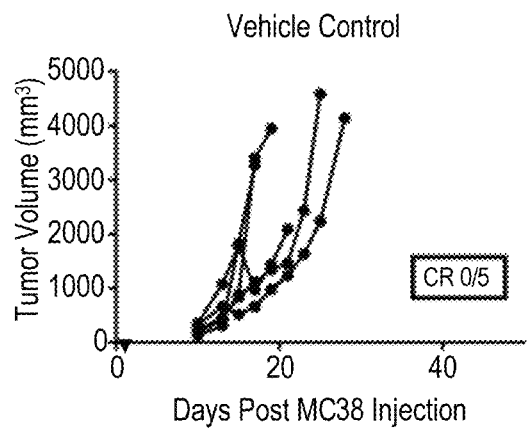
Figure 11B:
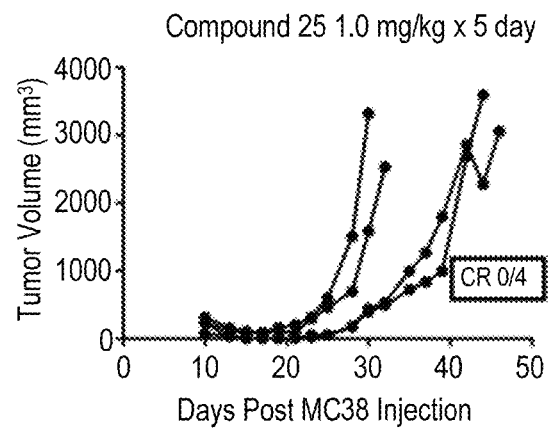
Figure 11C:
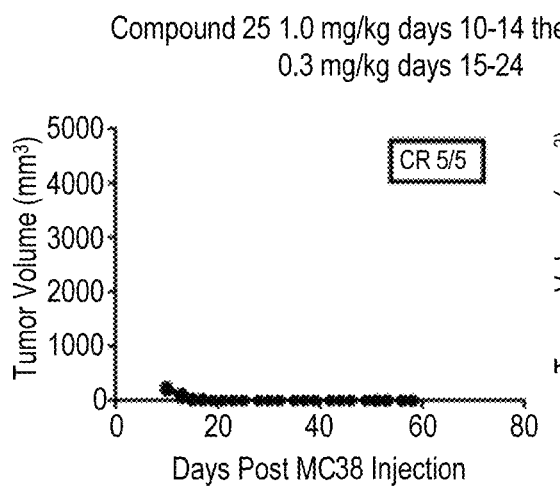
Figure 11D:
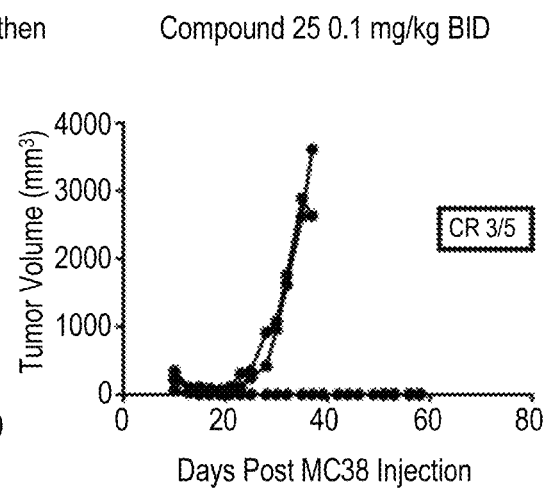
Figure 11E:
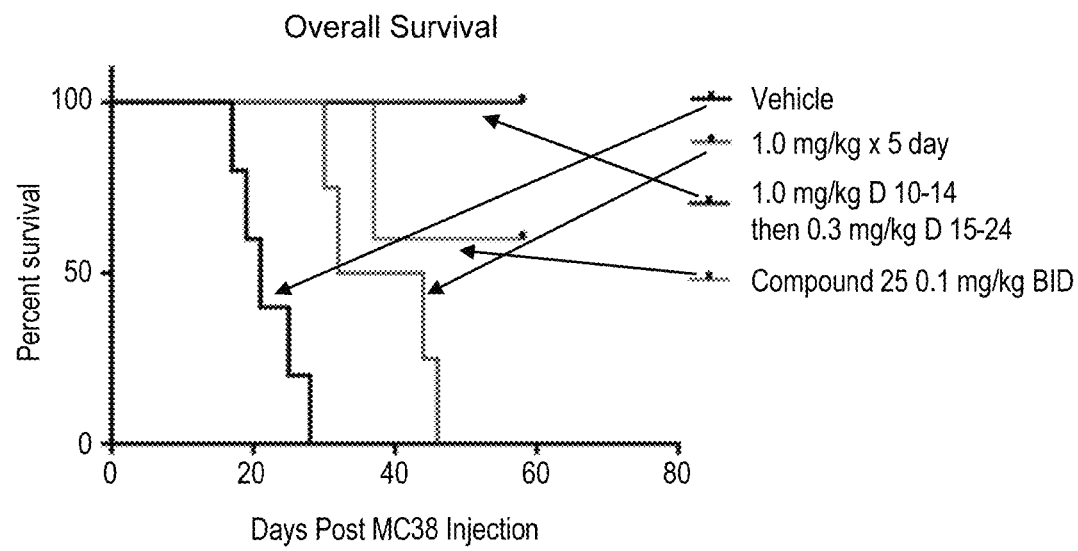
Figure 11F:
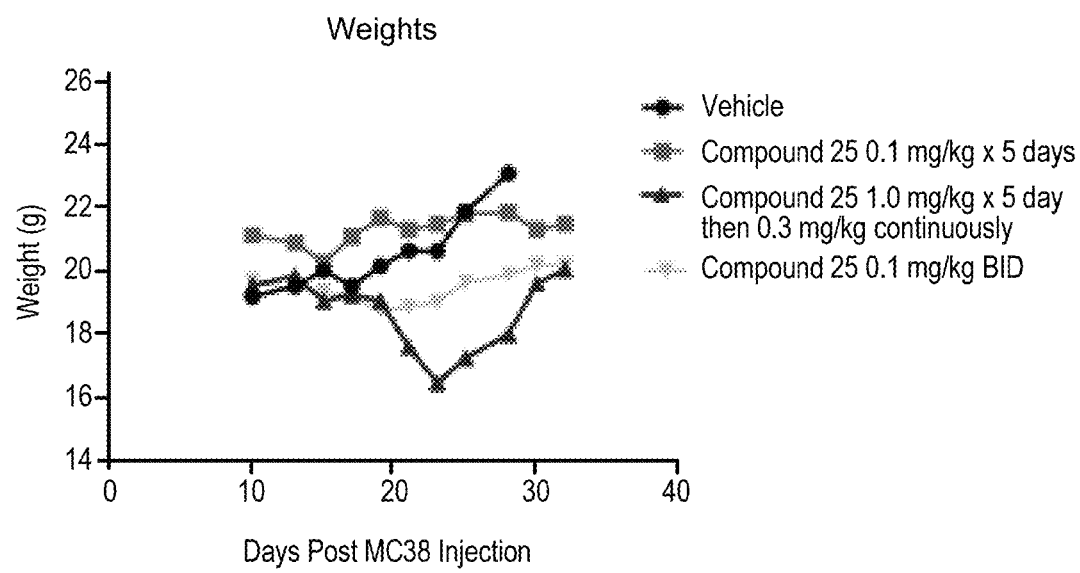
Figure 12A:
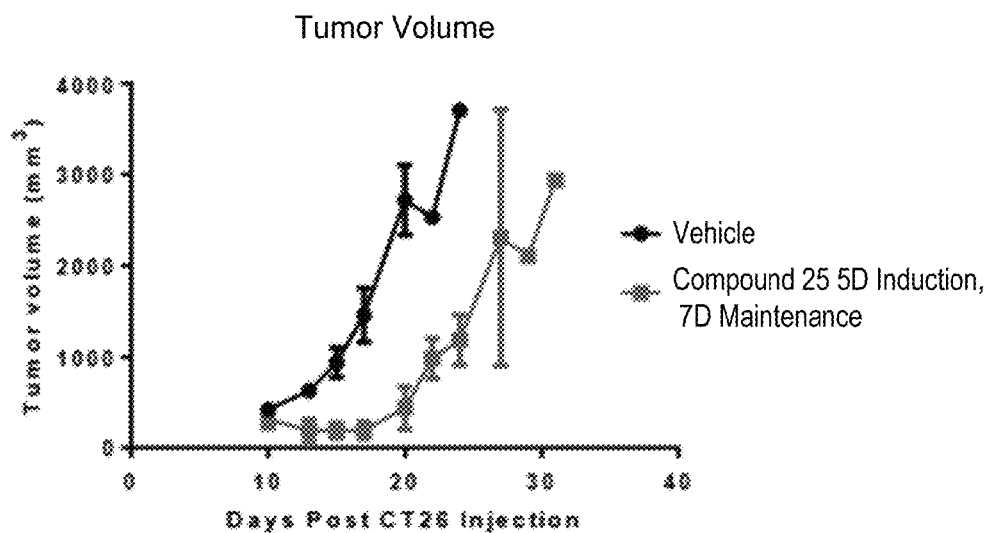
Figure 12B:
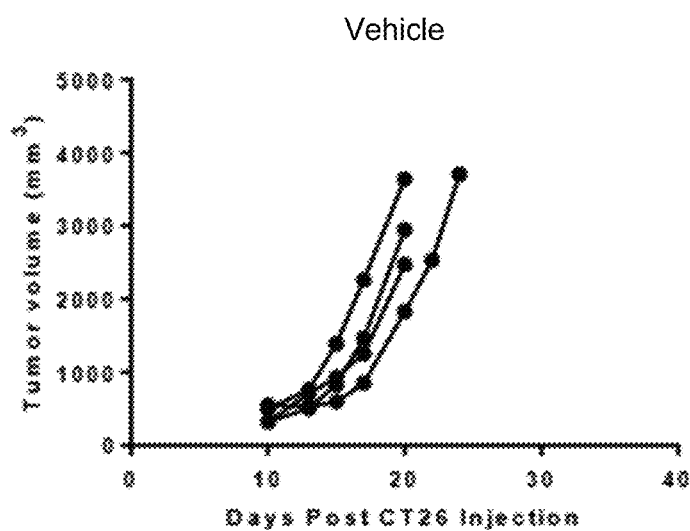
Figure 12C:
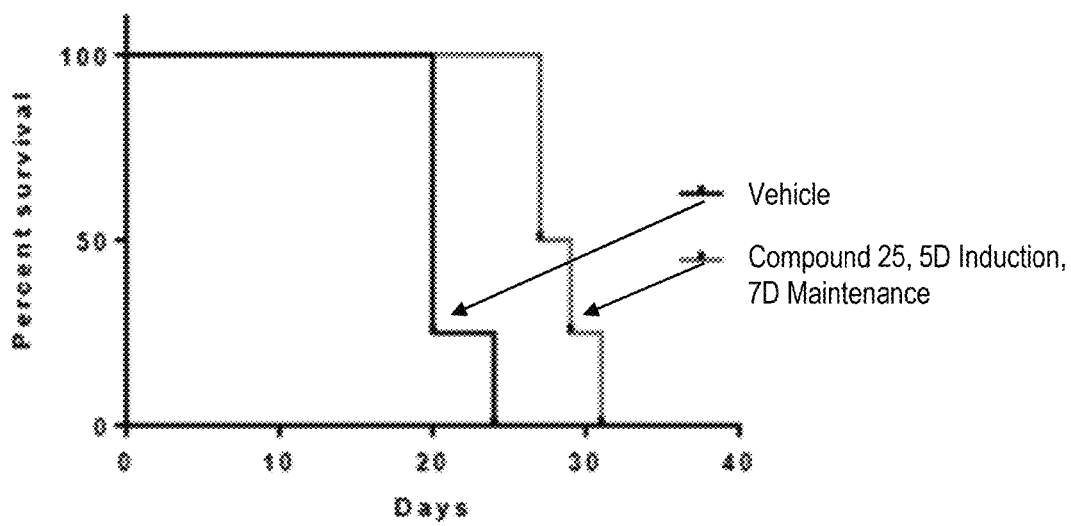
Figure 12D:
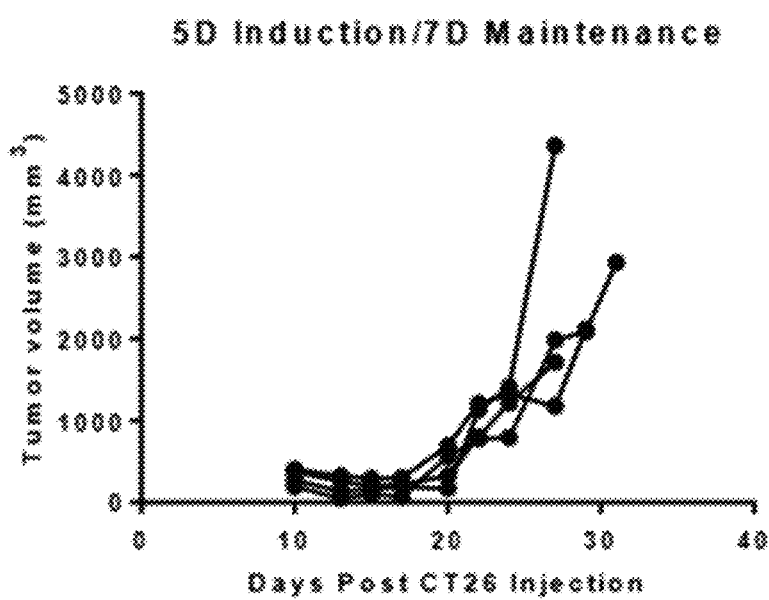
Figure 13A:
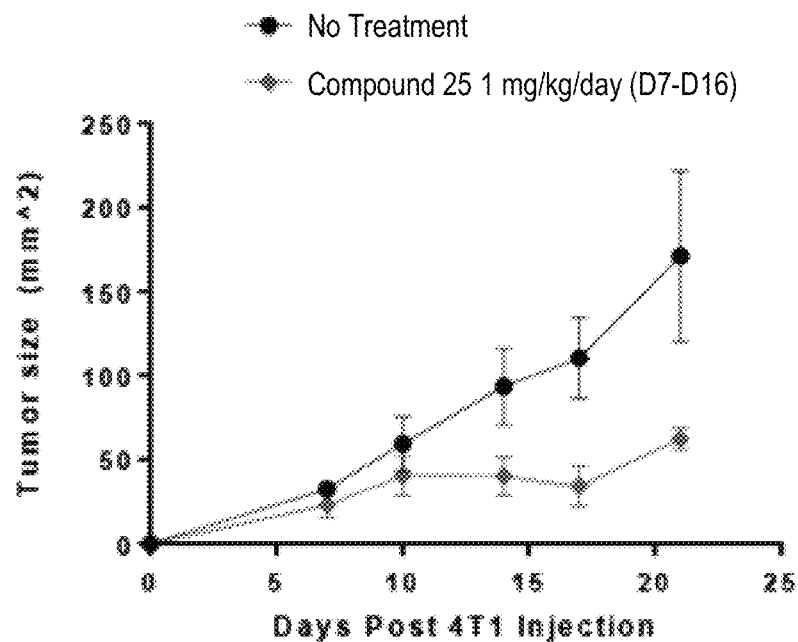
Figure 13B:
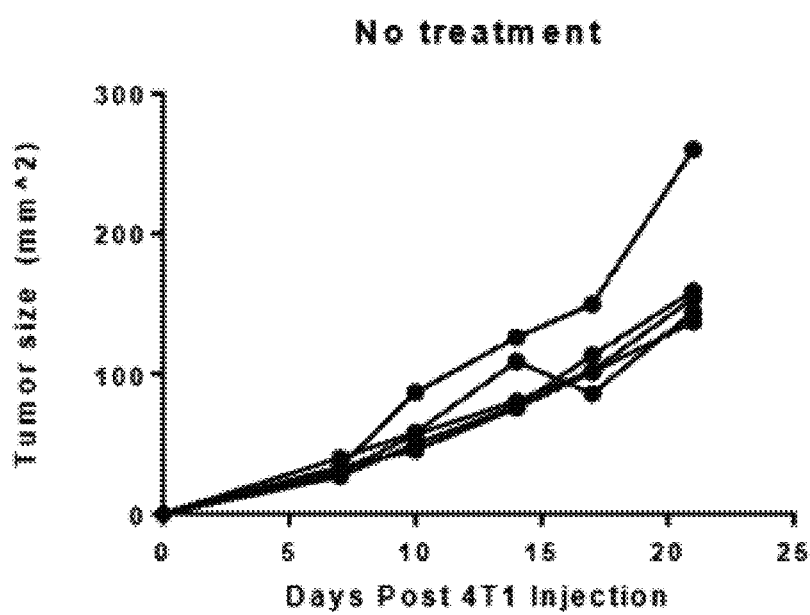
Figure 13C:
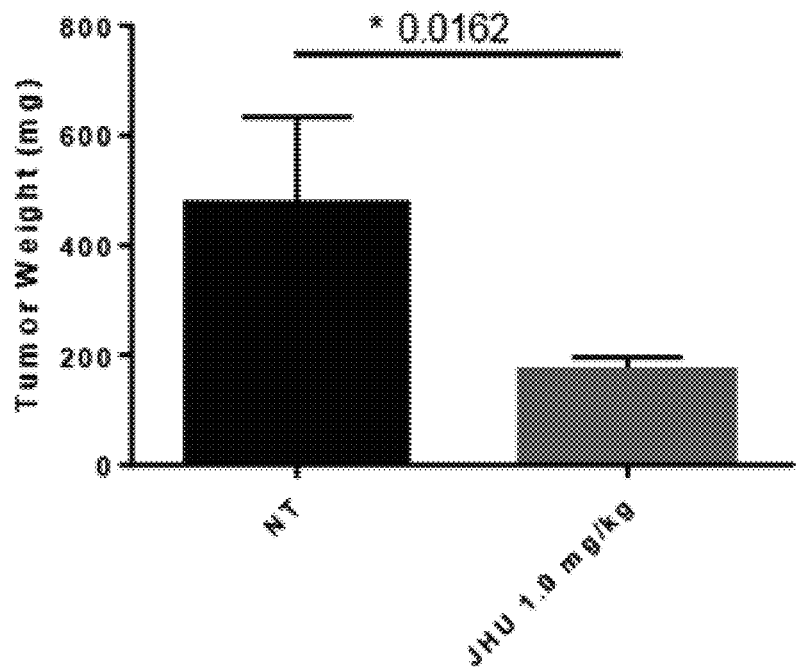
Figure 13D:
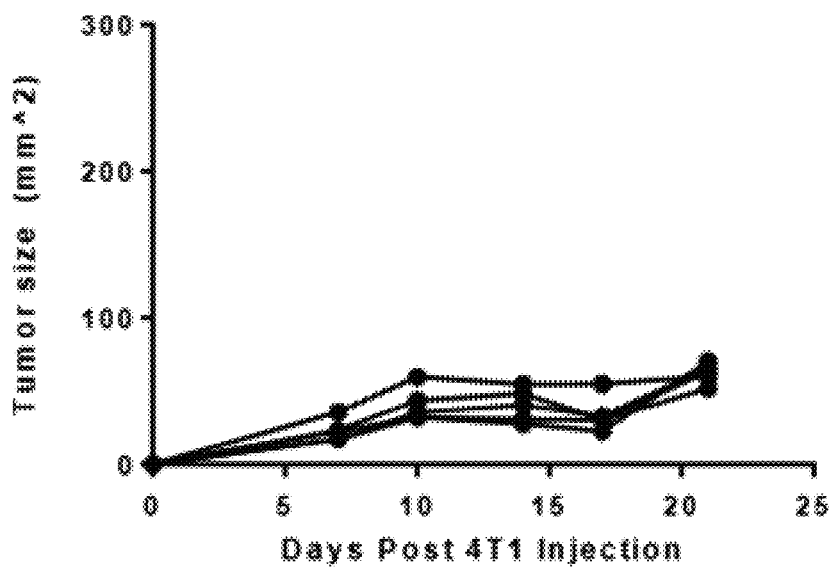
Figure 14A:
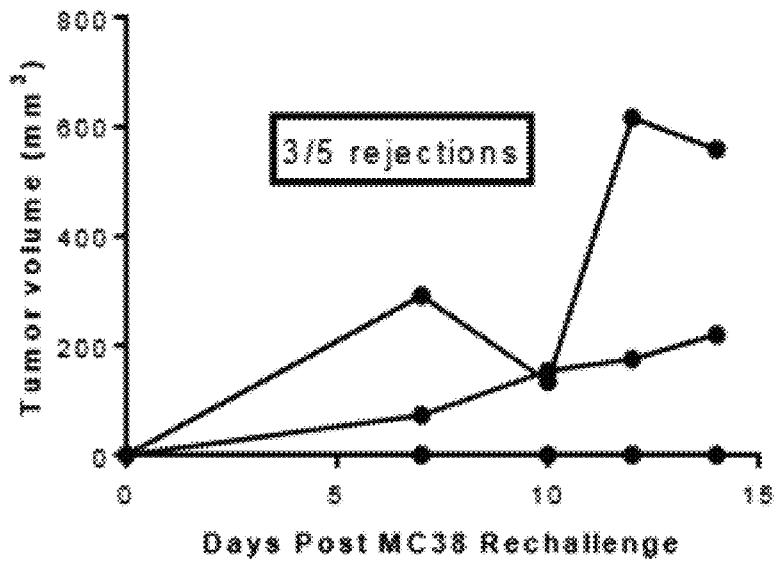
Figure 14B:
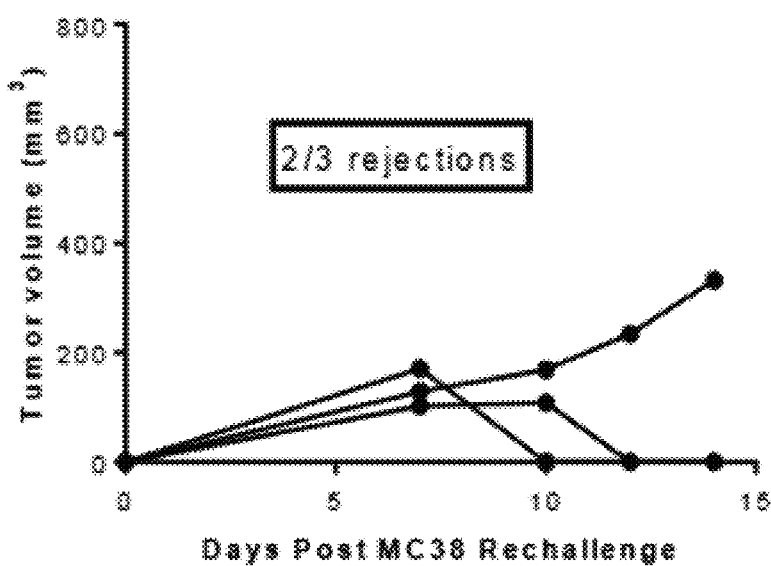
Figure 14C:
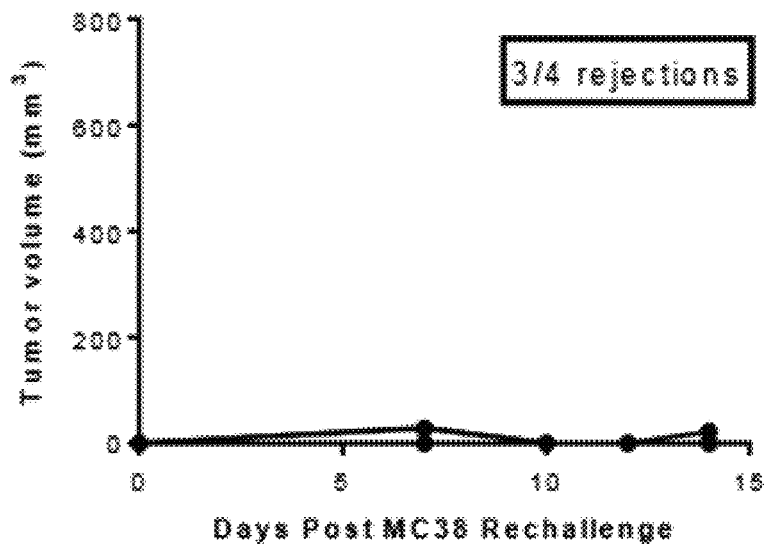
Figure 14D:
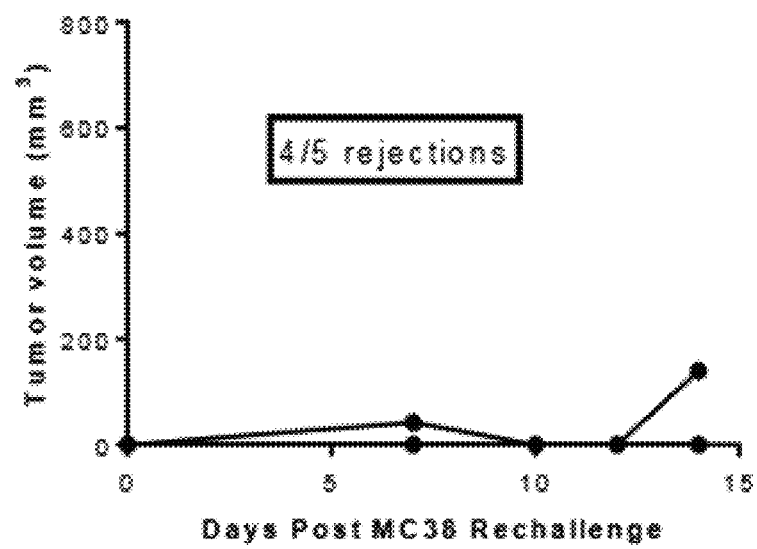
Figure 14E:
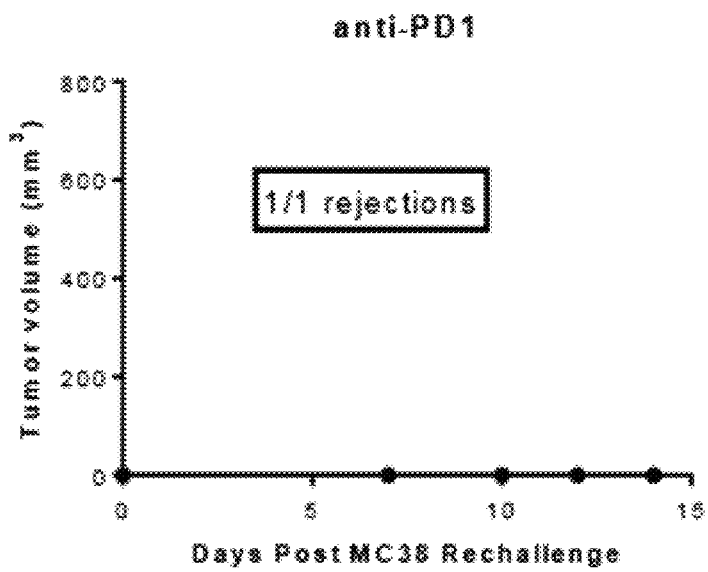
Figure 14F:
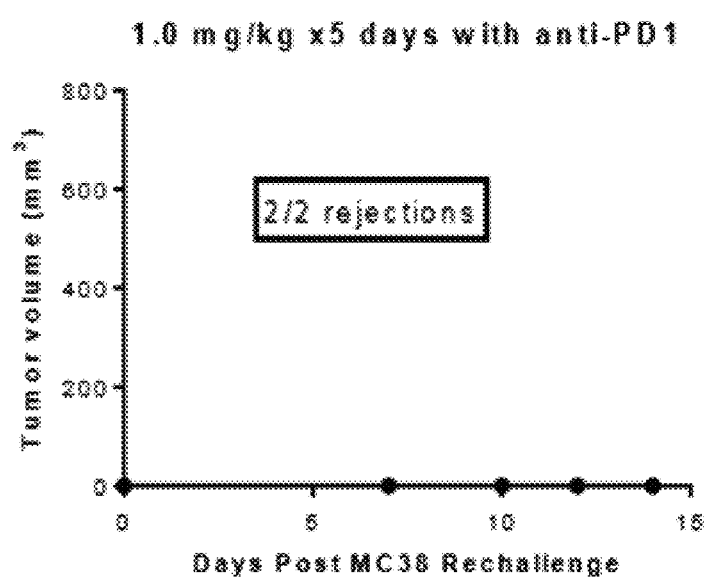
Figure 14G:
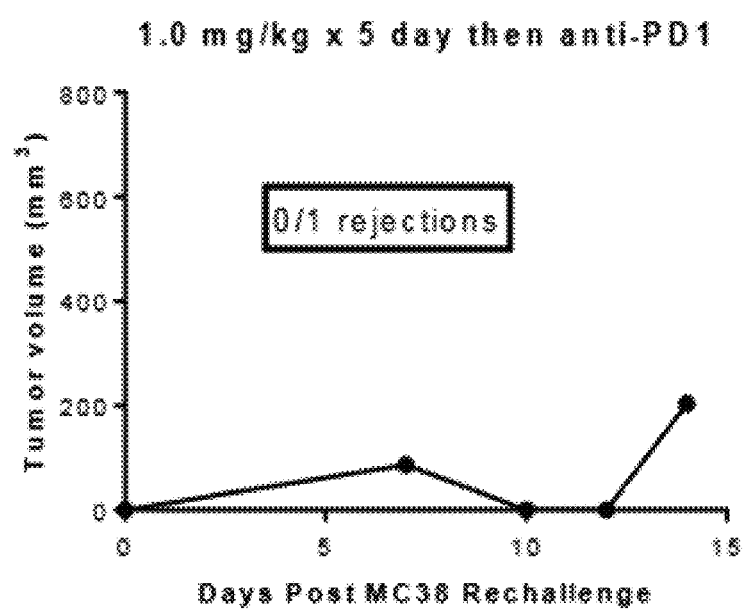
Figure 15A:
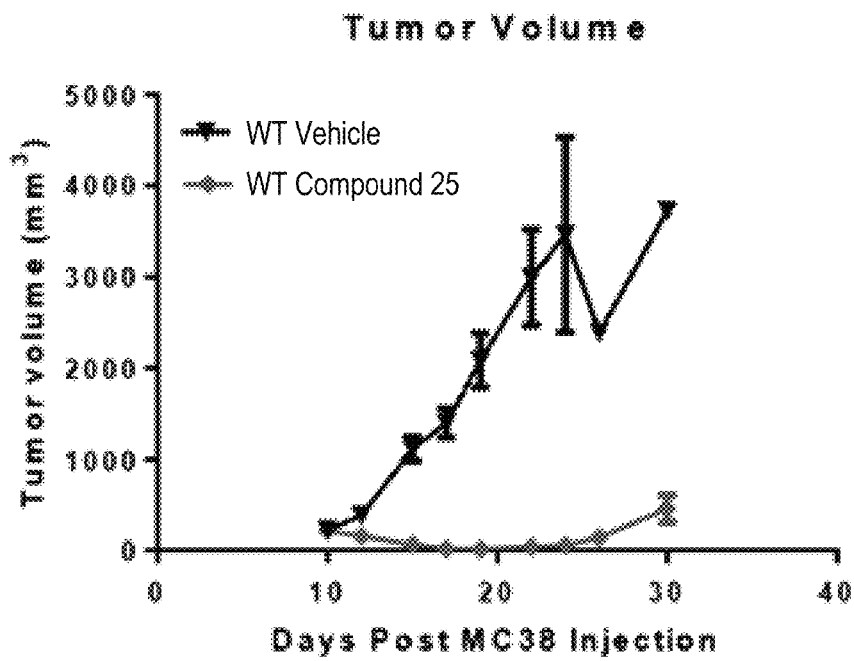
Figure 15B:
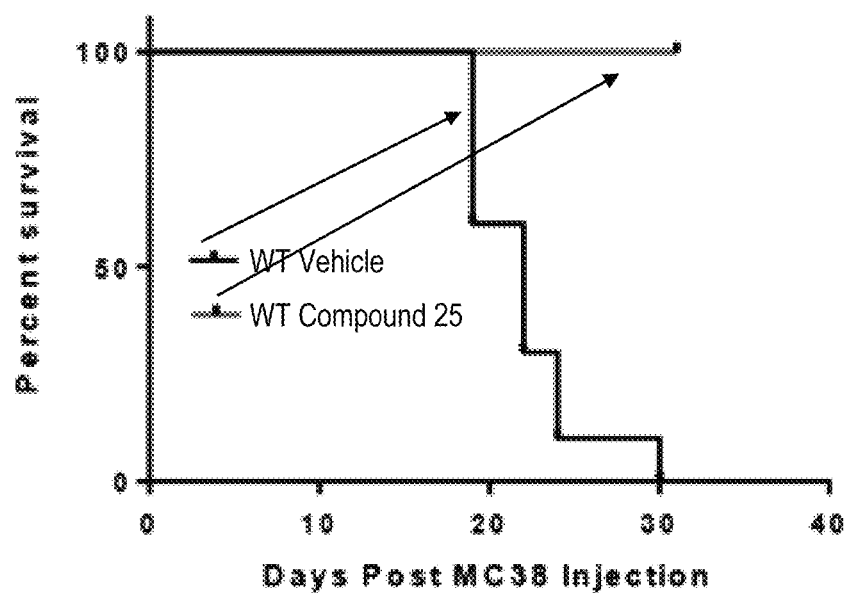
Figure 15C:
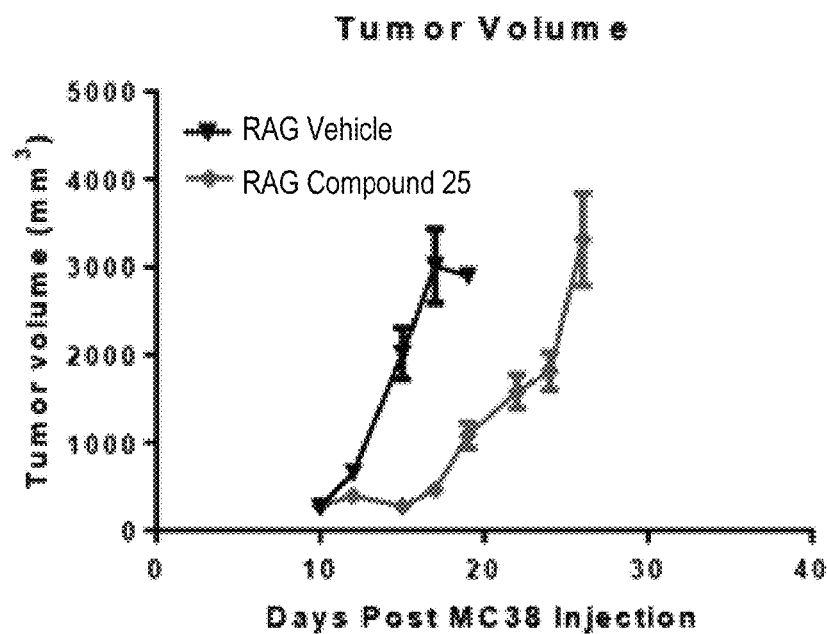
Figure 15D:
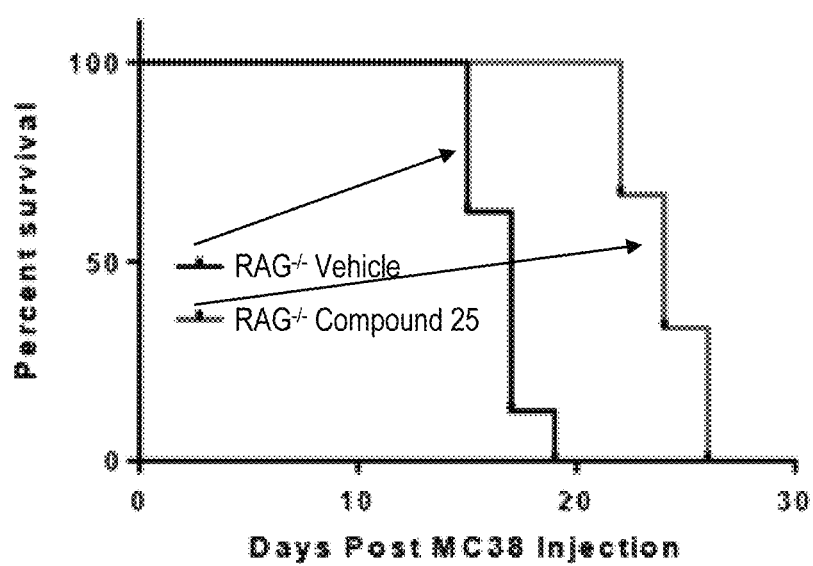
Figure 16A:
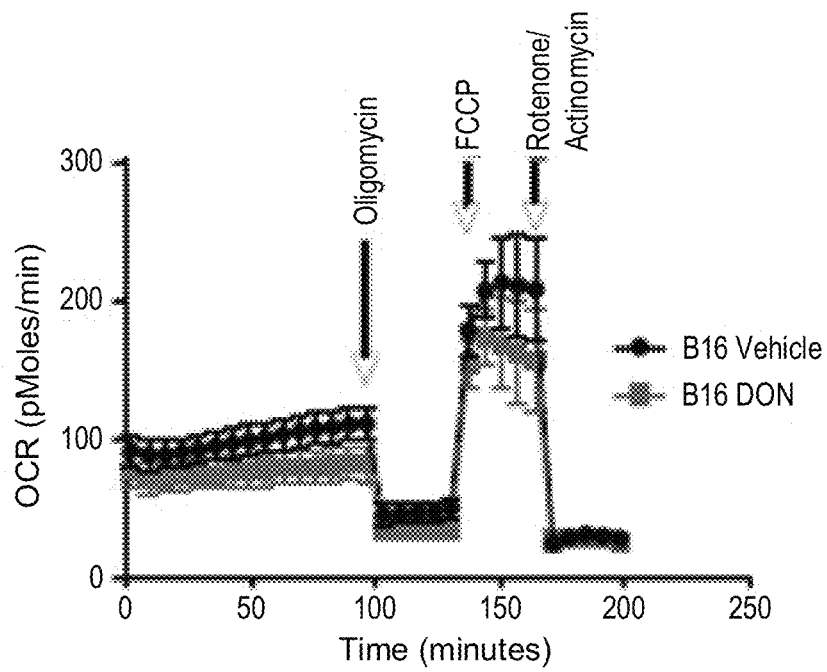
Figure 16B:
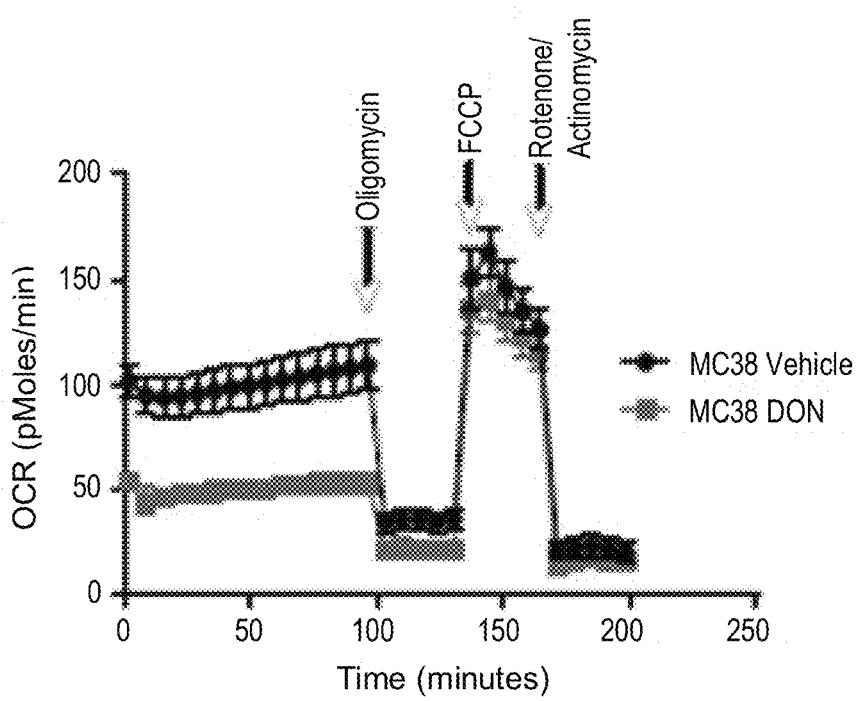
Figure 16C:
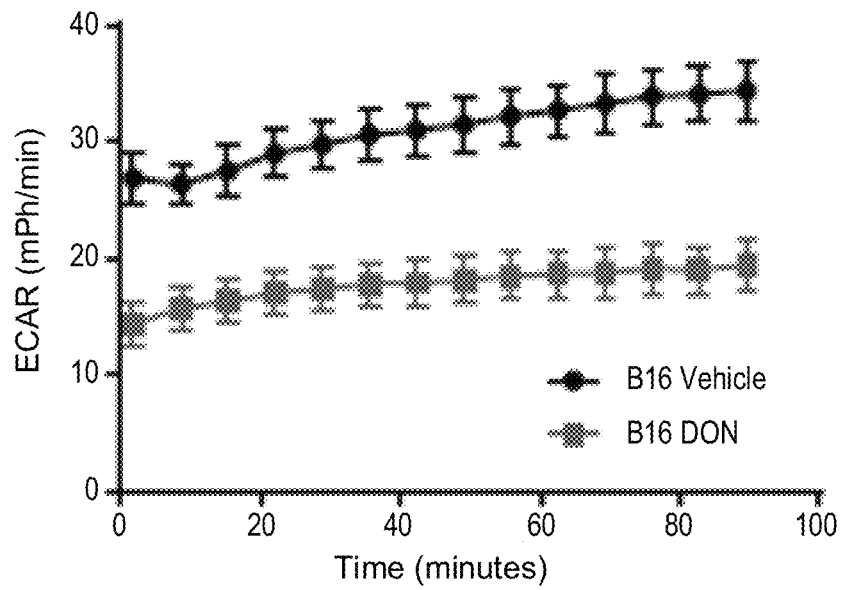
Figure 16D:
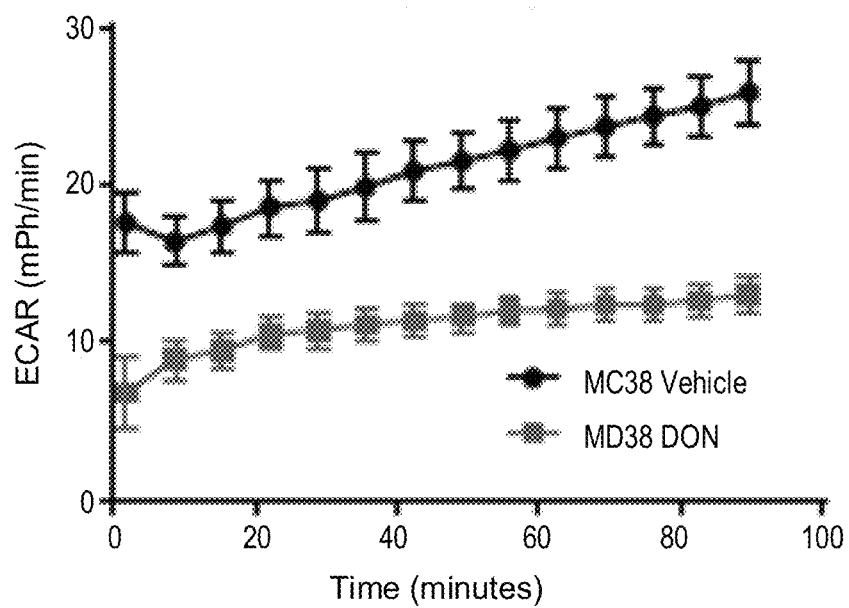
Figure 16E:
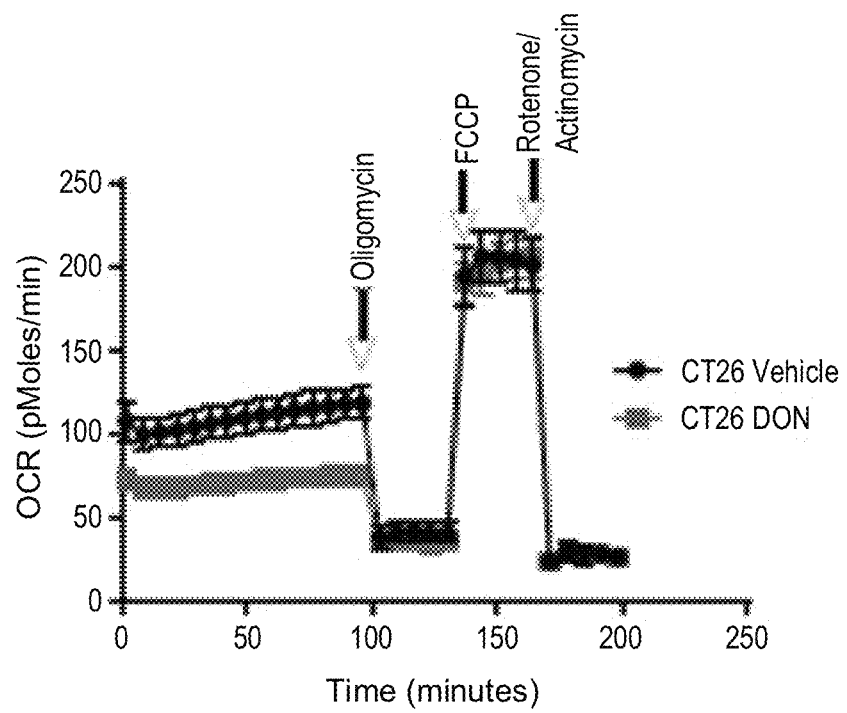
Figure 16F:
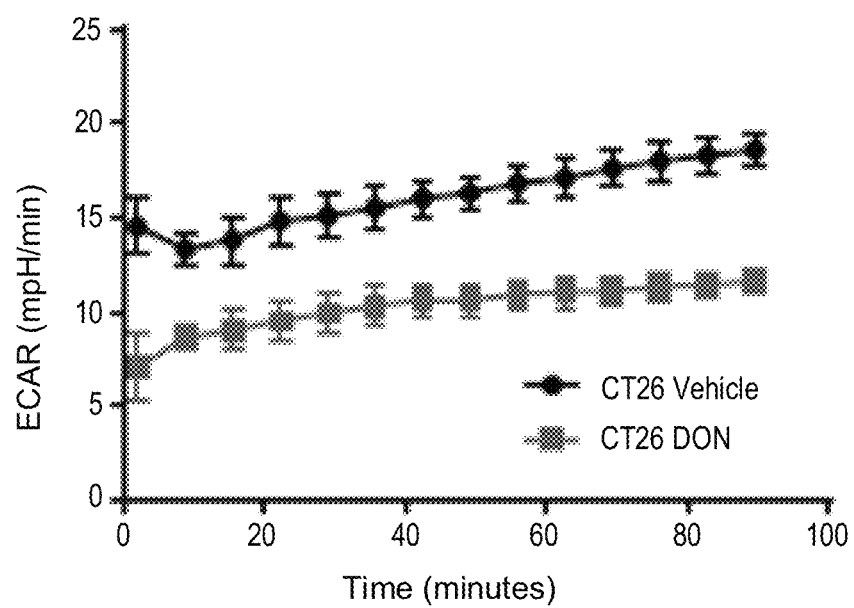
Figure 17A:
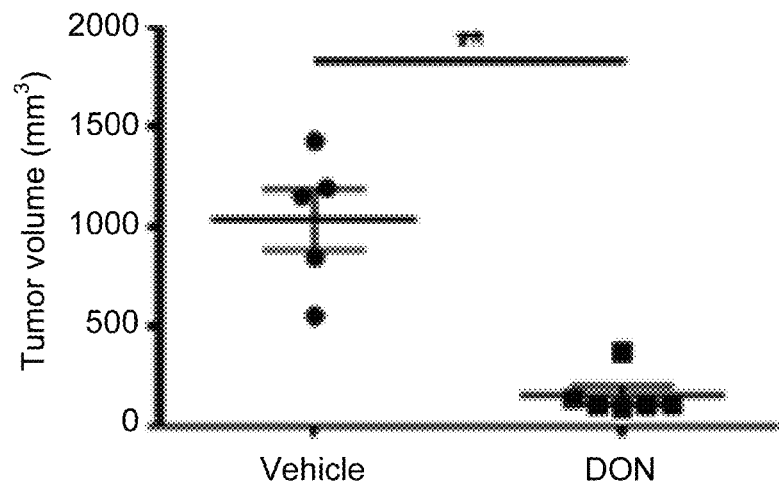
Figure 17B:
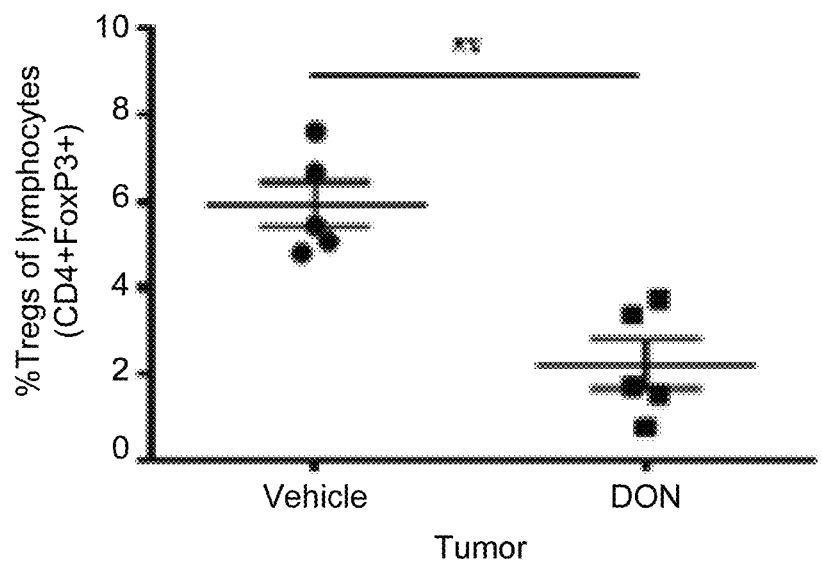
Figure 17C:
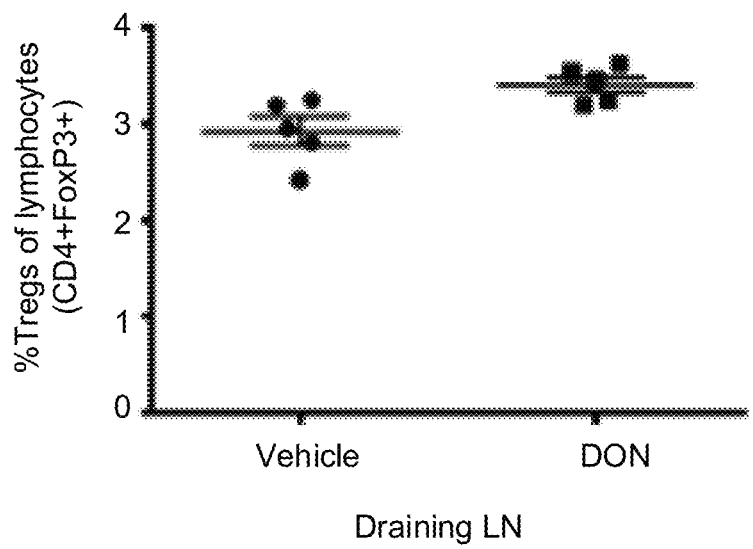
Figure 17D:
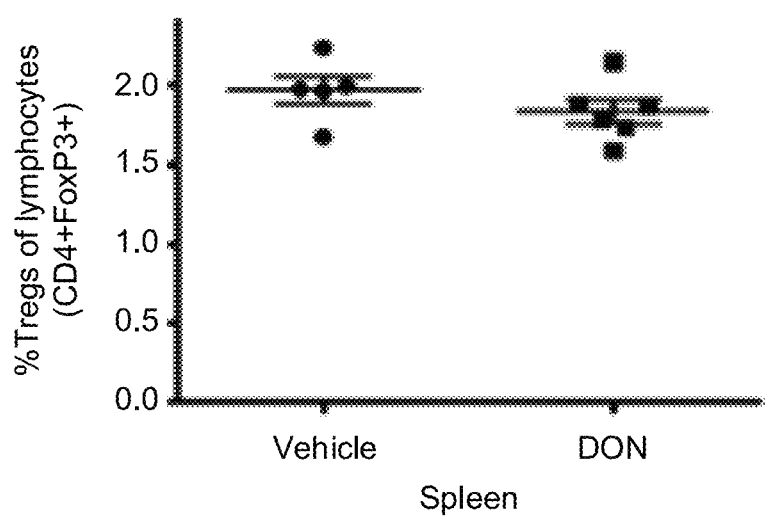
Figure 17E:
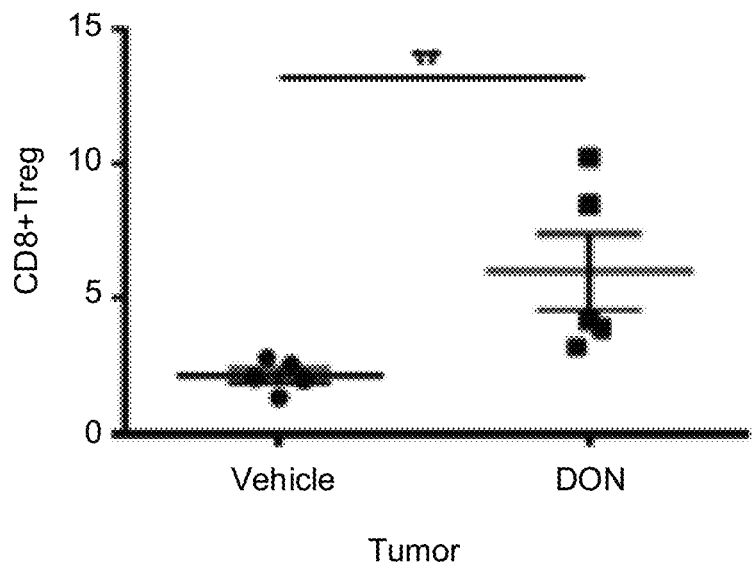
Figure 17F:
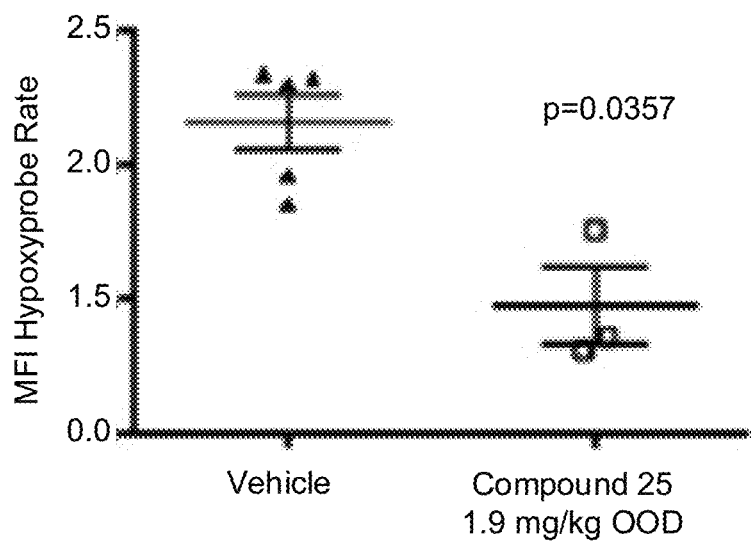
Figure 18A:
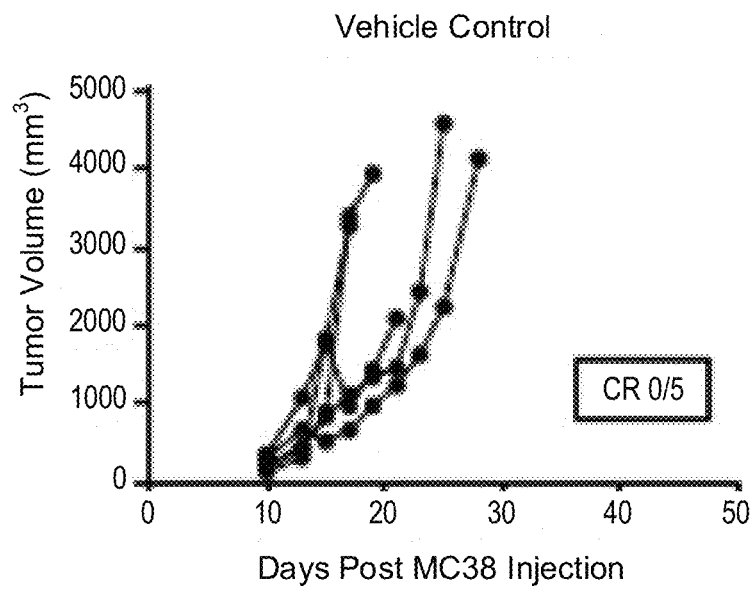
Figure 18B:
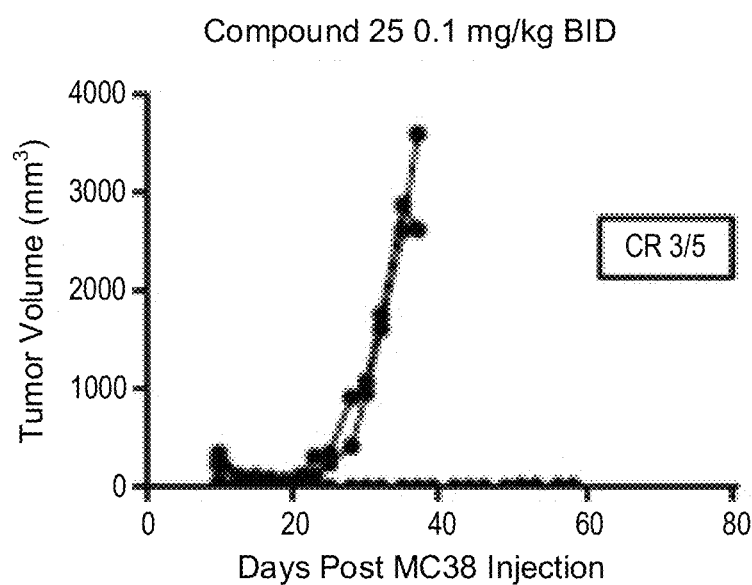
Figure 18C:
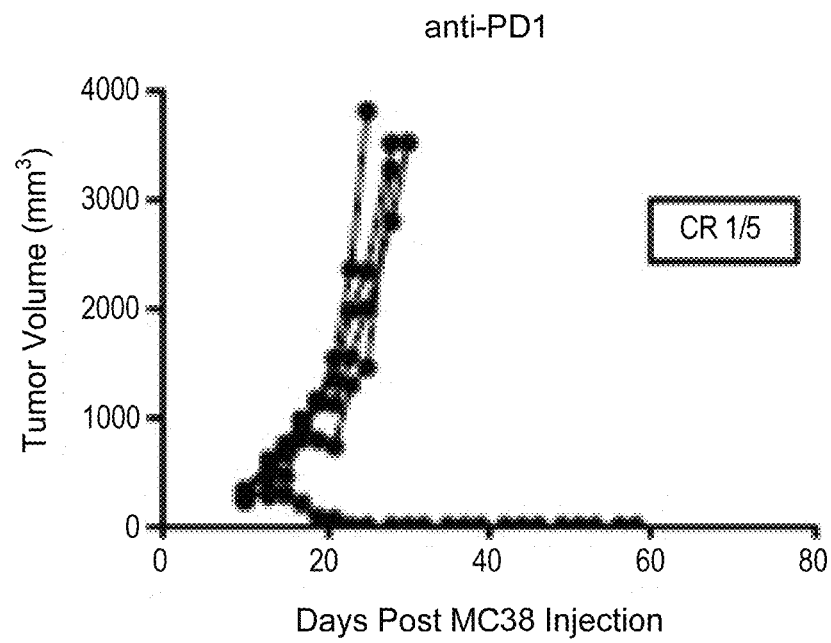
Figure 18D:
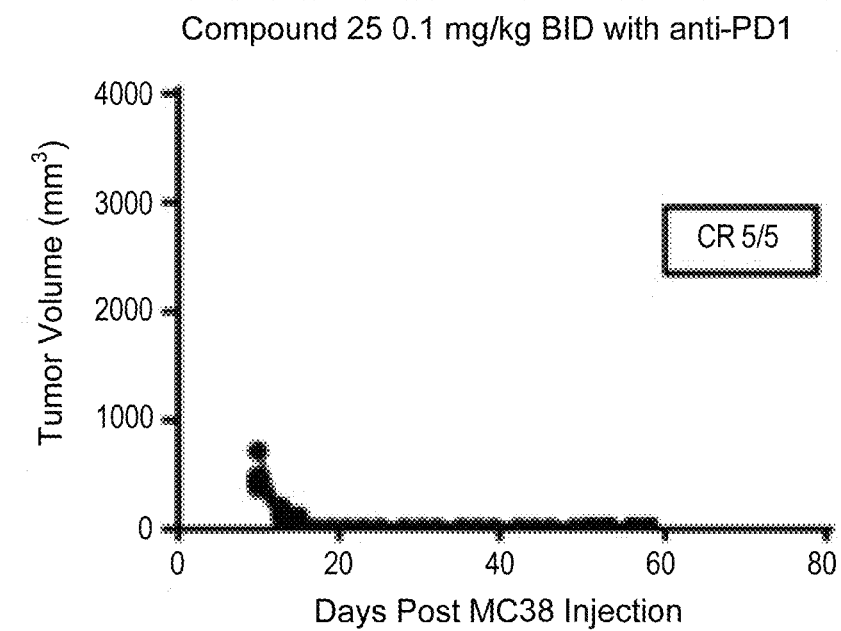
Figure 18E:
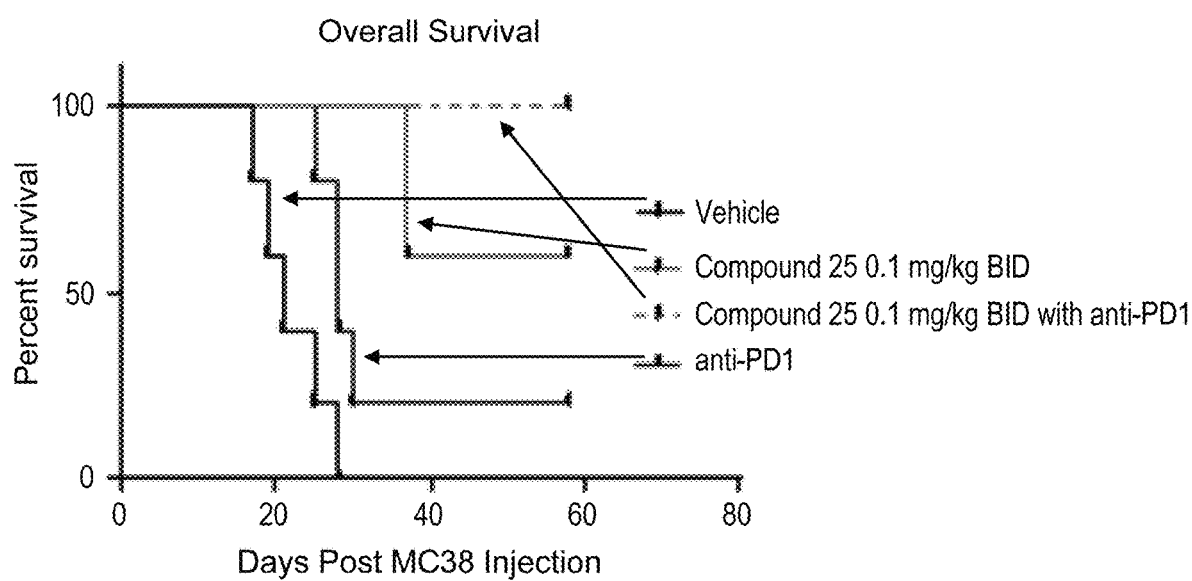
Figure 19A:
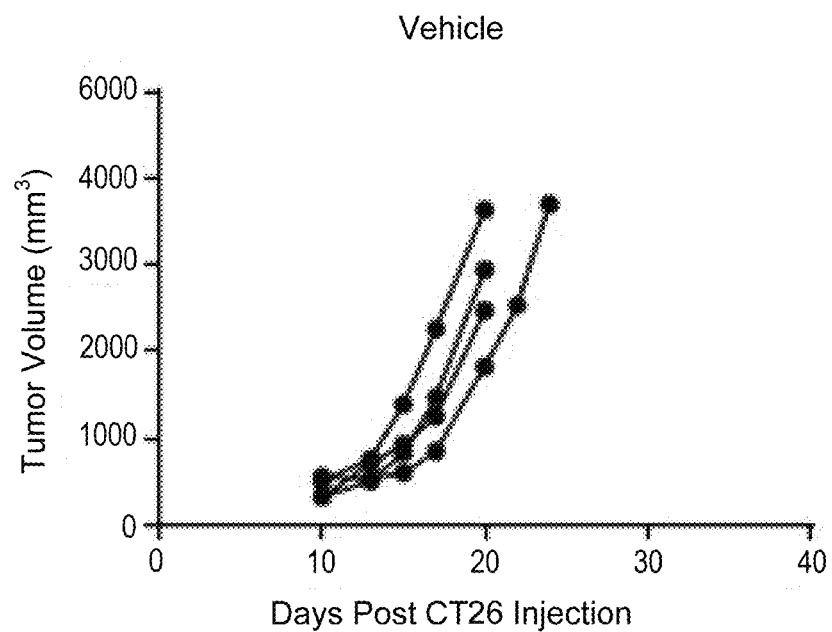
Figure 19B:
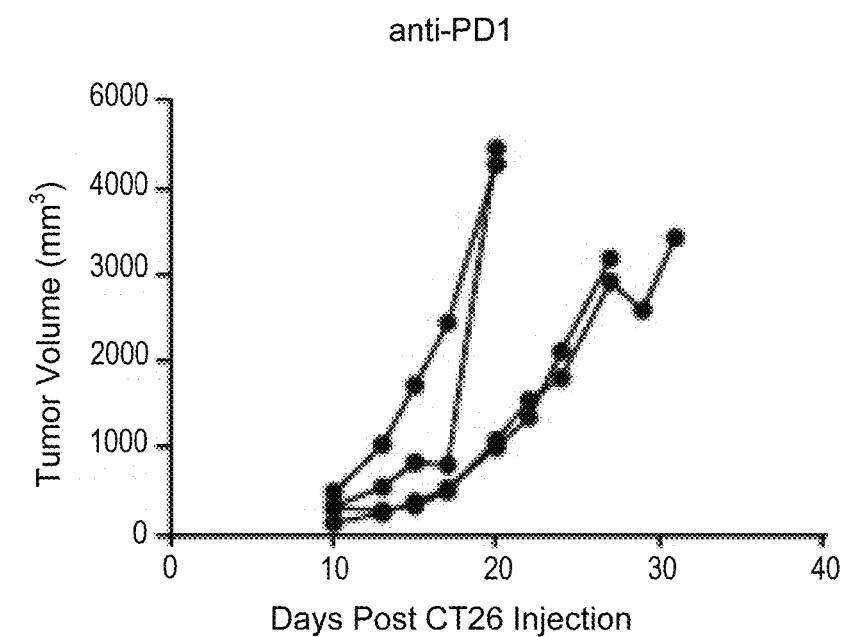
Figure 19C:
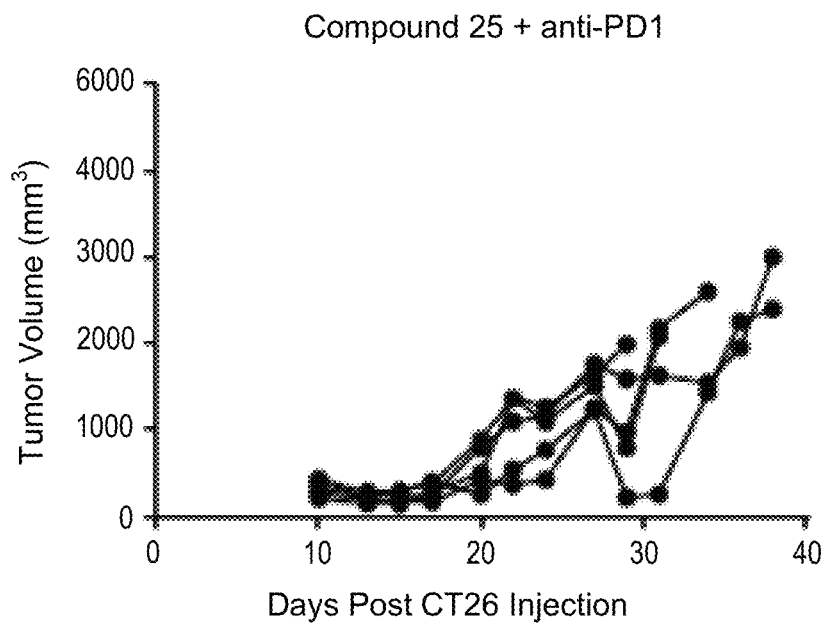
Figure 19D:
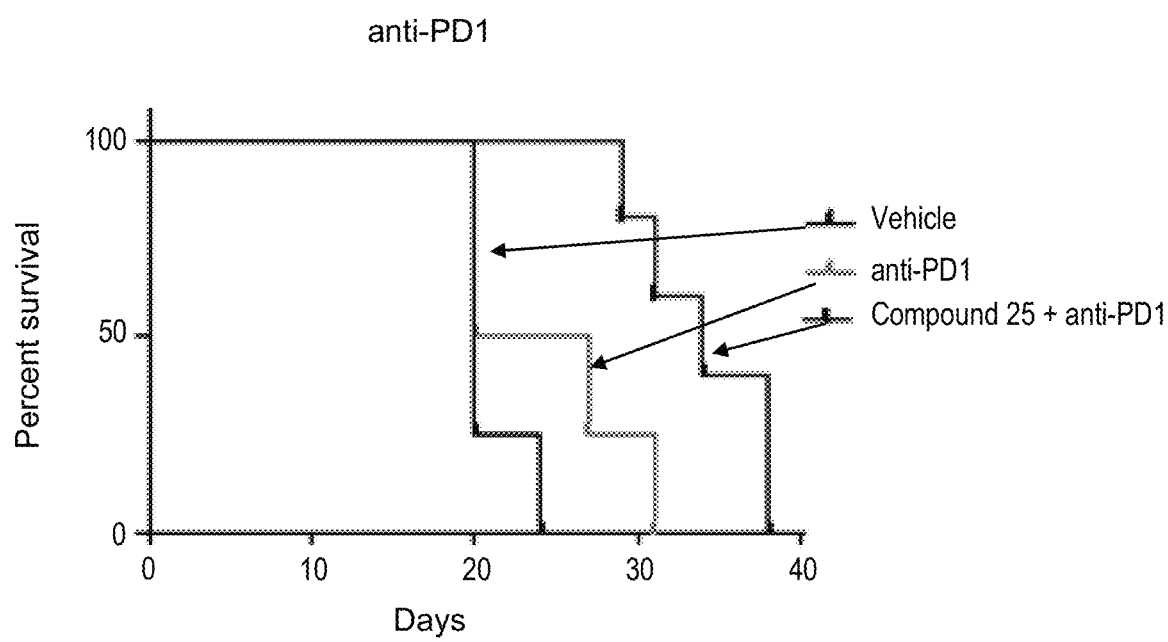
Figure 20A:
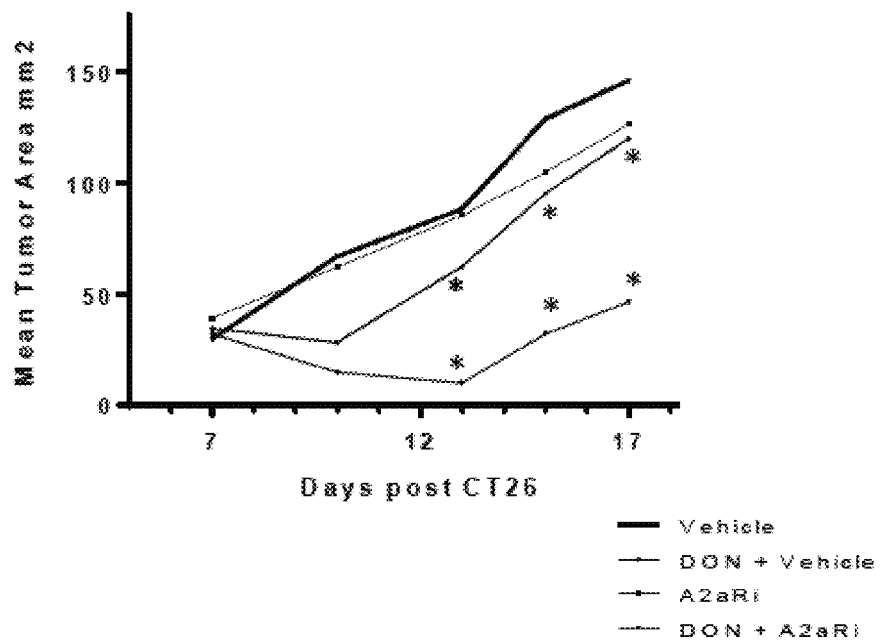
Figure 20B:
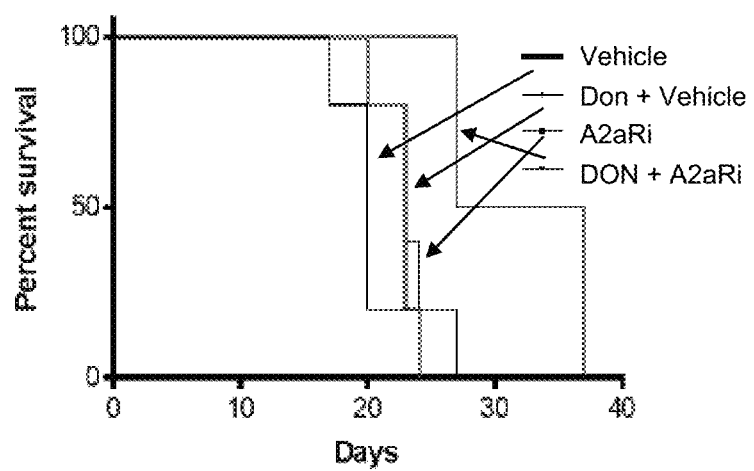
Figure 21A:
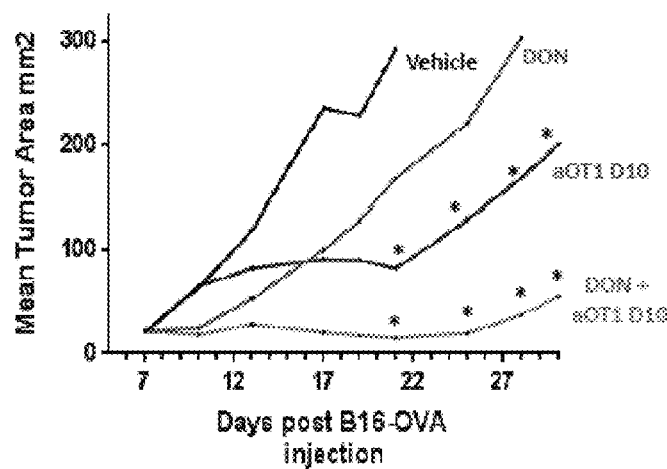
Figure 21B:
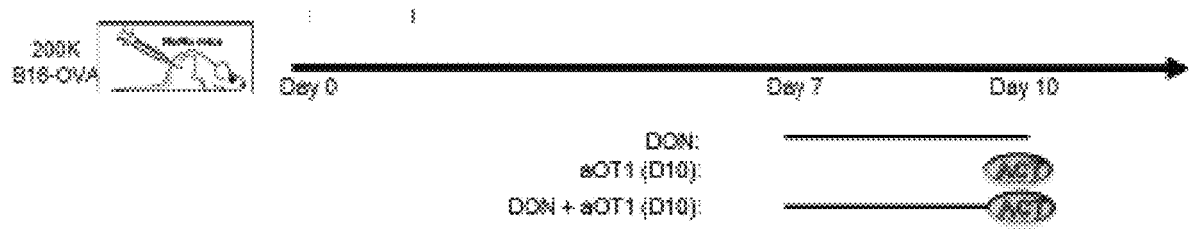
Figure 21C:
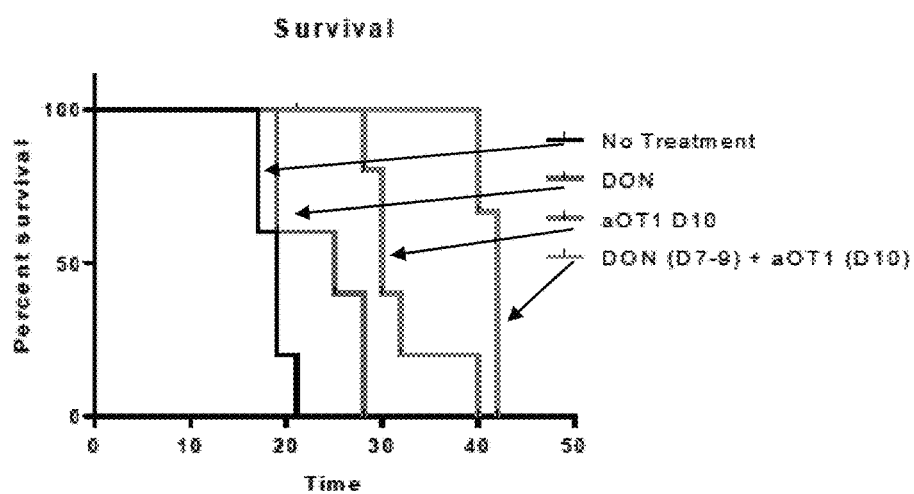
Figure 23:
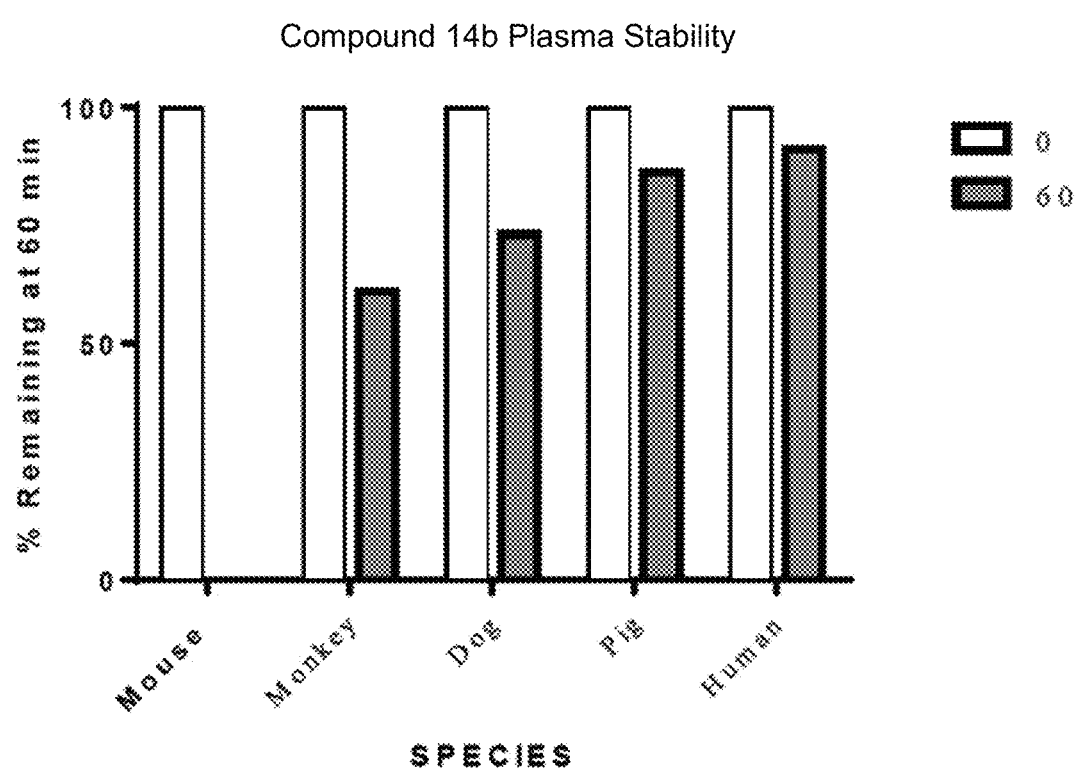
Figure 24:
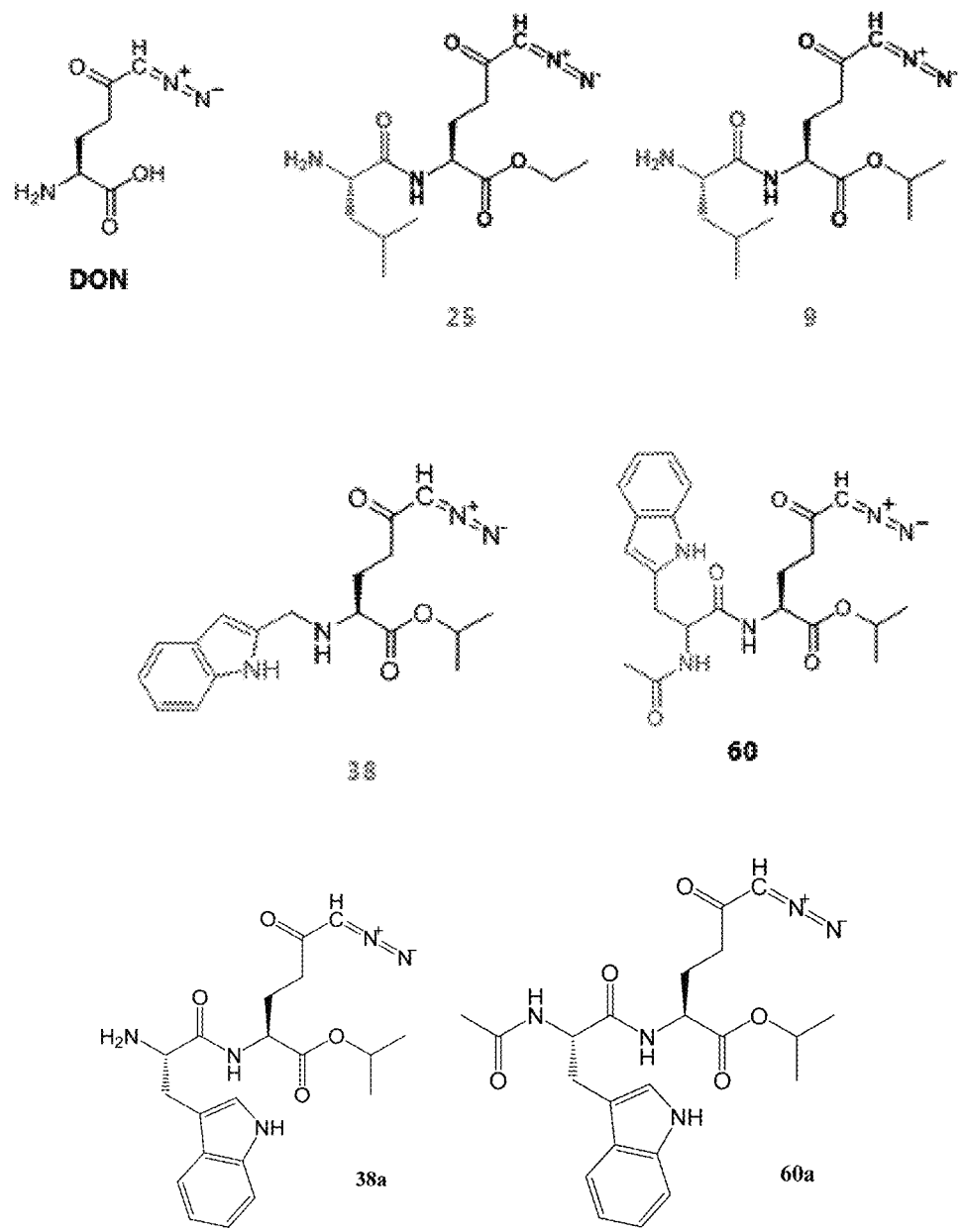
Figure 25A:
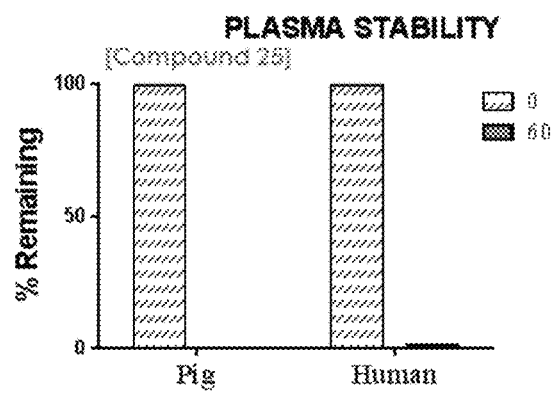
Figure 25B:
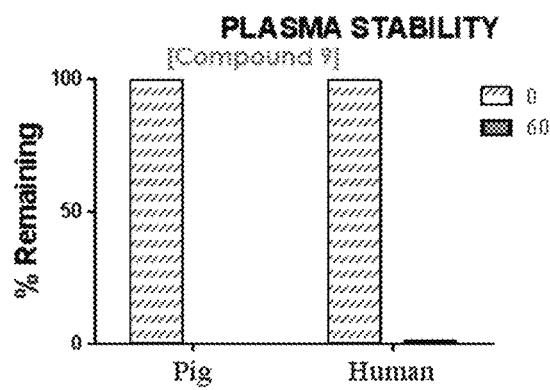
Figure 25C:
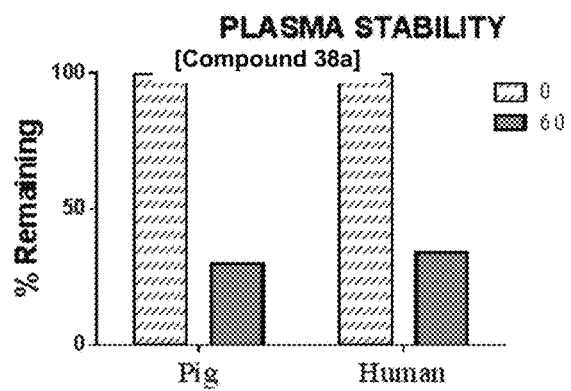
Figure 25D:
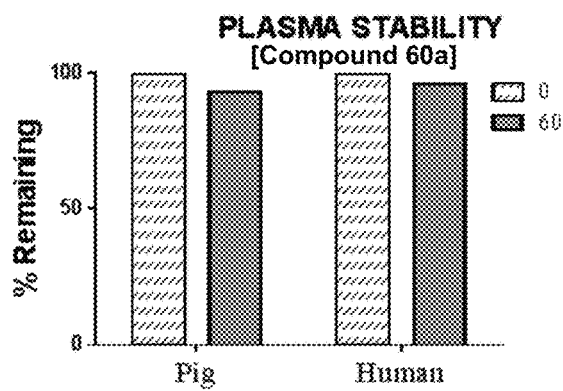
Figure 26A:
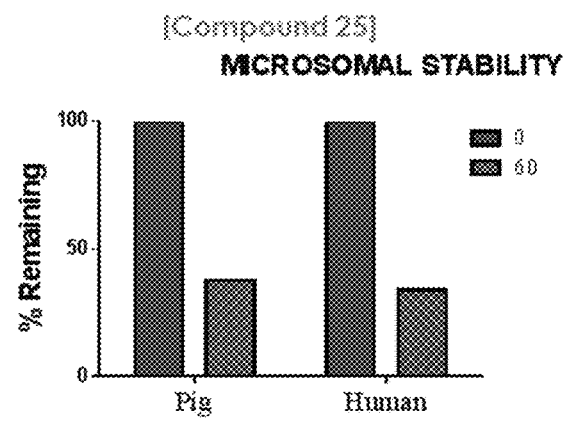
Figure 26B:
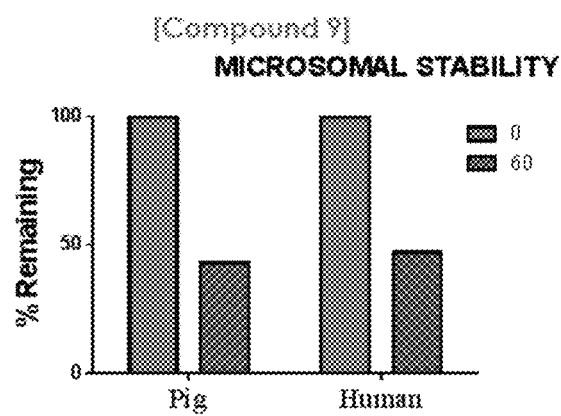
Figure 26C:
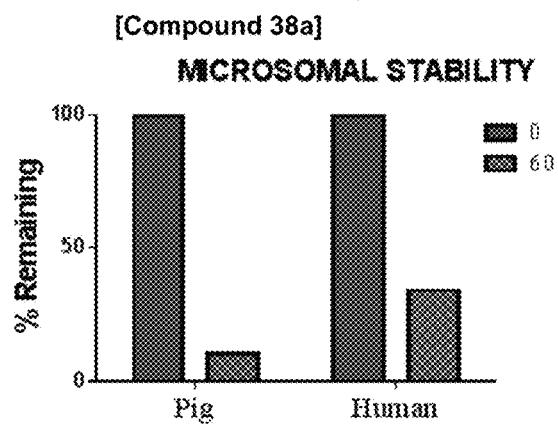
Figure 26D:
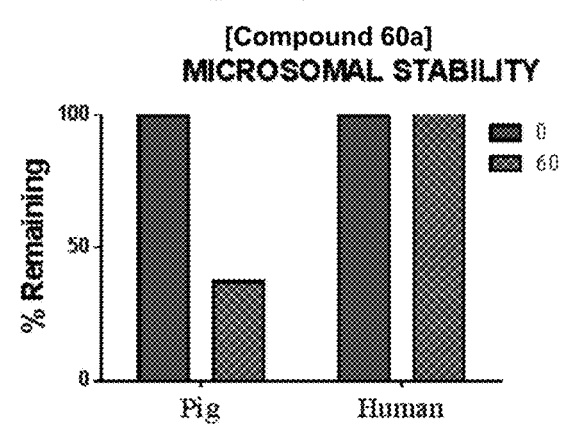
Figure 27A:
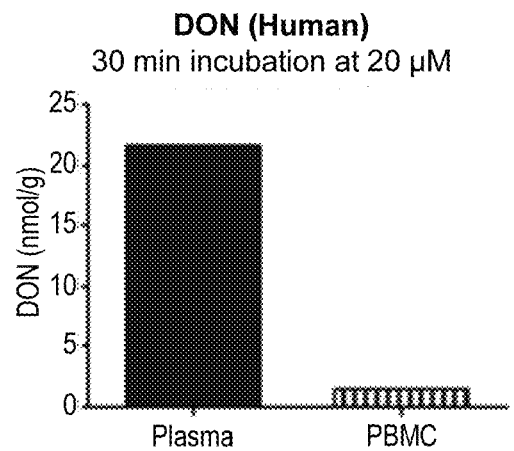
Figure 27B:
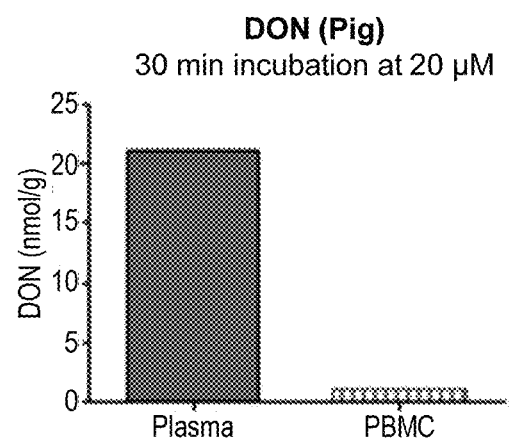
Figure 27C:
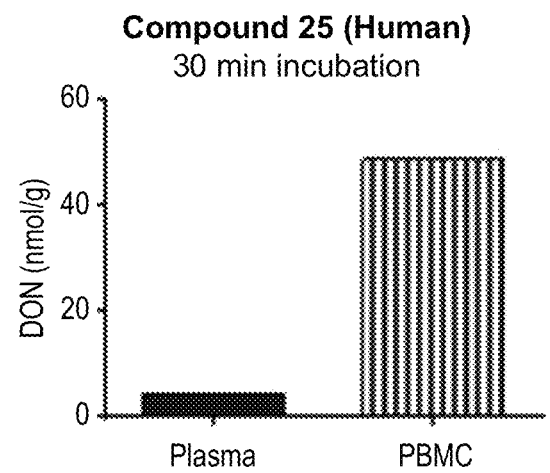
Figure 27D:
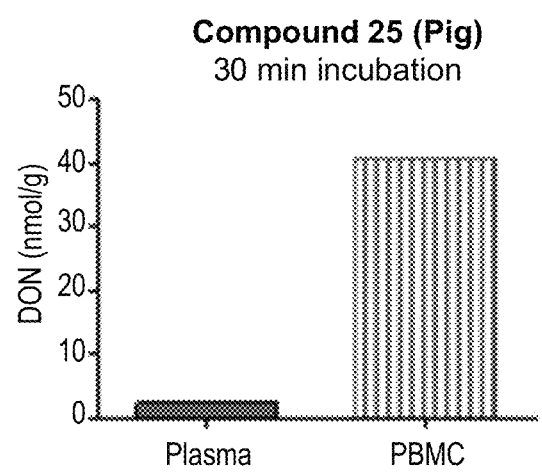
Figure 27E:
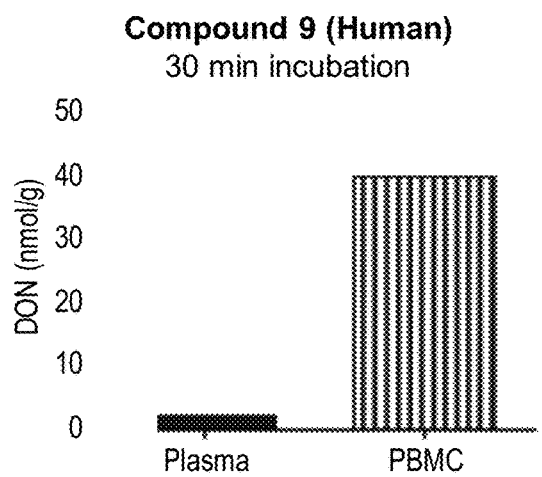
Figure 27F:
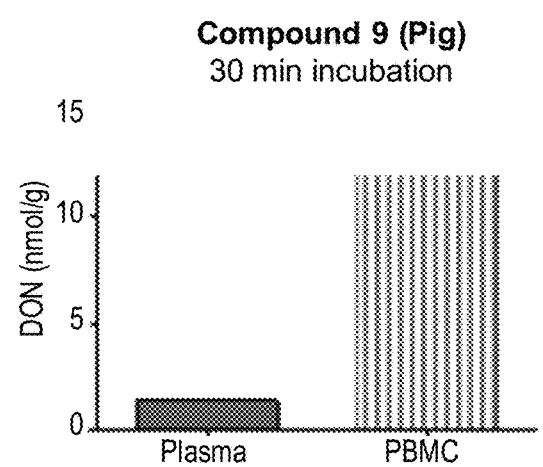
Figure 27G:
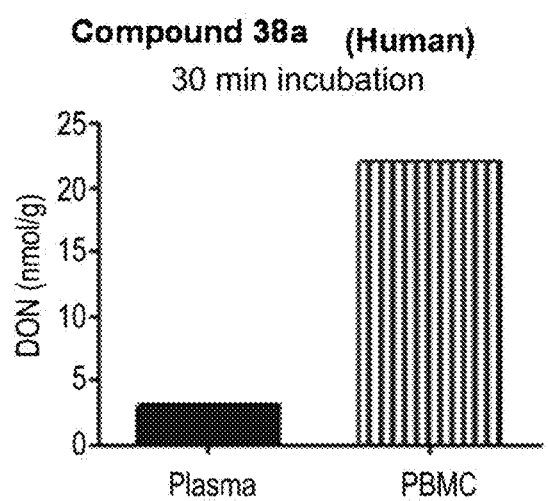
Figure 27H:
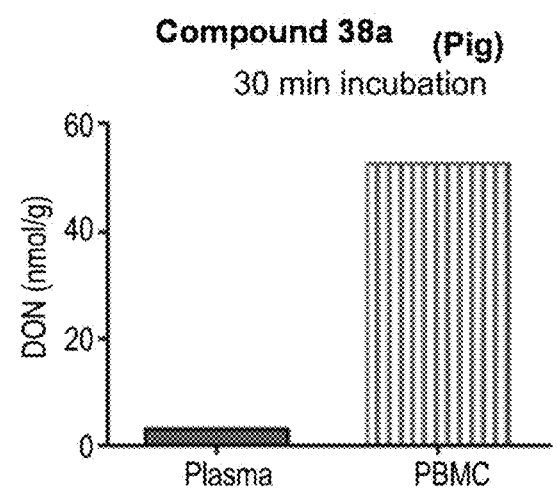
Figure 28A:
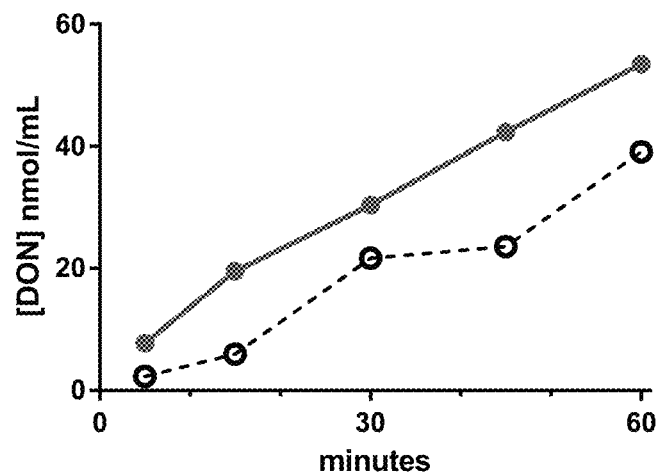
Figure 28B:
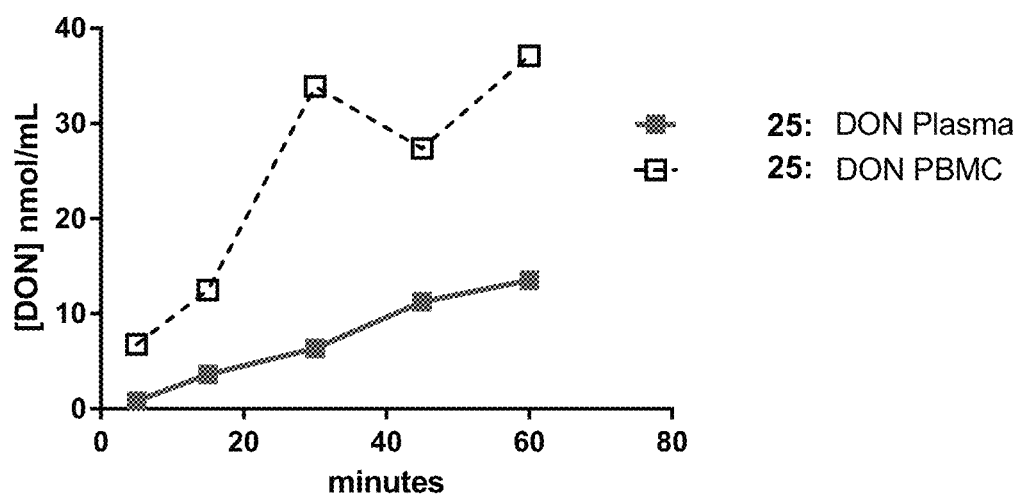
Figure 28C:
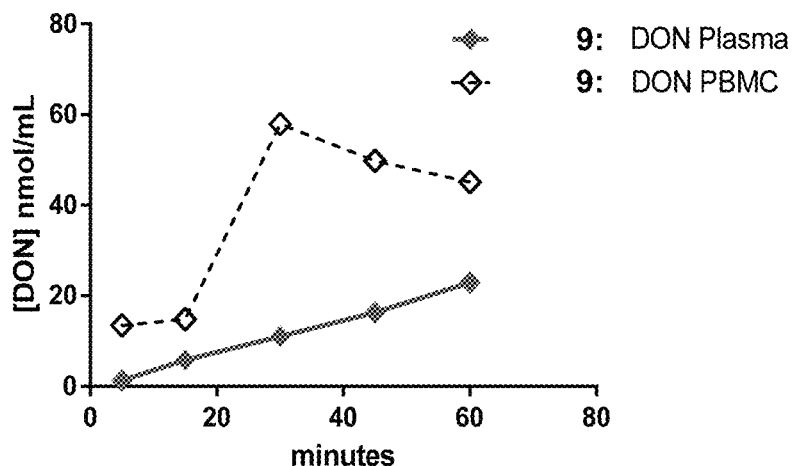
Figure 28D:
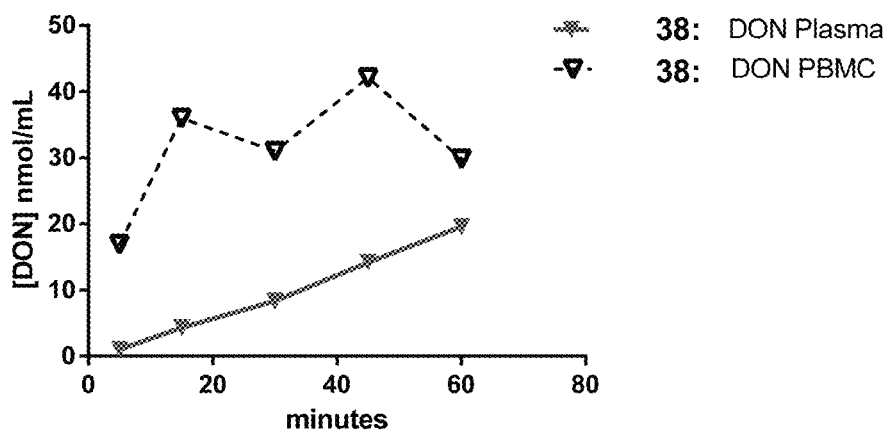
Figure 28E:
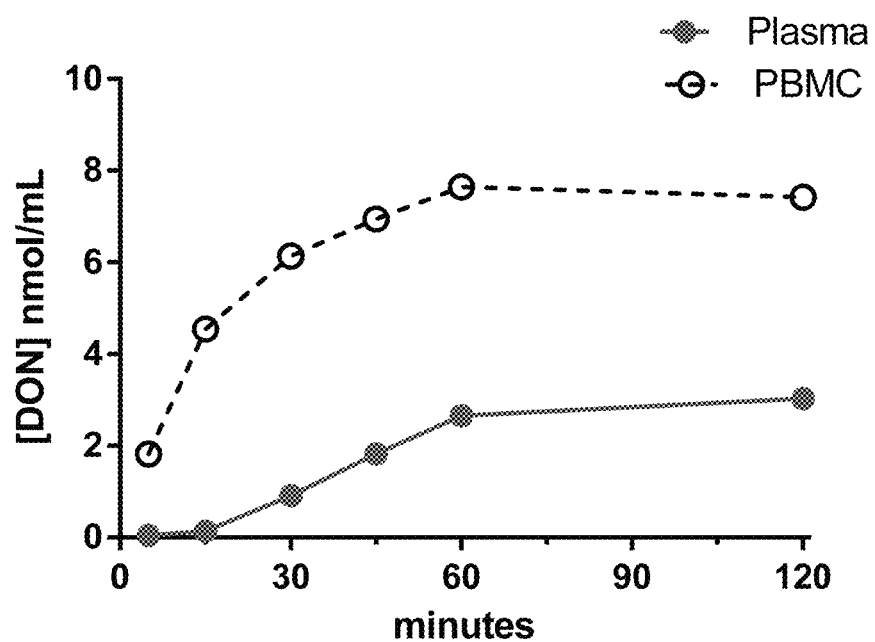
Figure 29A:
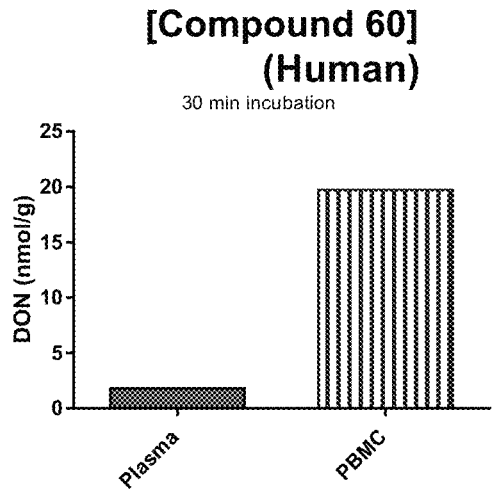
Figure 29B:
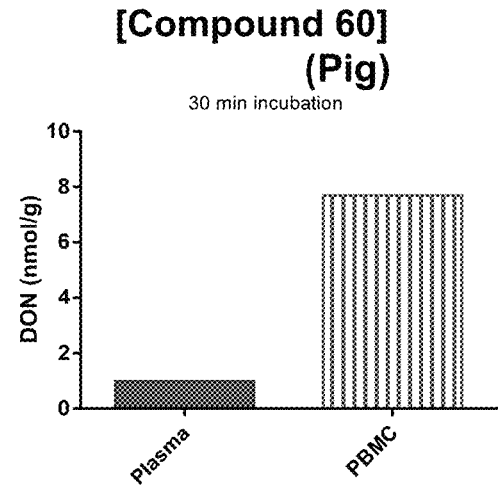
Figure 29C:
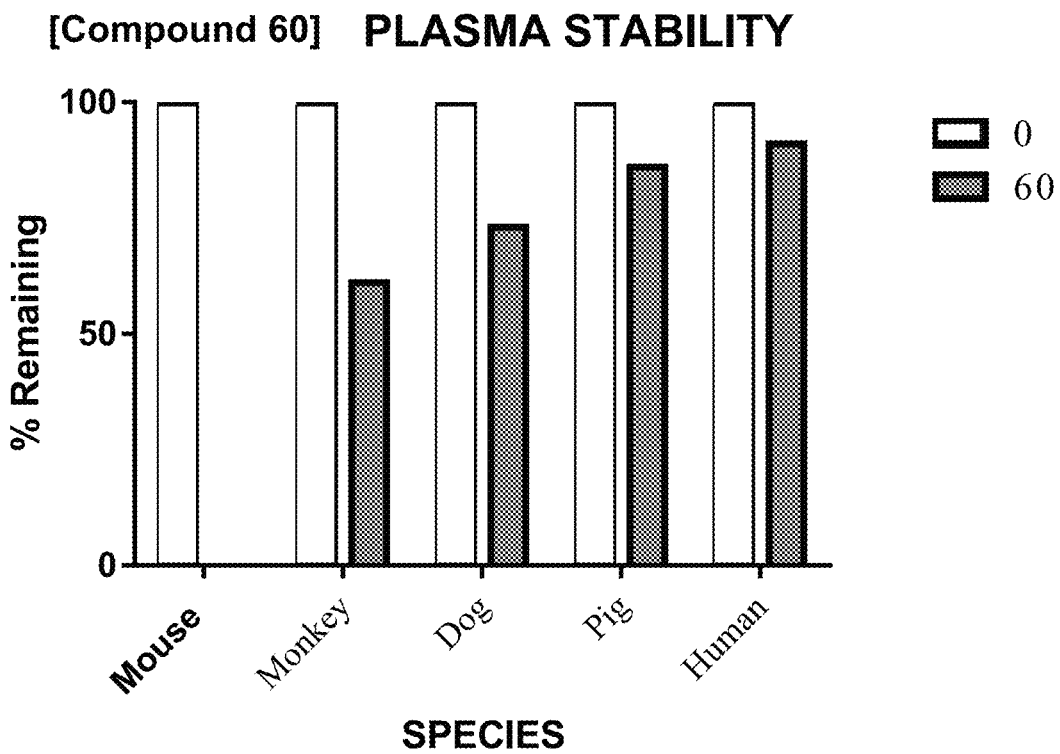
Figure 30:
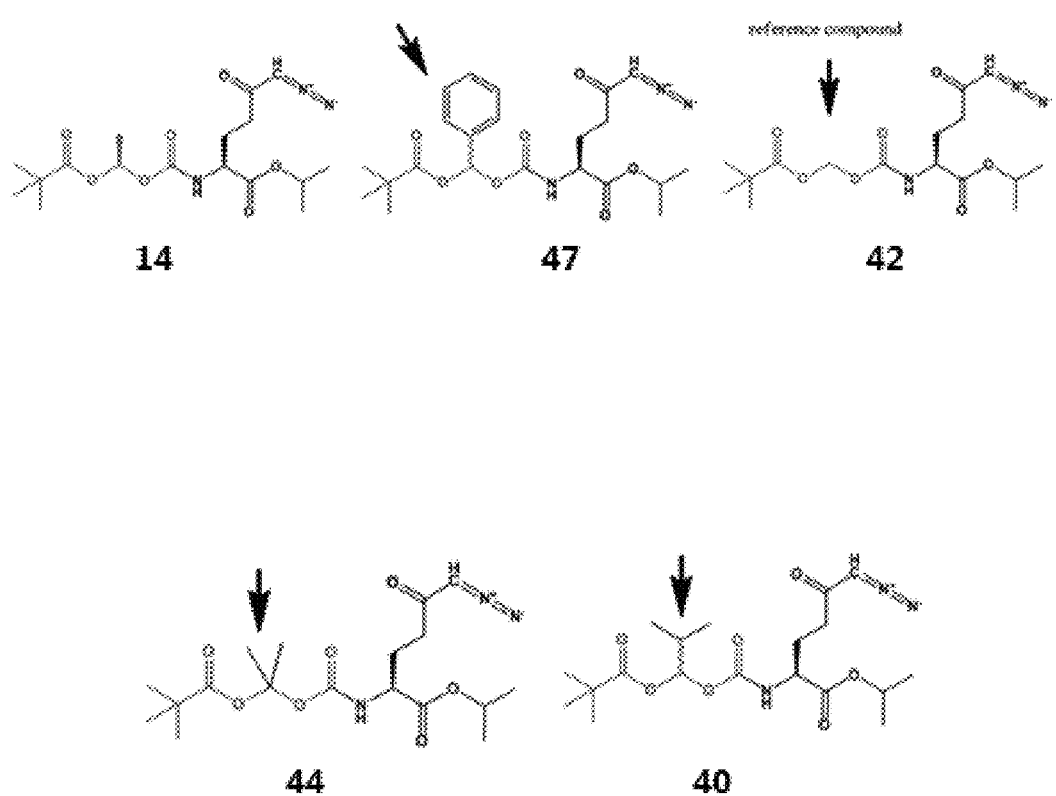
Figure 31:
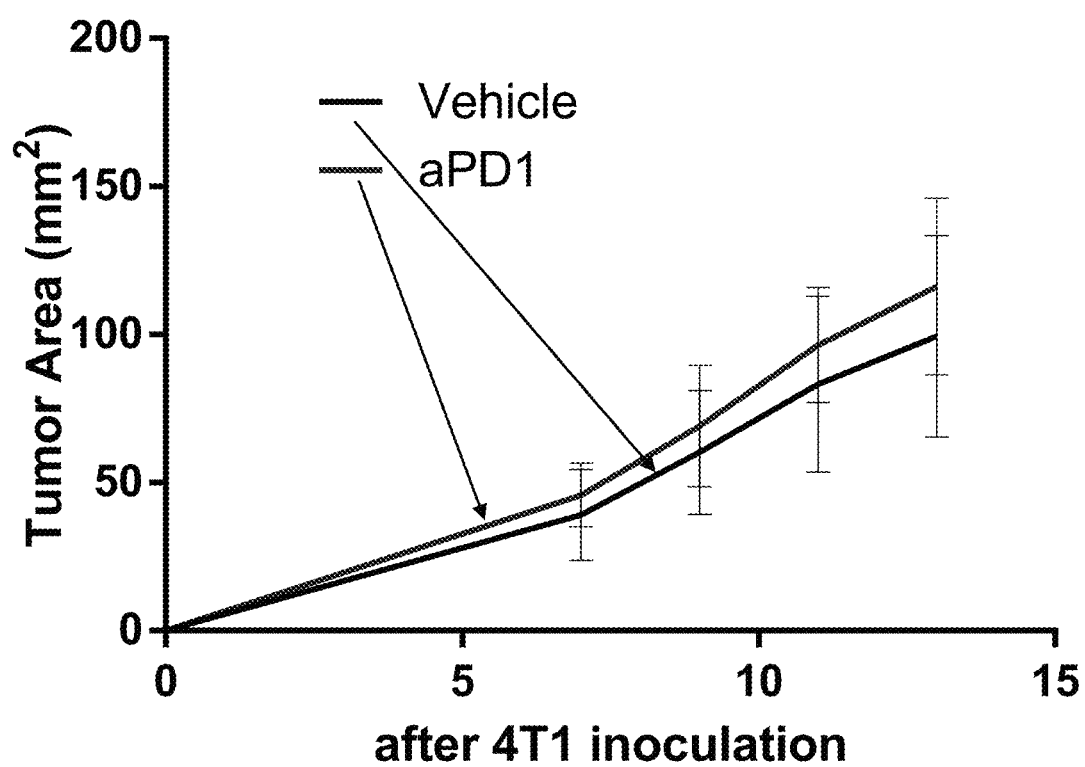
Figure 32A:
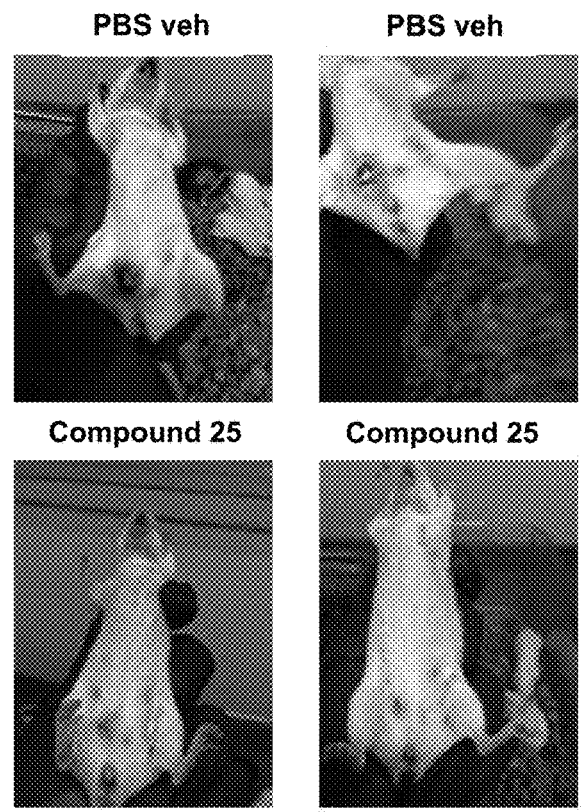
Figure 32B:
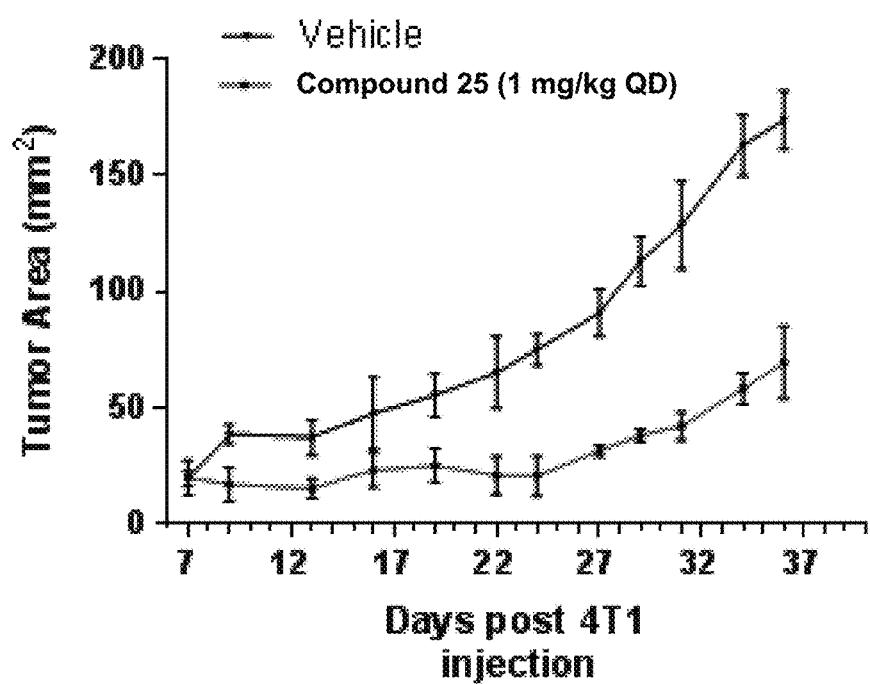

FIGS. 6A and 6B are lines graphs and FIG. 6C is a table showing in vivo brain and plasma pharmacokinetics of compound DON (1) following oral administration of DON (1) and 5c in mice. 1 and 5c were dosed in mice at 0.8 mg/kg equivalent, via oral gavage and plasma and brain concentrations of compound 1 were evaluated via LC/MS. Oral administration of compound 1 and 5c exhibited similar plasma and brain pharmacokinetic profiles due to complete and rapid metabolism of 5c to 1 in mouse plasma;

FIG. 7A is a line graph, FIG. 7B is a bar graph, FIG. 7C is a table, an FIG. 7D is an illustration showing in vivo pharmacokinetics of DON following i.v. administration of DON (1) and 5c in monkey plasma and CSF. 1 and 5c were dosed in two pigtail macaques at 1.6 mg/kg equivalent of 1 via i.v. administration and plasma (0.25-6 h) and CSF (30 min) concentrations of DON were evaluated via LC/MS. Relative to 1, 5c delivered substantially lower DON plasma concentration. Unexpectedly, the reverse was observed in CSF, where 5c delivered significantly higher DON CSF concentrations, achieving a 10-fold enhanced CSF to plasma ratio at 30 minute post dose;

FIG. 8A is a Kaplan-Meier graph, and FIG. 8B, FIG. 8C, FIG. 8D, and FIG. 8E are line graphs showing that 25 (5 day dosing starting on day 7) is superior to CB-839 (30 day dosing starting day 1) in CT26 tumor model:

FIG. 9 is a line graph showing that 25 (4 days starting on day 6) is superior to CB-839 (continuous twice daily dosing starting on day 1 prior to engraftment) in a CT26 tumor model. FIG. 9 shows mice received daily 25 (1.9 mg/kg) on days 6-9 vs BID glutaminase inhibitor on days 1-15:

FIG. 10 is a line graph showing that 25 (daily days 7-22) is superior to CB-839 (continuous twice daily dosing days 1-29) in a 4T1 breast cancer model. Mice received daily 25 (1.0 mg·kg/d) for days 7-22 as compared to BID glutaminase inhibitor for days 1-29;

FIGS. 11A-D and FIG. 11F are line graphs, and FIG. 11E is a Kaplan-Meier graph showing that 25 dosing of 1 mg/kg following by 0.3 mg/kg leads to a complete and durable response in the MC38 tumor;

FIG. 12A, FIG. 12B, and FIG. 12D are line graphs, and FIG. 12C is a Kaplan-Meier graph showing that 25 gives a robust response and improved overall survival in multiple tumor models including, for example, CT26 Colon Cancer;

FIG. 13A, FIG. 13B, and FIG. 13D are line graphs, and FIG. 13C is a bar graph showing that 25 provides a robust response and improved overall survival in multiple tumor models including, for example, 4T1 breast cancer:

FIGS. 14A-G are line graphs showing that mice cured with 25 alone immunologically reject tumors upon re-challenge, demonstrating that 25 monotherapy is immunotherapy;

FIG. 15A and FIG. 15C are line graphs and FIG. 15B and FIG. 15D are Kaplan-Meier graphs showing that 25 monotherapy is immunotherapy;

FIGS. 16A-F are line graphs showing that glutamine inhibition (e.g., DON) reduces the oxygen consumption and lactate production of tumor cells:

FIGS. 17A-F are graphs showing that glutamine inhibition (e.g., DON) improved the CD8/Treg ratio in the tumor and reduces hypoxia in the TILs;

FIGS. 18A-D are line graphs and FIG. 18E is a Kaplan-Meier graph showing that 25 conditions the tumor to be eliminated by anti-PD1 therapy in the MC38 Model, and in particular that 25 unexpectedly rescues anti-PD1 failures:

FIGS. 19A-C are line graphs and FIG. 19D is a Kaplan-Meier graph showing that even in the more difficult CT26 model, 25 enhances the response to anti-PD1 therapy;

FIG. 20A is a line graph, and FIG. 20B is a Kaplan-Meier graph showing that inhibiting glutamine metabolism also unexpectedly potentiates the anti-tumor response to adenosine A2a receptor (A2aR) blockade:

FIG. 21A is a line graph, FIG. 21B is an illustration, and FIG. 21C is a Kaplan-Meier graph showing that inhibiting glutamine metabolism unexpectedly enhances the efficacy of adoptive cellular therapy (ACT) in a B16-OVA model;

FIG. 22A is a line graph, FIG. 22B is a bar graph, and FIG. 22C is a table showing the in vivo pharmacokinetics of DON following i.v. administration of DON (1) and 14b in monkey plasma and cerebrospinal fluid (CSF). 1 and 14b were dosed in two pigtail macaques at 1.6 mg/kg equivalent of 1 via i.v. administration and plasma (0.25-6 h) and CSF (30 min) concentrations of DON were evaluated via LC/MS. Relative to 1, 14b delivered substantially lower DON plasma concentration. The reverse was observed in CSF, where 14b delivered significantly higher DON CSF concentrations, achieving an unexpected 10-fold enhanced CSF to plasma ratio at 30 minute post dose;

FIG. 23 is a bar graph showing species specific plasma stability of (14b); 14b is stable in plasma of human, pig, dog and monkeys, but rapidly metabolized in mice:

FIG. 24 is an illustration showing exemplary structures of DON and DON-based prodrugs 25, 9, 38, 38a, 60, and 60a; different N-amino acid promoieties (e.g. leucine, tryptophan) provide differential plasmas and microsomal stability;

FIG. 25A, FIG. 25B, FIG. 25C, and FIG. 25D are bar graphs showing the in vitro plasma stability of DON prodrugs 25, 9, 38a and 60a. Metabolism occurs via removal of N-protecting group; both ethyl and isopropyl esters are stable in plasma of pigs and humans:

FIG. 26A, FIG. 26B, FIG. 26C, and FIG. 26D are bar graphs showing the in vitro liver microsomal stability of DON prodrugs 25, 9, 38a and 60a; all prodrugs showed moderate-high stability in human and pig microsomes:

FIG. 27A, FIG. 27B, FIG. 27C, FIG. 27D, FIG. 27E, FIG. 27F, FIG. 27G, FIG. 27H, FIG. 27I, and FIG. 27J are bar graphs showing the results of ex-vivo studies in whole human and pig blood of 25, 9, 38a and 60a; DON prodrugs selectively deliver DON to PBMCs in both humans and pigs vs plasma; compared to DON, the PBMC/plasma ratio was unexpectedly enhanced 10-100+ fold;

FIG. 28A FIG. 28B, FIG. 28C, FIG. 28D and FIG. 28E are line graphs showing the results of pig in vivo studies with DON prodrugs of 25, 9, 38a and 60a; DON prodrugs selectively deliver DON to PBMCs vs plasma; compared to DON, the PBMC/plasma ratio was expectedly enhanced 6- to 10-fold:

FIG. 29A, FIG. 29B, and FIG. 29C are bar graphs showing the plasma stability of compound Methyl-POM 14b and its derivatives;

FIG. 30 is an illustration showing exemplary structures of N-acylalkyloxy DON-based prodrug analogs for intracellular targeting and brain penetration; the addition of steric bulk to the "bridge" might result in a slower hydrolysis;

FIG. 31 is a line graph showing that anti-PD1 monotherapy does not work in a 4T1 tumor model. 4T1 tumor cells (0.1 million) were injected into the mammary fat pads of 8-week-old female BALB/c mice. Anti-PD1 (5 mg/Kg) was administered on day 3, 5, 8, and 11 and tumor volume was measured 2-3 times weekly until tumors were evaluated for tumor infiltrating cells. Group: a-PD1 (d3, 5, 8, 11 100 ug/mouse)=5 mg/kg I.P.;

FIG. 32A is an illustration of mice and FIG. 32B is a line graph illustrating that compound 25 inhibits tumor growth. FIG. 32A shows mice after 30 days inoculation (8 days drug free). FIG. 32B shows tumor area vs. days post injection with 4T1 tumor cells. Mice were treated with compound 25 1 mg/kg every day (from d5-d22) or vehicle. 4T1 tumor cells (0.1 million) were injected into the mammary fat pads of 8-week-old female BALB/c mice. Mice received vehicle (PBS) or 1 mg/kg compound 25 daily from day 5 to day 22. Photos were taken on day 30 after tumor inoculation (FIG. 57A). Tumor volume was measured 2-3 times weekly until WT mice were sacrificed (when size reached to 20 mm length or necrosis occurred). Day 0: 100K 4T1 cells s.c. in 4th mammary pad. Day 5-22: Daily compound 25. The results show that compound 25 inhibited the growth of mammary carcinoma tumor cells.

Figure 33A:
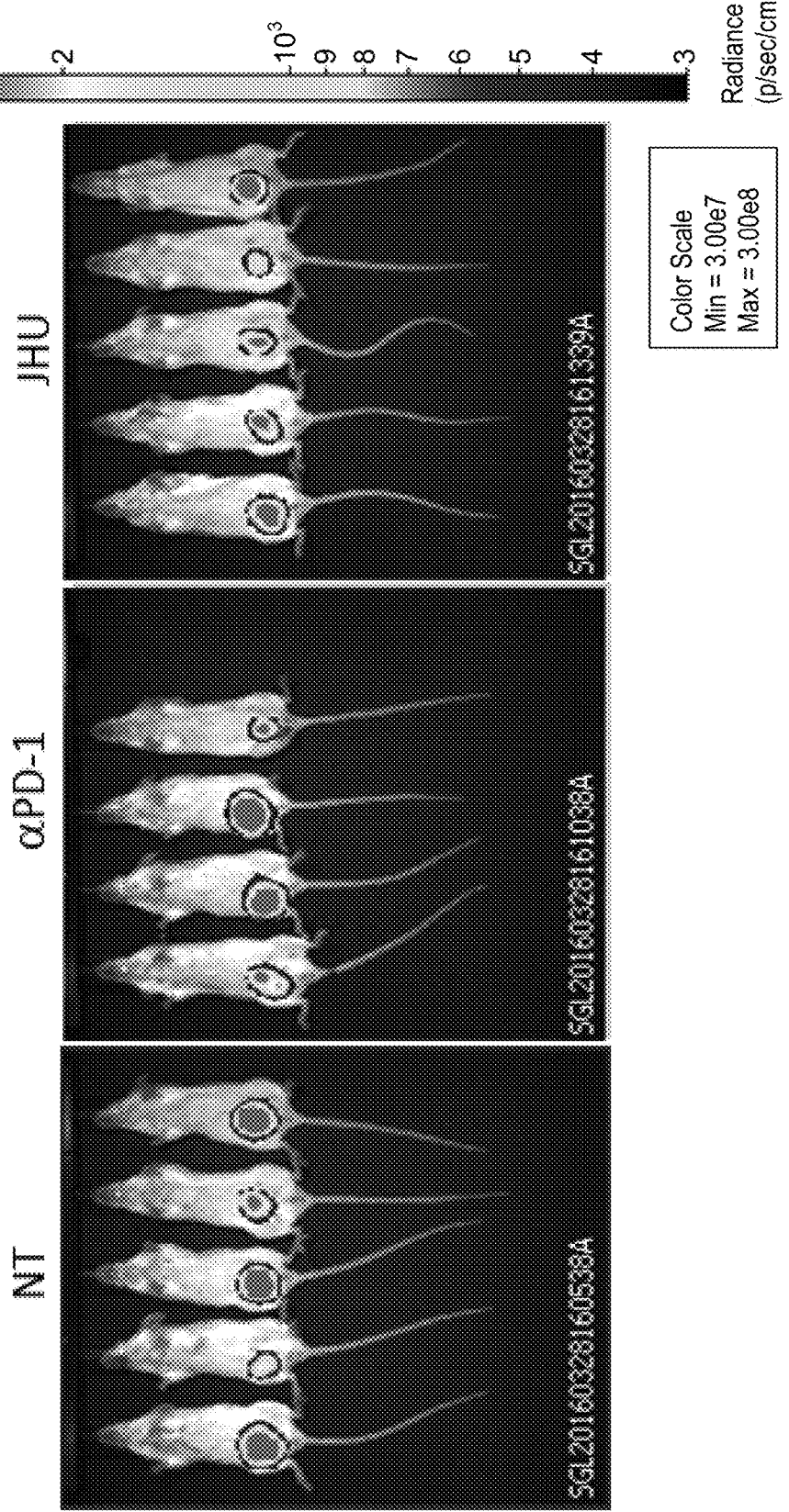
Figure 33B:
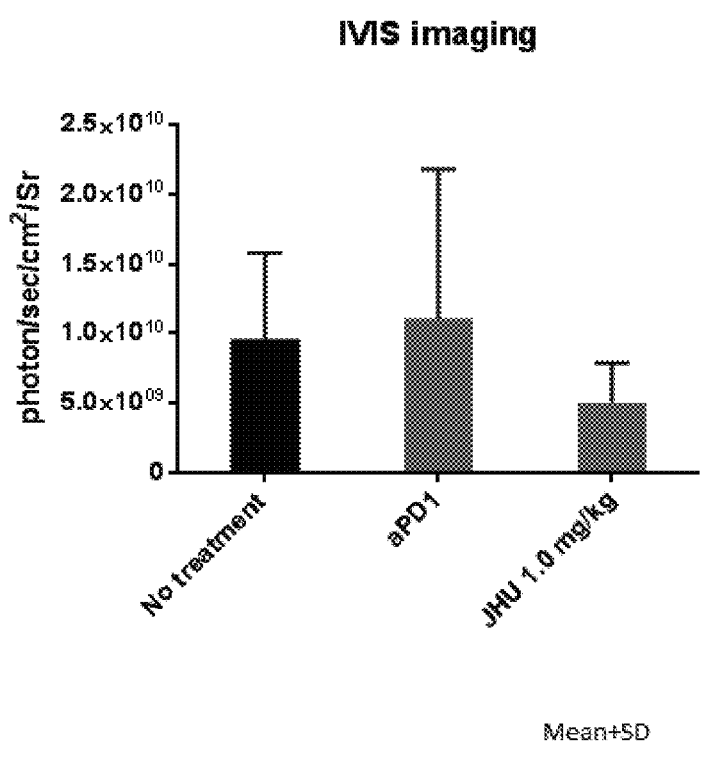

FIG. 33A is an illustration of mice and FIG. 33B is a bar graph illustrating that compound 25 inhibits tumor growth. 4T1-Luc tumor cells (0.1 million) were injected into the mammary fat pads of 8-week-old female BALB/c mice. Mice received vehicle (PBS) or 1 mg/kg compound 25 daily from day 7. Anti-PD1 antibody (5 mg/Kg) was administered on day 5, 8, and 12. Mice carrying 4T1-luc tumors are injected with Luciferin to measure luminescence from the tumor. IVIS imaging were taken on day 13. The results unexpectedly show that treatment with compound 25 as a single agent inhibited mammary carcinoma cell proliferation better than anti-PD1.

Figure 34A:
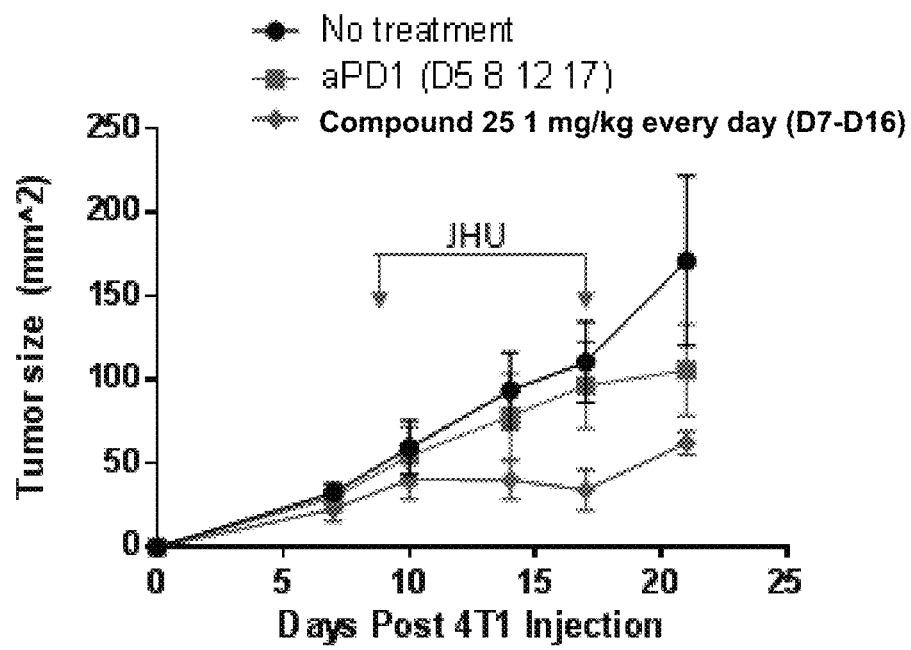
Figure 34B:
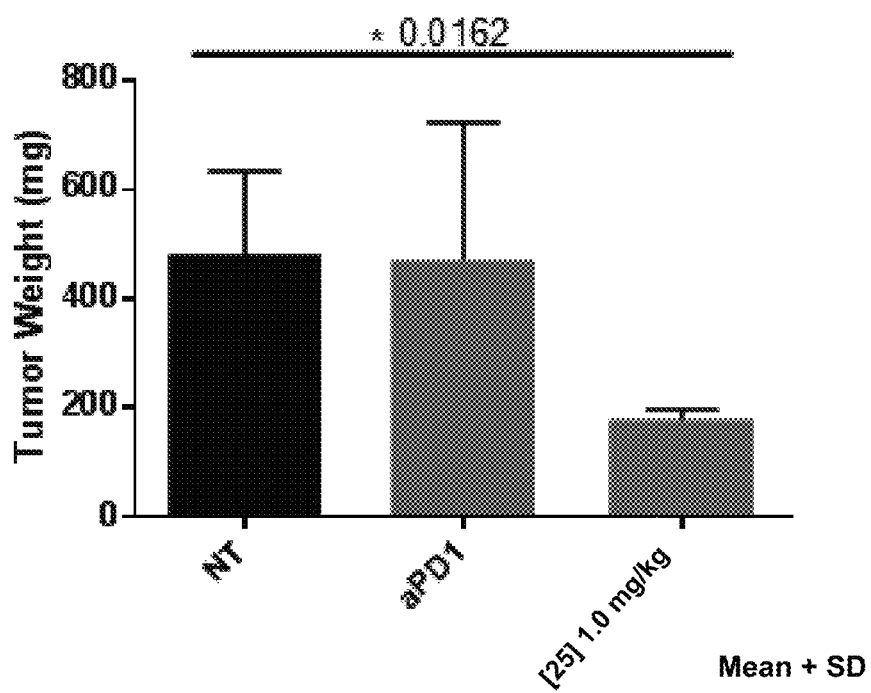
Figure 35A:
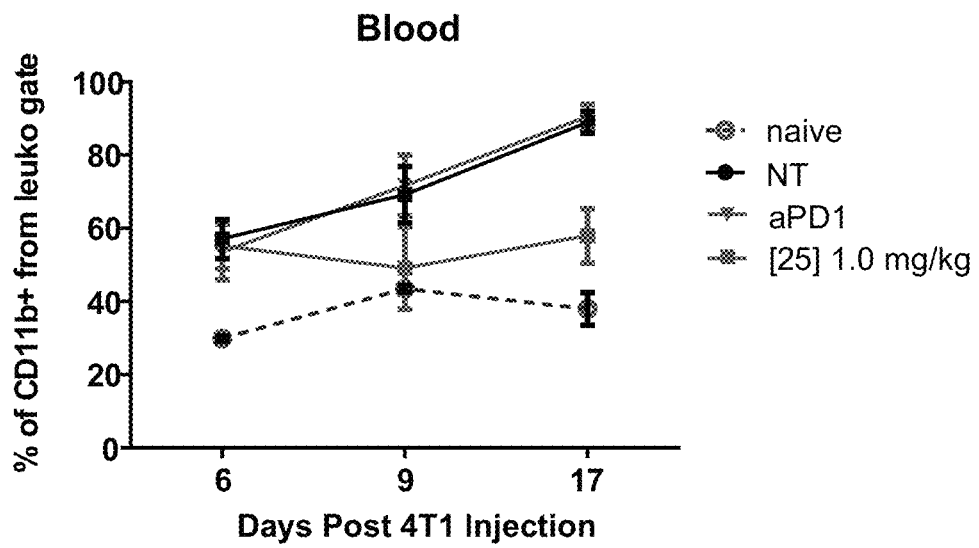
Figure 35B:
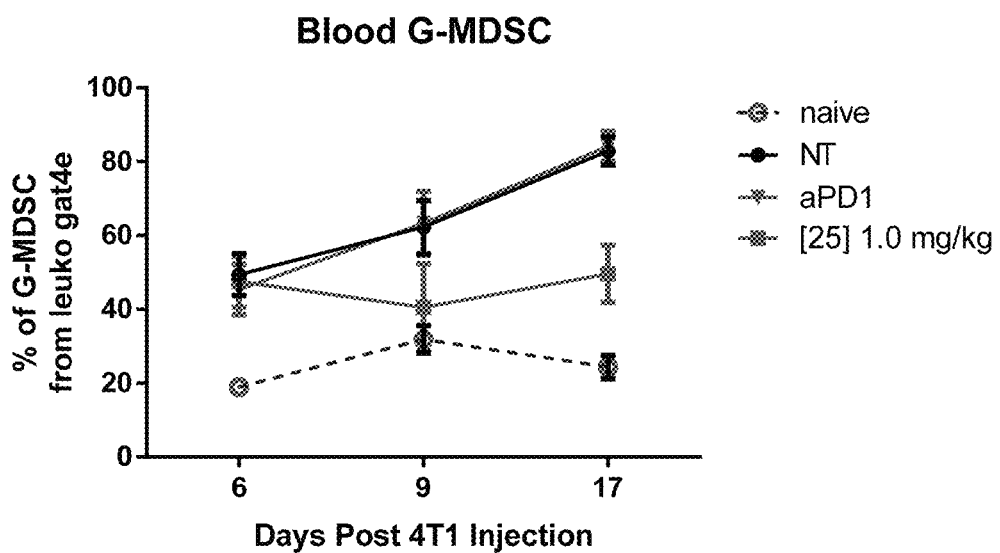
Figure 35C:
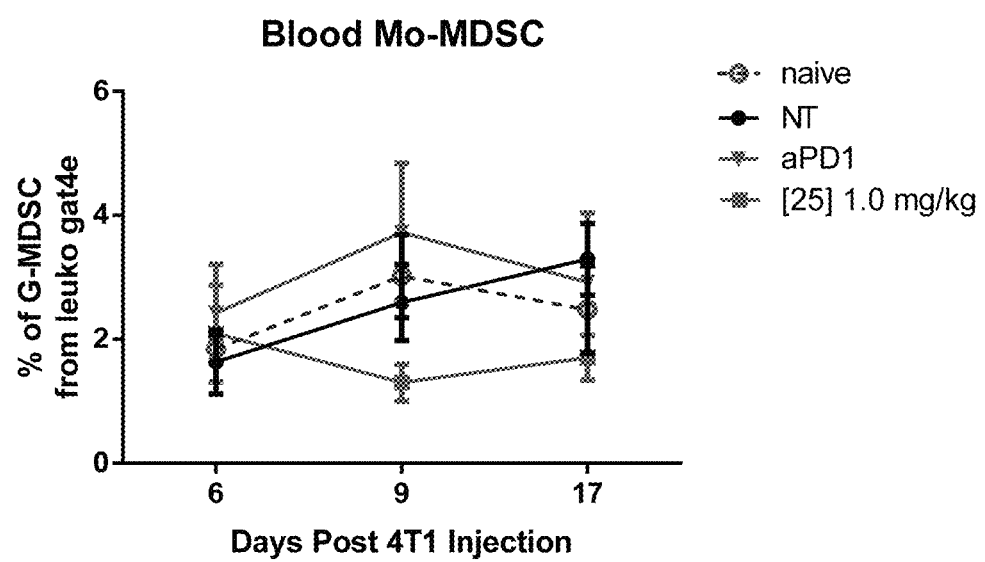
Figure 36:
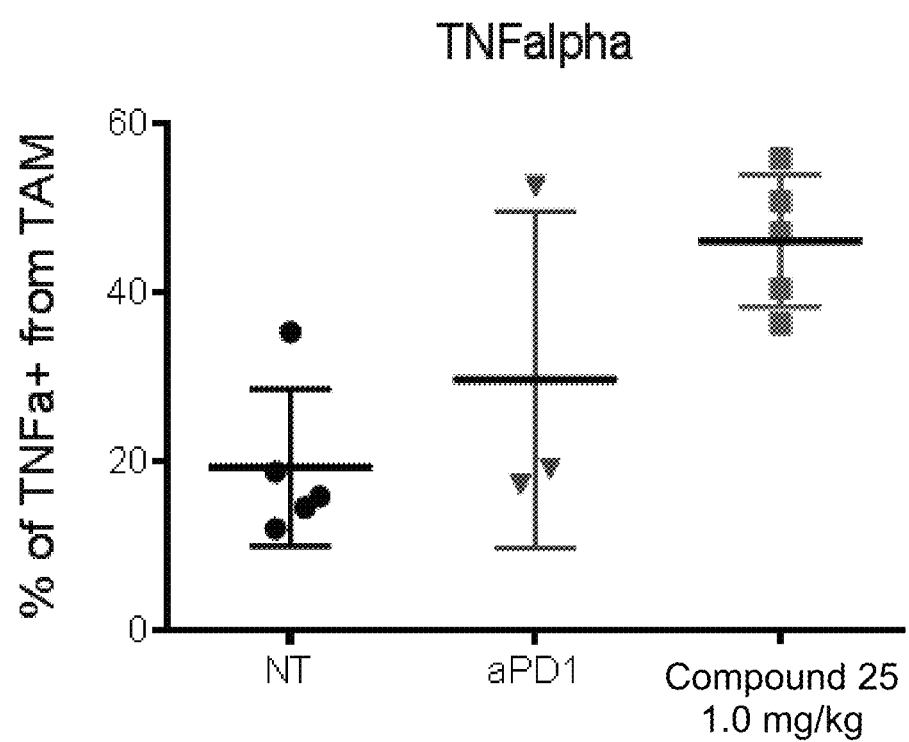
Figure 37A:
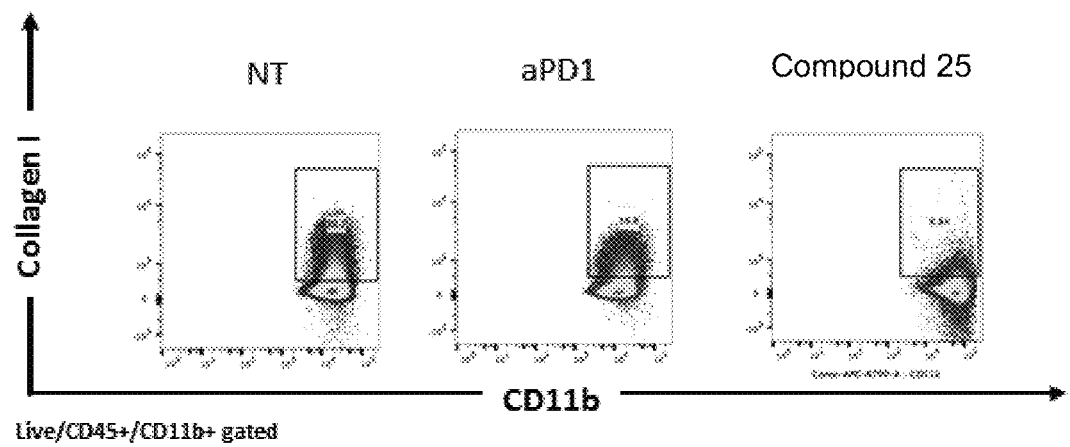
Figure 37B:
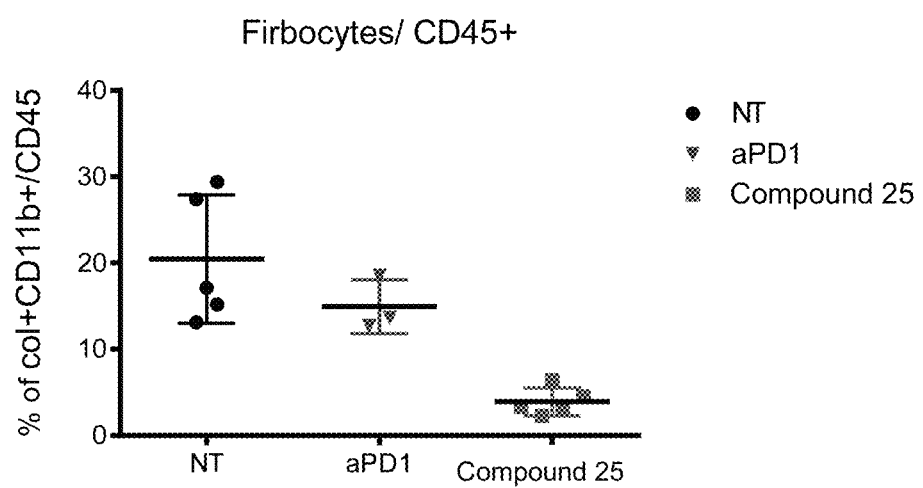
Figure 37C:
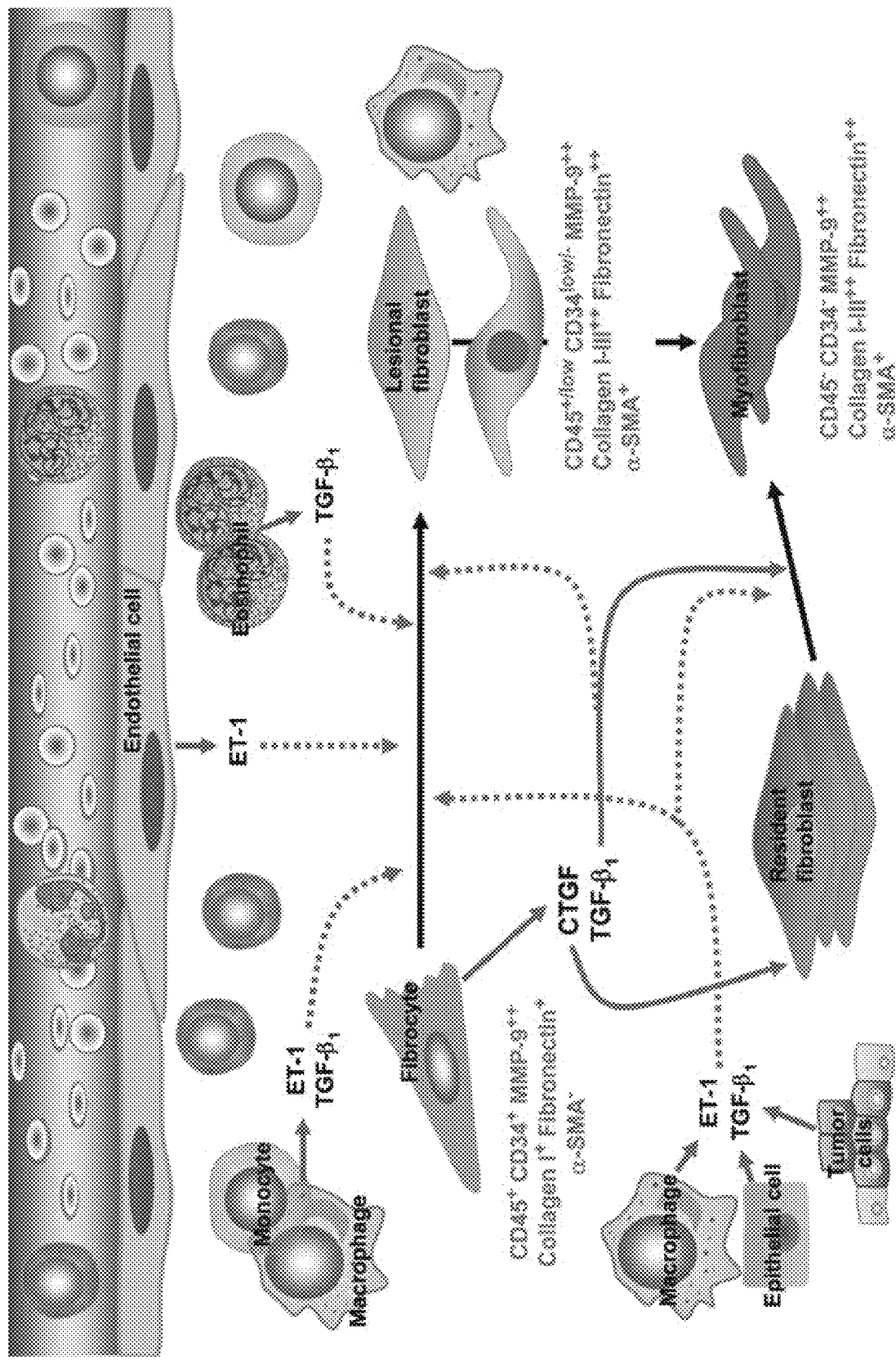

FIG. 34A is a line graph and FIG. 34B is a bar graph showing that compound 25 inhibits tumor growth. FIG. 34B shows tumor weight (mg) on harvest day 21. 4T1-Luc tumor cells (0.1 million) were injected into the mammary fat pads of 8-week-old female BALB/c mice. Mice received vehicle (PBS) or 1 mg/kg 25 daily from day 7 to day 16. Anti-PD1 antibody (5 mg/Kg) was administered on day 5, 8, 12 and 17. Tumor FIG. 40C is a line graph showing EO771 tumor growth in mice treated with vehicle.

Figure 40A:
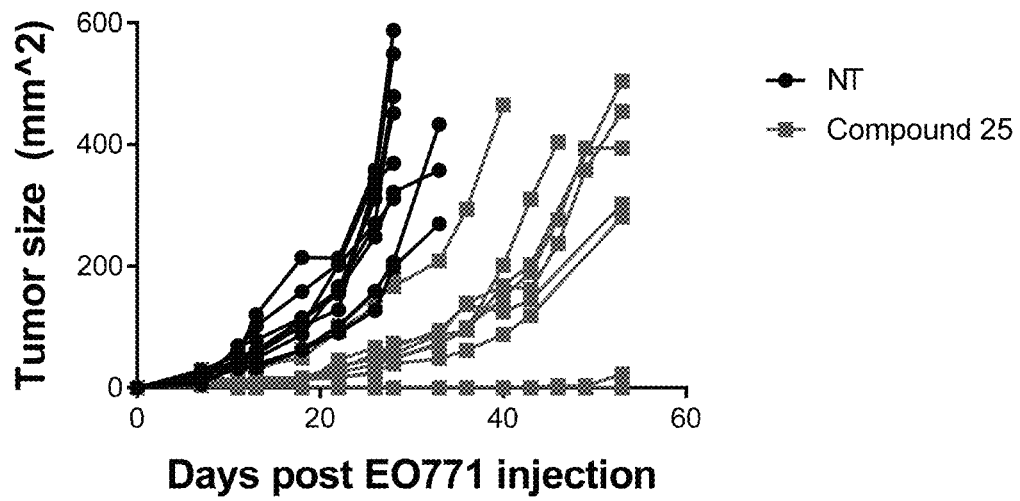
Figure 40B:
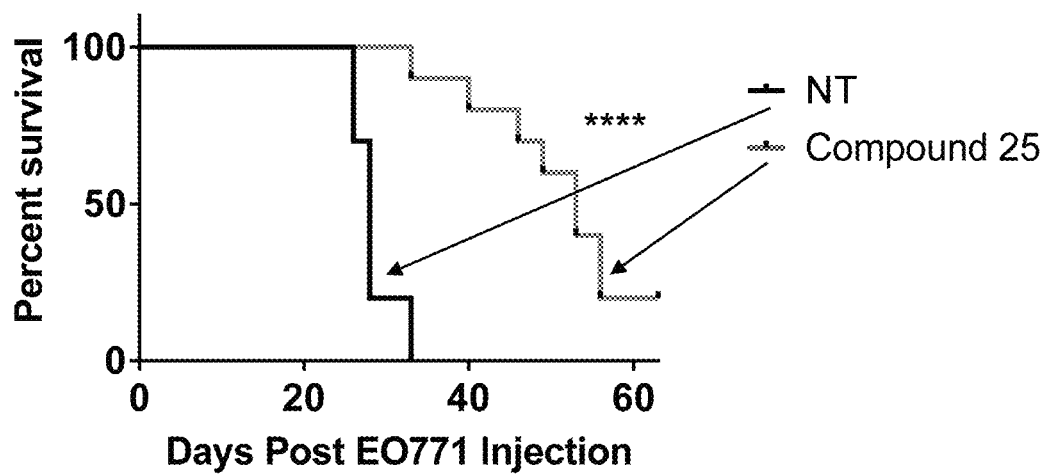
Figure 40C:
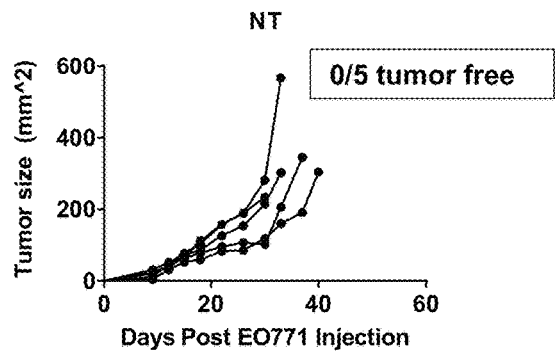
Figure 40D:
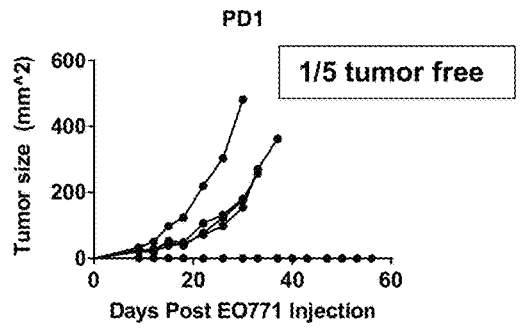

FIG. 40D is a line graph showing EO771 tumor growth in mice treated with anti-PD1.

Figure 40E:
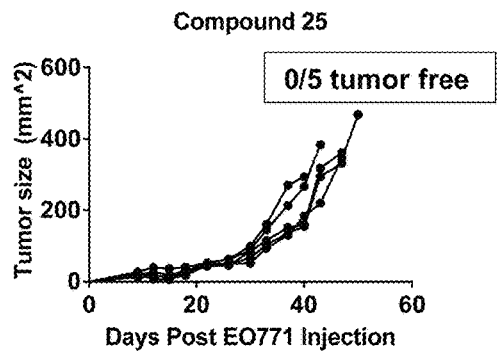

FIG. 40E is a line graph showing EO771 tumor growth in mice treated with compound 25.

Figure 40F:
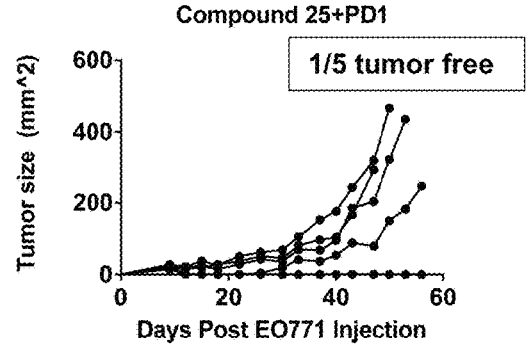

FIG. 40F is a line graph showing EO771 tumor growth in mice treated with combination of compound 25 and anti-PD-1.

Figure 40G:
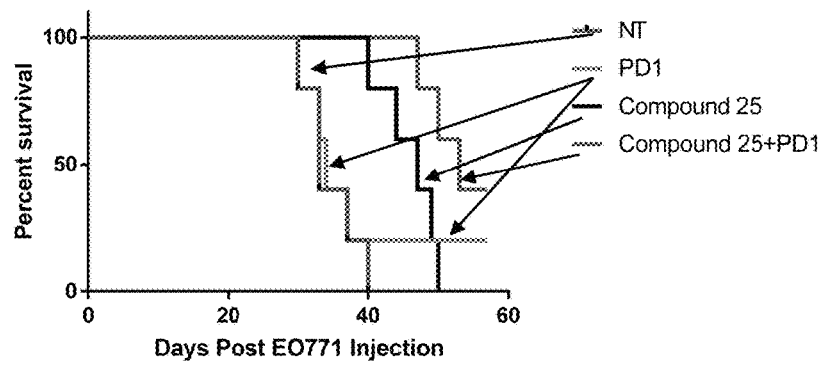

FIG. 40G is a line graph showing an increase in survival time with the combination of compound 25 and anti-PD-1 in EO771 tumor-bearing mice.

FIG. 41A is a line graph showing 4T1 tumor cells tumors were resistant to treatment with anti-PD1, anti-CTLA4, or combination of anti-PD1 and anti-CTLA4.

FIG. 41B is a graph showing percentages of Mo-MDSC (monocytic MDSC: CD11b+F4/80-Ly6ChiLy6Gneg) live cells from the blood.

FIG. 41C is a graph showing percentages of PMN-MDSC+TAN (CD11b+F4/80-Ly6CloLy6Ghi) live cells from the blood.

Figure 41D:
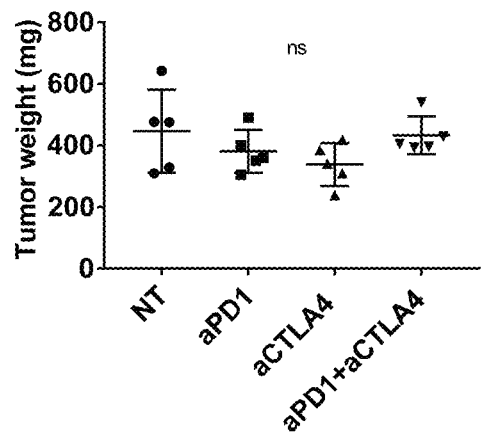

FIG. 41D is a graph showing 4T1 tumor weight in mice treated with vehicle, anti-PD1, anti-CTLA4, and combination of anti-PD1 and anti-CTLA4.

Figure 41E:
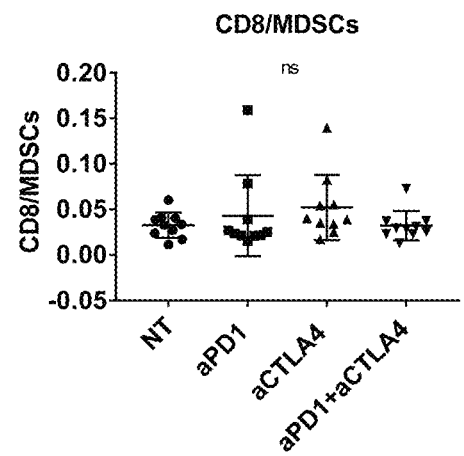

FIG. 41E is a graph showing the ratio of CD8 to MDSC in mice treated with vehicle, anti-PD1, anti-CTLA4, and combination of anti-PD1 and anti-CTLA4.

Figure 41F:
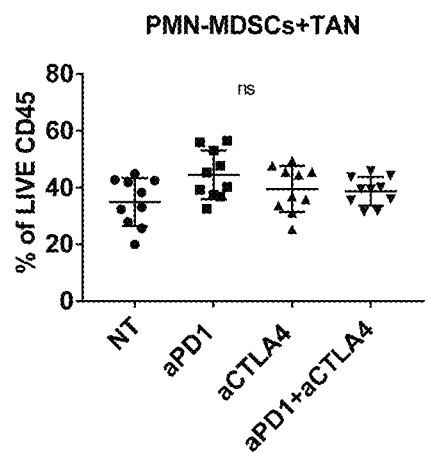

FIG. 41F is a graph showing the percentages of PMN-MDSC+TAN (CD11b+F4/80-Ly6CloLy6Ghi) in mice treated with vehicle, anti-PD1, anti-CTLA4, and combination of anti-PD1 and anti-CTLA4.

Figure 41G:
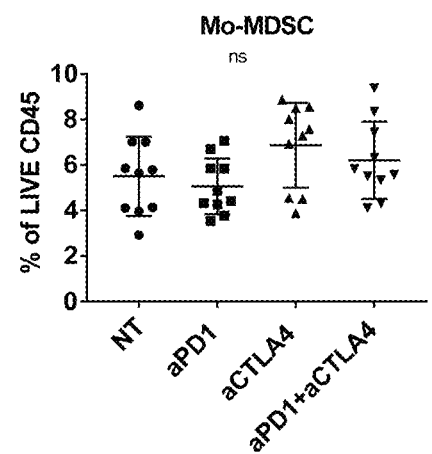

FIG. 41G is a graph showing percentages of Mo-MDSC (monocytic MDSC: CD11b+F4/80-Ly6ChiLy6Gneg) in mice treated with vehicle, anti-PD1, anti-CTLA4, and combination of anti-PD1 and anti-CTLA4.

Figure 41H:
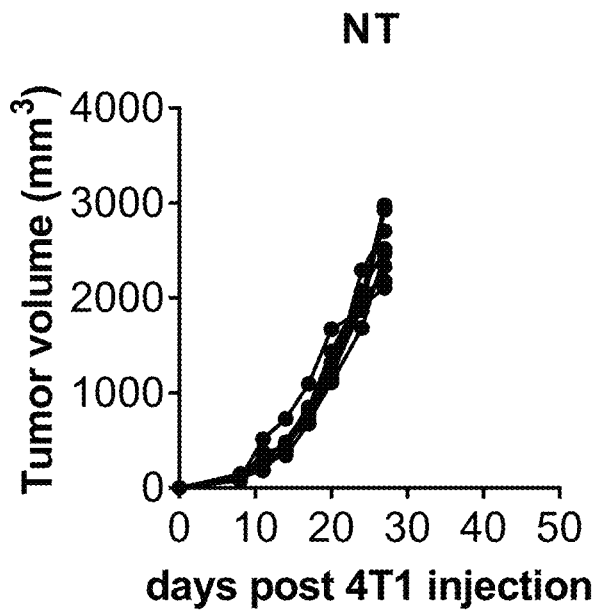

FIG. 41H is a line graph showing 4T1 tumor volume in mice treated with vehicle.

Figure 41I:
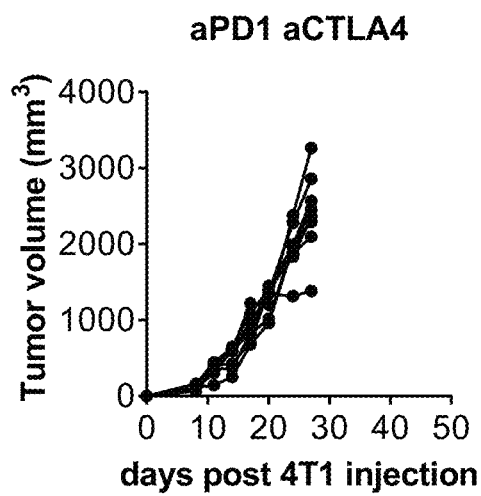

FIG. 41I is a line graph showing 4T1 tumor volume in mice treated with anti-CTLA4 and anti-PD1.

Figure 41J:
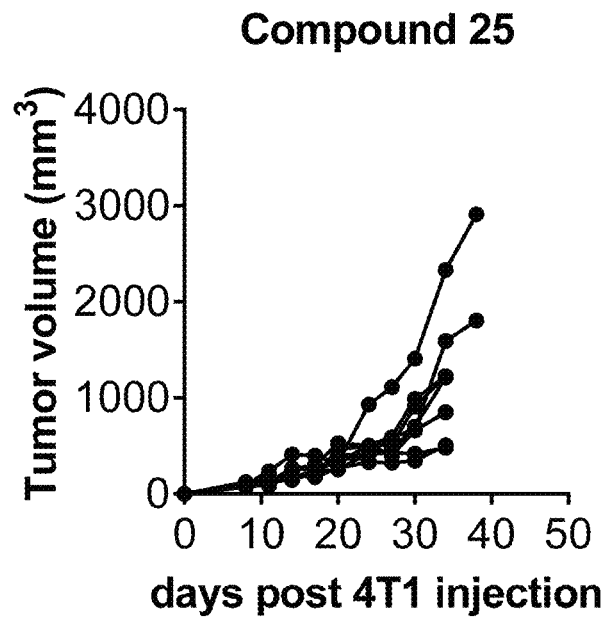

FIG. 41J is a line graph showing that the compound 25 treated group in the 4T1 tumor model displayed slow tumor growth and increased survival.

Figure 41K:
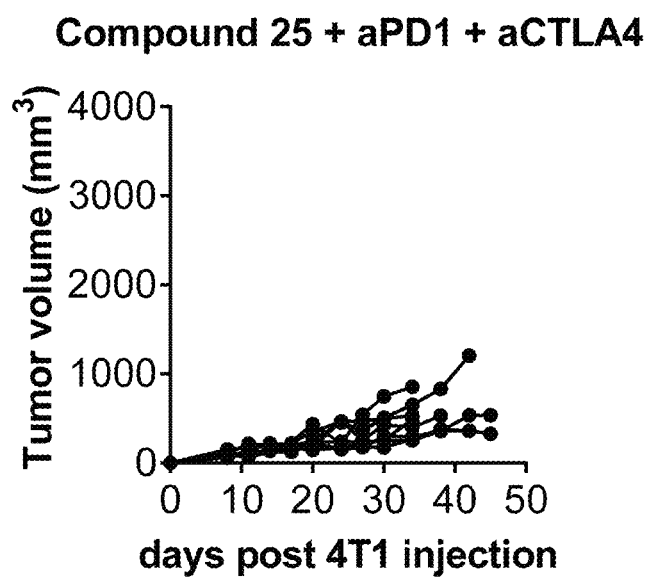

FIG. 41K is a line graph showing that combination of compound 25, anti-PD1 and anti-CTLA4 in the 4T1 tumor model further slowed tumor growth compared to the compound 25 alone group.

Figure 41L:
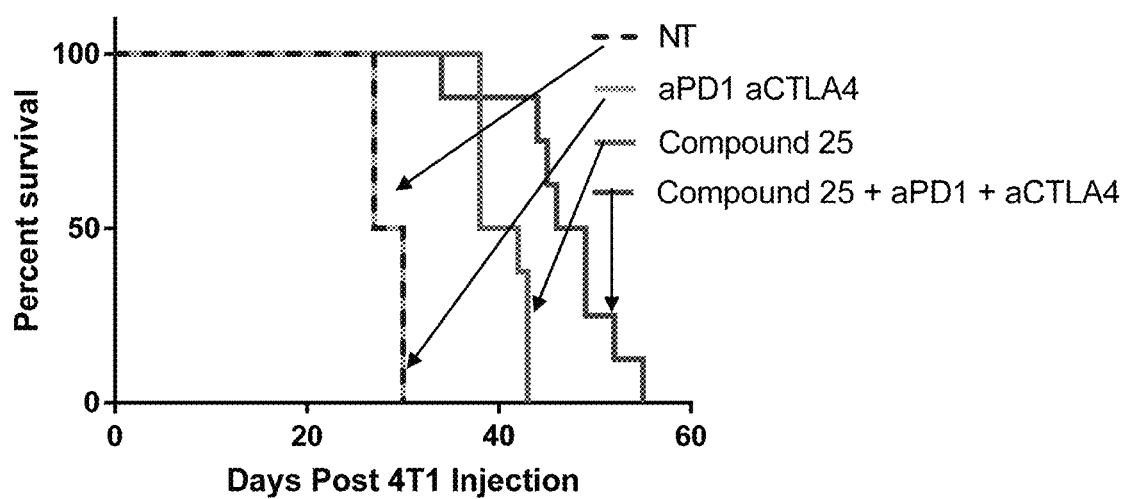

FIG. 41L is a line graph showing an increase in survival time with the combination of compound 25, anti-PD1 and anti-CTLA4 in the 4T1 tumor model.

Figure 42A:
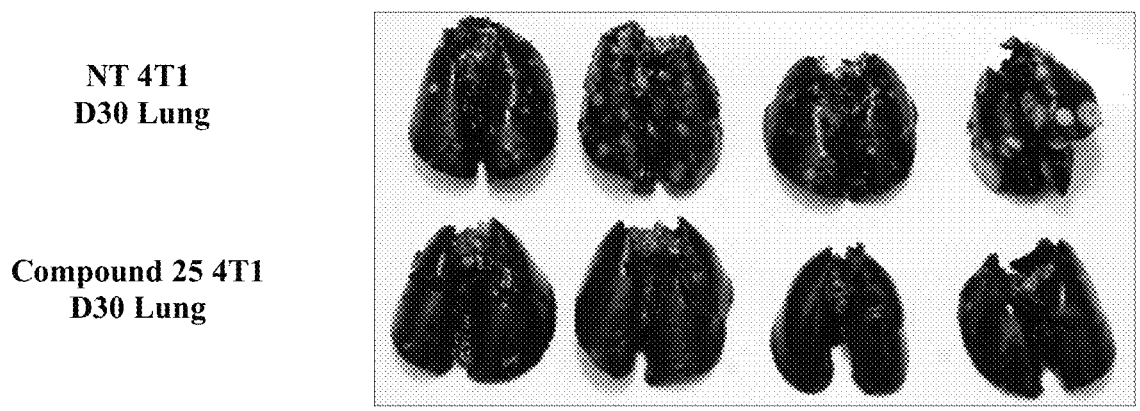

FIG. 42A is an illustration showing spontaneous lung metastasis in 4T1 tumor-bearing mice analyzed by inflation with 15% india ink to quantify tumor nodules.

Figure 42B:
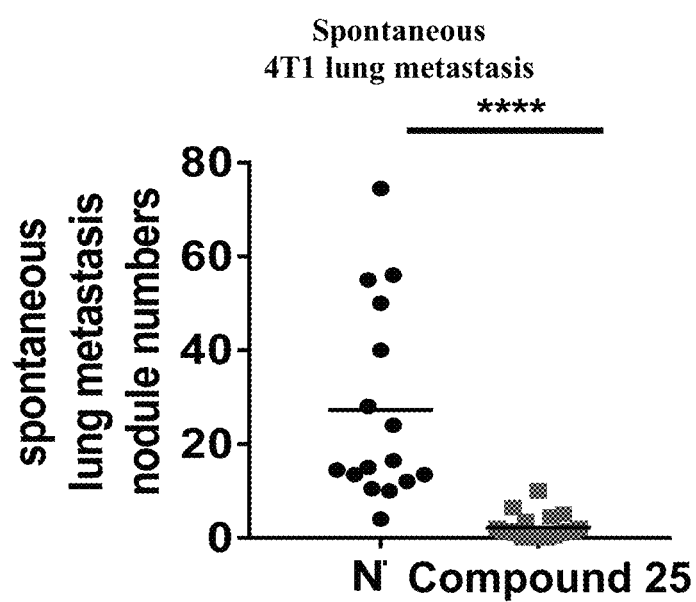

FIG. 42B is a graph showing numbers of spontaneous 4T1 lung metasteses in non-treated (NT) mice and mice treated with compound 25.

Figure 43A:
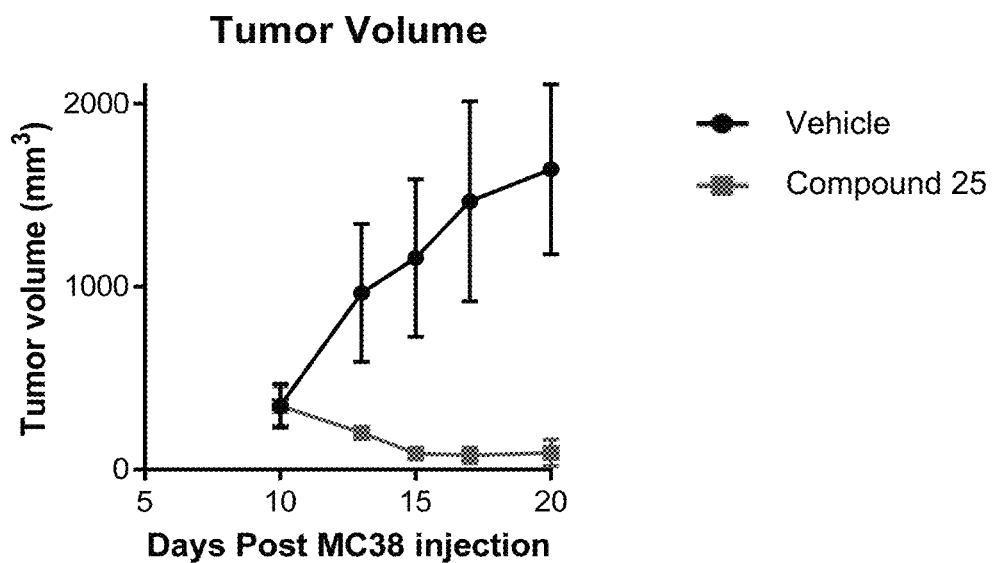

FIG. 43A is a line graph showing tumor growth curves of MC38-bearing mice treated with vehicle and with compound 25.

Figure 43B:
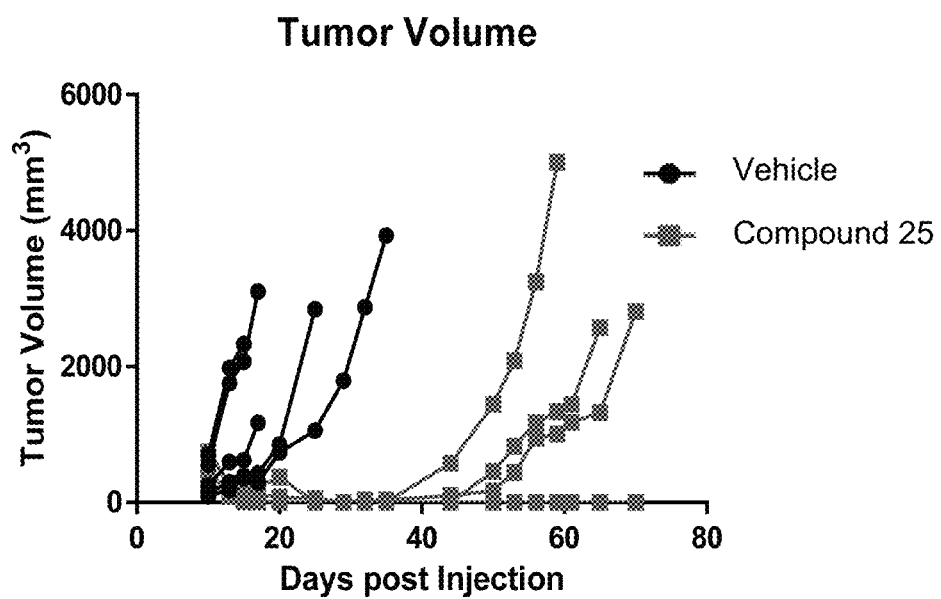

FIG. 43B is a line graph showing tumor volume of MC38-bearing mice treated with vehicle and with compound 25.

Figure 43C:
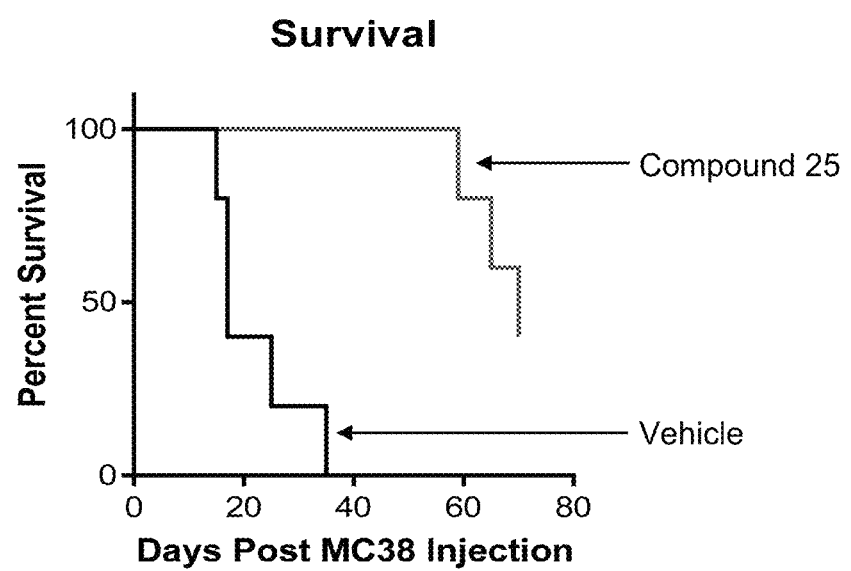

FIG. 43C is a line graph showing survival curves of MC38-bearing mice treated with vehicle and with compound 25.

Figure 44A:
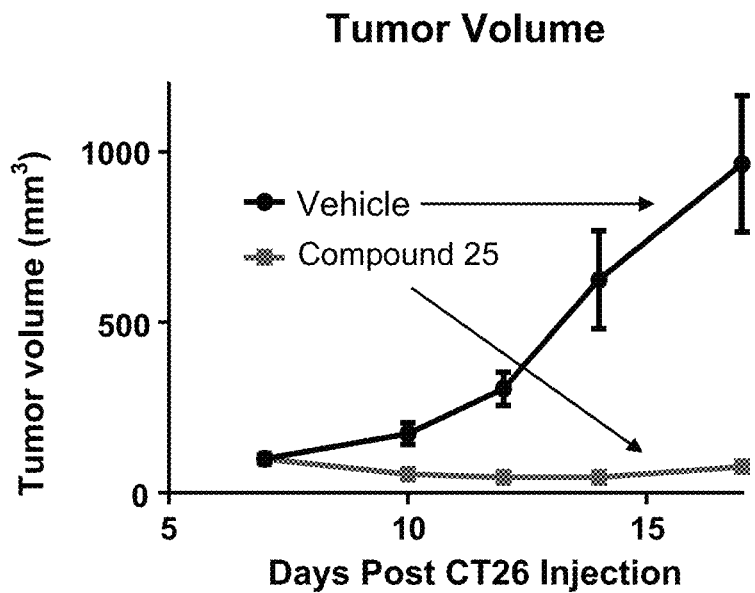

FIG. 44A is a line graph showing tumor growth curves of CT26 tumor-bearing mice treated with vehicle and with compound 25.

Figure 44B:
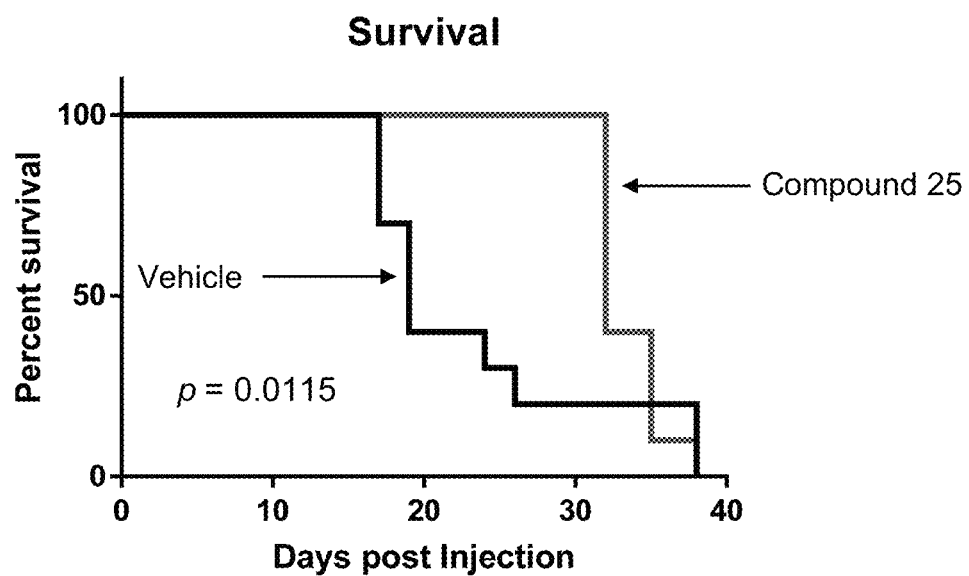

FIG. 44B is a line graph showing survival curves of CT26 tumor-bearing mice treated with vehicle and with compound 25.

Figure 45A:
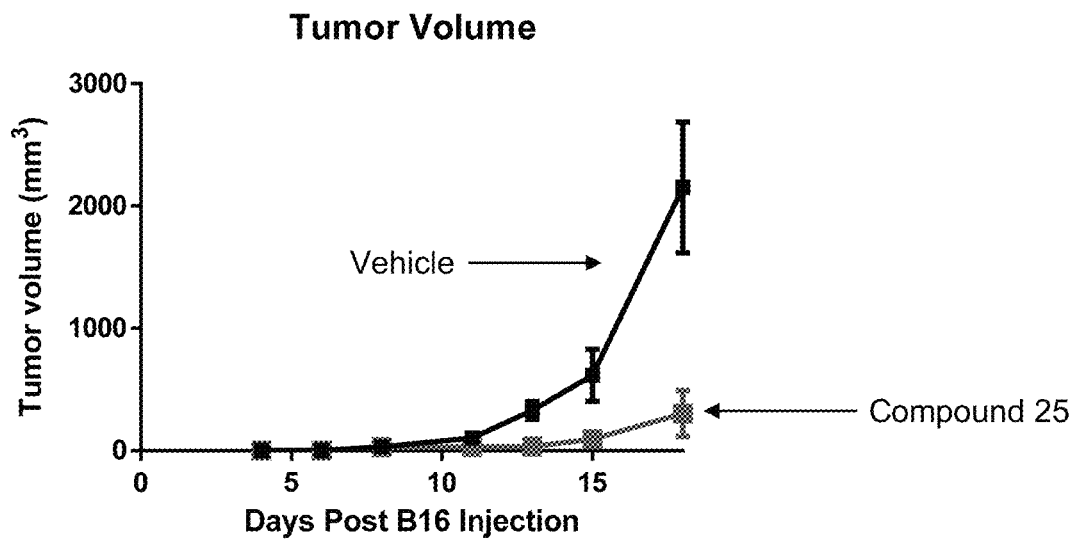

FIG. 45A is a line graph showing tumor growth curves of B16 tumor-bearing mice treated with vehicle and with compound 25.

Figure 45B:
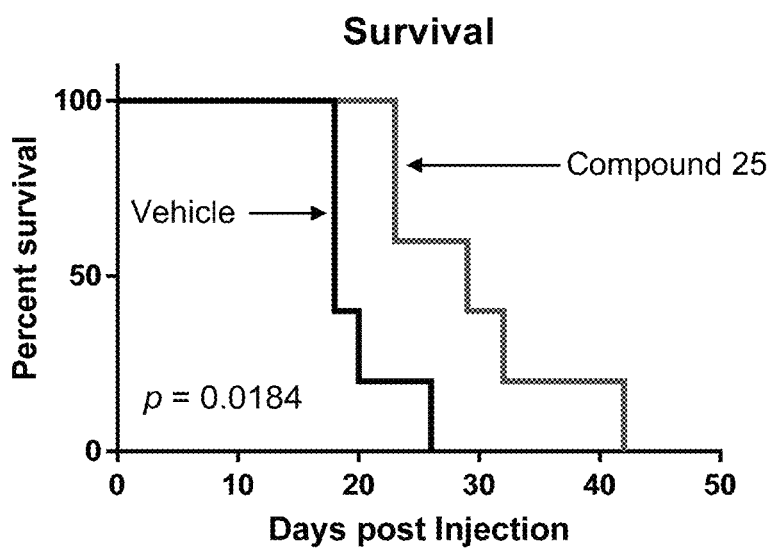

FIG. 45B is a line graph showing survival curves of B16 tumor-bearing mice treated with vehicle and with compound 25.

Figure 46A:
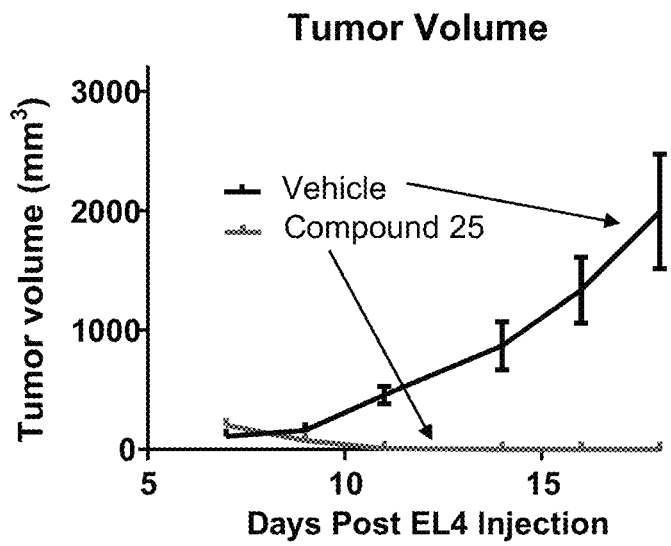

FIG. 46A is a line graph showing tumor growth curves of EL4 tumor-bearing mice treated with vehicle and with compound 25.

Figure 46B:
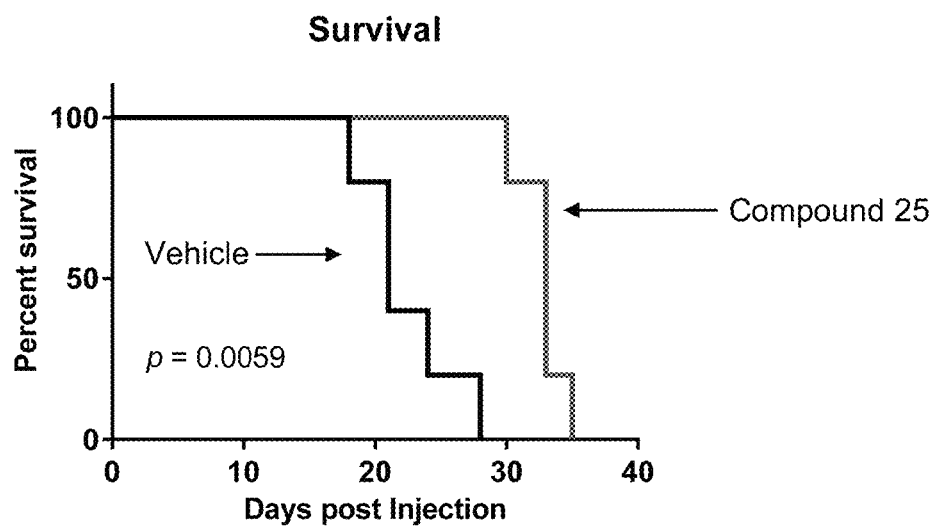

FIG. 46B is a line graph showing survival curves of EL4 tumor-bearing mice treated with vehicle and with compound 25.

Figure 47A:
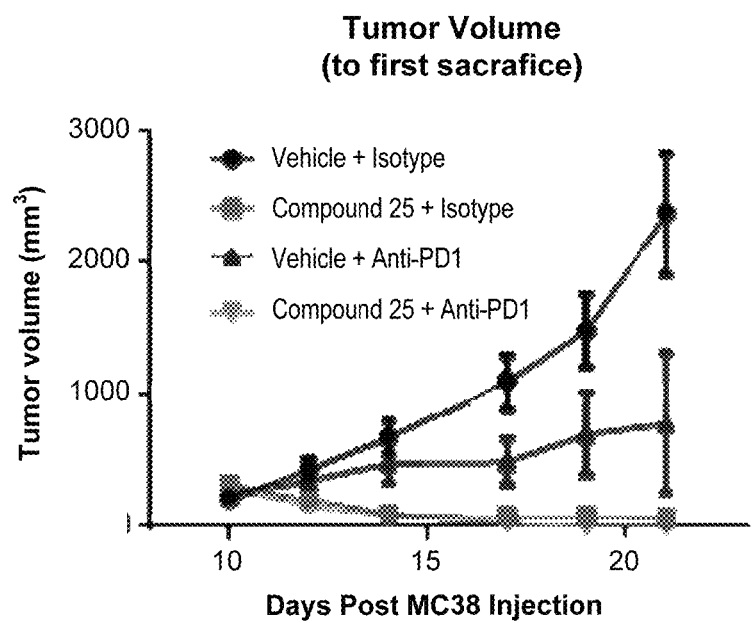

FIG. 47A is a line graph showing tumor growth of MC38 bearing C57BL/6 mice treated with vehicle, anti-PD-1, compound 25, or combination of compound 25 and anti-PD-1, beginning on day 10 after tumor inoculation.

Figure 47B:
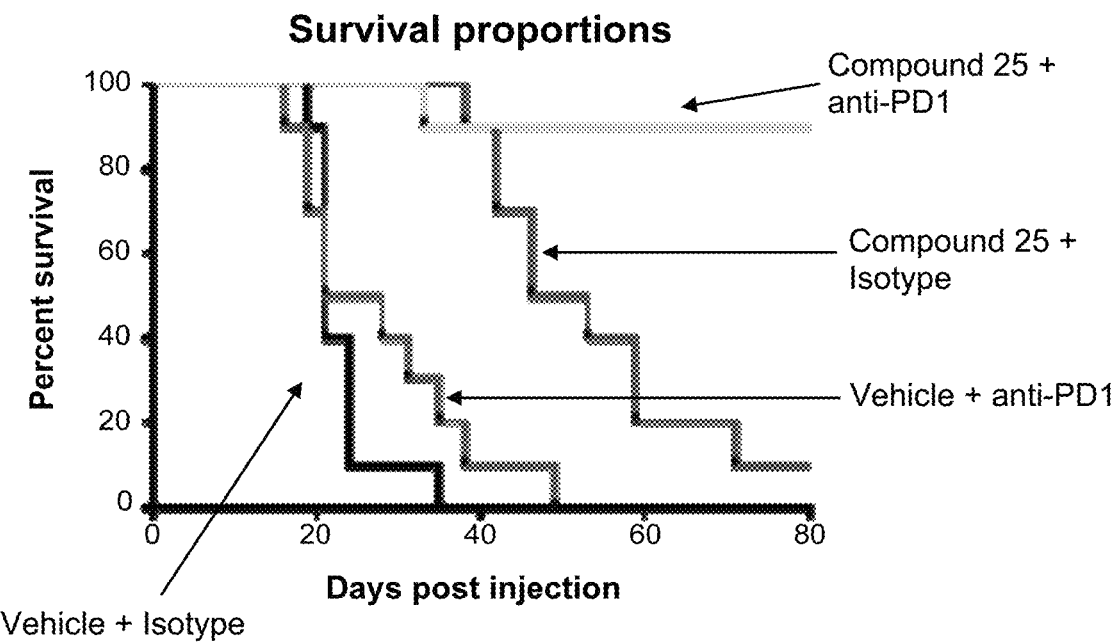

FIG. 47B is a line graph showing survival of MC38 bearing C57BL/6 mice treated with vehicle, anti-PD-1, compound 25, or combination of compound 25 and anti-PD-1, beginning on day 10 after tumor inoculation.

Figure 47C:
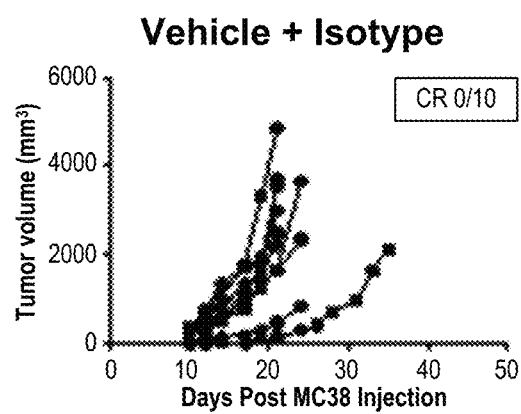

FIG. 47C is a line graph showing tumor cell growth of MC38 bearing C57BL/6 mice treated with vehicle.

Figure 47D:
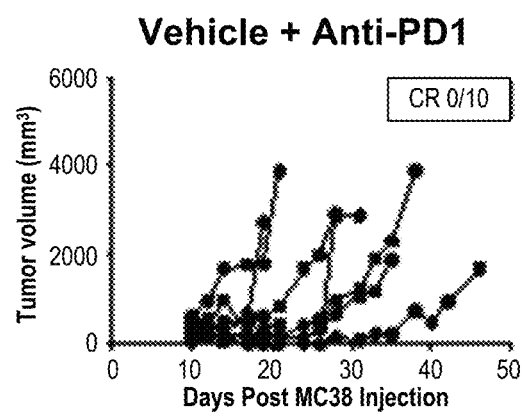

FIG. 47D is a line graph showing tumor cell growth of MC38 bearing C57BL/6 mice treated with anti-PD-1.

Figure 47E:
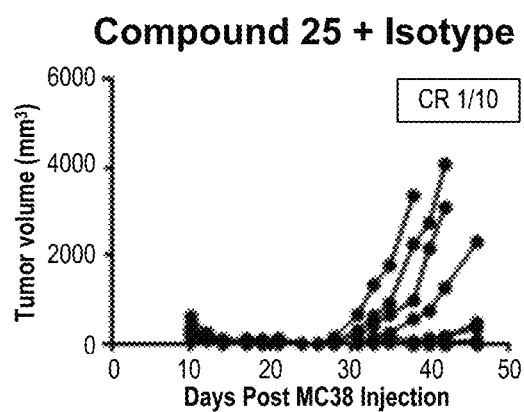

FIG. 47E is a line graph showing tumor cell growth of MC38 bearing C57BL/6 mice treated with compound 25.

Figure 47F:
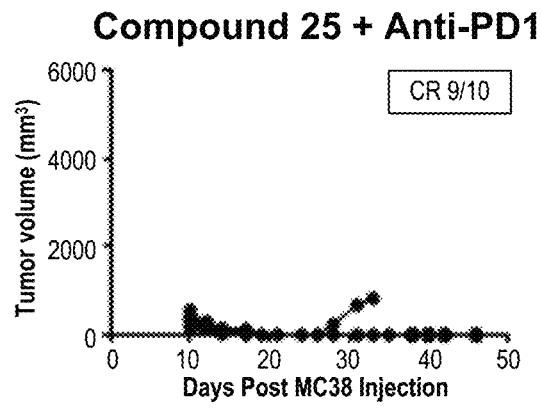

FIG. 47F is a line graph showing tumor cell growth of MC38 bearing C57BL/6 mice treated with combination of compound 25 and anti-PD-1 beginning on day 10 after tumor inoculation.

Figure 48A:
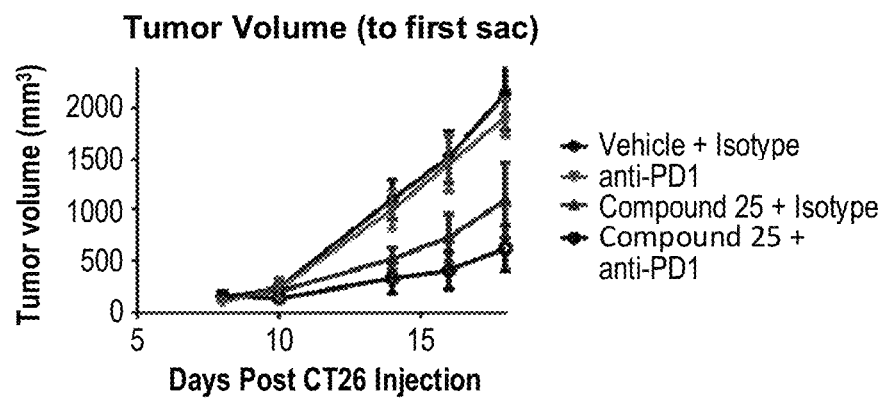

FIG. 48A is a line graph showing tumor growth of CT26 bearing BALB/c mice treated with vehicle, anti-PD-1, compound 25, or combination of compound 25 and anti-PD-1, beginning on day 10 after tumor inoculation.

Figure 48B:
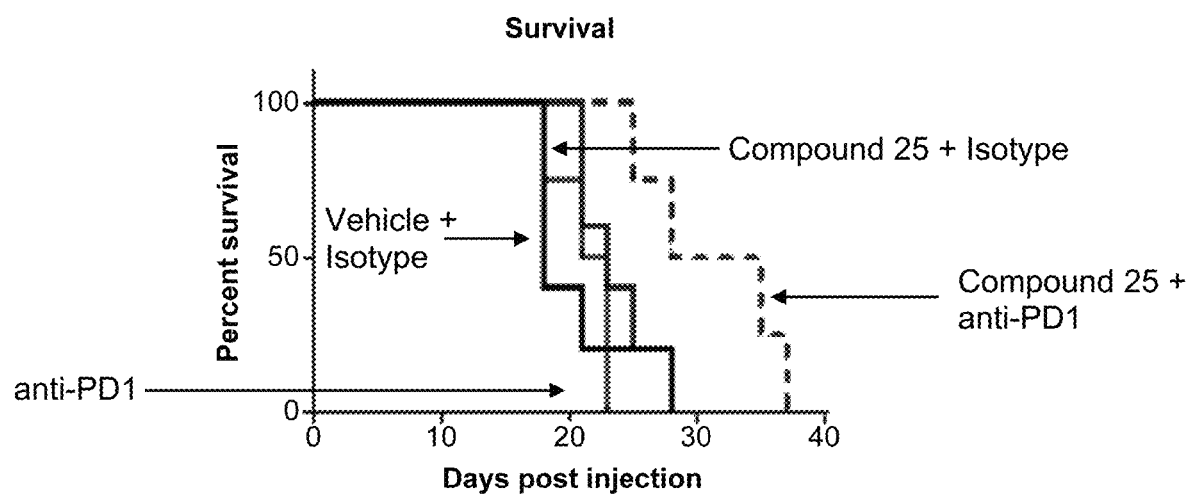

FIG. 48B is a line graph showing survival of CT26 bearing BALB/c mice treated with vehicle, anti-PD-1, compound 25, or combination of compound 25 and anti-PD-1, beginning on day 10 after tumor inoculation.

Figure 48C:
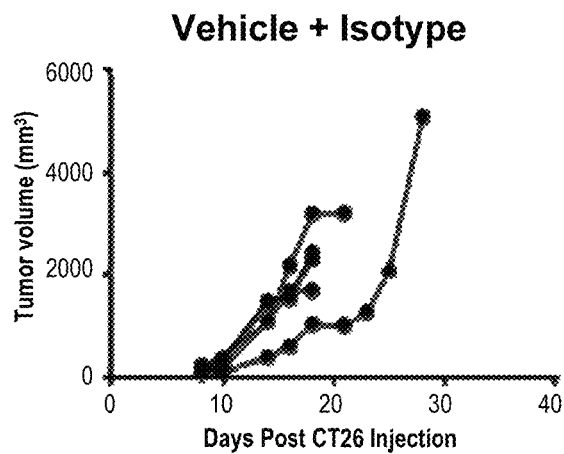

FIG. 48C is a line graph showing tumor growth of CT26 bearing BALB/c mice treated with vehicle.

Figure 48D:
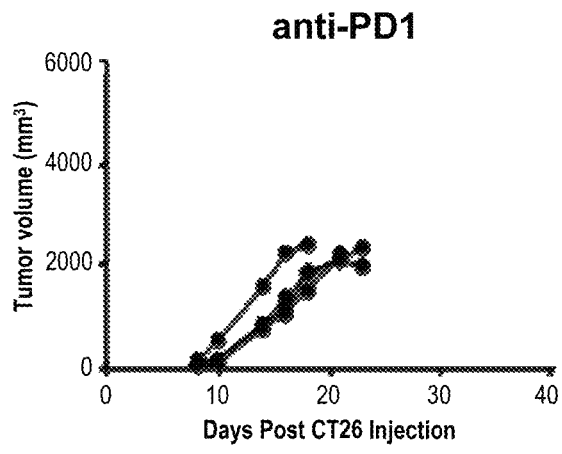

FIG. 48D is a line graph showing tumor growth of CT26 bearing BALB/c mice treated with anti-PD-1.

Figure 48E:
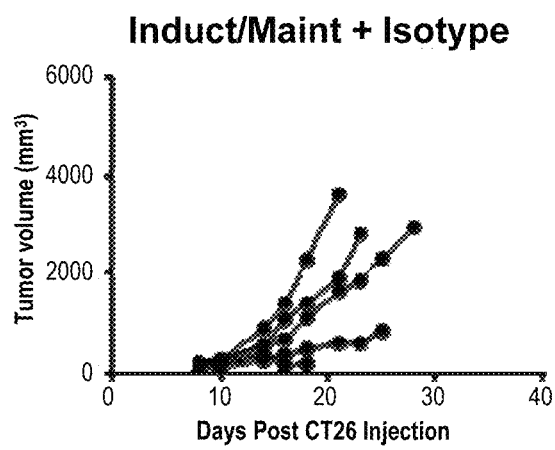

FIG. 48E is a line graph showing tumor growth of CT26 bearing BALB/c mice treated with compound 25.

Figure 48F:
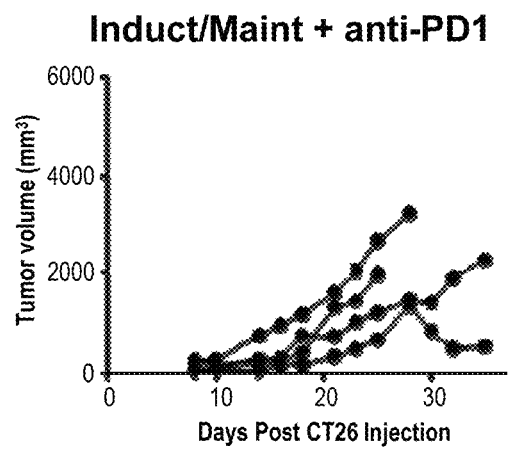

FIG. 48F is a line graph showing tumor growth of CT26 bearing BALB/c mice treated with combination of compound 25 and anti-PD-1, beginning on day 10 after tumor inoculation.

Figure 49A:
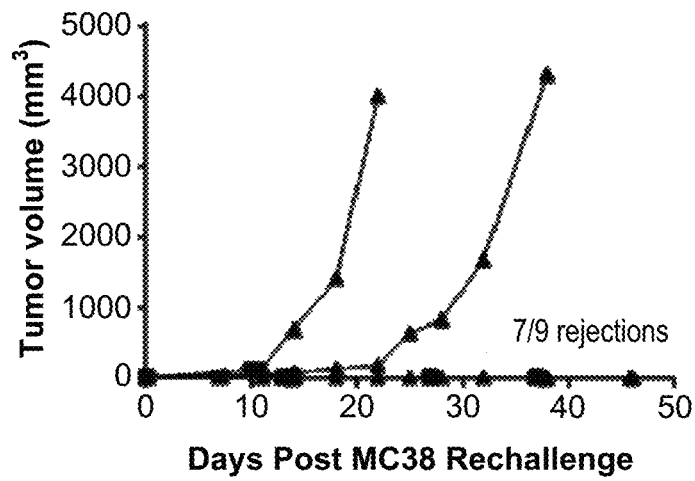

FIG. 49A is a line graph showing tumor growth of MC38 rechallenged mice.

Figure 49B:
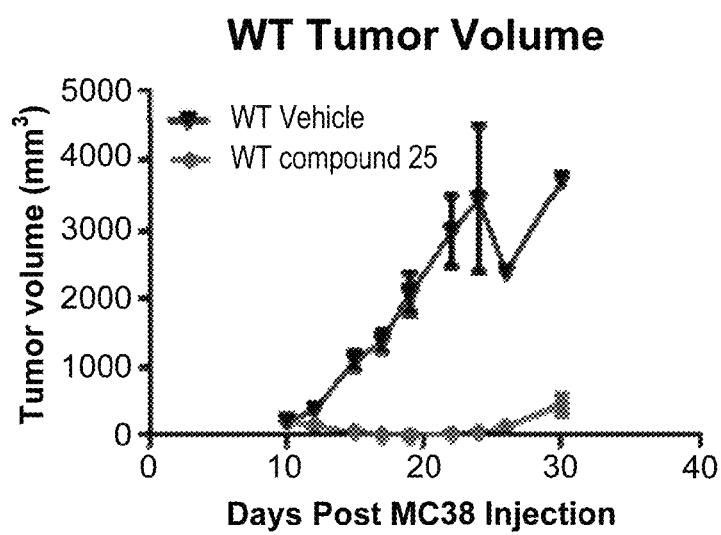

FIG. 49B is a line graph showing tumor growth of MC38-bearing C57BL/6 wild type.

Figure 49C:
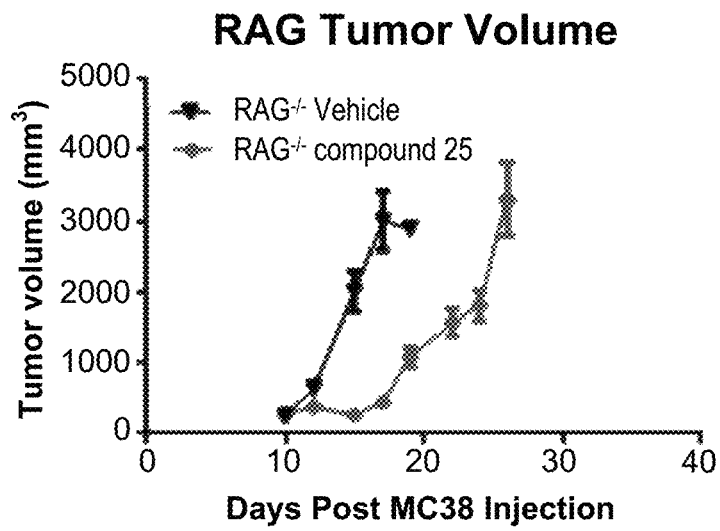

FIG. 49C is a line graph showing tumor growth of MC38-bearing C57BL/6 RAG$^{-/-}$ mice treated with compound 25 for 14 days.

Figure 49D:
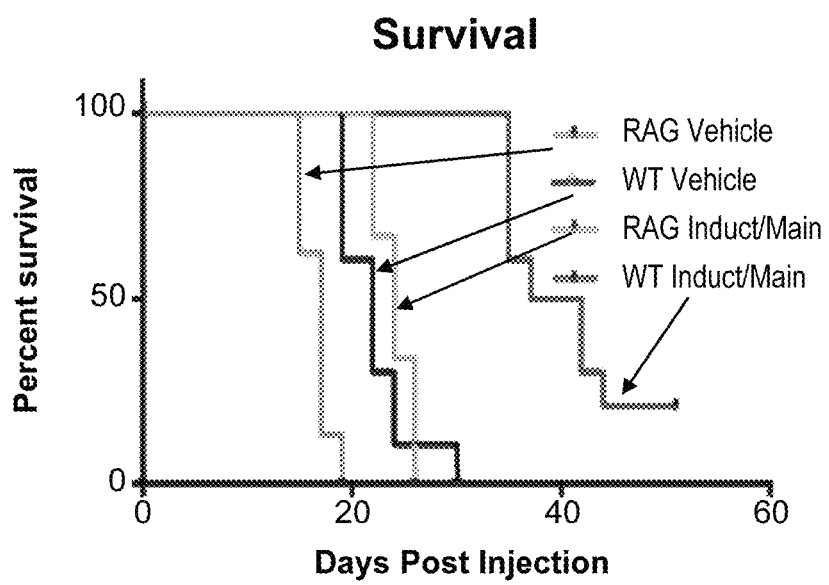

FIG. 49D is a line graph showing survival of MC38-bearing C57BL/6 wild type and RAG−/− mice treated with compound 25 for 14 days.

Figure 50A:
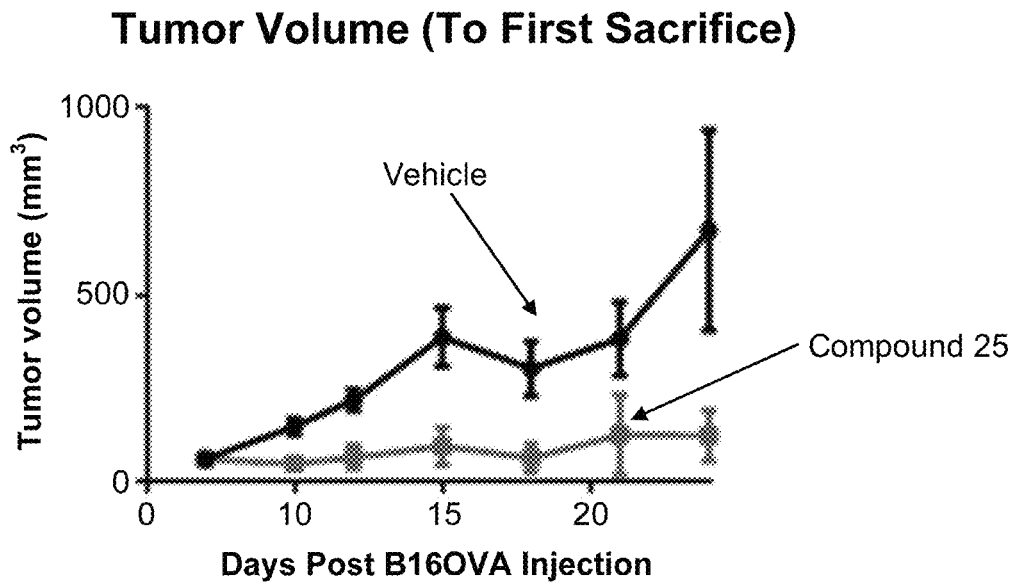

FIG. 50A is a line graph showing tumor growth of B16OVA-bearing C57BL/6 mice treated with compound 25 (1 mg/kg) or vehicle on days 7-9 after tumor inoculation. The mice received 1.5×10$^6$ activated OT1 T cells on day 10.

Figure 50B:
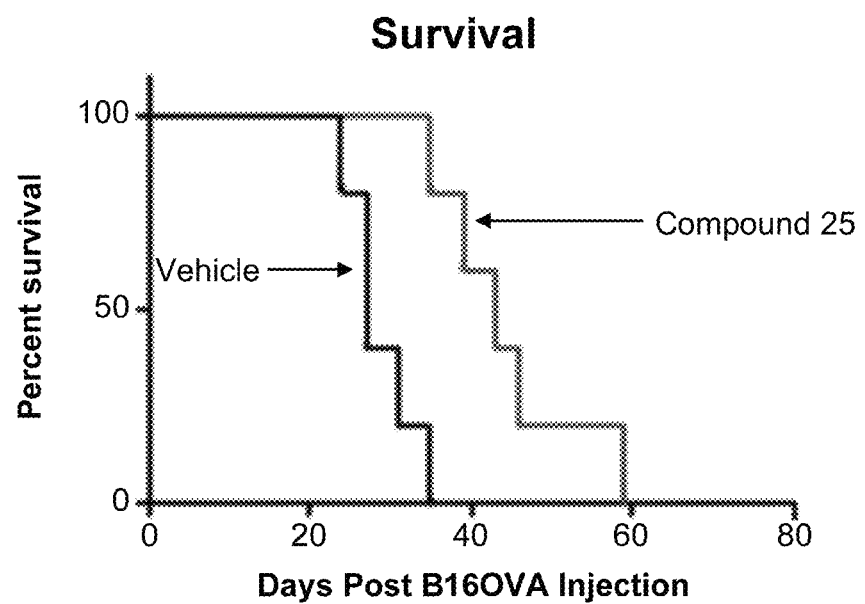

FIG. 50B is a line graph showing survival of B16OVA-bearing C57BL/6 mice treated with compound 25 (1 mg/kg)

or vehicle on days 7-9 after tumor inoculation. The mice received 1.5×10⁶ activated OT1 T cells on day 10.

Figure 50C:
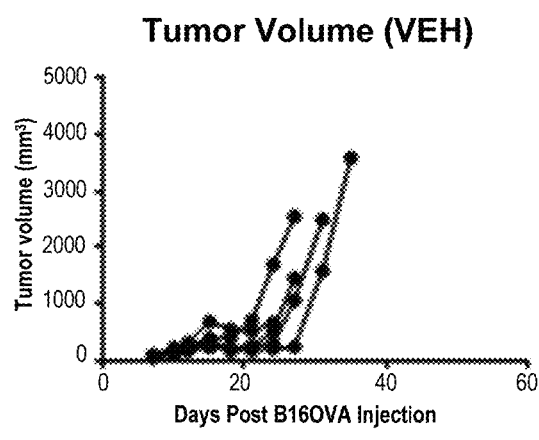

FIG. 50C is a line graph showing tumor growth of B16OVA-bearing C57BL/6 mice treated with vehicle on days 7-9 after tumor inoculation. The mice received 1.5×10⁶ activated OT1 T cells on day 10.

Figure 50D:
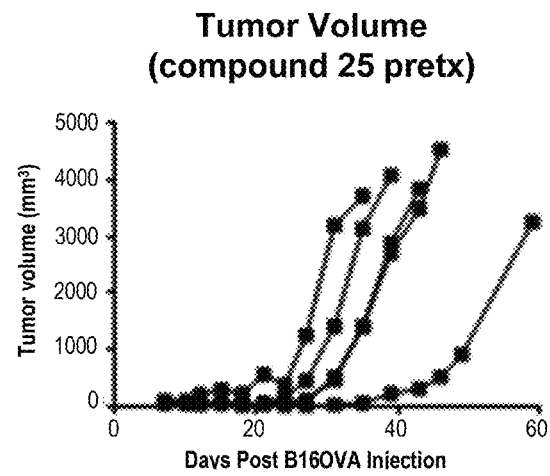

FIG. 50D is a line graph showing tumor growth of B16OVA-bearing C57BL/6 mice treated with compound 25 (1 mg/kg) on days 7-9 after tumor inoculation. The mice received 1.5×10⁶ activated OT1 T cells on day 10.

Figure 51A:
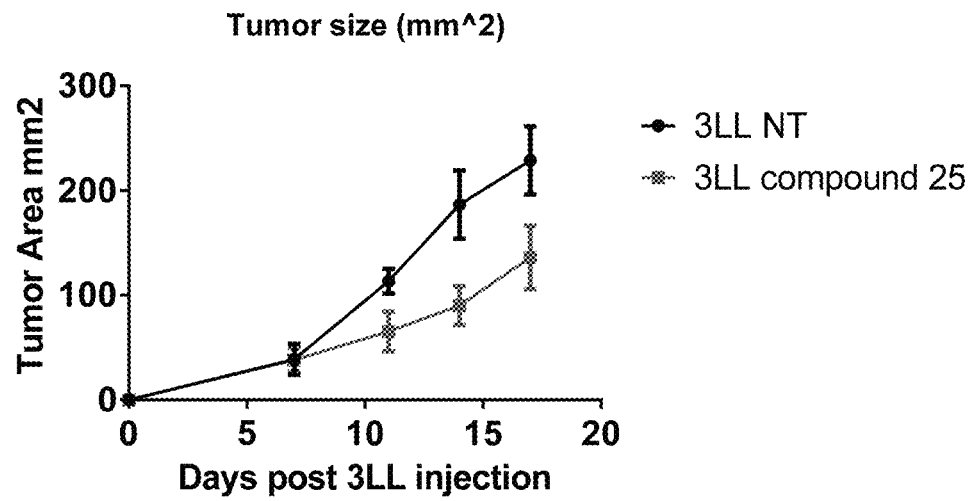

FIG. 51A is a line graph showing the tumor size of 3LL tumor-bearing mice treated with compound 25.

Figure 51B:
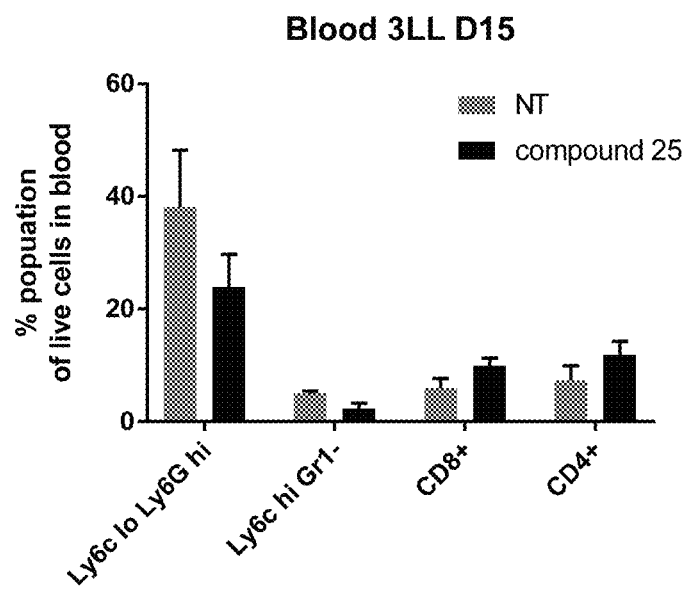

FIG. 51B is a bar graph showing the live cell percentages of Ly6c lo Ly6g hi, Ly6c hi Gr1, CD8+, and CD4+ of cells from blood in 3LL tumor bearing mice with no treatment (NT) and with compound 25.

FIG. 51C is a graph showing the ratio of CD8 cells to MDSCs+ and TANs in blood in 3LL tumor bearing mice with no treatment (NT) and with compound 25.

FIG. 51D is two graphs showing the ratio of CD8 cells to MDSCs+ and TANs in TIL in 3LL tumor bearing mice with no treatment (NT) and with compound 25.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

The presently disclosed subject matter demonstrates that certain conditions, diseases, and/or disorders involve metabolically reprogrammed cells whose activation, function, growth, proliferation, and/or survival in an abnormal, harmful, and/or unhealthy state depend on increased activity of at least one, at least two, or at least three metabolic pathways selected from the group consisting of glutamine metabolism, glycolysis, and fatty acid synthesis. It should be appreciated that the abnormal, harmful, and/or unhealthy state of the cell refers to its effect on or relative to the subject whose cells are affected by the condition, disease, or disorder rather than on or relative to the cell itself which exhibits an increased ability to thrive in the abnormal, harmful, and/or unhealthy state in a manner that is believed to be proportionate to the increase in the activity of at least one, at least two, or at least three metabolic pathways (e.g., glutamine metabolism, glycolysis, and/or fatty acid synthesis).

The presently disclosed subject matter have demonstrated that certain of such conditions, diseases, and/or disorders, referred to herein as "metabolic reprogramming disorders," are amenable to treatment using at least one, at least two, or at least three metabolic reprogramming agents that decrease activity of at least one, at least two, or at least three metabolic pathways selected from the group consisting of glutamine metabolism, glycolysis, and fatty acid synthesis. In some instances, the metabolic reprogramming disorders comprise conditions, diseases, or disorders that involve aberrant and/or excessive glutamine metabolism, aberrant and/or excessive glycolysis, or aberrant and/or excessive fatty acid synthesis.

As used herein, the term "excessive glutamine metabolism" means an increase in the amount of glutamine metabolic activity in a subject with a condition, disease, or disorder (e.g., a metabolic reprogramming disorder) as compared to the amount of glutamine metabolic activity in a subject without a similar disease or condition, such as an increase of approximately 100%, 100%, 200%, 300%, 400%, 500%, 600%, 700%, 800%, 900%, 1000%, or more. As used herein, the term "aberrant glutamine metabolism" means a change in the biological activity of glutamine in a subject with a condition, disease or disorder (e.g., a metabolic reprogramming disorder) as compared to the glutamine activity in a subject without a similar condition, disease, or disorder, such as increased utilization of glutamine in the growth and/or proliferation of malignant, neoplastic, or other pathologic cellular processes (e.g., immune disorders, neurodegenerative disorders, inflammatory disorders, etc.).

As used herein, the term "excessive glycolysis metabolism" means an increase in the amount of glycolytic metabolic activity in a subject with a condition, disease, or disorder (e.g., a metabolic reprogramming disorder) as compared to the amount of glycolytic metabolic activity in a subject without a similar disease or condition, such as an increase of approximately 100%, 100%, 200%, 300%, 400%, 500%, 600%, 700%, 800%, 900%, 1000%, or more. As used herein, the term "aberrant glycolytic metabolism" means a change in the biological activity of glycolysis in a subject with a condition, disease or disorder (e.g., a metabolic reprogramming disorder) as compared to the glycolytic activity in a subject without a similar condition, disease, or disorder, such as increased utilization of glucose in the growth and/or proliferation of malignant, neoplastic, or other pathologic cellular processes (e.g., immune disorders, neurodegenerative disorders, inflammatory disorders, etc.).

As used herein, the term "excessive fatty acid synthesis" means an increase in the amount of fatty acid synthesis in a subject with a condition, disease, or disorder (e.g., a metabolic reprogramming disorder) as compared to the amount of fatty acid synthesis in a subject without a similar condition, disease, or disorder, such as an increase of approximately 100%, 100%, 200%, 300%, 400%, 500%, 600%, 700%, 800%, 900%, 1000%, or more. As used herein, the term "aberrant fatty acid synthesis" means a change in the biological activity of fatty acid synthesis in a subject with a condition, disease or disorder (e.g., a metabolic reprogramming disorder) as compared to the fatty acid synthesis in a subject without a similar condition, disease, or disorder, such as increased utilization of fatty acids in the growth and/or proliferation of malignant, neoplastic, or other pathologic cellular processes (e.g., immune disorders, neurodegenerative disorders, inflammatory disorders, etc.).

As used herein, a "metabolically reprogrammed" cell refers to a cell in which the activity of at least one, at least two, or at least three metabolic pathways (e.g., glutamine metabolism, glycolysis, and fatty acid synthesis) has increased in response to the cells energetic and biosynthetic demands placed on the cell in order for the cell to become activated, function, grow, proliferate, and/or survive in the abnormal, harmful, and/or unhealthy state. As used herein, a "metabolic reprogramming agent" refers to an agent that is capable of reversing the metabolic reprogramming of a cell from a cell whose activation function, growth, proliferation, and/or survival in an abnormal, harmful, and/or unhealthy state depends on increased activity of at least one, at least two, or at least three metabolic pathways (e.g., glutamine metabolism, glycolysis, and fatty acid synthesis) to a cell that has a decreased capacity or has lost its ability to thrive (e.g., activate, function, grow, proliferate, and/or survive) in the abnormal, harmful and/or unhealthy state. In some contexts, a "metabolic reprogramming agent" inhibits at least one of, at least two of, or all of aberrant and/or excessive glutamine metabolism, aberrant and/or excessive glycolysis, and aberrant and/or excessive fatty acid synthesis.

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Methods of Treatment Using Metabolic Reprogramming Agents

In an aspect, the presently disclosed subject matter provides a method for treating a subject having a condition, disease, or disorder that involves metabolically reprogrammed cells whose activation, function, growth, proliferation, and/or survival depends on increased activity of at least one metabolic pathway selected from the group consisting of glutamine metabolism, glycolysis, and fatty acid synthesis, the method comprising administering to the subject at least one metabolic reprogramming agent that decreases activity of at least one metabolic pathway selected from the group consisting of glutamine metabolism, glycolysis, and fatty acid synthesis in an amount effective to treat the condition, disease, or disorder.

In some aspects, the presently disclosed subject matter provides a method for treating a subject having a condition, disease, or disorder that involves at least one of aberrant and/or excessive glutamine metabolism, aberrant and/or excessive glycolysis, or aberrant and/or excessive fatty acid synthesis, the method comprising administering to the subject at least one metabolic reprogramming agent that decreases activity of at least one metabolic pathway selected from the group consisting of glutamine metabolism, glycolysis, and fatty acid synthesis in an amount effective to treat the condition, disease, or disorder.

In general, the presently disclosed methods result in a decrease in the severity of a condition, disease, or disorder (e.g., a metabolic reprogramming disorder) in a subject. The term "decrease" is meant to inhibit, suppress, attenuate, diminish, arrest, or stabilize a symptom of the condition, disease, or disorder. As used herein, the terms "treat," "treating," "treatment," and the like refer to reducing or ameliorating a disease or condition, and/or symptoms associated therewith. It will be appreciated that, although not precluded, treating a disease or condition does not require that the disorder, condition or symptoms associated therewith be completely eliminated.

In some embodiments, the method comprises administering to the subject at least two metabolic reprogramming agents that decrease the activity of at least two metabolic pathways selected from the group consisting of glutamine metabolism, glycolysis, and fatty acid synthesis in an amount effective to treat the condition, disease, or disorder. In other embodiments, the method comprises administering to the subject at least three metabolic reprogramming agents that each decrease the activity of a different metabolic pathway selected from the group consisting of glutamine metabolism, glycolysis, and fatty acid synthesis in an amount effective to treat the condition, disease, or disorder.

The terms "subject" and "patient" are used interchangeably herein. The subject treated by the presently disclosed methods, uses, metabolic reprogramming agents and compositions comprising those agents in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease.

A. Cancer

Aspects of the invention involve the use of at least one, at least two, or at least three metabolic reprogramming agents, alone, or optionally together in combination with a chemotherapeutic agent, an immunotherapeutic agent, and/or a radiotherapeutic agent, for the treatment of a cancer. Accordingly, in some embodiments, the condition, disease, or disorder is a cancer. In such embodiments, the metabolically reprogrammed cells comprise malignant or cancerous cells. Examples of malignant or cancer cells whose activation, function, growth, proliferation, and/or survival in an abnormal, harmful, or unhealthy state depends on increased metabolic activity of at least one, at least two, or at least three metabolic pathways selected from the group consisting of glutamine metabolism, glycolysis and fatty acid synthesis include, but are not limited to, cMyc-dependent cancer cells, glutamine-dependent cancer cells, and combinations thereof. As used herein, a "glutamine-dependent cancer cell" is a cancer cell in which glutamine is an important fuel source for cellular energy in the cancer cell (e.g., hematopoietic tumors, hepatomas, Ehrlich carcinoma (see Huber et al., "Uptake of glutamine antimetabolites 6-diazo-5-oxo-L-norleucine (DON) and acivicin in sensitive and resistant tumor cell lines." *Int. J. Cancer.* 1988; 41:752-755)). As used herein, cMyc-dependent cancer cells" refers to cancer cells exhibiting activation, overexpression and/or amplification of c-Myc. In some contexts, a "Myc-dependent cancer" is a cancer in which c-Myc plays a role in increased glutamine metabolism in the cancer cells, i.e., cMyc-dependent glutamine addicted cancer cells. Examples of Myc-dependent cancers include, without limitation, lymphoma, neuroblastoma, and small cell lung cancer.

Aspects of the presently disclosed subject matter further involve the use of at least one metabolic reprogramming agent (e.g., a metabolic reprogramming agent that decreases glutamine metabolism) as a cancer maintenance therapy. As used herein, "cancer maintenance therapy" refers to a therapy administered to a cancer patient who is in cancer remission.

Accordingly, in one aspect, the presently disclosed subject matter provides a method of preventing a relapse or reducing the incidence of relapse of a cancer subject in remission, the method comprising administering to the subject a therapeutically effective amount of a metabolic reprogramming agent that decreases glutamine metabolism. In some embodiments, at least one metabolic reprogramming agent is a compound having any one of formula (I), formula (IIA), formula (IIB), or formula (III), below. As used herein, "remission" includes partial and complete remission and refers to a decrease in or disappearance of signs and symptoms of cancer. "Partial remission" means that the cancer responded to treatment with the primary therapy, but at least a portion of the tumor and/or at least a portion of the cancerous cells are still present in the subject, for example, at least 1%, 5%, 10%, 15%, 20%, 25%, 30%, 35%, 40%, 45%, or 49% of a measurable tumor and/or measurable cancerous cells are still present in the subject post-therapy. "Complete remission" means that the subject shows no signs or symptoms of cancer, for example, after a healthcare provider has used the most accurate and up-to-date tests available to detect the cancer and is unable to detect any signs or symptoms of cancer. It is to be understood that cancerous cells might still exist in a subject in complete remission at levels that are undetectable.

In some embodiments, the metabolic reprogramming agent is administered to the subject post transplant. As used herein, "post transplant" refers to a subject that has recently received a cell, tissue, or organ transplantation, including for example, subjects receiving immunosuppressive agents to prevent, or reduce the risk and/or severity of, a transplant rejection. In some embodiments, the metabolic reprogramming agent is administered to the subject post chemotherapy. In some embodiments, the metabolic reprogramming agent is administered to the subject post immunotherapy. In some embodiments, the metabolic reprogramming agent is administered to the subject post photodynamic therapy. In some embodiments, the metabolic reprogramming agent is administered to the subject post proton therapy. In some embodiments, the metabolic reprogramming agent is administered to the subject post radiotherapy. In some embodiments, the metabolic reprogramming agent is administered to the subject post surgery; and combinations thereof. In some embodiments, the metabolic reprogramming agent is administered to the subject at two or more of post transplant, post chemotherapy, post immunotherapy, post photodynamic therapy, post proton therapy, post radiotherapy, post surgery, and combinations thereof.

As used herein, a "cancer" in a subject refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells, for example, leukemic cells. A "tumor," as used herein, refers to all neoplastic cell growth and proliferation, whether malignant or benign, and all precancerous and cancerous cells and tissues. A "solid tumor", as used herein, is an abnormal mass of tissue that generally does not contain cysts or liquid areas. A solid tumor may be in the brain, colon, breasts, prostate, liver, kidneys, lungs, esophagus, head and neck, ovaries, cervix, stomach, colon, rectum, bladder, uterus, testes, and pancreas, as non-limiting examples. In some embodiments, the solid tumor regresses or its growth is slowed or arrested after the solid tumor is treated with the presently disclosed methods. In other embodiments, the solid tumor is malignant. In some embodiments, the cancer comprises Stage 0 cancer. In some embodiments, the cancer comprises Stage I cancer. In some embodiments, the cancer comprises Stage II cancer. In some embodiments, the cancer comprises Stage III cancer. In some embodiments, the cancer comprises Stage IV cancer. In some embodiments, the cancer is refractory and/or metastatic. For example, the cancer may be refractory to treatment with radiotherapy, chemotherapy or monotreatment with immunotherapy.

In particular embodiments, the cancer is a cancer of the central nervous system (CNS cancer). It is believed that certain of the presently disclosed metabolic reprogramming agents and compositions are particularly useful in the treatment of CNS cancers and cancers of CNS origin. In particular, the data described in FIG. 22A, FIG. 22B, FIG. 22C, FIG. 29A, FIG. 29B, FIG. 29C and FIG. 30 unexpectedly demonstrate that certain metabolic reprogramming agents (e.g., prodrugs of glutamine analogs, e.g., DON prodrugs, e.g., a compound having any one of formula (I), formula (IIA), formula (IIB), or formula (III), below.) effectively target and deliver DON to the brain, for example, achieving as much as a 10-fold enhanced CSF to plasma ratio at 30 minute post dosing. Accordingly, certain of the presently disclosed metabolic reprogramming agents are contemplated for use as cancer therapy (e.g., maintenance therapy), immunotherapy, and an enhancement to immunotherapy, for the treatment of CNS cancers and cancers of CNS origin.

Exemplary CNS cancers treatable with the presently disclosed methods, compositions and agents include, without limitation, gliomas, astrocytomas, oligodendrogliomas, ependymoas, mixed gliomas (e.g., oligoastrocytomas), meningiomas (e.g., atypical, invasive, anaplastic, etc.), medulloblastomas, gangliogliomas, schwannomas (neuroliemmomas), craniopharyngiomas, chordomas, non-Hodgkin lymphoma of CNS origin, and, pituitary tumors. In particular embodiments, the CNS cancer comprises glioblastoma multiform (GBM).

In particular embodiments, the cancer is a cancer that is associated with transplant and/or immunosuppression. It is well known that organ transplants (e.g., kidney, liver, heart, lung etc.) in the United States are at high risk of developing various types of cancer (see, e.g., Engels et al. 2011). In some instances, the cancer risk is elevated for infection-related cancer due to immunosuppression, for example, because of medications administered to suppress the immune system and prevent transplant rejection (e.g., organ). In some embodiments, the cancer associated with transplant and/or immunosuppression is related to an infectious agent. Examples of cancers associated with transplant and/or immunosuppression include, without limitation, anal cancer, Kaposi sarcoma, kidney cancer, liver cancer, lung cancer, melanoma, non-Hodgkin's lymphoma, and thyroid cancer. In particular embodiments, the subject is a child or elderly adult transplant recipient (e.g., liver, heart, kidney, etc.) who may or may not be infected with Epstein-Barr virus. In particular embodiments, the cancer is a cancer that is refractory to chemotherapy. In particular embodiments, the cancer is a cancer that is refractory to photodynamic therapy. In particular embodiments, the cancer is a cancer that is refractory to proton therapy.

In particular embodiments, the cancer is a cancer that is refractory to radiotherapy.

In particular embodiments, the cancer is a cancer that is refractory to surgery.

Cancer as used herein includes newly diagnosed or recurrent and/or refractory cancers, including without limitation, acute lymphoblastic leukemia, acute myelogenous leukemia, advanced soft tissue sarcoma, brain cancer, metastatic or aggressive breast cancer, breast carcinoma, bronchogenic carcinoma choriocarcinoma, chronic myelocytic leukemia, colon carcinoma, colorectal carcinoma, Ewing's sarcoma, gastrointestinal tract carcinoma, glioma, glioblastoma multiforme, head and neck squamous cell carcinoma, hepatocellular carcinoma, Hodgkin's disease, intracranial ependymoblastoma, large bowel cancer, leukemia, liver cancer, lung carcinoma, Lewis lung carcinoma, lymphoma, malignant fibrous histiocytoma, a mammary tumor, melanoma, mesothelioma, neuroblastoma, osteosarcoma, ovarian cancer, pancreatic cancer, a pontine tumor, premenopausal breast cancer, prostate cancer, rhabdomyosarcoma, reticulum cell sarcoma, sarcoma, small cell lung cancer, a solid tumor, stomach cancer, testicular cancer, and uterine carcinoma.

In particular embodiments, the cancer treated is a newly diagnosed, or recurrent, and/or refractory cancer selected from the group consisting of celnasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, brain cancer, oligodendroglioma, neuroblastoma, meningioma, spinal cord tumor, bone cancer, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, colorectal cancer, rectal cancer, esophagus cancer, gall bladder cancer, head cancer, eye cancer, neck cancer, kidney cancer, Wilms' tumor, liver cancer, Kaposi's sarcoma, prostate cancer, lung cancer, testicular cancer, Hodgkin's disease, non-Hodgkin's lymphoma, oral cancer, skin cancer, mesothelioma, multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer and tonsil cancer.

In some embodiments, the condition, disease, or disorder is lymphoma. Accordingly, in an aspect the presently disclosed subject matter provides a method for the treatment of lymphoma in a subject in need thereof, the method comprising administering to the subject at least one metabolic reprogramming agent that decreases glutamine metabolism in an amount effective to treat lymphoma in the subject.

In some embodiments, the condition, disease, or disorder is melanoma. Accordingly, in an aspect the presently disclosed subject matter provides a method for the treatment of melanoma in a subject in need thereof, the method comprising administering to the subject at least one metabolic reprogramming agent that decreases glutamine metabolism in an amount effective to treat melanoma in the subject.

In some embodiments, the methods include administering to the subject an effective amount of radiotherapy. In some embodiments, the methods include administering of the subject an effective amount of immunotherapy (e.g., a second immunotherapy). In some embodiments, the methods include administering to the subject an effective amount of photodynamic therapy. In some embodiments, the methods include administering to the subject an effective amount of proton therapy. In some embodiments, the methods include surgically resecting at least a portion of a tumor before, during, or after treatment with the at least one, at least two, or at least three metabolic reprogramming agents, and optionally at least one chemotherapeutic agent, immunotherapeutic agent, and/or radiotherapeutic agent.

In some embodiments, the condition, disease, or disorder is a newly diagnosed, or recurrent and/or refractory cancer selected from the group consisting of acute lymphoblastic leukemia, acute myelogenous leukemia, advanced soft tissue sarcoma, brain cancer, metastatic or aggressive breast cancer, breast carcinoma, bronchogenic carcinoma, choriocarcinoma, chronic myelocytic leukemia, colon carcinoma, colorectal carcinoma. Ewing's sarcoma, gastrointestinal tract carcinoma, glioma, glioblastoma multiforme, head and neck squamous cell carcinoma, hepatocellular carcinoma, Hodgkin's disease, intracranial ependymoblastoma, large bowel cancer, leukemia, liver cancer, lung carcinoma, Lewis lung carcinoma, lymphoma, malignant fibrous histiocytoma, a mammary tumor, melanoma, mesothelioma, neuroblastoma, osteosarcoma, ovarian cancer, pancreatic cancer, a pontine tumor, premenopausal breast cancer, prostate cancer, rhabdomyosarcoma, reticulum cell sarcoma, sarcoma, small cell lung cancer, a solid tumor, stomach cancer, testicular cancer, and uterine carcinoma.

In some embodiments, the cancer is not acute lymphoblastic leukemia. In some embodiments, the cancer is not acute myelogenous leukemia. In some embodiments, the cancer is not advanced soft tissue sarcoma. In some embodiments, the cancer is not brain cancer. In some embodiments, the cancer is not metastatic or aggressive breast cancer. In some embodiments, the cancer is not breast carcinoma. In some embodiments, the cancer is not bronchogenic carcinoma In some embodiments, the cancer is not choriocarcinoma. In some embodiments, the cancer is not chronic myelocytic leukemia. In some embodiments, the cancer is not colon carcinoma. In some embodiments, the cancer is not colorectal carcinoma. In some embodiments, the cancer is not Ewing's sarcoma. In some embodiments, the cancer is not gastrointestinal tract carcinoma. In some embodiments, the cancer is not glioma. In some embodiments, the cancer is not glioblastoma multiforme. In some embodiments, the cancer is not head and neck squamous cell carcinoma. In some embodiments, the cancer is not hepatocellular carcinoma. In some embodiments, the cancer is not Hodgkin's disease. In some embodiments, the cancer is not intracranial ependymoblastoma. In some embodiments, the cancer is not large bowel cancer. In some embodiments, the cancer is not leukemia. In some embodiments, the cancer is not liver cancer. In some embodiments, the cancer is not lung carcinoma. In some embodiments, the cancer is not Lewis lung carcinoma. In some embodiments, the cancer is not lymphoma. In some embodiments, the cancer is not malignant fibrous histiocytoma. In some embodiments, the cancer is not a mammary tumor. In some embodiments, the cancer is not melanoma. In some embodiments, the cancer is not mesothelioma. In some embodiments, the cancer is not neuroblastoma In some embodiments, the cancer is not osteosarcoma. In some embodiments, the cancer is not ovarian cancer. In some embodiments, the cancer is not pancreatic cancer. In some embodiments, the cancer is not a pontine tumor. In some embodiments, the cancer is not premenopausal breast cancer. In some embodiments, the cancer is not prostate cancer. In some embodiments, the cancer is not rhabdomyosarcoma. In some embodiments, the cancer is not reticulum cell sarcoma In some embodiments, the cancer is not sarcoma. In some embodiments, the cancer is not small cell lung cancer. In some embodiments, the cancer is not a solid tumor. In some embodiments, the cancer is not stomach cancer. In some embodiments, the cancer is not testicular cancer. In some embodiments, the cancer is not uterine carcinoma.

B. Immunotherapy

Aspects of the presently disclosed subject matter involve the use of at least one, at least two, or at least three metabolic reprogramming agents, alone, or optionally together in combination with an additional immunotherapy (e.g., checkpoint blockade, adoptive cellular therapy (ACT), vaccines (e.g., tumor vaccines), passive immunotherapy antibodies, for the treatment of cancer.

Accordingly, in one aspect, the presently disclosed subject matter provides a method for treating a cancer in a subject in need thereof, the method comprising: (a) administering a therapeutically effective amount of a first immunotherapy to the subject, wherein the first immunotherapy is a metabolic reprogramming agent; and (b) optionally administering a therapeutically effective amount of a second immunotherapy to the subject. In particular embodiments, the metabolic reprogramming agent is a glutamine antagonist. In particular embodiments, the metabolic reprogramming agent is a glutamine analog that interferes with a glutamine metabolic pathway. In particular embodiments, the metabolic reprogramming agent is selected from the group consisting of acivicin (L-(alpha S, 5S)-alpha-amino-3-chloro-4,5-dihydro-5-isoxazoleacetic acid), azaserine, and 6-diazo-5-oxo-norleucine (DON), and 5-diazo-4-oxo-L-norvaline (L-DONV). In particular embodiments, the metabolic reprogramming agent is a prodrug of a glutamine analog that interferes with a glutamine metabolic pathway. In particular embodiments, at least one metabolic reprogramming agent is a prodrug of acivicin, azaserine, DON, and L-DONV.

In some aspects, a prodrug of a glutamine antagonist, or a pharmaceutically acceptable salt or ester thereof has a structure of formula (I):

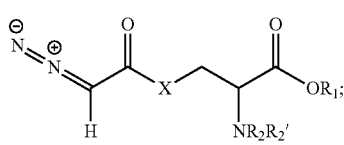

(I)

wherein: X is selected from the group consisting of a bond, —O—, and —(CH$_2$)$_n$—, wherein n is an integer selected from the group consisting of 1, 2, 3, 4, 5, 6, 7, and 8; R$_1$ is selected from the group consisting of H and a first prodrug-forming moiety capable of forming a salt or an ester; and R$_2$ is H or a second prodrug-forming moiety capable of forming an amide linkage, a carbamate linkage, a phosphoramidate linkage or a phosphorodiamidate linkage with the nitrogen adjacent to R$_2$; R$_2$' is selected from the group consisting of H, C$_1$-C$_6$ alkyl, substituted C$_1$-C$_6$ alkyl, or R$_2$ and R$_2$' together form a ring structure comprising —C(=O)-G-C(=O)—, wherein G is selected from the group consisting of C$_1$-C$_8$ alkylene, C$_1$-C$_8$ heteroalkylene, C$_5$-C$_8$ cycloalkylene, C$_6$-C$_{12}$ arvlene, C$_5$-C$_{14}$ heteroarylene, bivalent C$_4$-C$_{10}$ heterocycle, each of which can be optionally substituted; or R$_1$ and R$_2$' together form a 4- to 6-membered heterocylic ring comprising the oxygen atom adjacent to R$_1$ and the nitrogen atom adjacent to R$_2$'; provided that the compound has at least one prodrug-forming moiety selected from the group consisting of the first and the second prodrug-forming moieties.

As used herein, the term "amide linkage" comprises a structure represented by the formula:

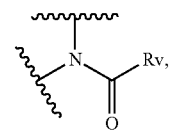

wherein R$_v$ is selected from the group consisting of alkyl, substituted alkyl, cycloalkyl, substituted cycloalkyl, aryl, substituted aryl, aralkyl, substituted aralkyl, heterocyclyl, substituted heterocyclyl, alkenyl, substituted alkenyl, cycloalkenyl, substituted cycloalkenyl, alkylamine, substituted alkylamine, heteroaryl, and substituted heteroaryl.

As used herein, the term "carbamate linkage" comprises a structure represented by the formula:

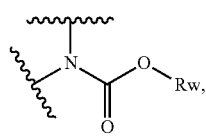

wherein R$_w$ is selected from the group consisting of alkyl, substituted alkyl, cycloalkyl, substituted cycloalkyl, aryl, substituted aryl, aralkyl, substituted aralkyl, heterocyclyl, substituted heterocyclyl, alkenyl, substituted alkenyl, cycloalkenyl, substituted cycloalkenyl, alkylamine, substituted alkylamine, heteroaryl, and substituted heteroaryl.

As used herein, the term "phosphoramidate linkage" comprises a structure represented by the formula:

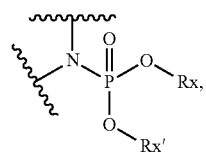

wherein R$_x$ and R$_x$' are each independently selected from the group consisting of alkyl, substituted alkyl, cycloalkyl, substituted cycloalkyl, aryl, substituted aryl, aralkyl, substituted aralkyl, heterocyclyl, substituted heterocyclyl, alkenyl, substituted alkenyl, cycloalkenyl, substituted cycloalkenyl, alkylamine, substituted alkylamine, heteroaryl, and substituted heteroaryl.

As used herein, the term "phosphorodiamidate linkage" comprises a structure represented by the formula:

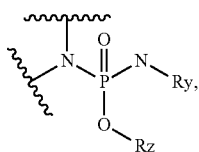

wherein $R_y$ and $R_z$ are each independently selected from the group consisting of H, alkyl, substituted alkyl, cycloalkyl, substituted cycloalkyl, heterocyclyl, substituted heterocyclyl, alkenyl, substituted alkenyl, cycloalkenyl, substituted cycloalkenyl, —$(CR_3R_4)_m$—Z, —$(CR_3R_4)_m$-Q-Z, aryl, substituted aryl, alkylamine, substituted alkylamine, heteroaryl, substituted heteroaryl, and

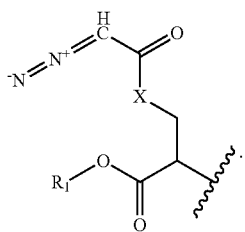

In some embodiments, X is —$CH_2$—, and n is 1.

In other embodiments, X is —O—. In some embodiments, the prodrug compound has both the first prodrug-forming moiety and the second prodrug-forming moiety. In some embodiments, the glutamine analog is a glutamine antagonist, i.e., the prodrug is a prodrug of a glutamine analog that antagonizes a glutamine pathway. Exemplary glutamine antagonists include, without limitation, 6-diazo-5-oxo-norleucine (DON), and aza-serine, and 5-diazo-4-oxo-L-norvaline (L-DONV).

In some embodiments, the presently disclosed subject matter provides a prodrug of DON. In some embodiments, the prodrug of DON has a structure of formula (I). In some embodiments, the presently disclosed subject matter provides a prodrug of L-DONV. In some embodiments, the prodrug of L-DONV has a structure of formula (I). In some embodiments, the presently disclosed subject matter provides a prodrug of azaserine. In some embodiments, the prodrug of azaserine has a structure of formula (I).

In some embodiments, $R_1$ of formula (I) comprises a residue $PRO_1$ of the prodrug-forming moiety, which, together with a basic moiety and the terminal hydroxyl group forms a salt.

In some embodiments, $R_1$ of formula (I) comprises a residue $PRO_1$ of the prodrug-forming moiety, which, together with an alkyl group and the oxygen of an adjoining hydroxyl group forms an ester.

In some embodiments. $R_1$ of formula (I) comprises a residue $PRO_1$ of the prodrug-forming moiety, which, together with an alkyl group and the nitrogen adjoining the $R_2'$ group, forms an azlactone or an oxazolidone.

In some embodiments, $R_1$ of formula (I) is selected from the group consisting of H, alkyl, substituted alkyl, cycloalkyl, substituted cycloalkyl, alkenyl, substituted alkenyl, alkynyl, substituted alkynyl, cycloalkenyl, substituted cycloalkenyl, tri(hydrocarbyl)ammonium, and tetra(hydrocarbyl)ammonium. Preferred alkyl group, cycloalkyl group, alkenyl group, alkynyl group, and cycloalkenyl group substituents include alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl.

In some embodiments, $R_1$ of formula (I) is not H. In some embodiments, $R_1$ of formula (I) is not H when $R_2$ and $R_2'$ are H. In some embodiments, $R_2$ and $R_2'$ of formula (I) are each H when and $R_1$ is not H.

In some embodiments, $R_1$ of formula (I) is selected from the group consisting of a $C_{1-6}$ straight-chain alkyl, a substituted $C_{1-6}$ straight-chain alkyl, a $C_{1-6}$ branched alkyl, a substituted $C_{1-6}$ branched alkyl, tri($C_1$-$C_8$-alkyl)ammonium, tetra($C_1$-$C_8$-alkyl)ammonium, triphenylammonium, tri(hydroxy-$C_1$-$C_8$-alkyl)ammonium, and tetra(hydroxy-$C_1$-$C_8$-alkyl)ammonium.

In some embodiments, $R_1$ of formula (I) is selected from the group consisting of methyl, ethyl, isopropyl, cyclopentyl, cyclohexyl, trimethylammonium, triethylammonium, tri(hydroxyethyl)ammonium, tripropylammonium, and tri(hydroxypropyl)ammonium. In some embodiments, $R_1$ of formula (I) is methyl. In some embodiments, $R_1$ of formula (I) is ethyl. In some embodiments, $R_1$ of formula (I) is isopropyl.

In some embodiments, $R_2$ of formula (I) comprises a residue $PRO_2$ of the second prodrug-forming moiety, which, together with a carbonyl, oxy carbonyl, or phosphonyl group and the nitrogen of the adjoining NH, forms an amide, a carbamate, phosphoramidate, or phosphorodiamidate linkage.

In some embodiments, $R_2$ of formula (I) comprises a moiety selected from the group consisting of an amino acid, an N-substituted amino acid, a peptide, a substituted peptide, a monocyclic ring, a substituted monocyclic ring, a bicyclic ring, a substituted bicyclic ring, a purine nucleoside, a substituted purine nucleoside, a pyrimidine nucleoside, and a substituted pyrimidine nucleoside.

In some embodiments, $R_2$ of formula (I) is selected from the group consisting of H, alkyl, —C(=O)—Ar, —C(=O)—Y—$(CR_3R_4)_m$—Ar, —C(=O)—Y—$(CR_3R_4)_m$—$NR_5R_6$, —P(=O)$(OR_7)_n(NHR_9)_o$, —C(=O)—Y—$(CR_3R_4)_m$—Ar—O—C(=O)—$R_8$, —C(=O)—Y—$(CR_3R_4)_m$—Ar—O—$R_8$, —C(=O)—O—$(CR_3R_4)_m$—O—C(O)—$R_{10}$, —C(=O)—O—$R_8$, —C(=O)—Y—$(CR_3R_4)_m$—Ar—O—C(=O)—Ar, and —C(=O)—Y—$(CR_3R_4)_m$—Ar—$NR_5R_6$; wherein: Y is —O— or a bond; m is an integer selected from the group consisting of 0, 1, 2, 3, 4, 5, 6, 7, and 8; each n and o is an integer from 0 to 2 provided that the sum of n and o is 2; $R_3$ and $R_4$ is independently H, $C_1$-$C_6$ alkyl or substituted $C_1$-$C_6$ alkyl, aryl or substituted aryl, —$(CR_3R_4)_m$—$NR_5R_6$, or

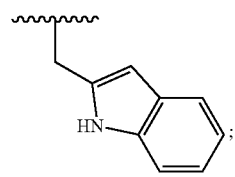 [SMILES: *Cc1cc2ccccc2[nH]1]

each $R_5$ and $R_6$ is independently H, alkyl, —C(=O)—$(CR_3R_4)_m$, —C(=O)—$(NR_5R_6)$, or —C(=O)—$(CR_3$ $R_4)_m$—$NR_5R_6$; each $R_7$ is independently selected from the group consisting of H, alkyl, substituted alkyl, cycloalkyl, substituted cycloalkyl, heterocyclyl, substituted heterocyclyl, alkenyl, substituted alkenyl, cycloalkenyl, substituted cycloalkenyl, —$(CR_3R_4)_m$—Z, —$(CR_3R_4)_m$-Q-Z, wherein Q is a monosaccharide, aryl, substituted aryl, heteroaryl, substituted heteroaryl, and wherein Z is

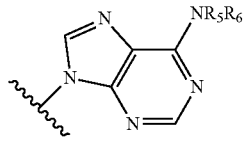

or wherein R7 together with the oxygen atom to which it is attached forms a purine or pyrimidine nucleoside; each $R_9$ is independently selected from the group consisting of H, alkyl, substituted alkyl, cycloalkyl, substituted cycloalkyl, heterocyclyl, substituted heterocyclyl, alkenyl, substituted alkenyl, cycloalkenyl, substituted cycloalkenyl, —$(CR_3R_4)_m$—Z, aryl, substituted aryl, heteroaryl, substituted heteroaryl, and

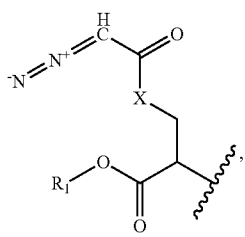

wherein $R_1$ and X are as defined above, provided that $R_1$ is not H; each $R_8$ is independently alkyl, substituted alkyl, cycloalkyl, substituted cycloalkyl, monosaccharide, acylated monosaccharide, aryl, substituted aryl, heteroaryl, substituted heteroaryl; each $R_{10}$ is independently alkyl, substituted alkyl, cycloalkyl, substituted cycloalkyl, monosaccharide, acylated monosaccharide, aryl, substituted aryl, heteroaryl, substituted heteroaryl; and Ar is aryl, substituted aryl, heteroaryl, or substituted heteroaryl. It should be appreciated that in addition to substitutions on the amino group of Z, one or more substitutions $R_3$, $R_4$, $R_5$, and/or $R_6$ can be made to the 5 or 6 membered rings of Z.

The disclosure also provides the following particular embodiments numbered Embodiments I-LXI.

Embodiment I

A method of treating cancer in a subject, the method comprising administering to the subject in need thereof a compound, or a pharmaceutically acceptable salt thereof, having formula (I):

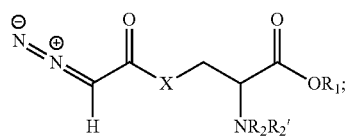

(I)

wherein:

X is selected from the group consisting of a bond, —O—, and —$(CH_2)_n$—, wherein n is an integer selected from the group consisting of 1, 2, 3, 4, 5, 6, 7, and 8;

$R_1$ is selected from the group consisting of $C_{1-6}$ alkyl and substituted $C_{1-6}$ alkyl;

$R_2$ is an amino acid, an N-substituted amino acid, or —C(=O)—O—$(CR_3R_4)_m$—O—C(=O)—$R_{10}$;

$R_2'$ is selected from the group consisting of H, $C_1$-$C_6$ alkyl, and substituted $C_1$-$C_6$ alkyl;

each $R_3$ and $R_4$ are independently H, $C_1$-$C_6$ alkyl, substituted $C_1$-$C_6$ alkyl, aryl, substituted aryl, —$(CR_3R_4)_m$—$NR_5R_6$, or

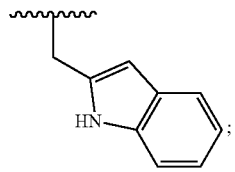 [SMILES: *Cc1cc2ccccc2[nH]1]

m is an integer selected from the group consisting of 1, 2, 3, 4, 5, 6, 7, and 8;

$R_5$ and $R_6$ are independently H or alkyl; and $R_{10}$ is selected from the group consisting of alkyl, substituted alkyl, cycloalkyl, substituted cycloalkyl, monosaccharide, acylated monosaccharide, aryl, substituted aryl, heteroaryl, and substituted heteroaryl.

Embodiment II

The method of Embodiment I, wherein X is —$CH_2$—.

Embodiment III

The method of Embodiment I, wherein X is —O—.

Embodiment IV

The method of Embodiment I, wherein $R_1$ is selected from the group consisting of methyl, ethyl, isopropyl, cyclopentyl, cyclohexyl, trimethylammonium, triethylammonium, tri(hydroxyethyl)ammonium, tripropylammonium, and tri(hydroxypropyl)ammonium.

Embodiment V

The method of Embodiment I, wherein $R_2$ is selected from the group consisting of —C(=O)—Y—$(CR_3R_4)_m$—$NR_5R_6$, and —C(=O)—O—$(CR_3R_4)_m$—O—C(=O)—$R_{10}$; wherein:

Y is —O— or a bond;

m is an integer selected from the group consisting of 1, 2, 3, 4, 5, 6, 7, and 8; and each $R_3$ and $R_4$ is independently H, $C_1$-$C_6$ alkyl or substituted $C_1$-$C_6$ alkyl, aryl or substituted aryl;

$R_{10}$ is selected from the group consisting of alkyl, substituted alkyl, cycloalkyl, substituted cycloalkyl, aryl, substituted aryl, heteroaryl, and substituted heteroaryl.

Embodiment VI

The method of Embodiment V, wherein:

Y is a bond;

m is 1;

$R_5$ and $R_6$ are each H.

Embodiment VII

The method of Embodiment 1, wherein $R_2$ is an amino acid.

Embodiment VIII

The method of Embodiment VII, wherein the amino acid is tryptophan.

Embodiment IX

The method of Embodiment I, wherein $R_2$ is a N-acyl amino acid.

Embodiment X

The method of Embodiment IX, wherein the amino acid is tryptophan.

Embodiment XI

The method of Embodiment I, wherein the compound having formula (I) is a compound having formula (IIA):

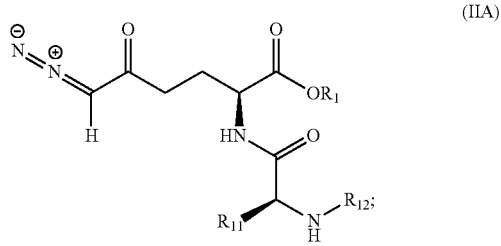

(IIA)

wherein:

$R_1$ is selected from the group consisting of H and $C_{1-6}$ alkyl;

$R_{11}$ is selected from the group consisting of H, methyl, isopropyl, sec-butyl, $CH_2CH(CH_3)_2$, benzyl, p-hydroxybenzyl $CH_2OH$, $CH(OH)CH_3$, $CH_2$-3-indoyl, $CH_2COOH$, $CH_2CH_2COOH$, $-CH_2C(O)NH_2$, $CH_2CH_2C(O)NH_2$, $CH_2SH$, $CH_2CH_2SCH_3$, $(CH_2)_4NH_2$, $(CH_2)_3NHC(=NH)NH_2$, and $CH_2$-3-imidazoyl;

$R_{12}$ is selected from the group consisting of H, $C_{1-4}$ alkyl, and $-C(=O)R_{13}$; and $R_{13}$ is $C_{1-4}$ alkyl.

Embodiment XII

The method of Embodiment 1, wherein the compound having formula (I) is a compound having formula (IIB):

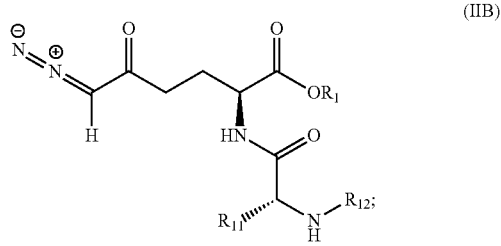

(IIB)

wherein:

$R_1$ is selected from the group consisting of H and $C_{1-6}$ alkyl;

$R_{11}$ is selected from the group consisting of H, methyl, isopropyl, sec-butyl, $CH_2CH(CH_3)_2$, benzyl, p-hydroxybenzyl $CH_2OH$, $CH(OH)CH_3$, $CH_2$-3-indoyl, $CH_2COOH$, $CH_2CH_2COOH$, $-CH_2C(O)NH_2$, $CH_2CH_2C(O)NH_2$, $CH_2SH$, $CH_2CH_2SCH_3$, $(CH_2)_4NH_2$, $(CH_2)_3NHC(=NH)NH_2$, and $CH_2$-3-imidazoyl;

$R_{12}$ is selected from the group consisting of H, $C_{1-4}$ alkyl, and $-C(=O)R_{13}$; and $R_{13}$ is $C_{1-4}$ alkyl.

Embodiment XIII

The method of Embodiments XI or XII, wherein:

$R_1$ is $C_{1-4}$ alkyl;

$R_{11}$ is selected from the group consisting of isopropyl, sec-butyl, $CH_2CH(CH_3)_2$, and $CH_2$-3-indoyl;

$R_{12}$ is selected from the group consisting of H and $-C(=O)R_{13}$; and $R_{13}$ is $C_{1-4}$ alkyl.

Embodiment XIV

The method of Embodiment I, wherein the compound of formula (I) is selected from the group consisting of:

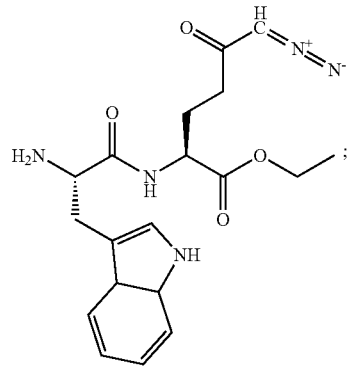

;

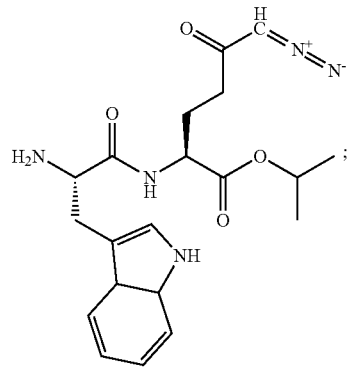

;

-continued

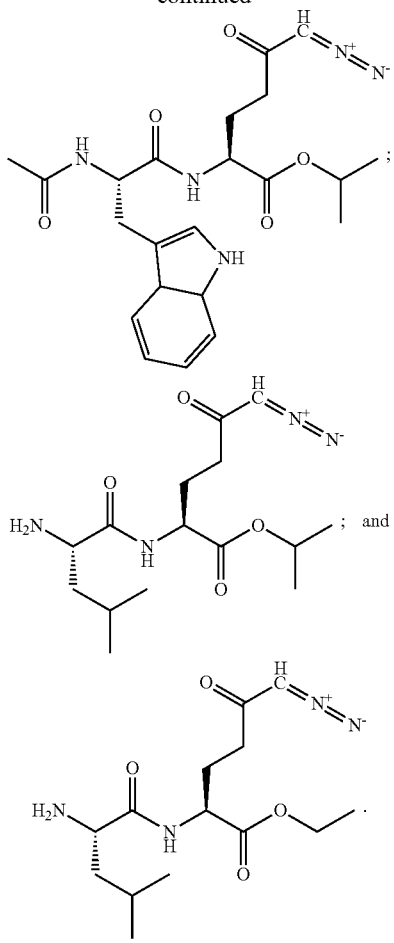

Embodiment XV

The method of Embodiment XIV, wherein the compound is:

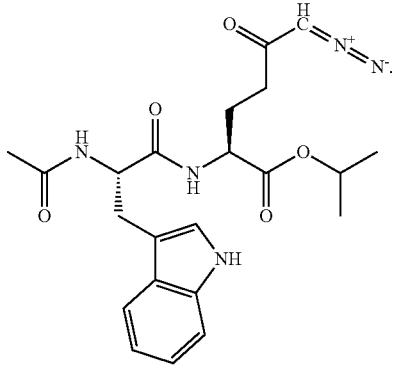

Embodiment XVI

The method of Embodiment I, wherein the compound having formula (I) is a compound having formula (III):

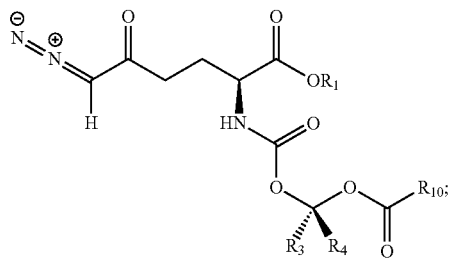

wherein:
$R_1$ is selected from the group consisting of H and $C_{1-4}$ alkyl;
$R_3$ and $R_4$ are independently selected from the group consisting of H, $C_1$-$C_6$ alkyl, substituted $C_1$-$C_6$ alkyl, aryl, and substituted aryl; and
$R_{10}$ is $C_{1-6}$ alkyl.

Embodiment XVII

The method of Embodiment XVI, wherein:
$R_3$ is selected from the group consisting of $C_1$-$C_6$ alkyl, substituted $C_1$-$C_6$ alkyl, aryl, and substituted aryl; and
$R_4$ is H.

Embodiment XVIII

The method of Embodiment XVII, wherein:
$R_3$ is H; and
$R_4$ is selected from the group consisting of $C_1$-$C_6$ alkyl, substituted $C_1$-$C_6$ alkyl, aryl, and substituted aryl.

Embodiment XIX

The method of Embodiment I, wherein the compound of formula (I) is selected from the group consisting of:

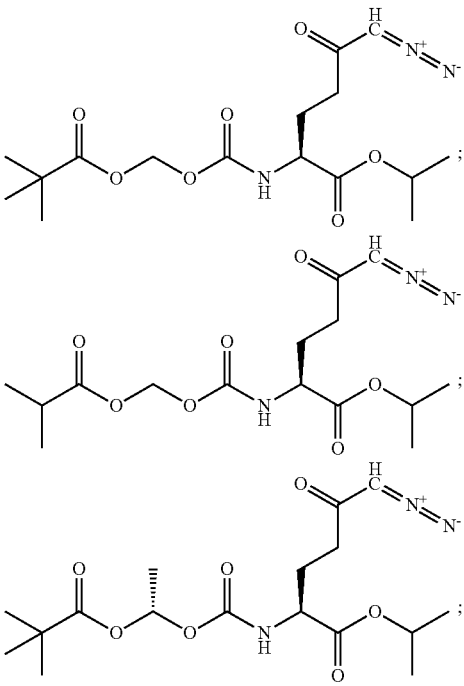

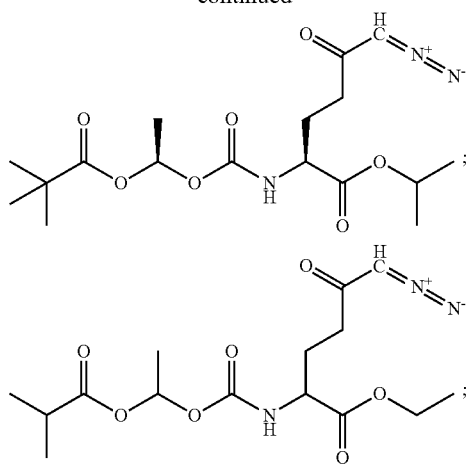
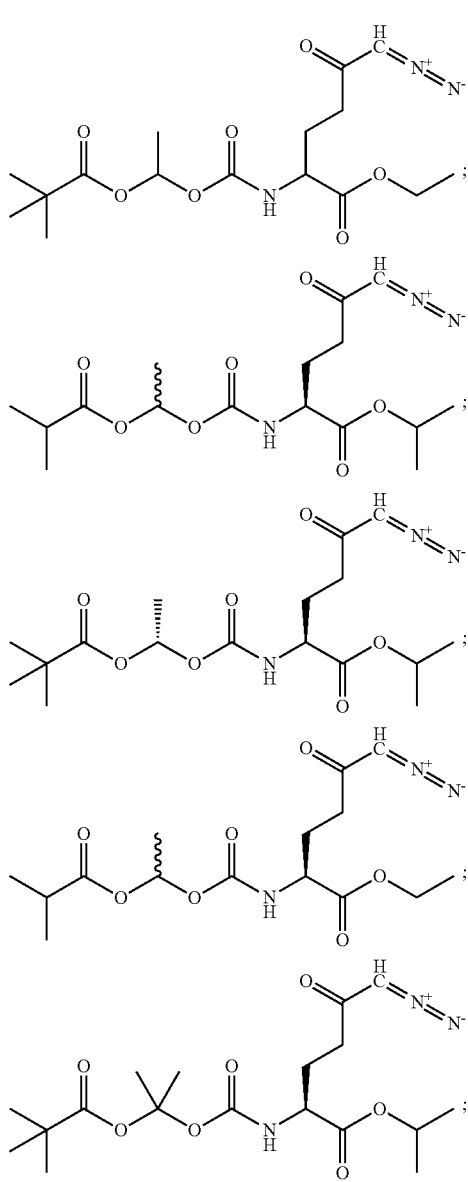
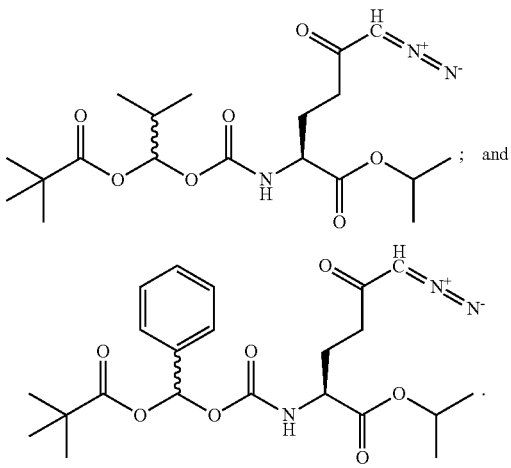
Embodiment XX
The method of Embodiment XIX, wherein the compound selected from the group consisting of:
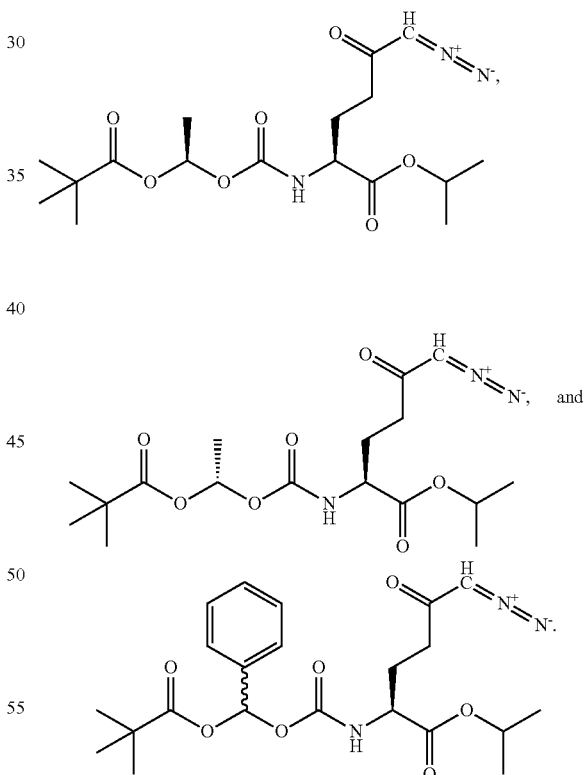
Embodiment XXI
A method of treating cancer in a subject, the method comprising administering to the subject in need thereof a compound, or a pharmaceutically acceptable salt thereof, selected from the group consisting of:

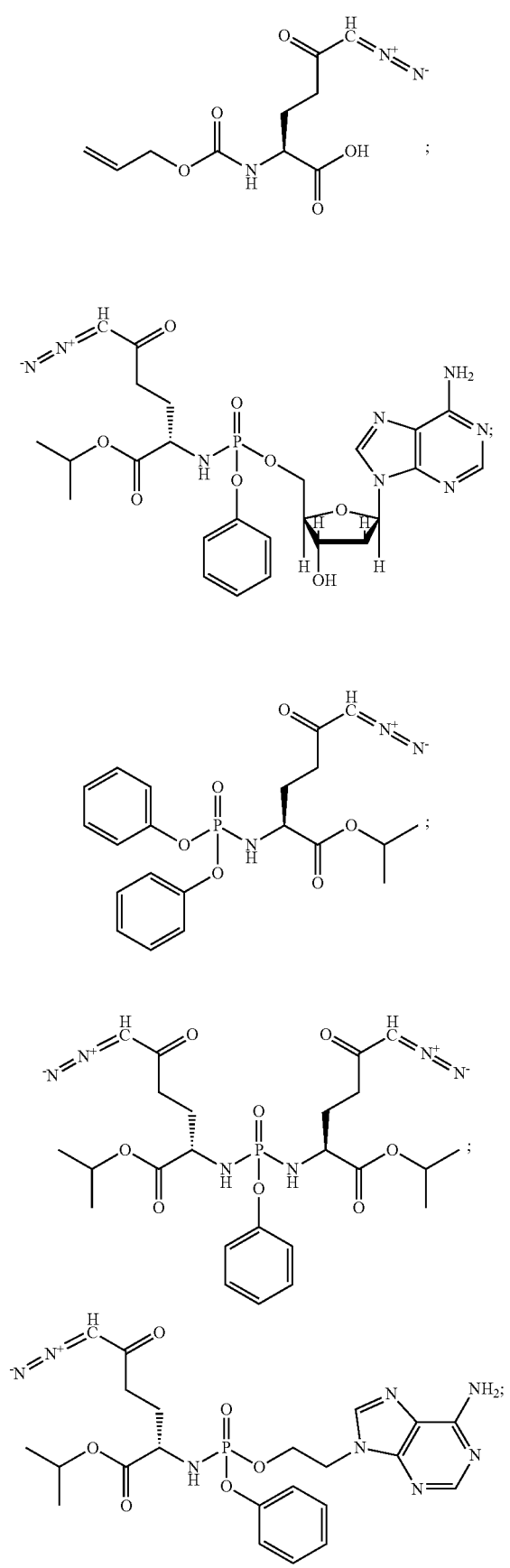
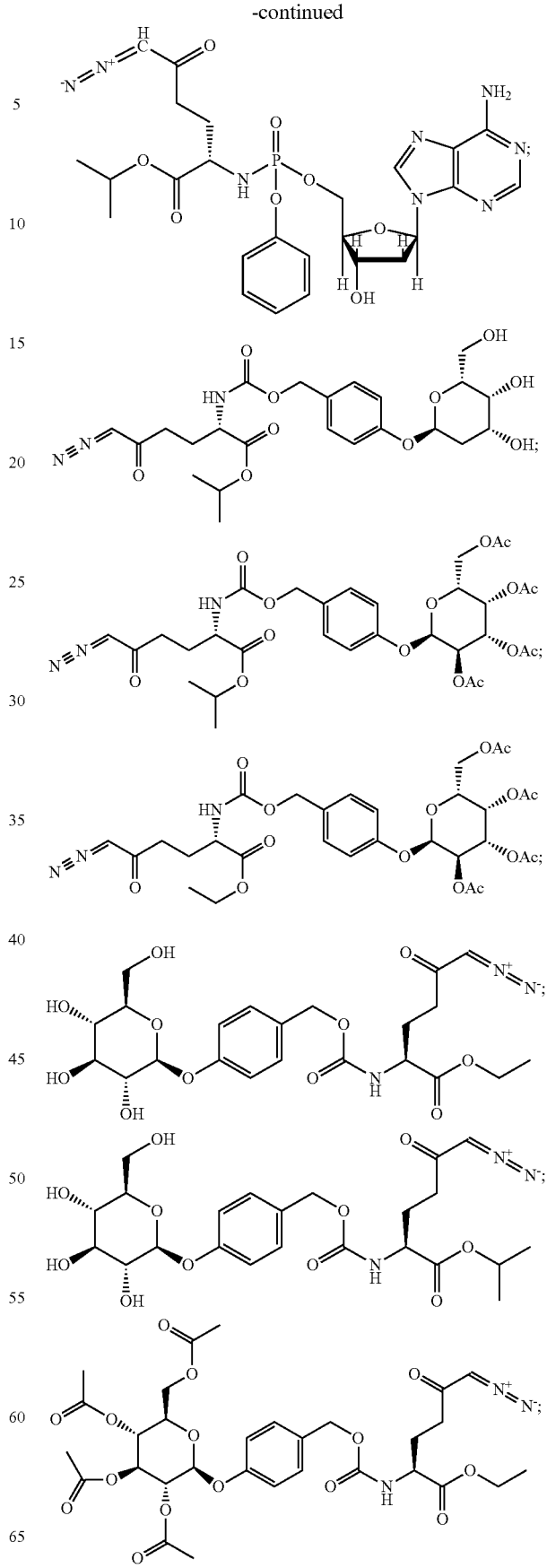

33
-continued
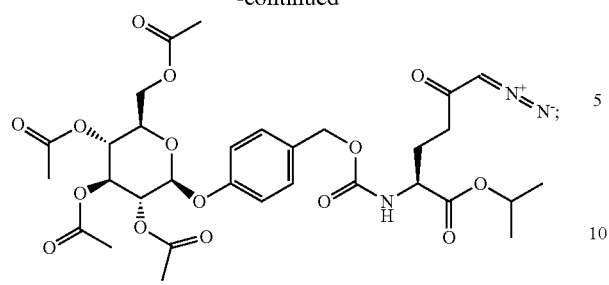
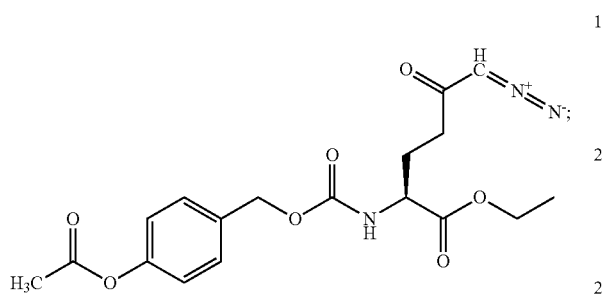
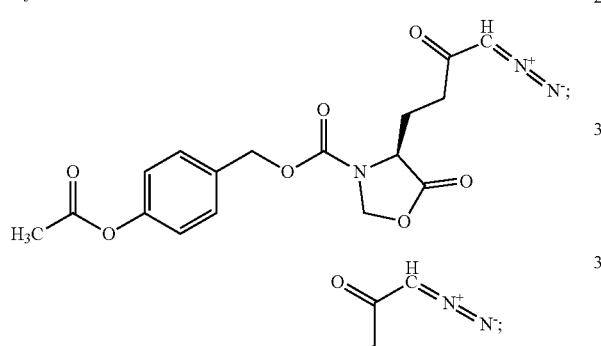
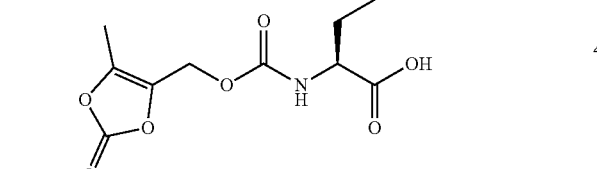
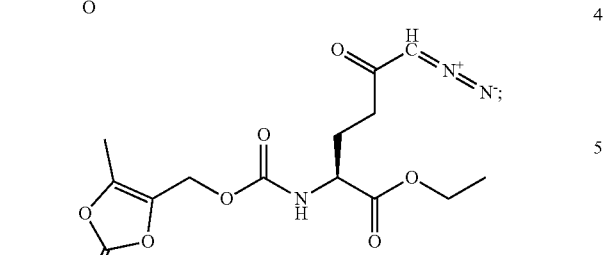
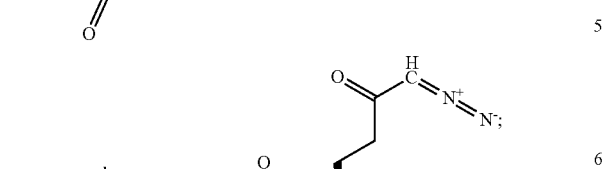
34
-continued
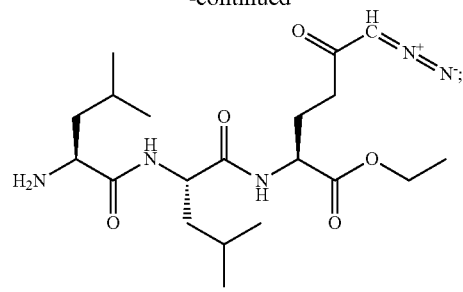
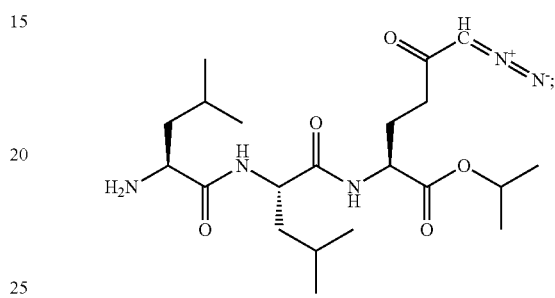
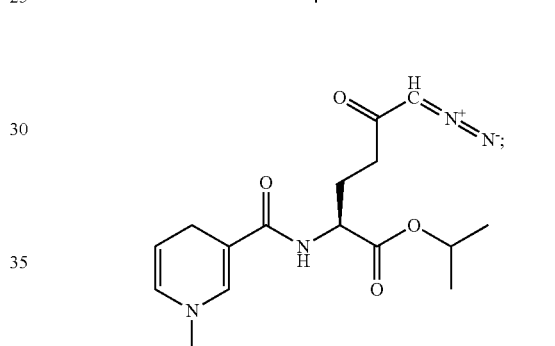
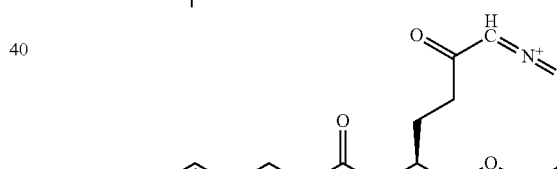
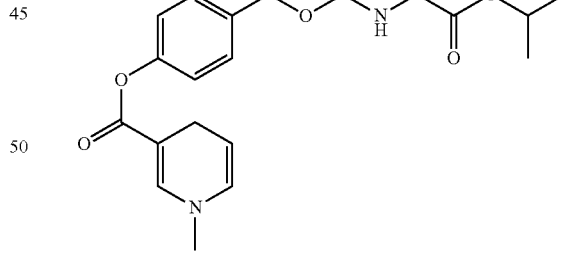
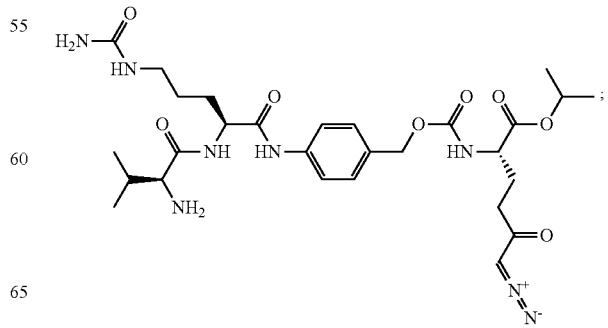

-continued

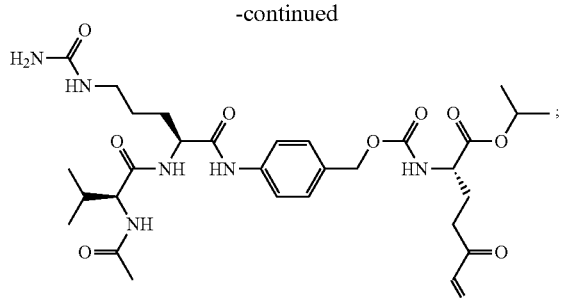

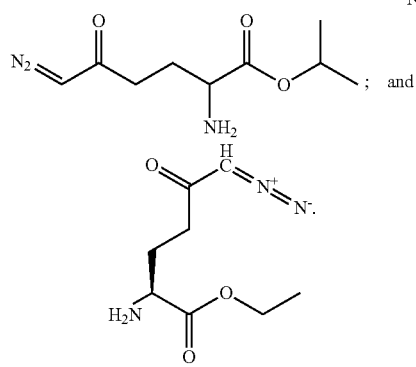

Embodiment XXII

The method of any one of Embodiments I-XXI further comprising simultaneously or sequentially administering a therapeutically effective amount of an immunotherapeutic agent to the subject.

Embodiment XXIII

The method of Embodiment XXII, wherein the immunotherapeutic agent is an immune checkpoint blockade therapy.

Embodiment XXIV

The method of Embodiment XXIII, wherein the immune checkpoint blockade therapy is selected from the group consisting of PD-1 antagonists, PD-L1 antagonists, CTLA-4 antagonists, LAG3 antagonists, and B7-H3 antagonists, and combinations thereof.

Embodiment XXV

The method of Embodiment XXII, wherein the immunotherapeutic agent is an adoptive cellular therapy.

Embodiment XXVI

The method of Embodiment XXII, wherein the immunotherapeutic agent is marrow-infiltrating lymphocytes (MILs).

Embodiment XXVII

The method of Embodiment XXII, wherein the immunotherapeutic agent is an adenosine A2aR inhibitor.

Embodiment XXVIII

The method of Embodiment XXII, wherein the immunotherapeutic agent is a tumor vaccine.

Embodiment XXIX

The method of Embodiment XXII, wherein the immunotherapeutic agent is a passive immunotherapy antibody.

Embodiment XXX

The method of Embodiment XXIX, wherein the passive immunotherapy antibody is selected from the group consisting of bevacizumab, cetuximab, rituximab, trastuzumab, alemtuzumab, ibritumomab tiuxetan, and panitumumab, and combinations thereof.

Embodiment XXXI

The method of any one of Embodiments I-XXX wherein the cancer is:
(i) a cancer of the central nervous system:
(ii) a cancer that is associated with transplant and/or immunosuppression;
(iii) a cancer that is refractory to chemotherapy;
(iv) a cancer that is refractory to photodynamic therapy;
(v) a cancer that is refractory to proton therapy;
(vi) a cancer that is refractory to radiotherapy; and
(vii) a cancer that is refractory to surgery.

Embodiment XXXII

The method of any one of Embodiments I-XXX, wherein the cancer is a newly diagnosed, recurrent, and/or refractory cancer selected from the group consisting of celnasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, brain cancer, oligodendroglioma, neuroblastoma, meningioma, spinal cord tumor, bone cancer, osteochondroma, chondrosarcoma. Ewing's sarcoma, cancer of unknown primary site, carcinoid, carcinoid of gastrointestinal tract, fibrosarcoma, breast cancer, Paget's disease, cervical cancer, colorectal cancer, rectal cancer, esophagus cancer, gall bladder cancer, head cancer, eye cancer, neck cancer, kidney cancer, Wilms' tumor, liver cancer, Kaposi's sarcoma, prostate cancer, lung cancer, testicular cancer, Hodgkin's disease, non-Hodgkin's lymphoma, oral cancer, skin cancer, mesothelioma, multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer and tonsil cancer.

Embodiment XXXIII

A method of preventing a relapse or reducing the incidence of relapse of a cancer subject in remission, the method comprising administering to the subject in need thereof a compound, or a pharmaceutically acceptable salt thereof, having formula (I):

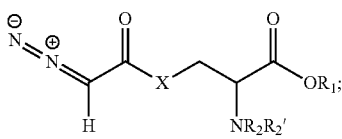

(I)

wherein:
X is selected from the group consisting of a bond, —O—, and —(CH$_2$)$_n$—, wherein n is an integer selected from the group consisting of 1, 2, 3, 4, 5, 6, 7, and 8;
R$_1$ is selected from the group consisting of C$_{1-6}$ alkyl and substituted C$_{1-6}$ alkyl;
R$_2$ is an amino acid, an N-substituted amino acid, or —C(=O)—O—(CR$_3$R$_4$)$_m$—O—C(=O)—R$_{10}$;
R$_2$' is selected from the group consisting of H, C$_1$-C$_6$ alkyl, and substituted C$_1$-C$_6$ alkyl;
each R$_3$ and R$_4$ are independently H, C$_1$-C$_6$ alkyl, substituted C$_1$-C$_6$ alkyl, aryl, substituted aryl, —(CR$_3$R$_4$)$_m$—NR$_5$R$_6$, or

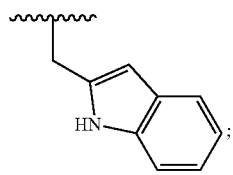 [SMILES: *Cc1cc2ccccc2[nH]1]

m is an integer selected from the group consisting of 1, 2, 3, 4, 5, 6, 7, and 8;
R$_5$ and R$_6$ are independently H or alkyl; and
R$_{10}$ is selected from the group consisting of alkyl, substituted alkyl, cycloalkyl, substituted cycloalkyl, monosaccharide, acylated monosaccharide, aryl, substituted aryl, heteroaryl, and substituted heteroaryl.

Embodiment XXXIV

The method of Embodiment XXXIII, wherein X is —CH$_2$—.

Embodiment XXXV

The method of Embodiment XXXIII, wherein X is —O—.

Embodiment XXXVI

The method of any one of Embodiments XXXIII-XXXV, wherein R$_1$ is selected from the group consisting of methyl, ethyl, isopropyl, cyclopentyl, cyclohexyl, trimethylammonium, triethylammonium, tri(hydroxyethyl)ammonium, tripropylammonium, and tri(hydroxypropyl)ammonium.

Embodiment XXXVII

The method of any one of Embodiments XXXIII-XXVI, wherein R$_2$ is selected from the group consisting of —C(=O)—Y—(CR$_3$R$_4$)$_m$—NR$_5$R$_6$, and —C(=O)—O—(CR$_3$R$_4$)$_m$—O—C(=O)—R$_{10}$:
wherein:
Y is —O— or a bond;
m is an integer selected from the group consisting of 1, 2, 3, 4, 5, 6, 7, and 8; and
each R$_3$ and R$_4$ is independently H, C$_1$-C$_6$ alkyl or substituted C$_1$-C$_6$ alkyl, aryl or substituted aryl;
R$_{10}$ is selected from the group consisting of alkyl, substituted alkyl, cycloalkyl, substituted cycloalkyl, aryl, substituted aryl, heteroaryl, and substituted heteroaryl.

Embodiment XXXVIII

The method of Embodiment XXXVII, wherein:
Y is a bond;
m is 1;
R$_5$ and R$_6$ are each H.

Embodiment XXXIX

The method of any one of Embodiments XXXIII-XXVI, wherein R$_2$ is an amino acid.

Embodiment XL

The method of Embodiment XXXIX, wherein the amino acid is tryptophan.

Embodiment XLI

The method of any one of Embodiment XXXIII-XXVI, wherein R$_2$ is a N-acyl amino acid.

Embodiment XLII

The method of Embodiment XLI, wherein the amino acid is tryptophan.

Embodiment XLIII

The method of Embodiment XXXIII, or a pharmaceutically acceptable salt thereof, having formula (IIA):

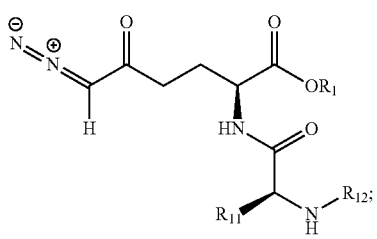

(IIA)

therein:
R$_1$ is selected from the group consisting of H and C$_{1-6}$ alkyl;
R$_{11}$ is selected from the group consisting of H, methyl, isopropyl, sec-butyl, CH$_2$CH(CH$_3$)$_2$, benzyl, p-hydroxybenzyl CH$_2$OH, CH(OH)CH$_3$, CH$_2$-3-indoyl, CH$_2$COOH, CH$_2$CH$_2$COOH, —CH$_2$C(O)NH$_2$, CH$_2$CH$_2$C(O)NH$_2$, CH$_2$SH, CH$_2$CH$_2$SCH$_3$, (CH$_2$)$_4$NH$_2$, (CH$_2$)$_3$NHC(=NH)NH$_2$, and CH$_2$-3-imidazoyl;
R$_{12}$ is selected from the group consisting of H, C$_{1-4}$ alkyl, and —C(=O)R$_{13}$; and
R$_{13}$ is C$_{1-4}$ alkyl.

Embodiment XLIV

The method of Embodiment XXXIII, wherein the compound having formula (I) is a compound having formula (IIB):

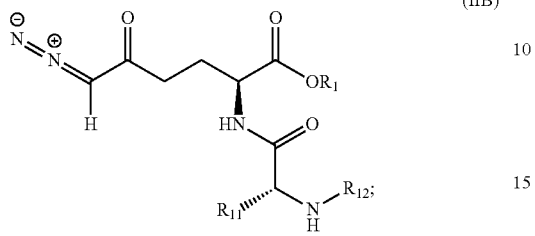

(IIB)

wherein:

$R_1$ is selected from the group consisting of H and $C_{1-6}$ alkyl;

$R_{11}$ is selected from the group consisting of H, methyl, isopropyl, sec-butyl, $CH_2CH(CH_3)_2$, benzyl, p-hydroxybenzyl $CH_2OH$, $CH(OH)CH_3$, $CH_2$-3-indoyl, $CH_2COOH$, $CH_2CH_2COOH$, —$CH_2C(O)NH_2$, $CH_2CH_2C(O)NH_2$, $CH_2SH$, $CH_2CH_2SCH_3$, $(CH_2)_4NH_2$, $(CH_2)_3NHC(=NH)NH_2$, and $CH_2$-3-imidazoyl:

$R_{12}$ is selected from the group consisting of H, $C_{1-4}$ alkyl, and —$C(=O)R_{13}$; and $R_{13}$ is $C_{1-4}$ alkyl.

Embodiment XLV

The method of Embodiments XLIII or XLIV, wherein:

$R_1$ is $C_{1-4}$ alkyl;

$R_{11}$ is selected from the group consisting of isopropyl, sec-butyl, $CH_2CH(CH_3)_2$, and $CH_2$-3-indoyl;

$R_{12}$ is selected from the group consisting of H and —$C(=O)R_{13}$; and $R_{13}$ is $C_{1-4}$ alkyl.

Embodiment XLVI

The method of Embodiment XXXIII, wherein the compound of formula (I) is selected from the group consisting of:

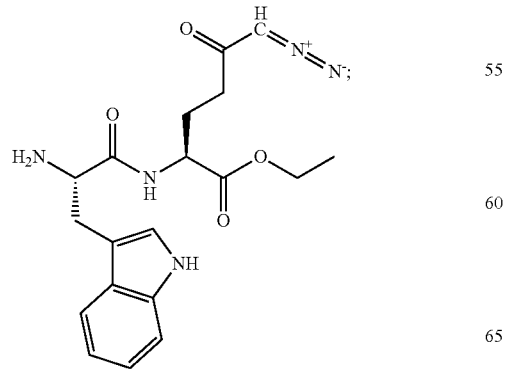

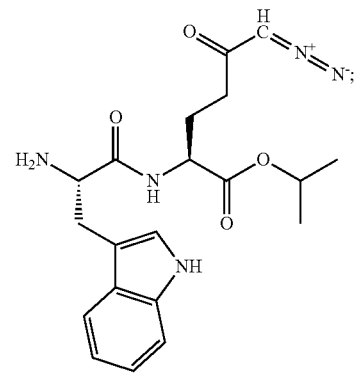

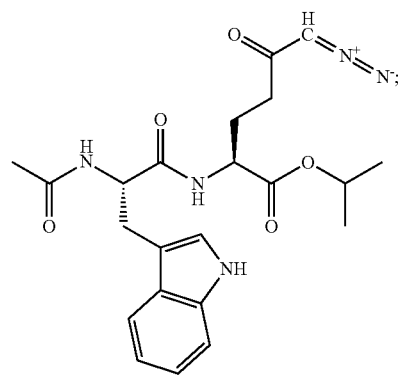

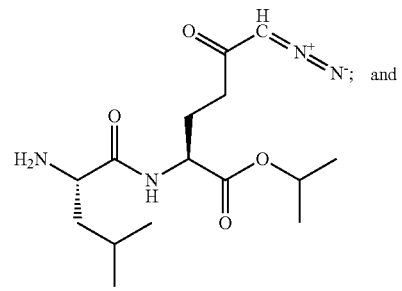

and

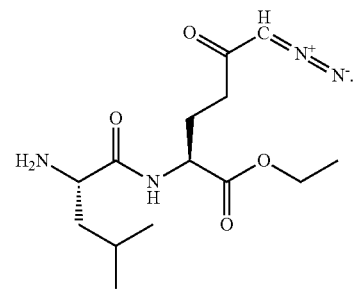

Embodiment XLVII

The method of Embodiment XLVI wherein the compound is:

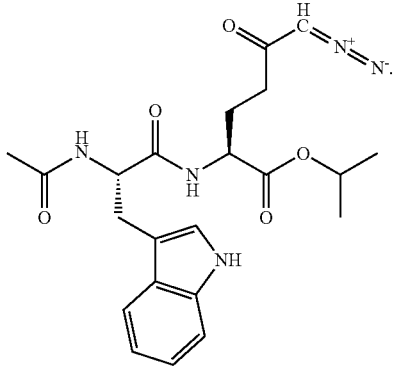

Embodiment XLVIII

The method of Embodiment XXXIII, wherein the compound having formula (I) is a compound having formula (III):

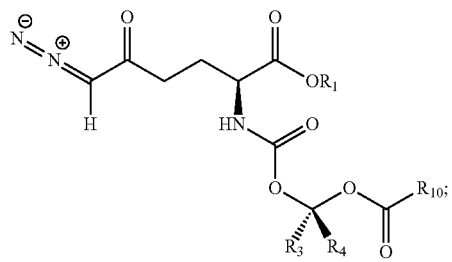

(III)

wherein:

R₁ is selected from the group consisting of H and $C_{1-6}$ alkyl;

R₃ and R₄ are independently selected from the group consisting of H, $C_1$-$C_6$ alkyl, substituted $C_1$-$C_6$ alkyl, aryl, and substituted aryl; and R₁₀ is $C_{1-6}$ alkyl.

Embodiment XLIX

The method of Embodiment XXXIII, wherein the compound of formula (I) is selected from the group consisting of

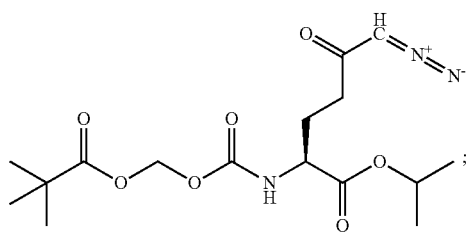

-continued

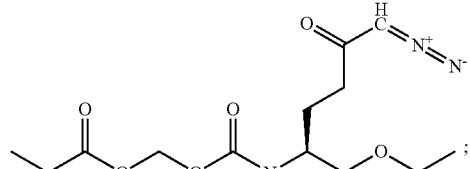

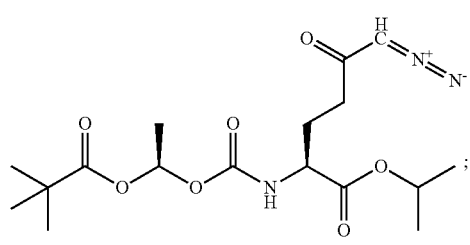

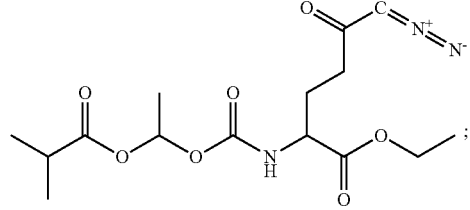

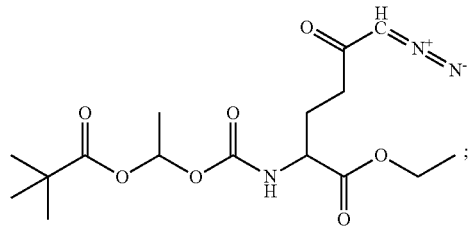

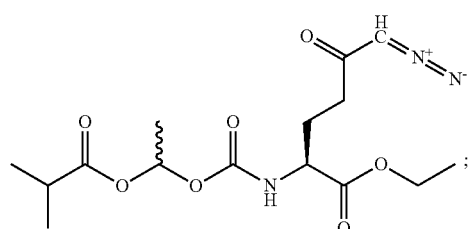

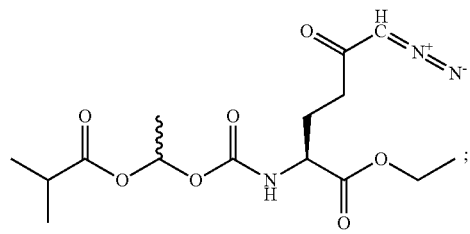

43

-continued

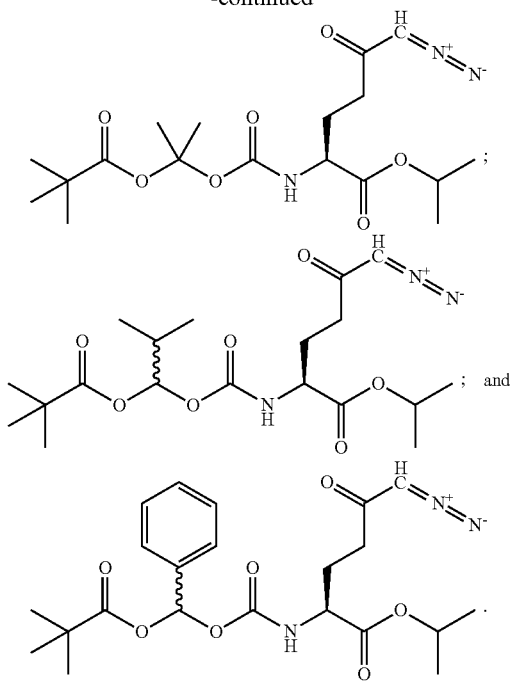

Embodiment L

The method of Embodiment XLIX selected from the group consisting of:

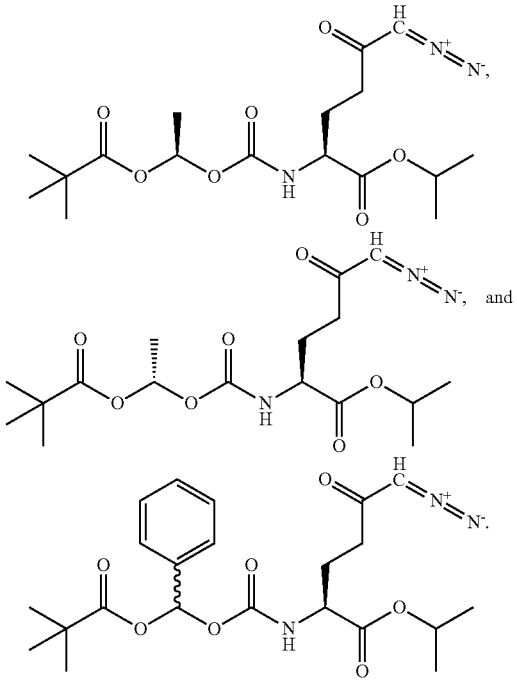

Embodiment LI

A method of preventing a relapse or reducing the incidence of relapse of a cancer subject in remission, the method comprising administering to the subject in need thereof a compound, or a pharmaceutically acceptable salt thereof, selected from the group consisting of:

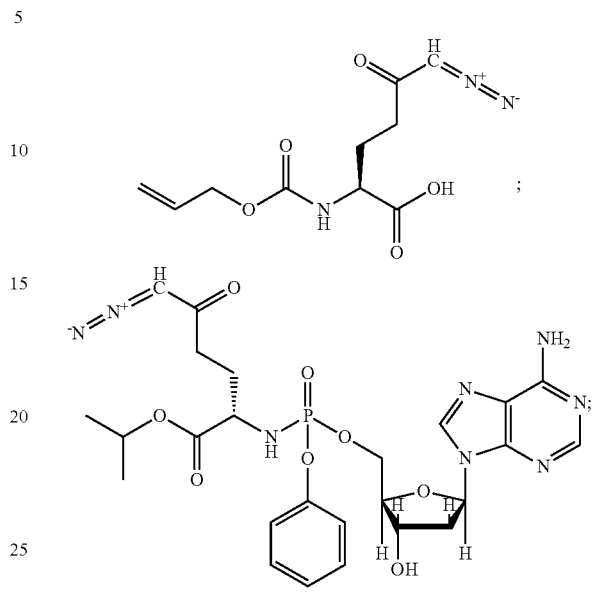

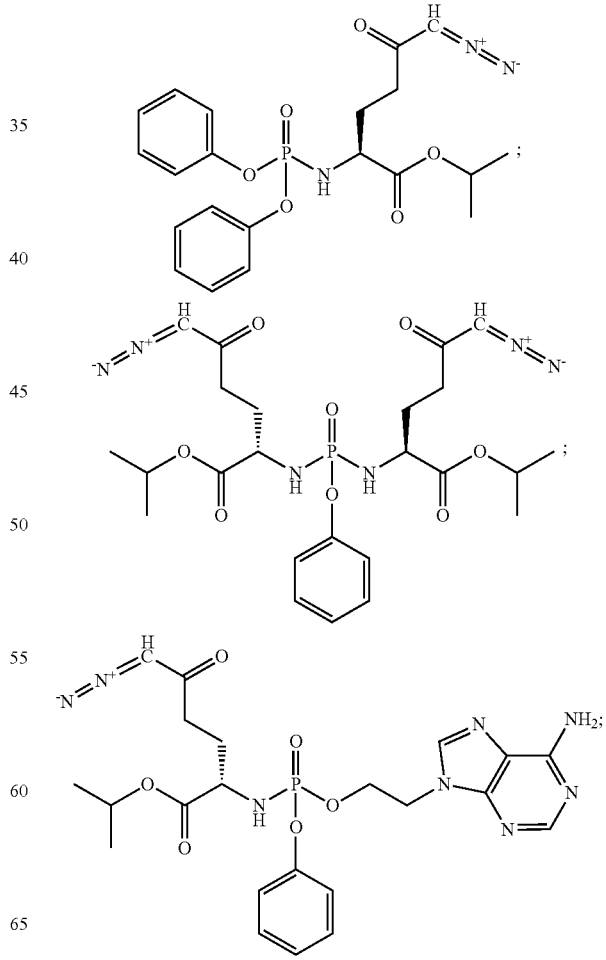

-continued
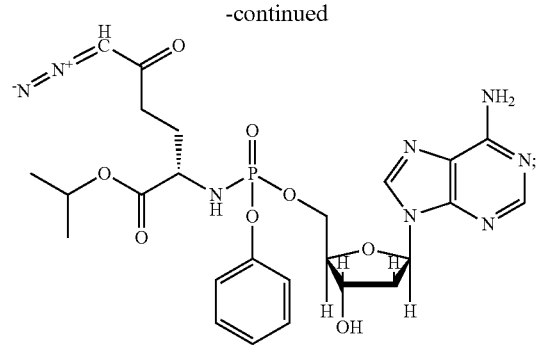
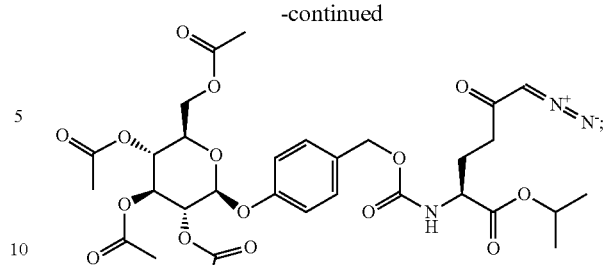
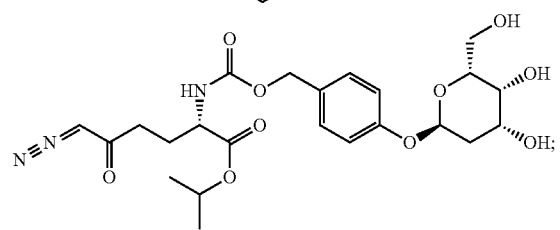
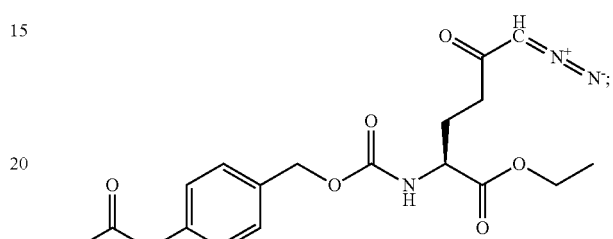
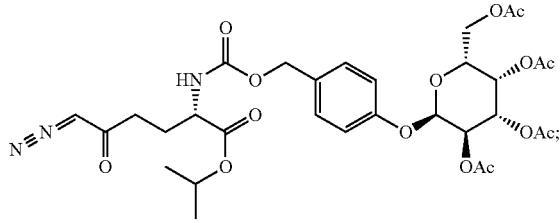
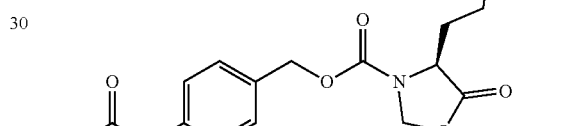
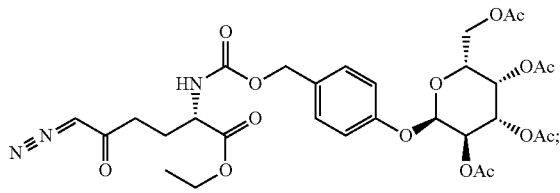
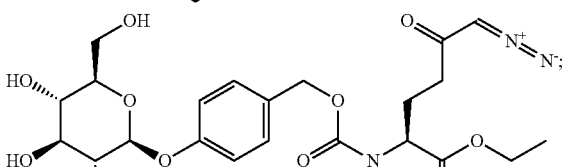
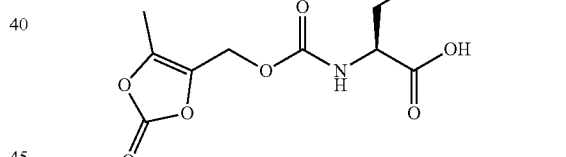
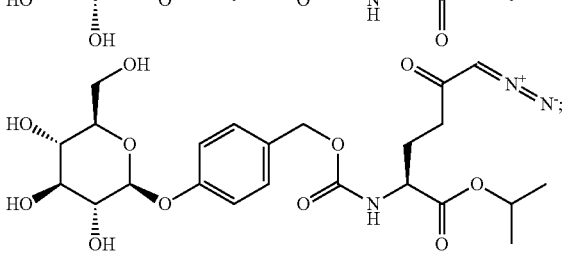
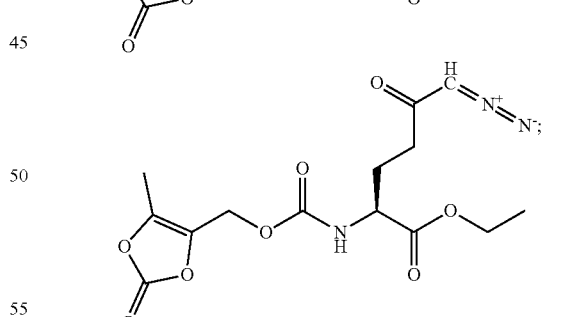
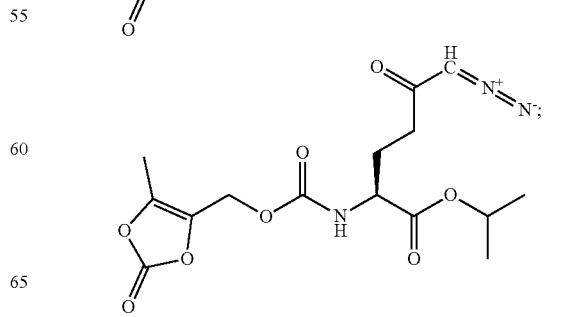

-continued

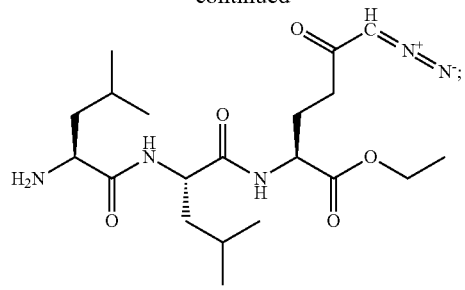

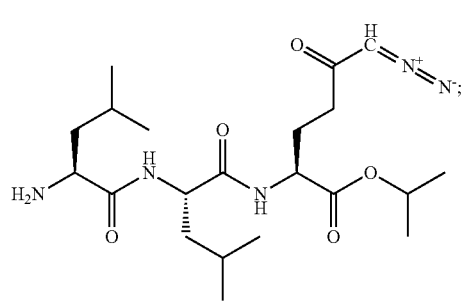

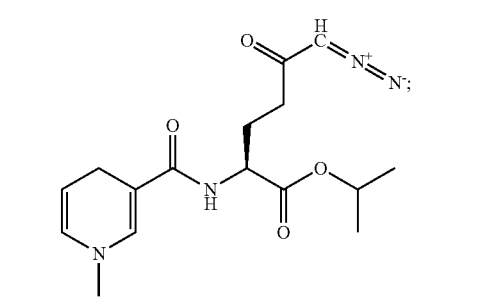

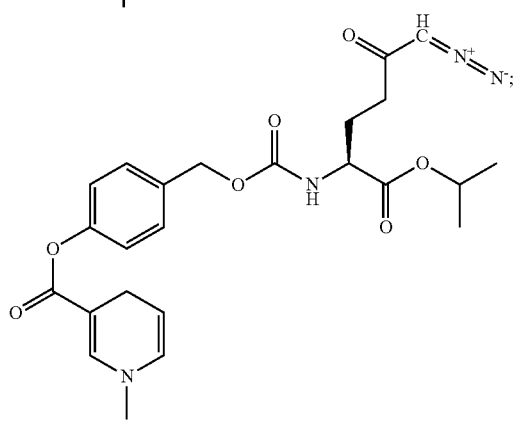

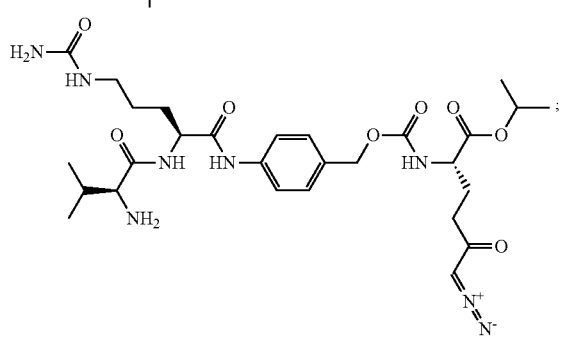

-continued

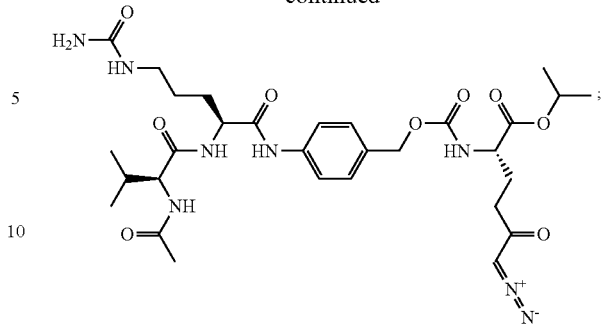

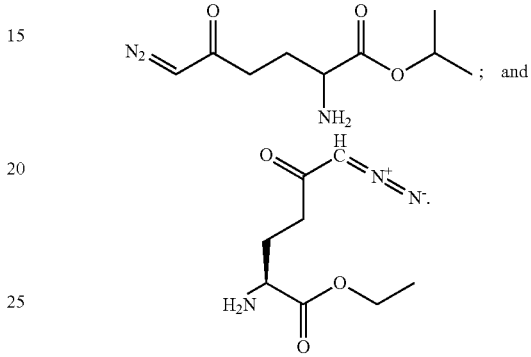

Embodiment LII

The method any one of Embodiments XXXIII-LI, wherein the compound is:
(i) administered to the subject post transplant;
(ii) administered to the subject post chemotherapy;
(iii) administered to the subject post immunotherapy;
(iv) administered to the subject post photodynamic therapy;
(v) administered to the subject post proton therapy;
(vi) administered to the subject post radiotherapy;
(vii) administered to the subject post surgery; or
(viii) after relapse of a cancer of a subject, and combinations thereof.

Embodiment LIII

The method of any one of Embodiments XXXIII-LII further comprising simultaneously or sequentially administering a therapeutically effective amount of an immunotherapeutic agent to the subject.

Embodiment LIV

The method of Embodiment LIII, wherein the immunotherapeutic agent is an immune checkpoint blockade therapy.

Embodiment LV

The method of Embodiment LIV, wherein the immune checkpoint blockade therapy is selected from the group consisting of PD-1 antagonists, PD-L1 antagonists, CTLA-4 antagonists, LAG3 antagonists, and B7-H3 antagonists, and combinations thereof.

Embodiment LVI

The method of Embodiment LIII, wherein the immunotherapeutic agent is an adoptive cellular therapy.

Embodiment LVII

The method of Embodiment LIII, wherein the immunotherapeutic agent is marrow-infiltrating lymphocytes (MILs).

Embodiment LVIII

The method of Embodiment LIII, wherein the immunotherapeutic agent is an adenosine A2aR inhibitor.

Embodiment LIX

The method of Embodiment LIII, wherein the immunotherapeutic agent is a tumor vaccine.

Embodiment LX

The method of Embodiment LIII, wherein the immunotherapeutic agent is a passive immunotherapy antibody.

Embodiment LXI

The method of Embodiment LX, wherein the passive immunotherapy antibody is selected from the group consisting of bevacizumab, cetuximab, rituximab, trastuzumab, alemtuzumab, ibritumomab tiuxetan, and panitumumab, and combinations thereof.

The disclosure also provides the following particular embodiments numbered Embodiments 1-20.

Embodiment 1

A method for treating a cancer in a subject in need thereof, the method comprising:
(a) administering a therapeutically effective amount of a first immunotherapy to the subject, wherein the first immunotherapy is a metabolic reprogramming agent that decreases glutamine metabolic activity; and
(b) optionally administering a therapeutically effective amount of a second immunotherapy to the subject.

Embodiment 2

The method of Embodiment 1, wherein the metabolic reprogramming agent is a glutamine antagonist.

Embodiment 3

The method of Embodiment 1, wherein the metabolic reprogramming agent is a glutamine analog that interferes with a glutamine metabolic pathway.

Embodiment 4

The method of Embodiment 1, wherein the metabolic reprogramming agent is selected from the group consisting of acivicin (L-(alpha S, 5S)-alpha-amino-3-chloro-4,5-dihydro-5-isoxazoleacetic acid), azaserine, and 6-diazo-5-oxo-norleucine (DON), and 5-diazo-4-oxo-L-norvaline (L-DONV).

Embodiment 5

The method of Embodiment 1, wherein the metabolic reprogramming agent is a prodrug of a glutamine analog that interferes with a glutamine metabolic pathway.

Embodiment 6

The method of Embodiment 1, wherein the at least one metabolic reprogramming agent is a prodrug of acivicin, azaserine, DON, and L-DONV.

Embodiment 7

The method of Embodiment 1, further comprising simultaneously or sequentially administering a therapeutically effective amount of the second immunotherapy to the subject, wherein the second immunotherapy is an immune checkpoint blockade therapy.

Embodiment 8

The method of Embodiment 7, wherein the immune checkpoint blockade therapy is selected from the group consisting of PD-1 antagonists, PD-L1 antagonists, CTLA-4 antagonists, LAG3 antagonists, B7-H3 antagonists, and combinations thereof.

Embodiment 9

The method of Embodiment 1, further comprising simultaneously or sequentially administering a therapeutically effective amount of the second immunotherapy to the subject, wherein the second immunotherapy is an adoptive cellular therapy.

Embodiment 10

The method of Embodiment 1, further comprising simultaneously or sequentially administering a therapeutically effective amount of the second immunotherapy to the subject, wherein the second immunotherapy is marrow-infiltrating lymphocytes (MILs).

Embodiment 11

The method of Embodiment 1, further comprising simultaneously or sequentially administering a therapeutically effective amount of the second immunotherapy to the subject, wherein the second immunotherapy is an adenosine A2aR blockade.

Embodiment 12

The method of Embodiment 1, further comprising simultaneously or sequentially administering a therapeutically effective amount of the second immunotherapy to the subject, wherein the second immunotherapy is a tumor vaccine.

Embodiment 13

The method of Embodiment 1, further comprising simultaneously or sequentially administering a therapeutically effective amount of the second immunotherapy to the subject, wherein the second immunotherapy is a passive immunotherapy antibody.

Embodiment 14

The method of Embodiment 14, wherein the passive immunotherapy antibody is selected from the group consisting of bevacizumab, cetuximab, rituximab, trastuzumab, alemtuzumab, ibritumomab tiuxetan, panitumumab, and combinations thereof.

Embodiment 15

The method of Embodiment 1, further comprising simultaneously or sequentially administering to the subject a therapeutically effective amount of a cancer therapy selected from the group consisting of: (i) chemotherapy; (ii) photodynamic therapy; (iii) proton therapy; (iv) radiotherapy; (v) surgery; and combinations thereof.

Embodiment 16

The method of Embodiment 1, wherein the first immunotherapy, and the second immunotherapy if administered, is/are administered to the subject in the absence of a cancer therapy selected from the group consisting of: (i) chemotherapy; (ii) photodynamic therapy; (iii) proton therapy; (iv) radiotherapy; (v) surgery; and combinations thereof.

Embodiment 17

The method of Embodiment 1, wherein the cancer is:
(i) a cancer of the central nervous system;
(ii) a cancer that is associated with transplant and/or immunosuppression;
(iii) a cancer that is refractory to chemotherapy;
(iv) a cancer that is refractory to photodynamic therapy;
(v) a cancer that is refractory to proton therapy;
(vi) a cancer that is refractory to radiotherapy;
(vii) a cancer that is refractory to surgery, or
(vii) a cancer that has relapsed.

Embodiment 18

The method of Embodiment 1, wherein the cancer is a newly diagnosed, recurrent, and/or refractory cancer selected from the group consisting of celnasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, oligodendroglioma, neuroblastoma, meningioma, spinal cord tumor, bone cancer, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, colorectal cancer, rectal cancer, esophagus cancer, gall bladder cancer, head cancer, eye cancer, neck cancer, kidney cancer, Wilms' tumor, liver cancer. Kaposi's sarcoma, prostate cancer, lung cancer, testicular cancer, Hodgkin's disease, non-Hodgkin's lymphoma, oral cancer, skin cancer, mesothelioma, multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer and tonsil cancer.

Embodiment 19

A method of preventing a relapse or reducing the incidence of relapse of a cancer subject in remission, the method comprising administering to the subject a therapeutically effective amount of a metabolic reprogramming agent, wherein the metabolic reprogramming agent is selected from the group consisting of acivicin (L-(alpha S, 5S)-alpha-amino-3-chloro-4,5-dihydro-5-isoxazoleacetic acid), azaserine, and 6-diazo-5-oxo-norleucine (DON), and 5-diazo-4-oxo-L-norvaline (L-DONV), and prodrugs thereof.

Embodiment 20

The method of Embodiment 20, wherein the metabolic reprogramming agent is:
(i) administered to the subject post transplant;
(ii) administered to the subject post chemotherapy;
(iii) administered to the subject post immunotherapy;
(iv) administered to the subject post photodynamic therapy;
(v) administered to the subject post proton therapy;
(vi) administered to the subject post radiotherapy;
(vii) administered to the subject post surgery; or
(vii) administered to a subject after relapse of a cancer, and combinations thereof.
Structures of representative DON prodrugs are provided in Table 1.

TABLE 1

Structures of Representative DON Prodrugs

| IOCB No./ Compound No. | Structure | MW |
|---|---|---|
| Compound 1 (DON) | 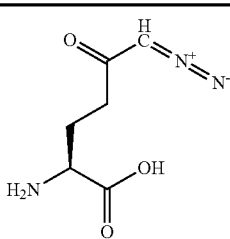 | 171.15 |

TABLE 1-continued

Structures of Representative DON Prodrugs

| IOCB No./<br>Compound No. | Structure | MW |
|---|---|---|
| Compound 3 | 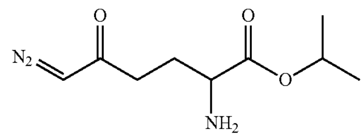 | 213.24 |
| Compound 4 | 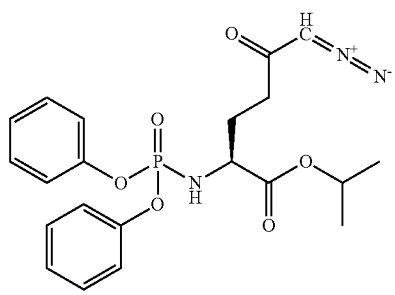 [SMILES: CC(C)OC(=O)[C@H](CCC(=O)C=[N+]=[N-])NP(=O)(Oc1ccccc1)Oc1ccccc1] | 445.41 |
| Compound 6 | 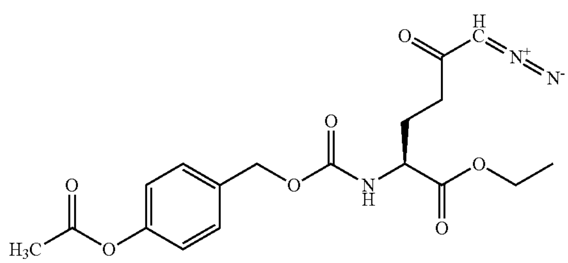 [SMILES: CCOC(=O)[C@H](CCC(=O)C=[N+]=[N-])NC(=O)OCc1ccc(OC(C)=O)cc1] | 391.38 |
| Compound 7 | 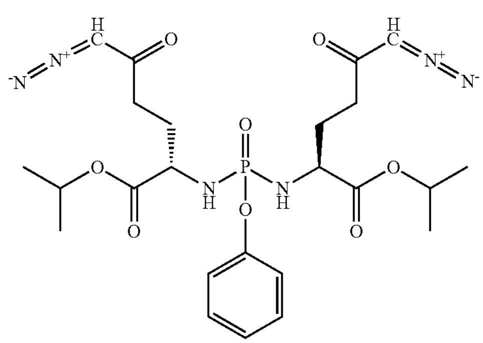 | 564.53 |
| Compound 9 | 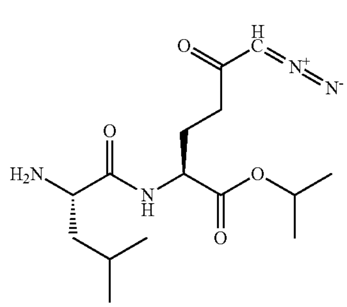 [SMILES: CC(C)C[C@H](N)C(=O)N[C@@H](CCC(=O)C=[N+]=[N-])C(=O)OC(C)C] | 326.39 |

TABLE 1-continued

Structures of Representative DON Prodrugs

| IOCB No./<br>Compound No. | Structure | MW |
|---|---|---|
| Compound 11 | (structure) | 439.55 |
| Compound 13 | (structure) | 369.18 |
| Compound 14a# | (structure) | 385.41 |
| Compound 14b# (or 5c) | (structure) | 385.41 |
| Compound 15 | (structure) | 371.39 |
| Compound 17 | (structure) | 375.33 |

TABLE 1-continued

Structures of Representative DON Prodrugs

| IOCB No./Compound No. | Structure | MW |
|---|---|---|
| Compound 20 | 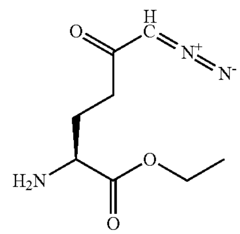 | 199.21 |
| Compound 22 | 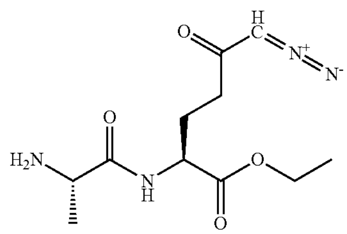 [SMILES: CCOC(=O)[C@H](CCC(=O)C=[N+]=[N-])NC(=O)[C@H](C)N] | 270.28 |
| Compound 23 | 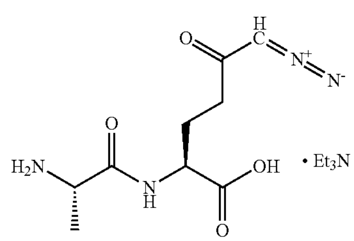 [SMILES: "· Et3N" ; C[C@H](N)C(=O)N[C@@H](CCC(=O)C=[N+]=[N-])C(=O)O] | 343.42 |
| Compound 25 | 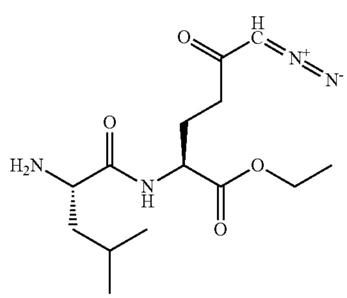 [SMILES: CCOC(=O)[C@H](CCC(=O)C=[N+]=[N-])NC(=O)[C@@H](N)CC(C)C] | 312.36 |
| Compound 26 | 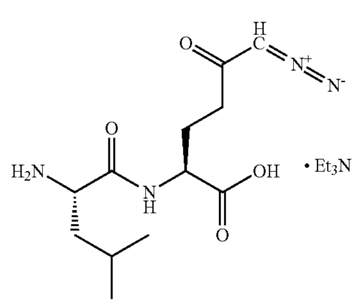 [SMILES: "· Et3N" ; CC(C)C[C@H](N)C(=O)N[C@@H](CCC(=O)C=[N+]=[N-])C(=O)O] | 385.50 |

TABLE 1-continued

Structures of Representative DON Prodrugs

| IOCB No./ Compound No. | Structure | MW |
|---|---|---|
| Compound 28 | 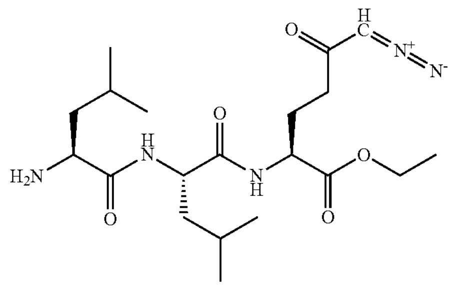 [SMILES: CCOC(=O)[C@H](CCC(=O)C=[N+]=[N-])NC(=O)[C@H](CC(C)C)NC(=O)[C@@H](N)CC(C)C] | 425.52 |
| Compound 29 | 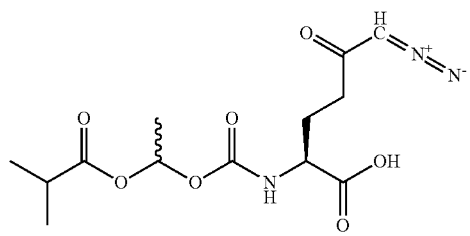 [SMILES: CC(OC(=O)N[C@@H](CCC(=O)C=[N+]=[N-])C(=O)O)OC(=O)C(C)C] | 329.31 |
| Compound 30 | 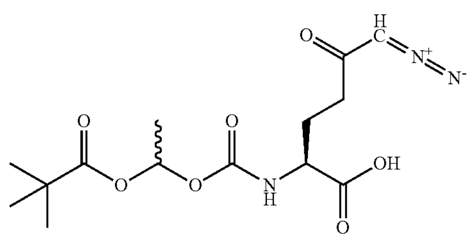 [SMILES: CC(OC(=O)N[C@@H](CCC(=O)C=[N+]=[N-])C(=O)O)OC(=O)C(C)(C)C] | 343.33 |
| Compound 31 | 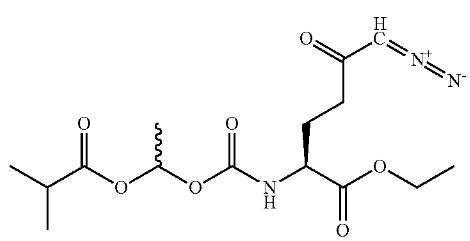 [SMILES: CCOC(=O)[C@H](CCC(=O)C=[N+]=[N-])NC(=O)OC(C)OC(=O)C(C)C] | 357.37 |
| Compound 32 | 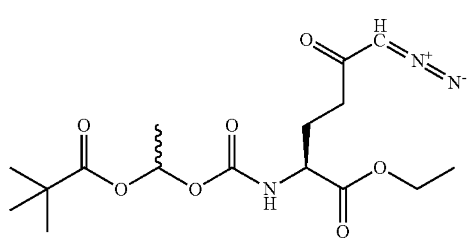 [SMILES: CCOC(=O)[C@H](CCC(=O)C=[N+]=[N-])NC(=O)OC(C)OC(=O)C(C)(C)C] | 371.39 |

TABLE 1-continued
Structures of Representative DON Prodrugs
| IOCB No./Compound No. | Structure | MW |
|---|---|---|
| Compound 34 | 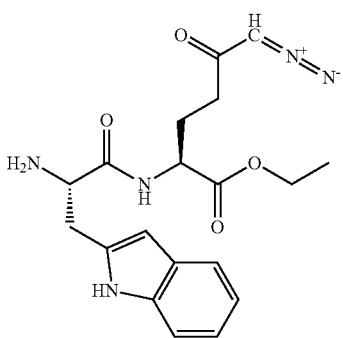 [SMILES: CCOC(=O)[C@H](CCC(=O)C=[N+]=[N-])NC(=O)[C@@H](N)Cc1cc2ccccc2[nH]1] | 385.42 |
| Compound 35 | 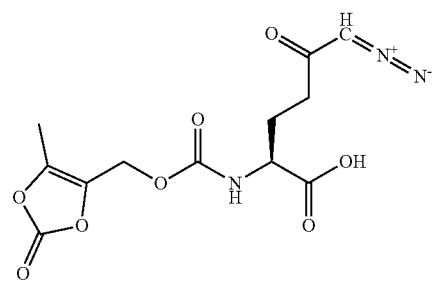 [SMILES: Cc1oc(=O)oc1COC(=O)N[C@@H](CCC(=O)C=[N+]=[N-])C(=O)O] | 327.25 |
| Compound 36 | 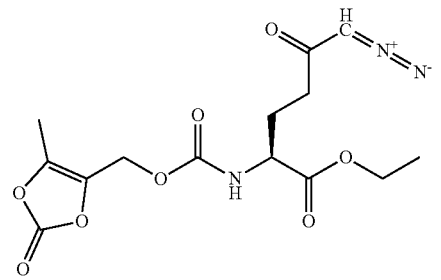 [SMILES: CCOC(=O)[C@H](CCC(=O)C=[N+]=[N-])NC(=O)OCc1oc(=O)oc1C] | 355.30 |
| Compound 38 | 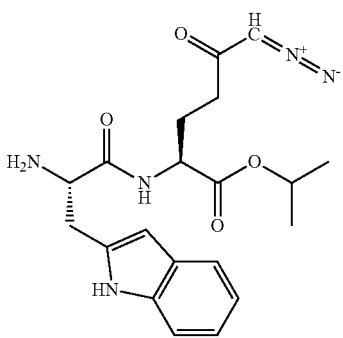 [SMILES: CC(C)OC(=O)[C@H](CCC(=O)C=[N+]=[N-])NC(=O)[C@@H](N)Cc1cc2ccccc2[nH]1] | 399.45 |

TABLE 1-continued

Structures of Representative DON Prodrugs

| IOCB No./Compound No. | Structure | MW |
|---|---|---|
| Compound 38a | 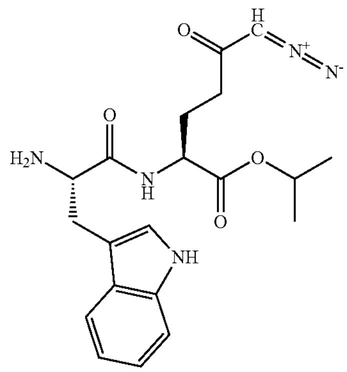 [SMILES: CC(C)OC(=O)[C@H](CCC(=O)C=[N+]=[N-])NC(=O)[C@@H](N)Cc1c[nH]c2ccccc12] | |
| Compound 40 | 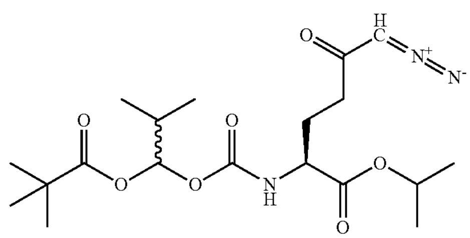 [SMILES: CC(C)OC(=O)[C@H](CCC(=O)C=[N+]=[N-])NC(=O)OC(OC(=O)C(C)(C)C)C(C)C] | 413.47 |
| Compound 42 | 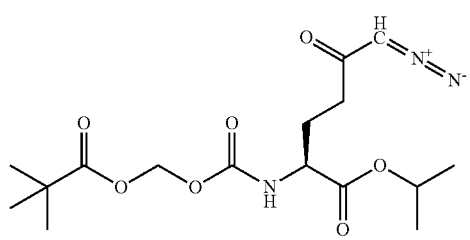 [SMILES: CC(C)OC(=O)[C@H](CCC(=O)C=[N+]=[N-])NC(=O)OCOC(=O)C(C)(C)C] | 371.39 |
| Compound 44 | 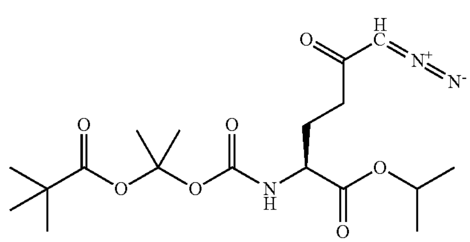 [SMILES: CC(C)OC(=O)[C@H](CCC(=O)C=[N+]=[N-])NC(=O)OC(C)(C)OC(=O)C(C)(C)C] | 2.44 |
| Compound 47 | 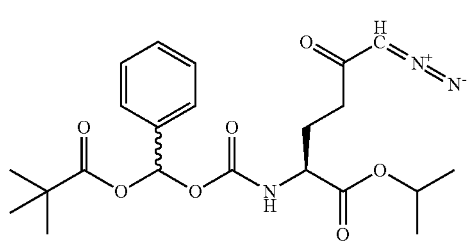 [SMILES: CC(C)OC(=O)[C@H](CCC(=O)C=[N+]=[N-])NC(=O)OC(OC(=O)C(C)(C)C)c1ccccc1] | 447.49 |

TABLE 1-continued

Structures of Representative DON Prodrugs

| IOCB No./ Compound No. | Structure | MW |
|---|---|---|
| Compound 49 | 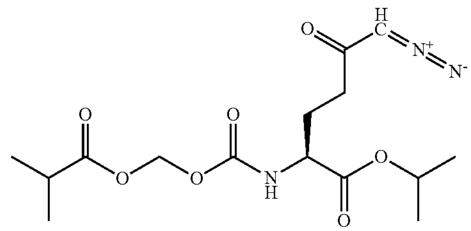 [SMILES: CC(C)OC(=O)[C@H](CCC(=O)C=[N+]=[N-])NC(=O)OCOC(=O)C(C)C] | 357.36 |
| Compound 51 | 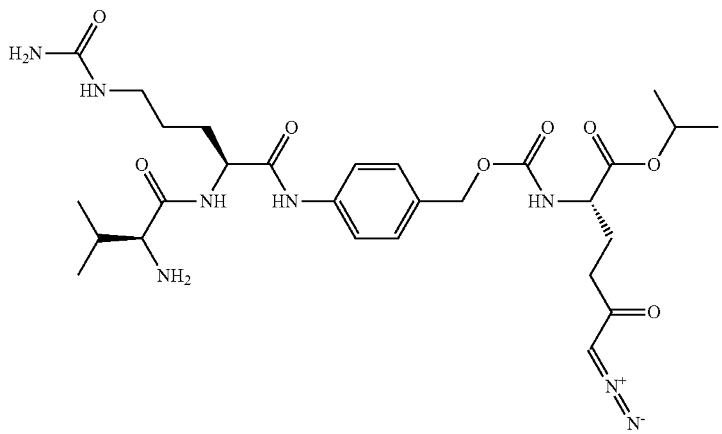 [SMILES: CC(C)OC(=O)[C@H](CCC(=O)C=[N+]=[N-])NC(=O)OCc1ccc(NC(=O)[C@H](CCCNC(N)=O)NC(=O)[C@@H](N)C(C)C)cc1] | 618.69 |
| Compound 52 | 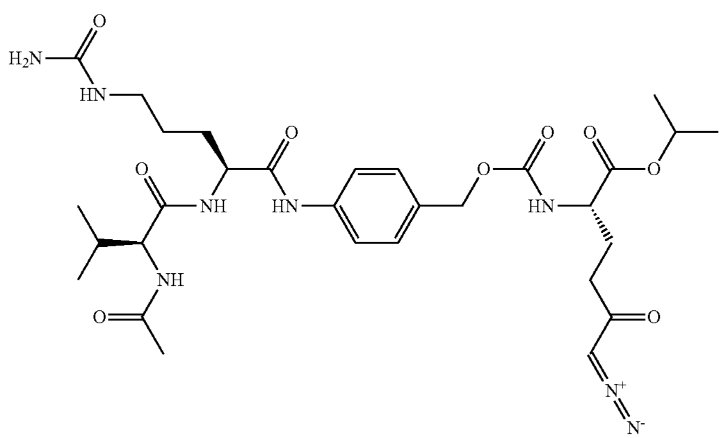 [SMILES: CC(=O)N[C@H](C(=O)N[C@@H](CCCNC(N)=O)C(=O)Nc1ccc(COC(=O)N[C@@H](CCC(=O)C=[N+]=[N-])C(=O)OC(C)C)cc1)C(C)C] | 660.73 |
| Compound 56 | 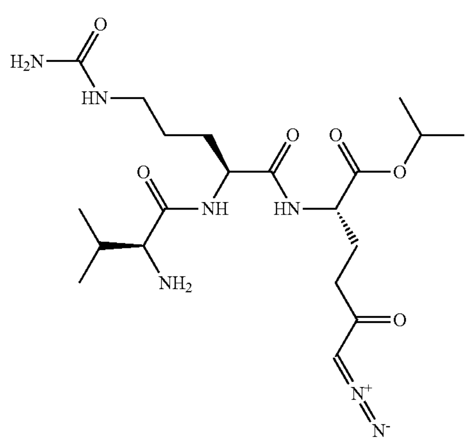 [SMILES: CC(C)OC(=O)[C@H](CCC(=O)C=[N+]=[N-])NC(=O)[C@H](CCCNC(N)=O)NC(=O)[C@@H](N)C(C)C] | 469.54 |

TABLE 1-continued

Structures of Representative DON Prodrugs

| IOCB No./Compound No. | Structure | MW |
|---|---|---|
| Compound 57 | 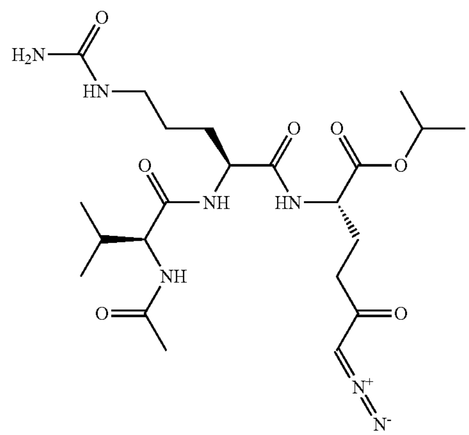 [SMILES: CC(=O)N[C@H](C(=O)N[C@@H](CCCNC(N)=O)C(=O)N[C@@H](CCC(=O)C=[N+]=[N-])C(=O)OC(C)C)C(C)C] | 511.58 |
| Compound 59 | 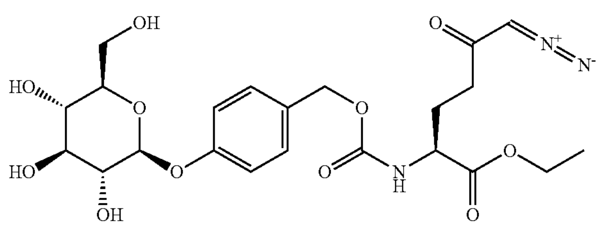 [SMILES: CCOC(=O)[C@H](CCC(=O)C=[N+]=[N-])NC(=O)OCc1ccc(O[C@@H]2O[C@H](CO)[C@@H](O)[C@H](O)[C@H]2O)cc1] | 511.48 |
| Compound 60 | 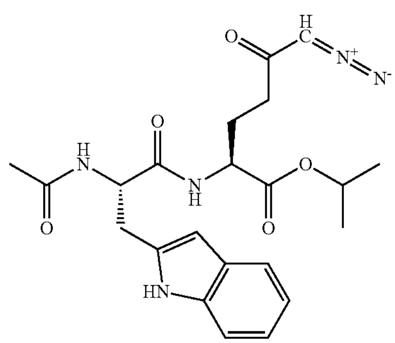 [SMILES: CC(=O)N[C@@H](Cc1cc2ccccc2[nH]1)C(=O)N[C@@H](CCC(=O)C=[N+]=[N-])C(=O)OC(C)C] | 464.19 |
| Compound 60a | 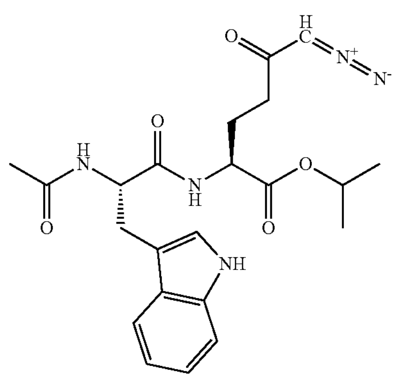 [SMILES: CC(=O)N[C@@H](Cc1c[nH]c2ccccc12)C(=O)N[C@@H](CCC(=O)C=[N+]=[N-])C(=O)OC(C)C] | |

TABLE 1-continued

Structures of Representative DON Prodrugs

| IOCB No./Compound No. | Structure | MW |
|---|---|---|
| A | 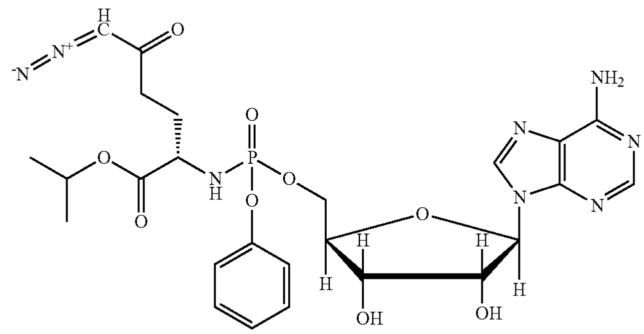 | 618.54 |
| B | 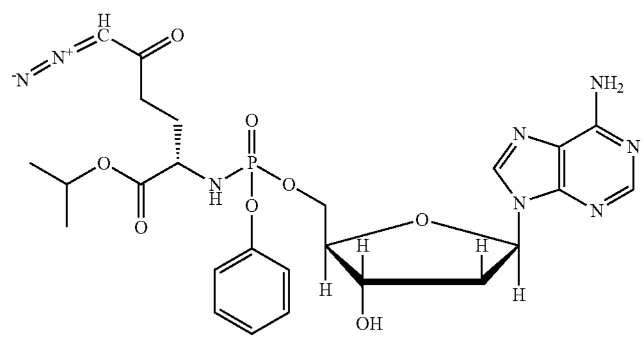 | 602.54 |
| C | 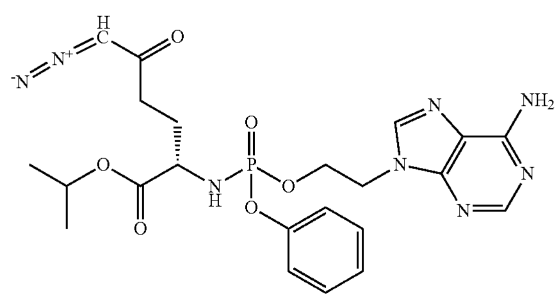 | 530.47 |
| D | 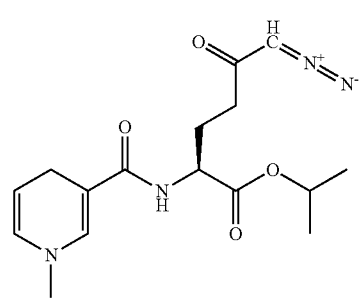 [SMILES: CC(C)OC(=O)[C@H](CCC(=O)C=[N+]=[N-])NC(=O)C1=CN(C)C=CC1] | 334.38 |

TABLE 1-continued

| Structures of Representative DON Prodrugs | | |
|---|---|---|
| IOCB No./ Compound No. | Structure | MW |
| E | 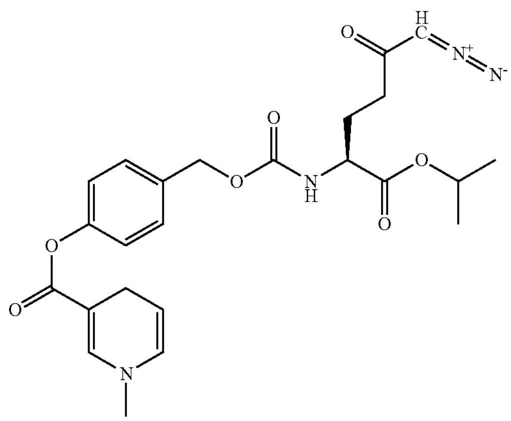 [SMILES: CC(C)OC(=O)[C@H](CCC(=O)C=[N+]=[N-])NC(=O)OCc1ccc(OC(=O)C2=CN(C)C=CC2)cc1]  | 484.51 |
| F | 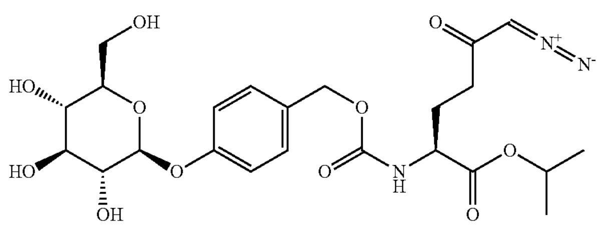  | 525.51 |
| G | 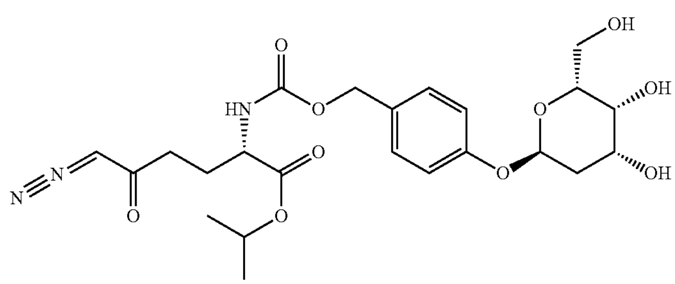 [SMILES: CC(C)OC(=O)[C@H](CCC(=O)C=[N+]=[N-])NC(=O)OCc1ccc(O[C@@H]2C[C@@H](O)[C@@H](O)[C@@H](CO)O2)cc1]  | 509.51 |
| LTP 073 | 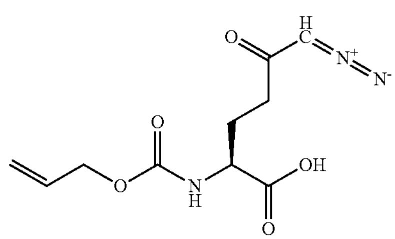 [SMILES: C=CCOC(=O)N[C@@H](CCC(=O)C=[N+]=[N-])C(=O)O]  | 255.23 |
| JAM0351 | 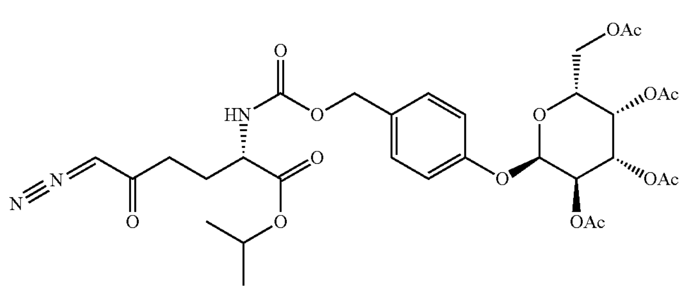 [SMILES: CC(=O)OC[C@H]1O[C@H](Oc2ccc(COC(=O)N[C@@H](CCC(=O)C=[N+]=[N-])C(=O)OC(C)C)cc2)[C@H](OC(C)=O)[C@@H](OC(C)=O)[C@H]1OC(C)=O]  | 693.66 |

TABLE 1-continued

Structures of Representative DON Prodrugs

| IOCB No./<br>Compound No. | Structure | MW |
|---|---|---|
| JAM0359 | 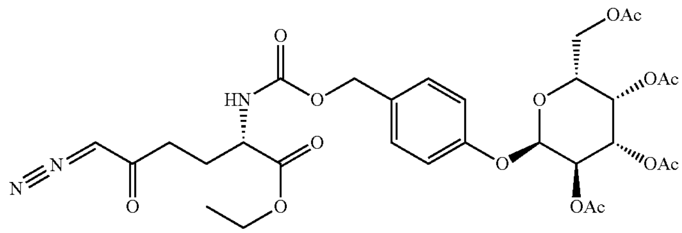 [SMILES: CCOC(=O)[C@H](CCC(=O)C=[N+]=[N-])NC(=O)OCc1ccc(O[C@H]2O[C@H](COC(C)=O)[C@H](OC(C)=O)[C@H](OC(C)=O)[C@H]2OC(C)=O)cc1] | 679.63 |

A diastereomeric mixture of isopropyl (2S)-6-diazo-5-oxo-2-(((1-(pivaloyloxy)ethoxy)carbonyl)amino)hexanoate was prepared and separated by column chromatography to give isopropyl (S)-6-diazo-5-oxo-2-((((S)-1-(pivaloyloxy)ethoxy)carbonyl)amino)hexanoate and isopropyl (S)-6-diazo-5-oxo-2-((((R)-1-(pivaloyloxy)ethoxy)carbonyl)amino)hexanoate. The S,S-isomer was arbitrarily designated compound 14a, and the S,R-isomer was arbitrarily designated compound 14b. The actual stereochemistry of the acetal methyl group was not determined. The diastereoisomer that was arbitrarily designated compound 14b was used in the biological studies described herein. See PCT/US2016/044767 (WO 2017/023774 A1), which is fully incorporated by reference herein.

1. Checkpoint Blockade

Aspects of the presently disclosed subject matter involve the use of metabolic reprogramming agents (e.g., DON, DON prodrugs, etc.) in a combination immunotherapy together with checkpoint blockade modulators, for example, to enhance checkpoint blockade therapies for the treatment of cancer. In some aspects, the presently disclosed subject matter involves the use of metabolic reprogramming agents (e.g., DON, DON prodrugs, etc.) in combination immunotherapy together with A2aR blockade, and optionally in combination with a third immunotherapy, a fourth immunotherapy, and/or a fifth immunotherapy, such as tumor vaccines, A2aR blockade, and/or adoptive cell therapy.

Accordingly, in some embodiments, the method of treating cancer further includes simultaneously or sequentially administering a therapeutically effective amount of the second immunotherapy to the subject, wherein the second immunotherapy is an immune checkpoint blockade modulator. As used herein, the term "immune checkpoint modulator" refers to an agent that totally or partially reduces, inhibits, interferes with, activates, or modulates one or more checkpoint proteins (i.e., an immune checkpoint receptor or a ligand for the immune checkpoint receptor).

Examples of immune checkpoint modulators of use herein include, but are not limited to, small organic molecules (e.g., haptens) or small inorganic molecules; saccharides; oligosaccharides; polysaccharides; a biological macromolecule selected from the group consisting of peptides (e.g., aptides), proteins, peptide analogs and derivatives; peptidomimetics; nucleic acids selected from the group consisting of miRNAs, siRNAs, shRNAs, antisense nucleic acids, such as antisense RNAs, ribozymes, and aptamers; an extract made from biological materials selected from the group consisting of bacteria, plants, fungi, animal cells, and animal tissues; naturally occurring or synthetic compositions; and any combination thereof. Other examples of immune checkpoint modulators include orthosteric inhibitors, allosteric regulators, interfacial binders, and molecular analogues of substrates that act as competitive inhibitors.

Specific examples of immune checkpoint modulators include, without limitation, PD-1 antagonists, PD-L1 antagonists, CTLA-4 antagonists, Lag-3 antagonists, CD137 antagonists, KIR antagonists, Tim3 antagonists, Ox40 agonists, B7-H3 antagonists, and combinations thereof.

Exemplary CTLA-4 antagonists include, without limitation, ipilimumab, tremelimumab and combinations thereof.

Anti-CTLA-4 antibodies are currently undergoing clinical trials for the treatment of melanoma.

Exemplary Lag-3 antagonists include, without limitation, BMS-986016 and IMP321.

Exemplary CD137 antagonists include, without limitation, CD137-specific antibody, peptide, organic small molecule, antisense oligonucleotide, siRNA, antisense expression vector or recombinant virus. In some embodiments, the CD137-specific antibody is clone BBK-2 or clone 4B4-1, as described in WIPO International Application Publication No. WO200405513A2, which is incorporated herein by reference in its entirety.

T-cell immunoglobulin and mucin domain 3 (TIM3) antagonists (e.g., anti-TIM3 antibodies) have been described for use as immunotherapy (see, e.g., Ngiow et al. 2011). Exemplary Tim3 antagonists include, without limitation, anti-TIM3 monoclonal antibodies, for example, as described in the poster presentation by Jun et al. "Generation of antagonistic anti-TIM-3 and anti-LAG-3 monoclonal antibodies for potential novel immunotherapy combinations", available on the world wide web at http://www.tesarobio-.com/documents/2014AACRposterLB266.pdf, which is incorporated herein by reference.

Ox40 agonists are described by Linch et al., "OX40 Agonists and Combination Immunotherapy: Putting the Pedal to the Metal" *Front Oncol* 5:34; 2015, which is incorporated herein by reference in its entirety. Exemplary Ox40 agonists include, without limitation, anti-Ox40 agonists antibodies. Other exemplary Ox40 agonists include, without limitation, OX86 and Fc-OX40L.

Exemplary B7-H3 antagonists include, without limitation, MGA271.

Exemplary PD-L1 antagonists include, without limitation, BMS-936559/MDX-1105, MEDI4736, MPDL3280A, MPDL3280A, MSB0010718C, and combinations thereof. PD-L1 antagonists are currently undergoing clinical trials, for example, for the treatment of melanoma, non-small cell lung cancer, renal cell carcinoma, and ovarian cancer.

PD-1 antagonists have been reviewed (see, e.g., Dolan and Gupta 2014). Exemplary PD-1 antagonists of use herein include, without limitation, AMP-224, AMP-554, nivolumab, pembrolizumab, pidilizumab, and combinations thereof.

In some embodiments, the PD-1 antagonists comprise anti-PD-1 antibodies. Exemplary anti-PD-1 antibodies include, without limitation, atezolizumab, nivolumab, pembrolizumab, pidilizumab, and combinations thereof. PD-1 antagonists are currently undergoing clinical trials, for example, for the treatment of colorectal cancer, gastric cancer, melanoma, non-small cell lung cancer, ovarian cancer, pancreatic cancer, and renal cell carcinoma.

In particular embodiments, the presently disclosed subject matter provides a method of treating an advanced solid tumor, the method comprising: (a) administering to the subject a therapeutically effective amount of BMS-936559; and (b) sequentially or simultaneously administering to the subject a therapeutically effective amount of a metabolic reprogramming agent that decreases glutamine metabolism.

In particular embodiments, the presently disclosed subject matter provides a method of treating an advanced solid tumor, the method comprising: (a) administering to the subject a therapeutically effective amount of MEDI4736; and (b) sequentially or simultaneously administering to the subject a therapeutically effective amount of a metabolic reprogramming agent that decreases glutamine metabolism.

In particular embodiments, the presently disclosed subject matter provides a method of treating melanoma, the method comprising: (a) administering to the subject a therapeutically effective amount of MPDL3280A in combination with vemurafenib; and (b) sequentially or simultaneously administering to the subject a therapeutically effective amount of a metabolic reprogramming agent that decreases glutamine metabolism.

In particular embodiments, the presently disclosed subject matter provides a method of treating melanoma, the method comprising: (a) administering to the subject a therapeutically effective amount of MEDI4736 in combination with dabrafenib and trametinib; and (b) sequentially or simultaneously administering to the subject a therapeutically effective amount of a metabolic reprogramming agent that decreases glutamine metabolism. In particular embodiments, the presently disclosed subject matter provides a method of treating melanoma, the method comprising: (a) administering to the subject a therapeutically effective amount of MEDI4736 in combination with trametinib; and (b) sequentially or simultaneously administering to the subject a therapeutically effective amount of a metabolic reprogramming agent that decreases glutamine metabolism.

In particular embodiments, the presently disclosed subject matter provides a method of treating non-small cell lung cancer, the method comprising: (a) administering to the subject a therapeutically effective amount of MPDL3280A; and (b) sequentially or simultaneously administering to the subject a therapeutically effective amount of a metabolic reprogramming agent that decreases glutamine metabolism. In some embodiments, MPDL3280A is administered in combination with erlotinib. In particular embodiments, the presently disclosed subject matter provides a method of treating non-small cell lung cancer, the method comprising: (a) administering to the subject a therapeutically effective amount of MEDI4736; and (b) sequentially or simultaneously administering to the subject a therapeutically effective amount of a metabolic reprogramming agent that decreases glutamine metabolism. In some embodiments, MEDI4736 is administered in combination with tremelimumab.

In particular embodiments, the presently disclosed subject matter provides a method of treating renal cell carcinoma, the method comprising: (a) administering to the subject a therapeutically effective amount of MPDL3280A; and (b) sequentially or simultaneously administering to the subject a therapeutically effective amount of a metabolic reprogramming agent that decreases glutamine metabolism. In some embodiments, MPDL3280A is administered in combination with bevacizumab.

In particular embodiments, the presently disclosed subject matter provides a method of treating a solid or hematological malignancy, the method comprising: (a) administering to the subject a therapeutically effective amount of MPDL3280A; and (b) sequentially or simultaneously administering to the subject a therapeutically effective amount of a metabolic reprogramming agent that decreases glutamine metabolism.

In particular embodiments, the presently disclosed subject matter provides a method of treating a solid tumor, the method comprising: (a) administering to the subject a therapeutically effective amount of MPDL3280A; and (b) sequentially or simultaneously administering to the subject a therapeutically effective amount of a metabolic reprogramming agent that decreases glutamine metabolism. In some embodiments. MPDL3280A is administered in combination with bevacizumab and/or chemotherapy. In some embodiments, MPDL3280A is administered in combination with cobimetinib.

In particular embodiments, the presently disclosed subject matter provides a method of treating a solid tumor, the method comprising: (a) administering to the subject a therapeutically effective amount of MEDI4736; and (b) sequentially or simultaneously administering to the subject a therapeutically effective amount of a metabolic reprogramming agent that decreases glutamine metabolism. In some embodiments, MEDI4736 is administered in combination with tremelimumab.

In particular embodiments, the presently disclosed subject matter provides a method of treating a solid tumor, the method comprising: (a) administering to the subject a therapeutically effective amount of MSB0010718C; and (b) sequentially or simultaneously administering to the subject a therapeutically effective amount of a metabolic reprogramming agent that decreases glutamine metabolism.

In particular embodiments, the presently disclosed subject matter provides a method of treating advanced cancer, the method comprising: (a) administering to the subject a therapeutically effective amount of AMP-224; and (b) sequentially or simultaneously administering to the subject a therapeutically effective amount of a metabolic reprogramming agent that decreases glutamine metabolism.

In particular embodiments, the presently disclosed subject matter provides a method of treating an advanced solid tumor, the method comprising: (a) administering to the subject a therapeutically effective amount nivolumab in combination with iliolumbar (anti-KIR); and (b) sequentially or simultaneously administering to the subject a therapeutically effective amount of a metabolic reprogramming agent that decreases glutamine metabolism.

In particular embodiments, the presently disclosed subject matter provides a method of treating a castration-resistant prostate cancer, hepatocellular carcinoma, melanoma, non-small cell lung cancer, or renal cell carcinoma, the method comprising: (a) administering to the subject a therapeutically effective amount of nivolumab; and (b) sequentially or simultaneously administering to the subject a therapeutically effective amount of a metabolic reprogramming agent that decreases glutamine metabolism.

In particular embodiments, the presently disclosed subject matter provides a method of treating colon cancer, gastric cancer, head and neck cancer, Hodgkin lymphoma, melanoma, myeloma, myelodysplastic syndrome, non-Hodgkin lymphoma, non-small cell lung cancer, solid tumors, or triple-negative breast cancer, the method comprising: (a) administering to the subject a therapeutically effective amount of pembrolizumab; and (b) sequentially or simultaneously administering to the subject a therapeutically effective amount of a metabolic reprogramming agent that decreases glutamine metabolism.

In particular embodiments, the presently disclosed subject matter provides a method of treating gastric cancer, pancreatic cancer, small-cell lung cancer, glioblastoma, or triple-negative breast cancer, the method comprising: (a) administering to the subject a therapeutically effective amount of nivolumab in combination with ipilimumab; and (b) sequentially or simultaneously administering to the subject a therapeutically effective amount of a metabolic reprogramming agent that decreases glutamine metabolism.

In particular embodiments, the presently disclosed subject matter provides a method of treating a malignant glioma, the method comprising: (a) administering to the subject a therapeutically effective amount of pidilizumab; and (b) sequentially or simultaneously administering to the subject a therapeutically effective amount of a metabolic reprogramming agent that decreases glutamine metabolism.

In particular embodiments, the presently disclosed subject matter provides a method of treating pancreatic cancer, the method comprising: (a) administering to the subject a therapeutically effective amount of pidilizumab in combination with gemcitabine; and (b) sequentially or simultaneously administering to the subject a therapeutically effective amount of a metabolic reprogramming agent that decreases glutamine metabolism.

In particular embodiments, the presently disclosed subject matter provides a method of treating renal cell carcinoma, the method comprising: (a) administering to the subject a therapeutically effective amount of pidilizumab in combination with dendritic cell/RCC fusion cell vaccine; and (b) sequentially or simultaneously administering to the subject a therapeutically effective amount of a metabolic reprogramming agent that decreases glutamine metabolism.

2. Adoptive Cellular Therapy

Adoptive cell therapies (ACT) are a useful approach for treating cancer. Adoptive cell transfer refers to the passive transfer of ex vivo grown cells, often immune-derived cells, into a host with the aim of transferring the immunologic functionality and characteristics of the transplant. Adoptive cell transfer can be autologous, as is common in adoptive T-cell therapies, or allogeneic. The adoptive transfer of autologous tumor infiltrating lymphocytes (TILs) or genetically re-directed peripheral blood mononuclear cells has been used to successfully treat patients with advanced solid tumors such as melanoma as well as patients with CD19-expressing hematologic malignancies. Exemplary cell types for use in ACT include, without limitation, T-cells (e.g., CD8+ cells, CD4+ cells, etc.), NK-cells, delta-gamma T-cells, regulatory T-cells and peripheral blood mononuclear cells. Such cells can be unmodified such as in TIL therapy or genetically modified. One way to achieve genetic targeting of T-cells to tumor specific targets is the transfer of a T-cell receptor with known specificity (TCR therapy) and with matched human leukocyte antigen (HLA, known as major histocompatibility complex in rodents) type. Another way is the modification of cells with artificial molecules such as chimeric antigen receptors (CAR), commonly known as CAR-T cell therapy. For example, single chain antibodies can be used and CARs can also incorporate co-stimulatory domains.

Aspects of the presently disclosed subject matter involve the use of metabolic reprogramming agents (e.g., DON, DON prodrugs, etc.) in combination immunotherapy together with adoptive cellular therapy, for example, to enhance adoptive cellular therapy for the treatment of cancer. In some aspects, the presently disclosed subject matter involves the use of metabolic reprogramming agents (e.g., DON, DON prodrugs, etc.) in combination immunotherapy together with adoptive cellular therapy, and optionally in combination with a third immunotherapy, a fourth immunotherapy, and/or a fifth immunotherapy, such as tumor vaccines, A2aR blockade, and/or checkpoint blockade.

Accordingly, in some embodiments, the method of treating cancer further includes simultaneously or sequentially administering a therapeutically effective amount of the second immunotherapy to the subject, wherein the second immunotherapy is an adoptive cellular therapy. In some embodiments, the adoptive cellular therapy is selected from the group consisting of T-cells, CD8+ cells, CD4+ cells, NK-cells, delta-gamma T-cells, marrow infiltrating lymphocytes (MILs), regulatory T-cells, and peripheral blood mononuclear cells. In some embodiments, the adoptive cellular therapy comprises a tumor infiltrating lymphocyte (TIL). In some embodiments, the adoptive cellular therapy comprises a T-cell receptor modified lymphocyte. In some embodiments, the adoptive cellular therapy comprises a chimeric antigen receptor modified lymphocyte. In some embodiments, the adoptive cellular therapy comprises a chimeric antigen receptor T (CAR-T) cell. In some embodiments, the adoptive cellular therapy comprises marrow infiltrating lymphocytes (MILs). In some embodiments, the method of treating cancer further includes simultaneously or sequentially administering a therapeutically effective amount of the second immunotherapy to the subject, wherein the second immunotherapy is marrow-infiltrating lymphocytes (MILs).

3. Adenosine A2aR Blockade

Adenosine A2a receptor (A2aR) blockade has been reviewed and is reported to enhance tumor vaccines, checkpoint blockade and adoptive T cell therapy (see, e.g., Powell et al. 2015). Accordingly, aspects of the presently disclosed subject matter involves the use of metabolic reprogramming agents (e.g., DON, DON prodrugs, etc.) in combination immunotherapy together with adenosine A2a receptor (A2aR) blockade, for example, to enhance A2aR blockade for the treatment of cancer. In some aspects, the presently disclosed subject matter involves the use of metabolic reprogramming agents (e.g., DON, DON prodrugs, etc.) in combination immunotherapy together with A2aR blockade, and optionally in combination with a third immunotherapy, a fourth immunotherapy, or a fifth immunotherapy, such as tumor vaccines, checkpoint blockade and/or adoptive cell therapy.

In some embodiments, the method of treating cancer further includes simultaneously or sequentially administering a therapeutically effective amount of the second immunotherapy to the subject, wherein the second immunotherapy is an adenosine A2aR blockade. Exemplary A2aR inhibitors of use in the A2aR blockade as an immunotherapy include, without limitation, SCH58261, SYN115, ZM241365 and FSPTP.

In particular embodiments, the presently disclosed subject matter provides a method for treatment of a subject with a CD73-expressing tumor, the method comprising: (a) administering a therapeutically effective amount of SCH58261 to the subject; and (b) sequentially or simultaneously administering to the subject a therapeutically effective amount of a metabolic reprogramming agent that decreases glutamine metabolism. Exemplary CD73-expressing tumors include, without limitation, breast tumors (e.g., breast adenocarcinoma, metastatic breast cancer) and melanoma (e.g., metastatic). In some embodiments, the CD73-expressing tumor is a metastatic tumor and administration of SCH58261 suppresses metastases in the CD73-expressing tumor. In some embodiments, the CD73-expressing tumor is melanoma and SCH58261 and the metabolic reprogramming agent are administered in combination with an anti-PD1 antibody to prolong survival and reduce the metastatic melanoma burden. In some embodiments, the CD73-expressing tumor is breast cancer and SCH58261 and the metabolic reprogramming agent are administered in combination with an anti-PD1 antibody to prolong survival and reduce the metastatic breast cancer burden. In some embodiments, the CD73-expressing tumor is a breast cancer tumor and SCH58261 and the metabolic reprogramming agent are administered in combination with a chemotherapeutic agent (e.g., doxorubicin) to increase the sensitivity of the breast cancer tumor to the chemotherapeutic agent.

In particular embodiments, the presently disclosed subject matter provides a method for treatment of a subject with a CD73-expressing tumor, the method comprising: (a) administering a therapeutically effective amount of SYN115 to the subject; and (b) sequentially or simultaneously administering to the subject a therapeutically effective amount of a metabolic reprogramming agent that decreases glutamine metabolism. In some embodiments, an anti-PD-1 antibody is administered in combination with SYN115 and the metabolic reprogramming agent.

In particular embodiments, the presently disclosed subject matter provides a method for treatment of melanoma, the method comprising: (a) administering a therapeutically effective amount of ZM241365 to the subject; and (b) sequentially or simultaneously administering to the subject a therapeutically effective amount of a metabolic reprogramming agent that decreases glutamine metabolism. In some embodiments, an anti-CTLA4 antibody is administered in combination with ZM241365 and the metabolic reprogramming agent.

In particular embodiments, the presently disclosed subject matter provides a method for treatment of bladder cancer, the method comprising: (a) administering a therapeutically effective amount of FSPTP to the subject; and (b) sequentially or simultaneously administering to the subject a therapeutically effective amount of a metabolic reprogramming agent that decreases glutamine metabolism. In some embodiments. FSPTP is administered via intratumoral injection.

4. Killer-Cell Immunoglobulin-Like Receptor (KIR) Blockade

Aspects of the presently disclosed subject matter involve the use of metabolic reprogramming agents (e.g., DON, DON prodrugs, e.g., compounds having any one of formula (I), formula (IIA), formula (IIB), or formula (III), below.) in combination immunotherapy together with killer-cell immunoglobulin-like receptor (KIR) blockade, for example, to enhance KIR blockade for the treatment of cancer. In some aspects, the presently disclosed subject matter involves the use of metabolic reprogramming agents (e.g., DON, DON prodrugs, etc.) in combination immunotherapy together with KIR blockade, and optionally in combination with a third immunotherapy, a fourth immunotherapy, and/or a fifth immunotherapy, such as tumor vaccines, adoptive cell therapy, A2aR blockade, and/or checkpoint blockade.

In some embodiments, the method of treating cancer further includes simultaneously or sequentially administering a therapeutically effective amount of the second immunotherapy to the subject, wherein the second immunotherapy is a KIR blockade.

Exemplary KIR inhibitors of use in the KIR blockade as an immunotherapy include, without limitation, IPH2102/BMS-986015 (lirilumab).

In particular embodiments, the presently disclosed subject matter provides a method of treating acute myeloid leukemia, the method comprising: (a) administering a therapeutically effective amount of lirilumab to the subject; and (b) sequentially or simultaneously administering to the subject a therapeutically effective amount of a metabolic reprogramming agent that decreases glutamine metabolism.

In particular embodiments, the presently disclosed subject matter provides a method of treating a solid tumor, the method comprising: (a) administering a therapeutically effective amount of lirilumab to the subject; and (b) sequentially or simultaneously administering to the subject a therapeutically effective amount of a metabolic reprogramming agent that decreases glutamine metabolism. In some embodiments, the solid tumor is a melanoma tumor, and lirilumab is administered in combination with nivolumab. In some embodiments, the solid tumor is a non-small cell lung cancer tumor, and lirilumab is administered in combination with nivolumab. In some embodiments, the solid tumor is a gastrointestinal tumor and lirilumab is administered in combination with nivolumab. In some embodiments, the solid tumor is a squamous cell carcinoma of the head and neck tumor and lirilumab is administered in combination with nivolumab. In some embodiments, the solid tumor is a hepatocellular carcinoma tumor and lirilumab is administered in combination with nivolumab.

In particular embodiments, the presently disclosed subject matter provides a method of treating a hematological tumor, the method comprising: (a) administering a therapeutically effective amount of lirilumab to the subject; and (b) sequentially or simultaneously administering to the subject a therapeutically effective amount of a metabolic reprogramming agent that decreases glutamine metabolism. In some embodiments, the hematological tumor is relapsed and/or refractory non-Hodgkin's lympohoma and lirilumab is administered in combination with nivolumab. In some embodiments, the hematological tumor is relapsed and/or refractory Hodgkin's lympohoma and lirilumab is administered in combination with nivolumab. In some embodiments, the hematological tumor is relapsed and/or refractory multiple myeloma and lirilumab is administered in combination with nivolumab. In some embodiments, the hematological tumor is relapsed and/or refractory chromic myelogenous leukemia and lirilumab is administered in combination with nivolumab.

In particular embodiments, the presently disclosed subject matter provides a method of treating relapsed and/or refractory multiple myeloma post autologous transplant, the method comprising: (a) administering a therapeutically effective amount of lirilumab to the subject optionally in combination with elotuzumab; and (b) sequentially or simultaneously administering to the subject a therapeutically effective amount of a metabolic reprogramming agent that decreases glutamine metabolism.

In particular embodiments, the presently disclosed subject matter provides a method of treating relapsed and/or refractory acute myeloid leukemia, the method comprising: (a) administering a therapeutically effective amount of lirilumab to the subject optionally in combination with 5-azacytidine; and (b) sequentially or simultaneously administering to the subject a therapeutically effective amount of a metabolic reprogramming agent that decreases glutamine metabolism.

5. Vaccines

Vaccines stimulate the body's immune system to attack abnormal or malignant ells, such as cancer, resulting in a reduction of the those cells. Cancer or tumor vaccines typically contain a tumor antigen in an immunogenic formulation that stimulates tumor antigen-specific helper cells, CTLs and/or B cells. Exemplary formulations of vaccines include, without limitations, dendritic cells (e.g., autologous dendritic cells pulsed with tumor cells or antigens), heterologous tumor cells transfected with immunostimulant agents, such as GM-CSF, recombinant virus, and/or peptides or proteins administered with adjuvants, such as CpG.

Aspects of the presently disclosed subject matter involve combination immunotherapy using metabolic reprogramming agents (e.g., that decrease glutamine metabolism (e.g., DON or a DON prodrug, e.g, compounds having any one of formula (I), formula (IIA), formula (IIB), or formula (III)) sequentially or simultaneously with vaccines, for example, for the treatment of cancer. It is believed that when used as a combination immunotherapy with vaccines the metabolic reprogramming agents can help delay or stop cancer cell growth, cause tumor shrinkage, prevent cancer from recurring, and/or eliminate cancer cells that have not been eradicated by other treatments.

Accordingly, in some embodiments, the method of treating cancer further includes simultaneously or sequentially administering a therapeutically effective amount of the second immunotherapy to the subject, wherein the second immunotherapy is a vaccine (e.g., tumor vaccine).

Exemplary such vaccines include, without limitation, peptide vaccines, dendritic cell (DC) vaccines. EGFRvIII vaccines, mesothilin vaccine, G-VAX, listeria vaccines, and a dentritic cell/RCC fusion cell vaccine.

In particular embodiments, the presently disclosed subject matter provides a method for the treatment or prevention of a human papillomavirus (HPV)-associated cancer in a subject in need thereof, the method comprising: (a) administering to the subject a therapeutically effective amount of a recombinant HPV vaccine; and (b) simultaneously or sequentially administering a therapeutically effective amount of a metabolic reprogramming agent that decreases glutamine metabolism.

In some embodiments, the subject has an oncogenic HPV-type 6 infection and the rHPV vaccine comprises a rHPV type 6 vaccine. In some embodiments, the subject has an oncogenic HPV-type 11 infection and the rHPV vaccine comprises a rHPV type 11 vaccine. In some embodiments, the subject has an oncogenic HPV-type 16 infection and the rHPV vaccine comprises a rHPV type 16 vaccine. In some embodiments, the subject has an oncogenic HPV-type 18 infection and the rHPV vaccine comprises a rHPV type 18 vaccine. In some embodiments, the subject is a female and the cancer is selected from the group consisting of cervical, vaginal and vulvar cancer. In some embodiments, the subject is a female between the 9 and 26 years old. In some embodiments, the subject is a female between 9 and 26 years old and the HPV-associated cancer is cervical cancer. In some embodiments, the subject is a female between 9 and 26 years old and the HPV-associated cancer is vaginal cancer. In some embodiments, the subject is a female between 9 and 26 years old and the HPV-associated cancer is vulvar cancer. In some embodiments, the subject is male or female and the HPV-associated cancer comprises anal cancer. In some embodiments, the subject is a male or female between 9 and 26 years old and the HPV-associated cancer is anal cancer. In some embodiments, the HPV vaccine comprises GARDASIL. In some embodiments, the subject is a female between 10 and 25 years old and the HPV-associated cancer is cervical cancer. In some embodiments, the HPV vaccine comprises CERVARIX. In some embodiments, the HPV vaccine is administered intramuscularly via injection as a suspension.

In particular embodiments, the presently disclosed subject matter provides a method for the treatment or prevention of a hepatitis B-associated cancer in a subject in need thereof, the method comprising: (a) administering to the subject a therapeutically effective amount of a hepatitis B vaccine; and (b) simultaneously or sequentially administering a therapeutically effective amount of a metabolic reprogramming agent that decreases glutamine metabolism. In some embodiments, the subject has a hepatitis B virus infection and the cancer is liver cancer.

6. Passive Immunotherapy

Aspects of the presently disclosed subject matter involve combination immunotherapy using metabolic reprogramming agents (e.g., that decrease glutamine metabolism (e.g., DON or a DON prodrug, e.g., compounds having any one of formula (I), formula (IIA), formula (IIB), or formula (III)) sequentially or simultaneously with passive immunotherapy antibodies for the treatment of cancer.

Accordingly, in some embodiments, the method of treating cancer further includes simultaneously or sequentially administering a therapeutically effective amount of the second immunotherapy to the subject, wherein the second immunotherapy is a passive immunotherapy antibody. As used herein, "passive immunotherapy antibody" refers to monoclonal antibodies targeted to cancer cell-surface specific antigens to provide cancer immunity without actively stimulating a patient's immune system.

Exemplary passive immunotherapy antibodies of use herein include, without limitation, bevacizumab (e.g., AVASTIN), cetuximab (e.g., ERBITUX), rituximab (e.g., RITUXAN), trastuzumab (e.g., HERCEPTIN), alemtuzumab (e.g., CAMPATH), ibritumomab tiuxetan (e.g., ZEVALIN), panitumumab (e.g., VECTIBIX).

In particular embodiments, the presently disclosed subject matter provides a method for treatment of a subject with metastatic colorectal cancer, the method comprising: (a) administering a therapeutically effective amount of bevacizumab to the subject; and (b) sequentially or simultaneously administering to the subject a therapeutically effective amount of a metabolic reprogramming agent that decreases glutamine metabolism. In some embodiments, bevacizumab is administered as a first- or second-line treatment in combination with intravenous 5-fluorouracil-based chemotherapy. In some embodiments, bevacizumab is administered as a second-line treatment in combination with fluoropyrimidine-based (combined with irinotecan or oxaliplatin) chemotherapy after cancer progression following a first-line treatment that includes bevacizumab.

In particular embodiments, the presently disclosed subject matter provides a method for treatment of a subject with non-small cell lung cancer, the method comprising: (a) administering a therapeutically effective amount of bevacizumab to the subject; and (b) sequentially or simultaneously administering to the subject a therapeutically effective amount of a metabolic reprogramming agent that decreases glutamine metabolism. In some embodiments, the non-small cell lung cancer comprises advanced nonsquamous non-small cell lung cancer and bevacizumab is administered to subjects who have not received chemotherapy for their advanced disease in combination with carboplatin and paclitaxel.

In particular embodiments, the presently disclosed subject matter provides a method for treatment of a subject with platinum-resistant ovarian cancer, the method comprising: (a) administering a therapeutically effective amount of bevacizumab to the subject; and (b) sequentially or simultaneously administering to the subject a therapeutically effective amount of a metabolic reprogramming agent that decreases glutamine metabolism. In some embodiments, the subject has had no more than two prior chemotherapy treatments and bevacizumab is used to treat plantinum-resistant recurrent epithelial ovarian, fallopian tube or primary peritoneal cancer in the subject in combination with paclitaxel, pegylated liposomal doxorubicin or topotecan.

In particular embodiments, the presently disclosed subject matter provides a method for treatment of a subject with advanced cervical cancer, the method comprising: (a) administering a therapeutically effective amount of bevacizumab to the subject; and (b) sequentially or simultaneously administering to the subject a therapeutically effective amount of a metabolic reprogramming agent that decreases glutamine metabolism. In some embodiments, the subject has persistent, recurrent, or metastatic cervical cancer and bevacizumab is administered in combination with paclitaxel and cisplatin. In some embodiments, the subject has persistent, recurrent, or metastatic cervical cancer and bevacizumab is administered in combination with paclitaxel and topotecan.

In particular embodiments, the presently disclosed subject matter provides a method for treatment of a subject with metastatic renal cell carcinoma, the method comprising: (a) administering a therapeutically effective amount of bevacizumab to the subject; and (b) sequentially or simultaneously administering to the subject a therapeutically effective amount of a metabolic reprogramming agent that decreases glutamine metabolism. In some embodiments, the subject has metastatic kidney cancer and bevacizumab is administered in combination with interferon alfa.

In particular embodiments, the presently disclosed subject matter provides a method for treatment of a subject with recurrent glioblastoma, the method comprising: (a) administering a therapeutically effective amount of bevacizumab to the subject; and (b) sequentially or simultaneously administering to the subject a therapeutically effective amount of a metabolic reprogramming agent that decreases glutamine metabolism. In some embodiments, the subject with recurrent glioblastoma is an adult.

In particular embodiments, the presently disclosed subject matter provides a method for treatment of a subject with head and neck cancer, the method comprising: (a) administering a therapeutically effective amount of cetuximab to the subject; and (b) sequentially or simultaneously administering to the subject a therapeutically effective amount of a metabolic reprogramming agent that decreases glutamine metabolism. In some embodiments, the subject has locally or regionally advanced squamous cell carcinoma of the head and neck and cetuximab is administered in combination with radiotherapy. In some embodiments, the subject has recurrent locoregional disease or metastatic squamous cell carcinoma of the head and neck and cetuximab is administered in combination with platinum-based therapy with 5-FU. In some embodiments, the subject has recurrent or metastatic squamous cell carcinoma of the head and neck and has failed to respond to prior platinum-based therapy.

In particular embodiments, the presently disclosed subject matter provides a method for treatment of a subject with metastatic colorectal cancer, the method comprising: (a) administering a therapeutically effective amount of cetuximab to the subject; and (b) sequentially or simultaneously administering to the subject a therapeutically effective amount of a metabolic reprogramming agent that decreases glutamine metabolism. In some embodiments, the metastatic colorectal cancer comprises KRAS wild-type, epidermal growth factor rector (EGFR)-expressing, metastatic colorectal cancer, and cetuximab is administered in combination with FOLFIRI (irinotecan, 5-fluorouracil, and lucovorin). In some embodiments, the metastatic colorectal cancer comprises KRAS wild-type, epidermal growth factor rector (EGFR)-expressing, metastatic colorectal cancer, the subject is refractory to irinotecan-based chemotherapy, and cetuximab is administered in combination with irinotecan. In some embodiments, the metastatic colorectal cancer comprises KRAS wild-type, epidermal growth factor rector (EGFR)-expressing, metastatic colorectal cancer, and the subject has failed to respond to oxaliplatin and irinotecan-based chemotherapy. In some embodiments, the metastatic colorectal cancer comprises KRAS wild-type, epidermal growth factor rector (EGFR)-expressing, metastatic colorectal cancer, and the subject is inteolerant to irinotecan.

In particular embodiments, the presently disclosed subject matter provides a method for treatment of a subject with non-Hodgkin's lymphoma, the method comprising: (a) administering a therapeutically effective amount of rituximab to the subject; and (b) sequentially or simultaneously administering to the subject a therapeutically effective amount of a metabolic reprogramming agent that decreases glutamine metabolism.

In some embodiments, the subject has recurrent or refractory low-grade or follicular CD20-positive non-Hodgkin's lymphoma. In some embodiment, the subject has newly diagnosed CD20-positive non-Hodgkin's lymphoma. In some embodiments, the subject has low-grade or follicular CD20-positive non-Hodgkin's lymphoma and responded to initial treatment with CVP chemotherapy (cyclophosphamide, vincristine and prednisone). In some embodiments, the subject has CD20-positive diffuse large B-cell non-Hodgkin's lymphoma and the rituximab is administered in combination with CHOP chemotherapy (cyclophosphamide, doxorubicin hydrochloride, vincristine and prednisolone). In some embodiments, the subject has newly diagnosed or recurrent CD20-positive chronic lymphocytic leukemia and the rituximab is administered in combination with FC chemotherapy (fludarabine and cyclophosphamide).

In particular embodiments, the presently disclosed subject matter provides a method for treatment of a subject with early-stage breast cancer that is human epidermal growth factor receptor 2-positive (HER2+), the method comprising: (a) administering a therapeutically effective amount of alemtuzumab to the subject; and (b) sequentially or simultaneously administering to the subject a therapeutically effective amount of a metabolic reprogramming agent that decreases glutamine metabolism.

In some embodiments, alemtuzumab is administered to the subject as part of a treatment course comprising doxorubicin, cyclophosphamide and either paclitaxel or docetaxel. In some embodiments, alemtuzumab is administered to the subject with docetaxel and carboplatin. In some embodiments, alemtuxumab is administered to the subject after treatment with anhtracylcine-based therapy. In some embodiments, the HER2+ breast cancer has spread into the subject's lymph nodes. In some embodiments, the HER2+ breast cancer has not spread into the subject's lymph nodes and the cancer is estrogen receptor/progesterone receptor (ER/PR)-negative or has one high risk feature selected from the group consisting of a tumor size >2 cm, age <35 years, or tumor grade of 2 or 3.

In particular embodiments, the presently disclosed subject matter provides a method for treatment of a subject with B-cell chronic lymphocytic leukemia (B-CLL), the method comprising: (a) administering a therapeutically effective amount of alemtuzumab to the subject; and (b) sequentially or simultaneously administering to the subject a therapeutically effective amount of a metabolic reprogramming agent that decreases glutamine metabolism.

In particular embodiments, the presently disclosed subject matter provides a method for treatment of a subject with low-grade or follicular B-cell non-Hodgkin's lymphoma (NHL) that has relapsed during or after treatment with other anticancer drugs or newly diagnosed follicular NHL following a response to initial anticancer therapy, the method comprising: (a) administering a therapeutically effective amount of ibritumomab tiuxetan to the subject; and (b) sequentially or simultaneously administering to the subject a therapeutically effective amount of a metabolic reprogramming agent that decreases glutamine metabolism. In some embodiments, administering ibritumomab tiuxetan comprises intravenous injection comprising two infusions of rituximab (e.g., to reduce the number of B-cells in the subject's blood) and one injection of Yttrium-90 ibritumomab tiuxetan.

In particular embodiments, the presently disclosed subject matter provides a method for treatment of a subject with wild-type KRAS (exon 2 in codons 12 or 13) metastatic colorectal cancer, the method comprising: (a) administering a therapeutically effective amount of panitumumab to the subject as a first-line therapy in combination with folinic acid, fluorouracil and oxaliplatin; and (b) sequentially or simultaneously administering to the subject a therapeutically effective amount of a metabolic reprogramming agent that decreases glutamine metabolism.

In particular embodiments, the presently disclosed subject matter provides a method for treatment of a subject with wild-type KRAS (exon 2 in codons 12 or 13) metastatic colorectal cancer, the method comprising: (a) administering a therapeutically effective amount of panitumumab following disease progression after prior treatment with fluoropyrimidine, oxalipltin, and irinotecan-containing chemotherapy; and (b) sequentially or simultaneously administering a therapeutically effective amount of a metabolic reprogramming agent that decreases glutamine metabolism.

7. Combination Immunotherapy

Aspects of the presently disclosed subject matter involve the use of metabolic reprogramming agents (e.g., DON, DON-prodrugs, e.g., compounds having any one of formula (I), formula (IIA), formula (IIB), or formula (III)) in combination immunotherapy together with a second, third, fourth, and/or fifth immunotherapy, for example, to enhance the immunotherapy for the treatment of cancer.

In some embodiments, the method of treating cancer further includes simultaneously or sequentially administering a therapeutically effective amount of a third immunotherapy to the subject, wherein the third immunotherapy is selected from the group consisting of checkpoint blockade, adoptive cell therapy, CAR-T cell therapy, marrow-infiltrating lymphocytes, A2aR blockade, KIR blockade, vaccines (e.g., tumor vaccines), passive immunotherapy antibodies, and combinations thereof.

In some embodiments, the method of treating cancer further includes simultaneously or sequentially administering a therapeutically effective amount of a third and/or fourth immunotherapy to the subject, wherein the third and/or fourth immunotherapy is selected from the group consisting of checkpoint blockade, adoptive cell therapy, CAR-T cell therapy, marrow-infiltrating lymphocytes, A2aR blockade, KIR blockade, vaccines (e.g., tumor vaccines), passive immunotherapy antibodies, and combinations thereof.

In some embodiments, the method of treating cancer further includes simultaneously or sequentially administering a therapeutically effective amount of a third, fourth, and/or fifth immunotherapy to the subject, wherein the third, fourth, and/or fifth immunotherapy is selected from the group consisting of checkpoint blockade, adoptive cell therapy, CAR-T cell therapy, marrow-infiltrating lymphocytes, A2aR blockade, KIR blockade, vaccines (e.g., tumor vaccines), passive immunotherapy antibodies, and combinations thereof.

8. Adjuvant to Cancer Therapy

Aspects of the presently disclosed subject matter involve the use of metabolic reprogramming agents (e.g., DON or a DON prodrug, e.g., compounds having any one of formula (I), formula (IIA), formula (IIB), or formula (III)) as an adjuvant to cancer therapy, for example, for the treatment or prevention of cancer.

Accordingly, in some embodiments, the method of treating cancer further includes simultaneously or sequentially administering to the subject a therapeutically effective amount of a cancer therapy selected from the group consisting of: (i) chemotherapy; (ii) photodynamic therapy; (iii) proton therapy; (iv) radiotherapy; (v) surgery; and combinations thereof.

In some embodiments, the first immunotherapy, and the second immunotherapy if administered, is/are administered to the subject in the absence of chemotherapy. In some embodiments, the first immunotherapy, and the second immunotherapy if administered, is/are administered to the subject in the absence of photodynamic therapy. In some embodiments, the first immunotherapy, and the second immunotherapy if administered, is/are administered to the subject in the absence of proton therapy. In some embodiments, the first immunotherapy, and the second immunotherapy if administered, is/are administered to the subject in the absence of radiotherapy. In some embodiments, the first immunotherapy, and the second immunotherapy if administered, is/are administered to the subject in the absence of surgery.

II. Metabolic Reprogramming Agents

The presently disclosed subject matter contemplates the use of various agents in connection with the methods, uses, and compositions described herein. Certain of the methods and compositions described herein relate to the metabolic reprogramming of cells using at least one metabolic reprogramming agent described herein to treat conditions, diseases, or disorders that involve metabolically reprogrammed cells whose activation, function, growth, proliferation, and/or survival depends on increased activity of at least one, at least two, or at least three metabolic pathways selected from the group consisting of glutamine metabolism, glycolysis, and fatty acid synthesis. Aspects of the methods and compositions described herein relate to the use of least one metabolic reprogramming agent described herein to treat conditions, diseases, or disorders that involve aberrant and/or excessive amounts of at least one, at least two, or at least three metabolic pathways selected from the group consisting of aberrant and/or excessive glutamine metabolism, aberrant and/or excessive glycolysis, or aberrant and/or excessive fatty acid synthesis.

As used herein, "metabolic reprogramming agent" generally refers to an agent that modulates the metabolic activity of at least one metabolic pathway in a cell, for example, to alter activation, function, growth, proliferation, and/or survival of the cell. As used herein. "modulate" broadly means to cause or facilitate a qualitative or quantitative change, alteration, or modification in a molecule, a process, pathway, or phenomenon of interest. Without limitation, such change may be an increase, decrease, a change in binding characteristics, or change in relative strength or activity of different components or branches of the process, pathway, or phenomenon. The term "modulator" broadly refers to any molecule or agent that causes or facilitates a qualitative or quantitative change, alteration, or modification in a process, pathway, or phenomenon of interest. As used herein, the term "modulator" comprises both inhibitors and activators of a metabolic pathway or target. For example, "modulator" comprises both inhibitors and activators of expression and/or activity of a component involved glutamine metabolism, a component involved in glycolysis, and/or a component involved in fatty acid metabolism (e.g., fatty acid synthesis or fatty acid oxidation).

As used herein, the phrase "modulation of a metabolic pathway" refers to modulation of activity of at least one component of the metabolic pathway. It is contemplated herein that modulator of the metabolic pathway can be, for example, a receptor ligand (e.g., a small molecule, an antibody, a siRNA), a ligand sequestrant (e.g., an antibody, a binding protein), a modulator of phosphorylation of a pathway component or a combination of such modulators. One of skill in the art can easily test an agent to determine if it modulates a metabolic pathway by assessing, for example, phosphorylation status of a receptor or expression or synthesis of downstream proteins or enzymes controlled by the pathway in cultured cells and comparing the results to cells not treated with a modulator. A modulator is determined to be a metabolic pathway modulator if the level of phosphorylation of the receptor or expression of or synthesis of downstream proteins or enzymes in a culture of cells is reduced by at least 20% compared to the level of phosphorylation of the receptor or expression or synthesis of downstream proteins or enzymes in cells that are cultured in the absence of the modulator; preferably the level of phosphorylation or expression or synthesis of downstream proteins or enzymes is altered by at least 30%, at least 40%, at least 50%, at least 60%, at least 70%, at least 80%, at least 90%, at least 95%, or at least 99% in the presence of a metabolic pathway modulator.

The terms "decrease", "reduced", "reduction", "decrease" or "inhibit" are all used herein generally to mean a decrease by a statistically significant amount. However, for avoidance of doubt, "reduced", "reduction", "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90%, where the decrease is less than 100%. In one embodiment, the decrease includes a 100% decrease (e.g. absent level as compared to a reference sample), or any decrease between 10-100% as compared to a reference level.

The terms "increased", "increase", "enhance" or "activate" are all used herein to generally mean an increase by a statically significant amount; for the avoidance of any doubt, the terms "increased", "increase", "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

Certain methods, compositions, and agents contemplated herein modulate an immune response. In the contexts of decreasing an immune response (e.g., inhibiting an immunosuppressive pathway, e.g., via checkpoint blockade, A2aR blockade, KIR blockade, etc.), the methods, compositions, and agents contemplated herein can decrease the immune response by at least about 10%, 20%, 30%, 40%, 50%, 60%, 70%, 80, 90%, or as much as 100% as compared to a reference level (e.g., an objective measure of the immune response before employing the method, composition, and/or agent). In the contexts of increasing an immune response (e.g., activating a T-cell co-stimulatory signal), the methods, compositions, and agents contemplated herein can increase the immune response by at least about 10%, 20%, 30%, 40%, 50%, 60%, 70%, 80, 90%, or as much as 100%, at least about a 2-fold, or at least about a 3-fold, or at least about a 4-fold, or at least about a 5-fold or at least about a 10-fold increase, or any increase between 2-fold and 10-fold or greater as compared to a reference level (e.g., an objective measure of the immune response before employing the method, composition, and/or agent).

Certain methods, compositions, and agents contemplated herein modulate growth, proliferation, metastasis, and invasion of malignant cells (e.g., cancer cells). In the contexts of inhibiting growth, proliferation, metastasis, invasion, and/or survival of malignant cells (e.g., cancer cells), the methods, compositions, and agents contemplated herein can decrease the growth, proliferation, metastasis, invasion, and/or survival of malignant cells (e.g., cancer cells) by at least about 10%/o, 20%, 30%, 40%, 50%, 60%, 70%, 80, 90%, or as much as 100% as compared to a reference level (e.g., an objective measure of the growth, proliferation, metastasis, invasion, and/or survival of malignant cells before employing the method, composition, and/or agent).

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

As used more particularly herein in some contexts, "modulates", "modulating", and "modulation" are used interchangeably and refer to any one or a combination of a decrease in glutamine metabolism, a decrease in glycolysis, and a decrease in fatty acid synthesis. In other contexts, "modulates", "modulating", and "modulation" are used interchangeably and refer to any one or a combination of an increase in glutamine metabolism, an increase in glycolysis, and an increase in fatty acid synthesis. In certain contexts, "modulates", "modulating", and "modulation" are used interchangeably and refer to any one or a combination of an increase in oxidative phosphorylation.

Glutamine (2-amino-4-carbamoylbutanoic acid), is used by the cell for both bioenergetic and biosynthetic needs. Glutamine can be used as an amino acid for protein synthesis, as a carbon source, or as the primary nitrogen donor for multiple essential biosynthetic reactions in the cell. Once taken up by the cell, much of the glutamine is converted to glutamate by mitochondrial glutaminase. Both glutamine and glutamate contribute to anabolic metabolism glutamine supplies nitrogen for nucleotide and hexosamine synthesis while glutamate is the nitrogen donor for the synthesis of many nonessential amino acids. Glutamate can be used to support the production of NADPH or converted to the metabolic intermediates pyruvate and α-ketoglutarate. As used herein, the term "glutamine metabolism" or "glutamine metabolic activity" refers to the chemical reactions, enzymes, and pathways involving glutamine. As used herein, the term "glutamine metabolic pathway" is a biochemical pathway that involves glutamine.

As can be envisioned by a person with skill in the art, a metabolic reprogramming agent can modulate any of the chemical reactions, enzymes and/or pathways involving glutamine. In some embodiments, at least one metabolic reprogramming agent can modulate chemical reactions, enzymes and/or pathways that do not directly involve glutamine, such as the conversion of pyruvate to acetyl CoA or the citric acid cycle, but indirectly affect any of the chemical reactions, enzymes and/or pathways involving glutamine. Certain methods, compositions, and metabolic reprogramming agents contemplated herein decrease glutamine metabolism in cells. In the context of decreasing glutamine metabolism in cells, the methods, compositions, and agents contemplated herein can decrease glutamine metabolism in cells by at least about 10%, 20%, 30%, 40%, 50%, 60%, 70%, 80, 90%, or as much as 100% as compared to a reference level (e.g., an objective measure of the glutamine metabolic activity before employing the method, composition, and/or agent).

In some embodiments, at least one metabolic reprogramming agent is a glutamine antagonist (i.e., an agent that decrease glutamine metabolism). As used herein, the term "glutamine antagonist" refers to an agent that blocks or interferes with the synthesis or use of glutamine in a cell, and preferably in a cell that is part of a living organism. When it is said that the glutamine antagonist interferes with the synthesis of glutamine, it is meant that the antagonist acts to reduce the amount or rate of glutamine synthesis to less than the amount or rate that would be experienced in the absence of the glutamine antagonist. When it is said that the glutamine antagonist interferes with the use of glutamine, it is meant that the antagonist acts to inhibit or block a metabolic pathway downstream of glutamine, that is, a pathway in which glutamine acts as a precursor of one or more non-glutamine compounds, or that the antagonist acts to deplete glutamine in a cell or an organism by reacting the glutamine to form a non-glutamine product, or by reversibly or irreversibly binding with glutamine to reduce its availability.

In some embodiments, at least one metabolic reprogramming agent of the presently disclosed subject matter can be a glutamine analog that interferes with a glutamine metabolic pathway, an antagonist that inhibits the synthesis of glutamine, a glutamine depleting enzyme, a compound that reacts with glutamine under intracellular conditions to form a non-glutamine product, an antagonist that inhibits glutamine uptake by cells, an agent that inhibits glutamine oxidation, an agent that inhibits a glutamine transporter, an agent that inhibits glutaminolysis (a series of biochemical reactions by which glutamine is lysed to glutamate, aspartate, carbon dioxide, pyruvate, lactate, alanine and/or citrate), or a glutamine binding compound that reduces the biological availability of glutamine. It should be recognized that a compound that is a useful metabolic reprogramming agent may have two or more of these characteristics. For example, a compound that is a glutamine analog that interferes with a glutamine metabolic pathway might also act as an antagonist that inhibits the synthesis of glutamine.

In some embodiments, at least one metabolic reprogramming agent can be an antagonist that inhibits the synthesis of glutamine. Examples of compounds having this activity include inhibitors of glutamine synthase (EC 6.3.1.2), such as L-methionine-DL-sulfoximine, and phosphinothricin; inhibitors of glutamate synthase (EC 1.4.1.13); inhibitors of amidophosphoribosyltransferase (EC 2.4.2.14); and inhibitors of glutamate dehydrogenase; and mixtures of any two or more of these.

In some embodiments, at least one metabolic reprogramming agent can be a glutamine depleting enzyme. Examples of such enzymes include carbamoyl-phosphate synthase (EC 6.3.5.5), glutamine-pyruvate transaminase (EC 2.6.1.15), glutamine-tRNA ligase (EC 6.1.1.18), glutaminase (EC 3.5.1.2), D-glutaminase (EC 3.5.1.35), glutamine N-acyltransferase (EC2.3.1.68), glutaminase-asparaginase (in particular glutaminase-asparaginase of *Pseudomonas* 7a and *Acinatobacter* sp.), and mixtures of any two or more of these.

In some embodiments, at least one metabolic reprogramming agent can be a compound that reacts with glutamine under intracellular conditions to form a non-glutamine product. An example of a compound having this property is phenylbutyrate (See Darmaun et al., Phenylbutyrate-induce glutamine depletion in humans: effect on leucine metabolism, pp. E801-E807, in Glutamine Depletion and Protein Catabolism, Am. Physiol. Soc. (1998)). Another example of a glutamine antagonist having this characteristic is phenylacetate (See, U.S. Pat. No. 6,362,226).

In some embodiments, at least one metabolic reprogramming agent can be an antagonist that inhibits glutamine uptake by cells. Examples of compounds having this property include alpha-methylaminoisobutyric acid (inhibits GynT plasma membrane glutamine transporter; See, Varoqui et al., *J. Biol. Chem.*, 275(6):4049-4054 (2000), wortmannin, and LY-294002 (inhibits hepatic glutamine transporter; See, Pawlik et al., *Am. J. Physiol. Gastrointest. Liver Physiol.*, 278:G532-G541 (2000)).

In some embodiments, at least one metabolic reprogramming agent can be a glutamine binding compound that reduces the biological availability of glutamine.

In some embodiments, at least one metabolic reprogramming agent can be a glutamine analog that interferes with a glutamine metabolic pathway (e.g., decreases glutamine metabolism/metabolic activity). Examples of compounds that can act in this manner include acivicin (L-(alpha S,5S)-alpha-amino-3-chloro-4,5-dihydro-5-isoxazoleacetic acid), DON (6-diazo-5-oxo-L-norleucine), azaserine, azotomycin, chloroketone (L-2-amino-4-oxo-5-chloropentanoic acid), $N^3$-(4-methoxyfumaroyl)-L-2,3-diaminopropanoic acid (FMDP) (inactivates glucosamine-6-phosphate synthase (EC 2.6.1.16), See, Zgòdka et al., *Microbiology* 147:1955-1959 (2001)), (3S,4R)-3,4-dimethyl-L-glutamine, (3S,4R)-3,4-dimethyl-L-pyroglutamic acid (See, Acevedo et al., *Tetrahedron.*, 57:6353-6359 (2001)), 1,5-N,N'-disubstituted-2-(substituted benzenesulphonyl) glutamamides (See, Srikanth et al., *Bioorganic and Medicinal Chemistry*, (2002)), or a mixture of any two or more of these. In some embodiments, at least one metabolic reprogramming agent is selected from the group consisting of acivicin (L-(alpha S, 5S)-alpha-amino-3-chloro-4,5-dihydro-5-isoxazoleacetic acid), azaserine, 6-diazo-5-oxo-norleucine (DON), and 5-diazo-4-oxo-L-norvaline (L-DONV).

In some embodiments, at least one metabolic reprogramming agent is a prodrug of a glutamine analog that interferes with a glutamine metabolic pathway (e.g., decreases glutamine metabolism/metabolic activity). In some embodiments, at least one metabolic reprogramming agent is a prodrug of acivicin (L-(alpha S, 5S)-alpha-amino-3-chloro-4,5-dihydro-5-isoxazoleacetic acid), azaserine, 6-diazo-5-oxo-norleucine (DON), and 5-diazo-4-oxo-L-norvaline (L-DONV). Suitable exemplary prodrugs of acivicin, azaserine, DON, and L-DONV can be found in "Prodrugs of Glutamine Analogs" (PCT/US2016/044767 (WO 2017/023774 A1), and herein incorporated by reference in its entirety).

Glycolysis is the metabolic pathway that converts glucose into pyruvate with the concurrent production of ATP. Pyruvate is a metabolic intermediate that can then enter the tricarboxylic acid (TCA) cycle within mitochondria to produce NADH and $FADH_2$. The first step in glycolysis is the phosphorylation of glucose by hexokinase to form glucose 6-phosphate.

In some embodiments, at least one metabolic reprogramming agent can modulate any of the chemical reactions and/or enzymes involved in glycolysis. In some embodiments, at least one metabolic reprogramming agent can modulate chemical reactions, enzymes and/or pathways that do not directly involve glycolysis, but indirectly affect any of the chemical reactions, enzymes and/or pathways involving glycolysis. Certain methods, compositions, and metabolic reprogramming agents contemplated herein decrease glycolysis in cells. In the context of decreasing glycolysis in cells, the methods, compositions, and agents contemplated herein can decrease glycolysis in cells by at least about 10%, 20%, 30%, 40%, 50%, 60%, 70%, 80, 90%, or as much as 100% as compared to a reference level (e.g., an objective measure of the glycolytic metabolic activity before employing the method, composition, and/or agent). As used herein, the term "glycolytic metabolic activity" refers to the chemical reactions and enzymes involving the glycolysis pathway.

In some embodiments, at least one metabolic reprogramming agent of the presently disclosed subject matter can be an agent that interferes with glycolysis or a related pathway that affects glycolysis; an agent that inhibits the synthesis of pyruvate and/or one of the intermediate products of glycolysis; an agent that inhibits one or more of the enzymes involved in glycolysis, such as hexokinase, phosphoglucose isomerase, phosphofructokinase, fructose-bisphosphate aldolase, triophosphate isomerase, glyceraldehyde phosphate dehydrogenase, phosphoglycerate kinase, phosphoglycerate mutase, enolase, and/or pyruvate kinase; an agent that depletes glucose-6-phosphate, one of the rate-limiting products in glycolysis; an agent that inhibits glucose uptake and/or transport across the plasma membrane by cells; or a glucose binding compound that reduces the biological availability of glucose. It should be recognized that a compound that is a useful metabolic reprogramming agent may have two or more of these characteristics.

In some embodiments, at least one metabolic reprogramming agent interferes or inhibits the expression and/or activity of hexokinase. Examples of inhibitors of hexokinase include, but are not limited to, 2-deoxyglucose (2-DG), 3-bromopyruvate (3-BrPA), lonidamine (LND), sodium fluoride, and potassium fluoride. In some embodiments, at least one metabolic reprogramming agent is 2-deoxy-D-glucose (2-DG).

Fatty acid synthesis is the process in the cell that creates fatty acids from acetyl-CoA and malonyl-CoA precursors. Fatty acid oxidation is the process by which fatty acid molecules are broken down in the mitochondria to generate acetyl-CoA, which enters the citric acid cycle, and NADH and $FADH_2$, which are used in the electron transport chain. The enzyme AMP-activated protein kinase (AMPK) plays a role in cellular energy homeostasis and is a stimulator of fatty acid oxidation.

In some embodiments, at least one metabolic reprogramming agent can modulate any of the chemical reactions and/or enzymes involved in fatty acid synthesis and/or fatty acid oxidation. In some embodiments, at least one metabolic reprogramming agent can modulate chemical reactions, enzymes and/or pathways that do not directly involve fatty acid synthesis and/or fatty acid oxidation, but indirectly affect any of the chemical reactions, enzymes and/or pathways involving fatty acid synthesis and/or fatty acid oxidation.

Certain methods, compositions, and metabolic reprogramming agents contemplated herein decrease fatty acid synthesis and/or increase fatty acid oxidation in cells. In the context of decreasing fatty acid synthesis and/or increasing fatty acid oxidation in cells, the methods, compositions, and agents contemplated herein can decrease fatty acid synthesis and/or increase fatty acid oxidation in cells by at least about 10%, 20%, 30%, 40%, 50%, 60%, 70%, 80, 90%, or as much as 100% as compared to a reference level (e.g., an objective measure of the synthesis of fatty before employing the method, composition, and/or agent).

In some embodiments, at least one metabolic reprogramming agent of the presently disclosed subject matter can be an agent that interferes with fatty acid synthesis and/or fatty acid oxidation or a related pathway that affects fatty acid synthesis and/or fatty acid oxidation; an agent that increases fatty acid oxidation; an agent that increases one or more of the products of fatty acid oxidation; an agent that increases the expression and/or activity of one or more of the enzymes involved in fatty acid oxidation, such as acyl CoA dehydrogenase, enoyl CoA hydratase, 3-hydroxyacyl-CoA dehydrogenase, and β-ketothiolase; an agent that increases expression and/or activity of AMP-activated protein kinase (AMPK); an agent that increases uptake and/or transfer of activated fatty acids across the mitochondrial membrane; and an agent that increases the expression and/or activity of enzymes involved in the uptake and/or transfer of activated fatty acids across the mitochondrial membrane. It should be recognized that a compound that is a useful metabolic reprogramming agent may have two or more of these characteristics. In some embodiments, at least one metabolic reprogramming agent is an activator of 5' AMP-activated protein kinase (AMPK) activity.

At least one metabolic reprogramming agent that is an activator of AMPK activity can be an agent that increases concentrations of AMP in the cell; an AMP analogue, such as 5-amino-4-imidazolecarboxamide ribotide (ZMP); an agent that increases phosphorylation of AMPK, such as an agent that increases the expression and/or activity of a kinase that can phosphorylate AMPK; and an agent that is an allosteric modulator of AMPK, such as one that can modify AMPK to make it a better substrate for a kinase that can phosphorylate AMPK.

In some embodiments, at least one metabolic reprogramming agent is metformin.

It should be appreciated that modulation of glutamine metabolism, glycolysis, and fatty acid metabolism may result in modulation of one or more genes or expression products of genes or biosynthesis or degradation of one or more enzymes.

The term "expression" means the process by which information from a gene or nucleic acid (e.g., DNA) is used in the synthesis of gene products (e.g., mRNA, RNA and/or proteins) and includes, but is not limited to, one or more of the steps of replication, transcription and translation. The steps of expression which may be modulated by the agents contemplated herein may include, for example, transcription, splicing, translation and post-translational modification of a protein. Those skilled in the art will appreciate that the method of modulating any particular protein may depend on the type of protein (e.g., protein kinase, transcriptional regulator, enzyme, etc.), its function (e.g., transcriptional regulation, catalysis, phosphorylation, signal transduction, etc.), and its subcellular localization (e.g., extracellular space, cytoplasm, nucleus, membrane, etc.). Those skilled in the art will readily appreciate appropriate agents to be used for modulation depending on the particular context (e.g., type of protein, biological function, subcellular localization, composition, method of use, mode of inhibition, etc.). For example, an agent can be used to inhibit enzymatic activity of an enzyme (e.g., at least one metabolic reprogramming agent that inhibits glutaminolysis catalyzed by glutaminase (e.g., a glutamine antagonist), at least one metabolic reprogramming agent that inhibits glycolysis catalyzed in part by hexokinase (e.g., 2-DG), etc.), inhibits the level or activity of phosphorylation of a protein kinase, inhibit activation of transcription or a signaling pathway.

The metabolic reprogramming agents, chemotherapeutic agents, cytotoxic agents, immunotherapeutic agents, immunosuppressant agents, radiotherapeutic agents, anti-inflammatory agents, and neuroprotective agents described herein can be any type of agent. Exemplary types of agents that can be used as such agents in the methods, compositions, and uses described herein include small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; microcarrier or nanocarrier consisting of one or more polymers, proteins, nucleic acids, lips, or metals; and any combination thereof.

As used herein, the term "small molecule" can refer to agents that are "natural product-like," however, the term "small molecule" is not limited to "natural product-like" agents. Rather, a small molecule is typically characterized in that it contains several carbon-carbon bonds, and has a molecular weight of less than 5000 Daltons (5 kD), preferably less than 3 kD, still more preferably less than 2 kD, and most preferably less than 1 kD. In some cases it is preferred that a small molecule have a molecular weight equal to or less than 700 Daltons.

As used herein, an "RNA interference molecule" refers to an agent which interferes with or inhibits expression of a target gene or genomic sequence by RNA interference (RNAi). Such RNA interfering agents include, but are not limited to, nucleic acid molecules including RNA molecules which are homologous to the target gene or genomic sequence, or a fragment thereof, short interfering RNA (siRNA), short hairpin or small hairpin RNA (shRNA), microRNA (miRNA) and small molecules which interfere with or inhibit expression of a target gene by RNA interference (RNAi).

The term "polynucleotide" is used herein interchangeably with "nucleic acid" to indicate a polymer of nucleosides. Typically a polynucleotide is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. Polynucleotide sequence" as used herein can refer to the polynucleotide material itself and/or to the sequence information (e.g. the succession of letters used as abbreviations for bases) that biochemically characterizes a specific nucleic acid. A polynucleotide sequence presented herein is presented in a 5' to 3' direction unless otherwise indicated.

The nucleic acid molecules that modulate the metabolic pathways or targets described herein can, in some embodiments, be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. Proc. Natl. Acad. Sci. USA 91:3054-3057, 1994). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The terms "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids, such as the 20 L-amino acids that are most commonly found in proteins. However, other amino acids and/or amino acid analogs known in the art can be used. One or more of the amino acids in a polypeptide may be modified, for example, by the addition of a chemical entity, such as a carbohydrate group, a phosphate group, a fatty acid group, a linker for conjugation, functionalization, etc. A polypeptide that has a non-polypeptide moiety covalently or non-covalently associated therewith is still considered a "polypeptide". Exemplary modifications include glycosylation and palmitoylation. Polypeptides may be purified from natural sources, produced using recombinant DNA technology, synthesized through chemical means, such as conventional solid phase peptide synthesis, etc. The term "polypeptide sequence" or "amino acid sequence" as used herein can refer to the polypeptide material itself and/or to the sequence information (e.g., the succession of letters or three letter codes used as abbreviations for amino acid names) that biochemically characterizes a polypeptide. A polypeptide sequence presented herein is presented in an N-terminal to C-terminal direction unless otherwise indicated.

The term "identity" as used herein refers to the extent to which the sequence of two or more nucleic acids or polypeptides is the same. The percent identity between a sequence of interest and a second sequence over a window of evaluation, e.g., over the length of the sequence of interest, may be computed by aligning the sequences, determining the number of residues (nucleotides or amino acids) within the window of evaluation that are opposite an identical residue allowing the introduction of gaps to maximize identity, dividing by the total number of residues of the sequence of interest or the second sequence (whichever is greater) that fall within the window, and multiplying by 100. When computing the number of identical residues needed to achieve a particular percent identity, fractions are to be rounded to the nearest whole number. Percent identity can be calculated with the use of a variety of computer programs known in the art. For example, computer programs, such as BLAST2, BLASTN, BLASTP, Gapped BLAST, etc., generate alignments and provide percent identity between sequences of interest. The algorithm of Karlin and Altschul (Karlin and Altschul, Proc. Natl. Acad. Sci. USA 87:22264-2268, 1990) modified as in Karlin and Altschul, Proc. Natl. Acad. Sci. USA 90:5873-5877, 1993 is incorporated into the NBLAST and XBLAST programs of Altschul et al. (Altschul, et al., J. MoT Biol. 215:403-410, 1990). To obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs may be used. A PAM250 or BLOSUM62 matrix may be used. Software for performing BLAST analyses is publicly available through the National Center for Biotechnology Information (NCBI). See the Web site having URL www.ncbi.nlm.nih.gov for these programs. In a specific embodiment, percent identity is calculated using BLAST2 with default parameters as provided by the NCBI.

Generally, at least one metabolic reprogramming agent described herein can be used in combination with an additional therapeutic agent (e.g., a pharmaceutically active agent, e.g., a drug approved by a regulatory agency). The therapeutic agent may act synergistically with the agent described herein, or they may independently exert their intended effects. The disclosure contemplates any therapeutic agent which a skilled artisan would use in connection with a method, use, or composition described herein. Examples of therapeutic agents contemplated for use in the presently disclosed methods, uses and compositions in combination with the metabolic reprogramming agents include, but are not limited to, chemotherapeutic agents/chemotherapy, immunotherapeutic agents/immunotherapy, immunosuppressant agents, anti-inflammatory agents, neuroprotective agents, neuroregenerative agents, neurotrophic factors, radiotherapeutic agents/radiotherapy, proton therapy, photodynamic therapy, and stem and progenitor cells used to replace and/or repair endogenous populations of abnormal, harmful, or unhealthy cells.

Chemotherapy and chemotherapeutic agent are used synonymously herein. A "chemotherapeutic agent" is used to connote a compound or composition that is administered in the treatment of cancer. Chemotherapeutic agents contemplated for use in combination with at least one metabolic reprogramming agent, at least two metabolic reprogramming agents, or at least three metabolic reprogramming agents described herein include, but are not limited to, alkylating agents, such as thiotepa and cyclophosphamide; alkyl sulfonates, such as busulfan, improsulfan and piposulfan; aziridines, such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards, such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas, such as carmustine, chlorozotocin, fotemustine, lomustine, nimustine, ranimustine; antibiotics, such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, such as methotrexate and 5-fluorouracil (5-FU); folic acid analogues, such as denopterin, methotrexate, pteropterin, trimetrexate; purine analogs, such as fludarabine, 6-mercaptopurine, thiamiprine, thioguanine; pyrimidine analogs, such as ancitabine, azacitidine, 6-azauridine, carmofur, cytosine arabinoside, dideoxyuridine, doxifluridine, enocitabine, floxuridine, 5-FU; androgens, such as calusterone, dromostanolone propionate, epitiostanol, mepitiostane, testolactone; anti-adrenals, such as aminoglutethimide, mitotane, trilostane; folic acid replenishers, such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); taxoids, e.g., paclitaxel and docetaxel; chlorambucil; gemcitabine; 6-thioguanine; mercaptopurine; platinum analogs, such as cisplatin and carboplatin; vinblastine; platinum; etoposide; ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylornithine; retinoic acid; esperamicins; capecitabine; and pharmaceutically acceptable salts, acids or derivatives of any of the above. Chemotherapeutic agents also include anti-hormonal agents that act to regulate or inhibit hormone action on tumors, such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens, such as flutamide, nilutamide, bicalutamide, leuprolide, and goserelin; and pharmaceutically acceptable salts, acids or derivatives of any of the above.

In some embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide, and irinotecan, as well as pharmaceutically acceptable salts, acids, or derivatives of any of these.

In some embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these.

In certain embodiments, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain alternative embodiments, the antimitotic agent comprises a vinca alkaloid, such as vincristine, binblastine, vinorelbine, or vindesine, or pharmaceutically acceptable salts, acids, or derivatives thereof.

As used herein, the term "immunotherapeutic agent" refers to a molecule that can aid in the treatment of a disease by inducing, enhancing, or suppressing an immune response in a cell, tissue, organ or subject. Examples of immunotherapeutic agents contemplated for use in combination with at least one metabolic reprogramming agent, at least two metabolic reprogramming agents, or at least three metabolic reprogramming agents described herein include, but are not limited to, immune checkpoint molecules (e.g., antibodies to immune checkpoint proteins), interleukins (e.g., IL-2, IL-7, IL-12, IL-15), cytokines (e.g., interferons, G-CSF, imiquimod), chemokines (e.g., CCL3, CCL26, CXCL7), vaccines (e.g., peptide vaccines, dendritic cell (DC) vaccines, EGFRvIII vaccines, mesothilin vaccine, G-VAX, listeria vaccines), and adoptive T cell therapy including chimeric antigen receptor T cells (CAR T cells).

As used herein, "immunosuppressant agent" means an agent which may be used in immunotherapy to reduce or prevent an immune response in a cell, organ, tissue, or subject. Examples of immunosuppressant agents contemplated for use in combination with at least one metabolic reprogramming agent, at least two metabolic reprogramming agents, or at least three metabolic reprogramming agents include, without limitation, corticosteriods, calcineurin inhibitors, antiproliferative agents, SIP receptor agonists, kinase inhibitors, monoclonal antilymphocyte antibodies and polyclonal antilymphocyte antibodies. Non-limiting examples of corticosteroids include Prednisone (Deltasone® and Orasone®) and Methylprednisolone (SoluMedrol®). Non-limiting examples of calcineurin inhibitors include Cyclosporine (Cyclosporin A, SangCya, Sandimmune®, Neoral®, Gengraf®), ISA, Tx247, ABT-281, ASM 981 and Tacrolimus (Prograf®, FK506). Non-limiting examples of antiproliferative agents include Mycophenolate Mofetil (CellCept®), Azathioprene (Imuran®), and Sirolimus (Rapamune®). Non-limiting examples of SIP receptor agonists include FTY 720 or analogues thereof. Non-limiting examples of kinase inhibitors include mTOR kinase inhibitors, which are compounds, proteins or antibodies that target, decrease or inhibit the activity and/or function of members of the serine/threonine mTOR family. These include, without limitation, CCI-779, ABT578, SAR543, rapamycin and derivatives or analogs thereof, including 40-O-(2-hydroxyethyl)-rapamycin, rapalogs, including AP23573, AP23464, AP23675 and AP23841 from Ariad, Everolimus (CERTICAN, RAD001), biolimus 7, biolimus 9 and sirolimus (RAPAMUNE). Kinase inhibitors also include protein kinase C inhibitors, which include the compounds described the PCT publications WO 2005/097108 and WO 2005/068455, which are herein incorporated by reference in their entireties. Non-limiting examples of monoclonal anti-lymphocyte antibodies include Muromonab-CD3 (Orthoclone OKT3®), Interleukin-2 Receptor Antagonist (Basiliximab, Simulect®), and Daclizumab (Zenapax®). Non-limiting examples of polyclonal antilymphocyte antibodies include Antithymocyte globulin-equine (Atgam®) and Antithymocyte globulin-rabbit (RATG, Thymoglobulin®). Other immunosuppressants include, without limitation, SERP-1, a serine protease inhibitor produced by malignant rabbit fibroma virus (MRV) and myxoma virus (MYX), described in US Patent Publication No. 2004/0029801, which is incorporated herein by reference.

Immunosuppressant agents can be classified according to their specific molecular mode of action. The four main categories of immunosuppressant drugs currently used in treating patients with transplanted organs are the following. Calcineurin inhibitors inhibit T-cell activation, thus preventing T-cells from attacking the transplanted organ. Azathioprines disrupt the synthesis of DNA and RNA as well as the process of cell division. Monoclonal antibodies inhibit the binding of interleukin-2, which in turn slows down the production of T-cells in the patient's immune system. Corticosteroids suppress inflammation associated with transplant rejection.

Immunosuppressants can also be classified according to the specific organ that is transplanted. Basiliximab (Simulect) is also used in combination with such other drugs as cyclosporine and corticosteroids in kidney transplants. IL-2 blockers, including Simulect from Novartis, FK506 or Cy A, MMF, prednisone or Rapamycin are also used in kidney transplants. Daclizumab (Zenapax) is also used in combination with such other drugs as cyclosporin and corticosteroids in kidney transplants. Similar drugs are used in heart transplants, but anti-lymphocyte globulin (ALG) is often used instead of Simulect. Muromonab CD3 (Orthoclone OKT3) is used along with cyclosporine in kidney, liver and heart transplants. Tacrolimus (Prograf) is used in liver and kidney transplants. It is under study for bone marrow, heart, pancreas, pancreatic island cell and small bowel transplantation.

As used herein, "photodynamic therapy", also known as photoradiation therapy, phototherapy, and photochemotherapy, refers to a treatment that uses photosensitizing agents in combination with light to kill cancer cells. The photosensitizing agents kill cancer cells upon light activation.

As used herein, "proton therapy", also known as proton beam therapy, refers to a treatment that uses a beam of protons to irradiate and kill cancer cells.

As used herein, "anti-inflammatory agent" refers to an agent that may be used to prevent or reduce an inflammatory response or inflammation in a cell, tissue, organ, or subject. Exemplary anti-inflammatory agents contemplated for use in combination with at least one metabolic reprogramming agent, at least two metabolic reprogramming agents, or at least three metabolic reprogramming agents include, without limitation, steroidal anti-inflammatory agents, a nonsteroidal anti-inflammatory agent, or a combination thereof. In some embodiments, anti-inflammatory agents include clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. The anti-inflammatory agent may also be a biological inhibitor of proinflammatory signaling molecules including antibodies to such biological inflammatory signaling molecules.

Exemplary neuroprotective agents include, without limitation, L-dopa, dopamine agonists (e.g., apomorphine, bromocriptine, pergolide, ropinirole, pramipexole, or cabergoline), adenosine A2a antagonists (Shah et al., Curr. Opin. Drug Discov. Devel. 13:466-80 (2010)); serotonin receptor agonists; continuous-release levodopa (Sinemet CR®, MSD, Israel); continuous duodenal levodopa administration (Duodopa®, Abbott, UK); catechol-O-methyltransferase (COMT) inhibitors (e.g., Stalevo®, Novartis Pharma, USA; entacapone (Comtan®, Novartis Pharma, USA)); tolcapone; coenzyme Q10, and/or MAO-B inhibitors (e.g., Selegiline or Rasagiline). Additional neuroprotective agents are described in. e.g., Hart et al., Mov. Disord. 24: 647-54 (2009).

As used herein, a "radiotherapeutic agent" refers to those agents conventionally adopted in the therapeutic field of cancer treatment and includes photons having enough energy for chemical bond ionization, such as, for instance, alpha ($\alpha$), beta ($\beta$), and gamma ($\gamma$) rays from radioactive nuclei as well as x-rays. The radiation may be high-LET (linear energy transfer) or low-LET. LET is the energy transferred per unit length of the distance. High LET is said to be densely ionizing radiation and Low LET is said to be sparsely ionizing radiation. Representative examples of high-LET are neutrons and alpha particles. Representative examples of low-LET are x-ray and gamma rays. Low LET radiation including both x-rays and γrays is most commonly used for radiotherapy of cancer patients. The radiation may be used for external radiation therapy that is usually given on an outpatient basis or for internal radiation therapy that uses radiation that is placed very close to or inside the tumor. In case of internal radiation therapy, the radiation source is usually sealed in a small holder called an implant. Implants may be in the form of thin wires, plastic tubes called catheters, ribbons, capsules, or seeds. The implant is put directly into the body. Internal radiation therapy may require a hospital stay. The ionizing radiation source is provided as a unit dose of radiation and is preferably an x-ray tube since it provides many advantages, such as convenient adjustable dosing where the source may be easily turned on and off, minimal disposal problems, and the like. A unit dose of radiation is generally measured in gray (Gy). The ionizing radiation source may also comprise a radioisotope, such as a solid radioisotopic source (e.g., wire, strip, pellet, seed, bead, or the like), or a liquid radioisotopic filled balloon. In the latter case, the balloon has been specially configured to prevent leakage of the radioisotopic material from the balloon into the body lumen or blood stream. Still further, the ionizing radiation source may comprise a receptacle in the catheter body for receiving radioisotopic materials like pellets or liquids. The radioisotopic material may be selected to emit $\alpha$, $\beta$ and $\gamma$. Usually, $\alpha$ and $\beta$ radiations are preferred since they may be quickly absorbed by the surrounding tissue and will not penetrate substantially beyond the wall of the body lumen being treated. Accordingly, incidental irradiation of the heart and other organs adjacent to the treatment region can be substantially eliminated. The total number of units provided will be an amount determined to be therapeutically effective by one skilled in treatment using ionizing radiation. This amount will vary with the subject and the type of malignancy or neoplasm being treated. The amount may vary but a patient may receive a dosage of about 30-75 Gy over several weeks.

Exemplary radiotherapeutic agents contemplated for use in combination with at least one metabolic reprogramming agent, at least two metabolic reprogramming agents, or at least three metabolic reprogramming agents include, factors that cause DNA damage, such as γ-rays, X-rays, and/or the directed delivery of radioisotopes to tumor cells. Other forms of DNA damaging factors are also contemplated, such as microwaves and UV-irradiation. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the target cell. In some embodiments, the radiotherapeutic agent is selected from the group consisting of $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb, $^{212}$B, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193}$MPt, $^{197}$H, $^{43}$K, $^{43}$K, $^{52}$Fe, $^{57}$Co, $^{67}$Cu, $^{67}$Ga, $^{68}$Ga, $^{77}$Br, $^{81}$Rb/$^{81}$MKr, $^{87}$MSr, $^{99}$MTc, $^{111}$In, $^{113}$MIn, $^{127}$Cs, $^{129}$Cs, $^{132}$I, $^{197}$Hg, $^{203}$Pb and $^{206}$Bi, as described in U.S. Pat. No. 8,946,168, the entirety of which is incorporated herein by reference.

In some contexts, an agent described herein can be administered with an antigen (e.g., to induce an immune response). In some embodiments, an adjuvant can be used in combination with the antigen.

An agent described herein can also be used in combination with an imaging agent. An agent (e.g., a metabolic reprogramming agent) can be attached to imaging agents for imaging and diagnosis of various diseased organs, tissues or cell types. The agent can be labeled or conjugated a fluorophore or radiotracer for use as an imaging agent. Many appropriate imaging agents are known in the art, as are methods for their attachment to agents (e.g., attaching an imaging agent to a proteins or peptides using metal chelate complexes, radioisotopes, fluorescent markers, or enzymes whose presence can be detected using a colorimetric markers (such as, but not limited to, urease, alkaline phosphatase, (horseradish) hydrogen peroxidase and glucose oxidase)). An agent may also be dual labeled with a radioisotope in order to combine imaging through nuclear approaches and be made into a unique cyclic structure and optimized for binding affinity and pharmacokinetics. Such agents can be administered by any number of methods known to those of ordinary skill in the art including, but not limited to, oral administration, inhalation, subcutaneous (sub-q), intravenous (I.V.), intraperitoneal (I.P.), intramuscular (I.M.), intrathecal injection, or intratumoral injection. The methods, compositions, and uses described herein can be used alone or in combination with other techniques, to diagnose access and monitor and direct therapy of metabolic reprogramming disorders. In some contexts, the imaging agent can be used for detecting and/or monitoring tumors or sites of metastasis in a subject. For example, an agent (e.g., a metabolic reprogramming agent) can be administered in vivo and monitored using an appropriate label. Exemplary methods for detecting and/or monitoring an agent labeled with an imaging agent in vivo include Gamma Scintigraphy, Positron Emission Tomography (PET), Single Photon Emission Computer Tomography (SPECT), Magnetic Resonance Imaging (MRI), X-ray, Computer Assisted X-ray Tomography (CT). Near Infrared Spectroscopy, and Ultrasound. These techniques provide information regarding detection of neoplastic involvement, particularly of inaccessible nodes in subjects with malignant diseases. Knowledge on the size of the node and the filling of nodes can also be instructive. For example, agents or compositions targeted to the lymph nodes in detection applications will contain suitable contrast or imaging agents, such as ferromagnetic materials like iron oxide, perfluorochemicals such as perfluorooctylbromide, or gamma emitting radiolabels such as Technetium-99m, Indium-111, Gallium-67, Thallium-201, Iodine-131, 125, or 123, positron emitting radiolabels, such as Fluorine-18, or those produced by neutron activation, such as Samarium-153.

Imaging agents of use in the present disclosure include radioisotopes and dyes. Any conventional method according to radiolabeling which is suitable for labeling isotopes for in vivo use will be generally suitable for labeling detection agents according to the disclosure. Internal detection procedures include intraoperative, intravascular or endoscopic, including laparoscopic, techniques, both surgically invasive and noninvasive. For example, when detecting a lymph node, a high signal-to-background ratio should to be achieved. Therapy also requires a high absolute accretion of the therapeutic agent in the lymph node, as well as a reasonably long duration of uptake and binding.

Suitable radioisotopes for the methods of the disclosure include: Actinium-225, Astatine-211, Iodine-123, Iodine-125, Iodine-126, Iodine-131, Iodine-133, Bismuth-212, Bromine-77, Indium-111, Indium-113m, Gallium-67, Gallium-68, Ruthenium-95, Ruthenium-97, Ruthenium-103, Ruthenium-105, Mercury-107, Mercury-203, Rhenium-186, Rhenium-188, Tellurium-121m, Tellurium-122m, Tellurium-125m, Thulium-165, Thulium-167, Thulium-168, Technetium-99m, Fluorine-18, Silver-111, Platinum-197, Palladium-109, Copper-67, Phosphorus-32, Phosphorus-33, Yttrium-90, Scandium-47, Samarium-153, Lutetium-177, Rhodium-105, Praseodymium-142, Praseodymium-143, Terbium-161, Holmium-166, Gold-199, Cobalt-57, Cobalt-58, Chromium-51, Iron-59, Selenium-75, Thallium-201, and Ytterbium-169. The most preferred radioisotope for use in the presently disclosed subject matter is Technetium-99m. Preferably the radioisotope will emit a particle or ray in the 10-7,000 keV range, more preferably in the 50-1,500 keV range, and most preferably in the 80-250 keV range.

Isotopes preferred for external imaging include: Iodine-123, Iodine-131, Indium-111, Gallium-67, Ruthenium-97, Technetium-99m, Cobalt-57, Cobalt-58, Chromium-51, Iron-59, Selenium-75, Thallium-201, and Ytterbium-169. Technetium-99m is the most preferred radioisotope for external imaging in the disclosure.

Isotopes most preferred for internal detection include: Iodine-125, Iodine-123, Iodine-131, Indium-111, Technetium-99m and Gallium-67. Technetium-99m is the most preferred isotope for internal detection.

III. Uses of Metabolic Reprogramming Agents

The presently disclosed subject matter contemplates the use of at least one, at least two, or at least three metabolic reprogramming agents that decrease activity of at least one metabolic pathway selected from the group consisting of glutamine metabolism, glycolysis, and fatty acid synthesis, alone, or optionally together with one or more additional therapeutic agents described herein. Accordingly, in an aspect the presently disclosed subject matter involves the use of at least one metabolic reprogramming agent that decreases activity of at least one metabolic pathway selected from the group consisting of glutamine metabolism glycolysis, and fatty acid synthesis for treating a condition, disease, or disorder that involves (i) metabolically reprogrammed cells whose activation, function, growth, proliferation, and/or survival depends on increased activity of at least one metabolic pathway selected from the group consisting of glutamine metabolism, glycolysis, and fatty acid synthesis or (ii) at least one of aberrant and/or excessive glutamine metabolism, aberrant and/or excessive glycolysis, or aberrant and/or excessive fatty acid synthesis.

In some embodiments, the presently disclosed subject matter involves the use of at least two metabolic reprogramming agents. In some embodiments, the presently disclosed subject matter involves the use of at least three metabolic reprogramming agents.

In some aspects, the presently disclosed subject matter involves the use of at least one metabolic reprogramming agent that decreases glutamine metabolism as an immunotherapy to treat a cancer. In other aspects, the presently disclosed subject matter involves the use of at least one metabolic reprogramming agent that decreases glutamine metabolism as an immunotherapy in combination with an additional immunotherapy to treat a cancer. Examples of additional immunotherapy contemplated for use in combination with the at least one metabolic reprogramming agent include, without limitation, checkpoint blockade, adoptive cellular therapy, CAR-T cell therapy, marrow-infiltrating lymphocytes, A2aR blockade, KIR blockade, vaccines (e.g., tumor vaccines), passive immunotherapy antibodies, and combinations thereof.

In an aspect, the presently disclosed subject matter involves the use of an effective amount of at least one metabolic reprogramming agent that decreases glutamine metabolism to treat lymphoma in a subject in need thereof.

In an aspect, the presently disclosed subject matter involves the use of an effective amount of at least one metabolic reprogramming agent that decreases glutamine metabolism to treat melanoma in a subject in need thereof.

In some embodiments, a use described herein further comprises using an effective amount of at least one metabolic reprogramming agent that decreases glycolysis. In some embodiments, a use described herein further comprises uses an effective amount of at least one metabolic reprogramming agent that increases fatty acid oxidation.

IV. Pharmaceutical Compositions Comprising Metabolic Reprogramming Agents

The presently disclosed subject matter also contemplates pharmaceutical compositions comprising one or more metabolic reprogramming agents for the treatment of certain conditions, diseases, and/or disorders involving metabolically reprogrammed cells. In some embodiments, the presently disclosed methods comprise the use of the presently disclosed metabolic reprogramming agents for the manufacture of a medicament for the treatment of certain conditions, diseases, and/or disorders involve metabolically reprogrammed cells. The disclosure contemplates various pharmaceutical compositions comprising at least one, at least two, and or at least three metabolic reprogramming agents.

Accordingly, in an aspect the presently disclosed subject matter provides a pharmaceutical composition comprising an effective amount of at least one, at least two, or at least three metabolic reprogramming agents that decrease the activity of at least one metabolic pathway selected from the group consisting of glutamine metabolism, glycolysis, and fatty acid synthesis, and a pharmaceutically acceptable carrier, diluent, or excipient.

In some aspects, the presently disclosed subject matter provides a pharmaceutical composition comprising at least one metabolic reprogramming agent that decreases glutamine metabolism as an immunotherapy to treat a cancer, and a pharmaceutically acceptable carrier, diluent, or excipient. It should be appreciated that additional forms of immunotherapy are contemplated for use in combination with the pharmaceutical composition comprising at least one metabolic reprogramming agent, such as checkpoint blockade, adoptive cellular therapy, CAR-T cell therapy, marrow-infiltrating lymphocytes, A2aR blockade, KIR blockade, vaccines (e.g., tumor vaccines), passive immunotherapy antibodies, and combinations thereof.

In some embodiments, the metabolic reprogramming composition comprises one or more additional therapeutic agents described herein. Generally, the presently disclosed compositions (e.g., comprising at least one metabolic reprogramming agent) can be administered to a subject for therapy by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articular, intra-sternal, intrasynovial, intra-hepatic, intralesional, intracranial, intraperitoneal, intranasal, intraocular injections, intratumoral injections, intracisternally, topically, as by powders, ointments or drops (including eyedrops), including buccally and sublingually, transdermally, through an inhalation spray, or other modes of delivery known in the art.

The phrases "systemic administration". "administered systemically". "peripheral administration" and "administered peripherally" as used herein mean the administration of compositions comprising at least one metabolic reprogramming agent, such that it enters the patient's system and, thus, are subject to metabolism and other like processes, for example, subcutaneous administration.

The phrases "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

The presently disclosed pharmaceutical compositions can be manufactured in a manner known in the art, e.g. by means of conventional mixing, dissolving, granulating, dragee-making, levitating, emulsifying, encapsulating, entrapping or lyophilizing processes.

In some embodiments, the presently disclosed pharmaceutical compositions can be administered by rechargeable or biodegradable devices. For example, a variety of slow-release polymeric devices have been developed and tested in vivo for the controlled delivery of drugs, including proteinacious biopharmaceuticals. Suitable examples of sustained release preparations include semipermeable polymer matrices in the form of shaped articles, e.g., films or microcapsules. Sustained release matrices include polyesters, hydrogels, polylactides (U.S. Pat. No. 3,773,919; EP 58,481), copolymers of L-glutamic acid and gamma ethyl-L-glutamate (Sidman et al., Biopolymers 22:547, 1983), poly (2-hydroxyethyl-methacylate) (Langer et al. (1981) *J. Biomed. Mater. Res.* 15:167; Langer (1982), *Chem. Tech.* 12:98), ethylene vinyl acetate (Langer et al. (1981) *J. Biomed. Mater. Res.* 15:167), or poly-D-(−)-3-hydroxybutyric acid (EP 133,988A). Sustained release compositions also include liposomally entrapped compositions comprising at least one metabolic reprogramming agent which can be prepared by methods known in the art (Epstein et al. (1985) *Proc. Natl. Acad. Sci. U.S.A.* 82:3688; Hwang et al. (1980) *Proc. Natl. Acad. Sci. U.S.A.* 77:4030; U.S. Pat. Nos. 4,485,045 and 4,544,545, and EP 102,324A). Ordinarily, the liposomes are of the small (about 200-800 angstroms) unilamelar type in which the lipid content is greater than about 30 mol % cholesterol, the selected proportion being adjusted for the optimal therapy. Such materials can comprise an implant, for example, for sustained release of the presently disclosed compositions, which, in some embodiments, can be implanted at a particular, pre-determined target site.

In another embodiment, the presently disclosed pharmaceutical compositions may comprise PEGylated therapeutics (e.g., PEGylated antibodies). PEGylation is a well established and validated approach for the modification of a range of antibodies, proteins, and peptides and involves the attachment of polyethylene glycol (PEG) at specific sites of the antibodies, proteins, and peptides (Chapman (2002) *Adv. Drug Deliv. Rev.* 54:531-545). Some effects of PEGylation include: (a) markedly improved circulating half-lives in vivo due to either evasion of renal clearance as a result of the polymer increasing the apparent size of the molecule to above the glomerular filtration limit, and/or through evasion of cellular clearance mechanisms; (b) improved pharmacokinetics; (c) improved solubility—PEG has been found to be soluble in many different solvents, ranging from water to many organic solvents, such as toluene, methylene chloride, ethanol and acetone; (d) PEGylated antibody fragments can be concentrated to 200 mg/ml, and the ability to do so opens up formulation and dosing options, such as subcutaneous administration of a high protein dose; this is in contrast to many other therapeutic antibodies which are typically administered intravenously; (e) enhanced proteolytic resistance of the conjugated protein (Cunningham-Rundles et. al. (1992) *J. Immunol. Meth.* 152:177-190); (f) improved bioavailability via reduced losses at subcutaneous injection sites; (g) reduced toxicity has been observed; for agents where toxicity is related to peak plasma level, a flatter pharmacokinetic profile achieved by sub-cutaneous administration of PEGylated protein is advantageous; proteins that elicit an immune response which has toxicity consequences may also benefit as a result of PEGylation; and (h) improved thermal and mechanical stability of the PEGylated molecule.

Pharmaceutical compositions for parenteral administration include aqueous solutions of compositions comprising at least one metabolic reprogramming agent. For injection, the presently disclosed pharmaceutical compositions can be formulated in aqueous solutions, for example, in some embodiments, in physiologically compatible buffers, such as Hank's solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of compositions include fatty oils, such as sesame oil, or synthetic fatty acid esters, such as ethyl oleate or triglycerides, or liposomes. Optionally, the suspension also can contain suitable stabilizers or agents that increase the solubility of the compositions comprising at least one metabolic reprogramming agent to allow for the preparation of highly concentrated solutions.

For nasal or transmucosal administration generally, penetrants appropriate to the particular barrier to be permeated are used in the formulation. Such penetrants are generally known in the art.

Additional ingredients can be added to compositions for topical administration, as long as such ingredients are pharmaceutically acceptable and not deleterious to the epithelial cells or their function. Further, such additional ingredients should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, buffering agents, and the like can be present. The pH of the presently disclosed topical composition can be adjusted to a physiologically acceptable range of from about 6.0 to about 9.0 by adding buffering agents thereto such that the composition is physiologically compatible with a subject's skin.

Regardless of the route of administration selected, the presently disclosed compositions are formulated into pharmaceutically acceptable dosage forms, such as described herein or by other conventional methods known to those of skill in the art.

In general, the "effective amount" or "therapeutically effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like.

The term "combination" is used in its broadest sense and means that a subject is administered at least two agents. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

Further, the presently disclosed compositions can be administered alone or in combination with adjuvants that enhance stability of the agents, facilitate administration of pharmaceutical compositions containing them in certain embodiments, provide increased dissolution or dispersion, increase activity, provide adjuvant therapy, and the like, including other active ingredients. Advantageously, such combination therapies utilize lower dosages of the conventional therapeutics, thus avoiding possible toxicity and adverse side effects incurred when those agents are used as monotherapies.

The timing of administration of at least one metabolic reprogramming agent can be varied so long as the beneficial effects of the combination of these agents are achieved. Accordingly, the phrase "in combination with" refers to the administration of at least one metabolic reprogramming agent, at least two metabolic reprogramming agents, or at least three metabolic reprogramming agents, and optionally additional agents either simultaneously, sequentially, or a combination thereof. Therefore, a subject administered a combination of at least one, at least two, or at least three metabolic reprogramming agents, and optionally additional agents can receive at least one metabolic reprogramming agent, at least two metabolic reprogramming agents, and at least three metabolic reprogramming agents, and optionally additional agents at the same time (i.e., simultaneously) or at different times (i.e., sequentially, in either order, on the same day or on different days), so long as the effect of the combination of all agents is achieved in the subject.

When administered sequentially, the agents can be administered within 1, 5, 10, 30, 60, 120, 180, 240 minutes or longer of one another. In other embodiments, agents administered sequentially, can be administered within 1, 2, 3, 4, 5, 10, 15, 20 or more days of one another. Where the agents are administered simultaneously, they can be administered to the subject as separate pharmaceutical compositions, each comprising either at least one metabolic reprogramming agent, at least two metabolic reprogramming agents, or at least three metabolic reprogramming agents, and optionally additional agents, or they can be administered to a subject as a single pharmaceutical composition comprising all agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of an agent and at least one additional therapeutic agent is greater than the sum of the biological activities of the respective agents when administered individually.

Synergy can be expressed in terms of a "Synergy Index (SI)," which generally can be determined by the method described by F. C. Kull et al. Applied Microbiology 9, 538 (1961), from the ratio determined by:

$$Q_a Q_A + Q_b Q_B = \text{Synergy Index (SI)}$$

wherein:

$Q_A$ is the concentration of a component A, acting alone, which produced an end point in relation to component A:

$Q_a$ is the concentration of component A, in a mixture, which produced an end point;

$Q_B$ is the concentration of a component B, acting alone, which produced an end point in relation to component B; and $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

In another aspect, the presently disclosed subject matter provides a pharmaceutical composition including at least one metabolic reprogramming agent, at least two metabolic reprogramming agents, at least three metabolic reprogramming agents, and optionally additional agents, alone or in combination with one or more additional therapeutic agents in admixture with a pharmaceutically acceptable excipient.

More particularly, the presently disclosed subject matter provides a pharmaceutical composition comprising at least one metabolic reprogramming agent, at least two metabolic reprogramming agents, at least three metabolic reprogramming agents, and optionally additional agents, and a pharmaceutically acceptable carrier.

In therapeutic and/or diagnostic applications, the compounds of the disclosure can be formulated for a variety of modes of administration, including systemic and topical or localized administration. Techniques and formulations generally may be found in Remington: The Science and Practice of Pharmacy (20$^{th}$ ed.) Lippincott, Williams and Wilkins (2000).

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 100 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The term "instructing" a patient as used herein means providing directions for applicable therapy, medication, treatment, treatment regimens, and the like, by any means, but preferably in writing. Instructing can be in the form of prescribing a course of treatment, or can be in the form of package inserts or other written promotional material. Accordingly, aspects of the presently disclosed subject matter include instructing a patient to receive a method of treatment or use an agent to treat a metabolic reprogramming disorder described herein.

The term "promoting" as used herein means offering, advertising, selling, or describing a particular drug, combination of drugs, or treatment modality, by any means, including writing, such as in the form of package inserts. Promoting herein refers to promotion of a metabolic reprogramming agent for an indication, where such promoting is authorized by the Food and Drug Administration (FDA) as having been demonstrated to be associated with statistically significant therapeutic efficacy and acceptable safety in a population of subjects. In some embodiments, promoting is not authorized by the Food and Drug Administration (FDA) (or other health regulatory agency, such as the European Medicines Agency (EMA), and promoting is for an off-label use. Accordingly, aspects of the presently disclosed subject matter include promoting a method of treatment or use described herein.

V. General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of Formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups R$_1$, R$_2$, and the like, or variables, such as "m" and "n"), can be identical or different. For example, both R$_1$ and R$_2$ can be substituted alkyls, or R$_1$ can be hydrogen and R$_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., C$_1$-C$_{10}$ means one to ten carbons, including 1, 2, 3, 4, 5, 6, 7, 8, 9, and 10 carbons). In particular embodiments, the term "alkyl" refers to C$_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a C$_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to C$_{1-8}$ straight-chain alkyls. In other embodiments, "alkyl" refers, in particular, to C$_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —$CH_2$—$CH_2$—$N(CH_3)$—$CH_3$, —$CH_2$—S—$CH_2$—$CH_3$, —$CH_2$—$CH_{2S}$—S(O)—$CH_3$, —$CH_2$—$CH_2$—$S(O)_2$—$CH_3$, —CH=CH—O—$CH_3$, —$Si(CH_3)_3$, —$CH_2$—CH=N—$OCH_3$, —CH=CH—$N(CH_3)$—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—$Si(CH_3)_3$.

As described above, heteroalkyl groups, as used herein, include those groups that are attached to the remainder of the molecule through a heteroatom, such as —C(O)NR', —NR'R", —OR', —SR, —S(O)R, and/or —$S(O_2)R'$. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$=$CH_2$—); propylene (—$(CH_2)_3$—); cyclohexylene (—$C_6H_{10}$—); —CH=CH—CH=CH—; —CH=CH—$CH_2$—; —$CH_2CH_2CH_2CH_2$—, —$CH_2$CH=$CHCH_2$—, —$CH_2$CsCC$H_2$—, —$CH_2CH_2$CH$(CH_2CH_2CH_3)CH_2$—, —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxy (—O—CH$_2$—O—); and ethylenedioxy (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(l-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

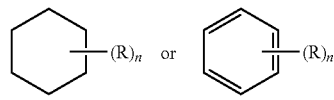

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

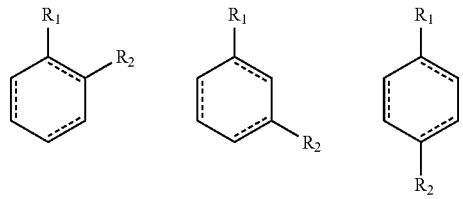

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ⁓⁓⁓ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such groups. R', R''', R'''' and R''''' each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R'', R''' and R'''' groups when more than one of these groups is present. When R' and R'' are attached to the same nitrogen atom, they can be combined with the nitrogen atom to form a 4-, 5-, 6-, or 7-membered ring. For example, —NR'R'' is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —$C(O)CH_3$, —$C(O)CF_3$, —$C(O)CH_2OCH_3$, and the like).

Similar to the substituents described for alkyl groups above, exemplary substituents for aryl and heteroaryl groups (as well as their divalent derivatives) are varied and are selected from, for example: halogen, —OR', —NR'R'', —SR', —SiR'R''R''', —OC(O)R', —C(O)R', —$CO_2$R', —C(O)NR'R'', —OC(O)NR'R'', —NR''C(O)R', —NR'—C(O)NR''R''', —NR''C(O)OR', —NR—C(NR'R''R''')=NR'''', —NR—C(NR'R'')=NR'''—S(O)R', —S(O)$_2$R', —S(O)$_2$NR'R'', —NRSO$_2$R', —CN and —NO$_2$, —R', —N$_3$, —CH(Ph)$_2$, fluoro($C_1$-$C_4$)alkoxo, and fluoro($C_1$-$C_4$)alkyl, in a number ranging from zero to the total number of open valences on aromatic ring system; and where R', R'', R''' and R'''' may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R'', R''' and R'''' groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C''R''')$_d$—, where s and d are independently integers of from 0 to 3, and X' is —O—, —NR'—, —S—, —S(O)—, —S(O)$_2$—, or —S(O)$_2$NR'—. The substituents R, R', R'' and R''' may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as a 2-(furan-2-yl)acetyl- and a 2-phenylacetyl group. Specific examples of acyl groups include acetyl and benzoyl. Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include $C_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., $C_6H_5$—$CH_2$—O—. An aralkyloxyl group can optionally be substituted.

"Alkoxycarbonyl" refers to an alkyl-O—C(=O)— group. Exemplary alkoxycarbonyl groups include methoxycarbonyl, ethoxycarbonyl, butyloxycarbonyl, and tert-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

"Carbamoyl" refers to an amide group of the formula —C(=O)NH$_2$. "Alkylcarbamoyl" refers to a R'RN—C(=O)— group wherein one of R and R' is hydrogen and the other of R and R' is alkyl and/or substituted alkyl as previously described. "Dialkylcarbamoyl" refers to a R'RN—C(=O)— group wherein each of R and R' is independently alkyl and/or substituted alkyl as previously described.

The term carbonyldioxyl, as used herein, refers to a carbonate group of the formula —O—C(=O)—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R''', wherein R', R", and R''' are each independently selected from the group consisting of alkyl groups. Additionally, R', R", and/or R''' taken together may optionally be —$(CH_2)_k$— where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(=O)— group, and can include an aldehyde group represented by the general formula R—C(=O)H.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms, such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —S($O_2$)R.

The term "sulfoxide" refers to a compound having a sulfinyl group —S(O)R

The term ureido refers to a urea group of the formula —NH—CO—$NH_2$.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure. i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids, such as glutamic acid. These salts may be prepared by methods known to those skilled in art. Also included are base addition salts, such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent or by ion exchange. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids, such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The term "wild type" refers to an organism which occurs in nature or may be isolated from the environment and does not carry any genetically engineered mutations.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments±50%, in some embodiments±20%, in some embodiments±10%, in some embodiments±5%, in some embodiments±1%, in some embodiments±0.5%, and in some embodiments±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

General Methods a. Flow Cytometry

Single cell-suspensions were stained with antibodies after Fc blocking (BD bioscience). The following antibodies and staining reagents were purchased from Biolegend: anti-CD45 (30-F11), anti-F4/80 (BM8), anti-CD11b (M1/70), Ly6C (HK1.4), Ly6G (RB6-8C5), MHC Class II (M5/114.15.2), CD90.1 (OX-7), CD8 (53-6.7), CD4 (RM4-5). Cell signaling: Calreticulin (D3E6), Thermofisher: LIVE/DEAD® Fixable Near-IR Dead Cell Stain Kit, TLR4 (UT41), CellROX™ Deep Red Flow Cytometry Assay Kit, Fixation and Permeabilization Buffer Set, and BD bioscience: TNF (MP6-XT22), GM-CSF (MP1-22E9), 7-AAD, BD, BD Cytofix/Cytoperm Plus Kit (with BD GolgiPlug) and staining were followed manufacture's protocol. Cells were acquired using BD FACSCalibur or BD FACSCelesta, and data were analyzed using FlowJo (Tree Star).

b. Generation of BMDMs

For preparation of bone marrow cell suspensions, the bones of both hind limbs (two tibias and two femurs) were flushed with ice-cold DMEM supplemented with 10% FBS, 1% penicillin/streptomycin and 2 mM L-glutamine (cell media) plus 20% L929-conditioned media. The cells were incubated at 37° C., and on day 4, non-adherent cells were removed, and washed with PBS. On day 7. BMDMs were lifted using Cellstripper (Mediatech, Manassas, Va.). BMDMs were seeded in 12-well plates, and treated with 6-Diazo-5-oxo-L-norleucine (DON, Sigma Aldrich). To make tumor-conditioned media, tumor cells were cultured in the presence or absence of DON (0.5 µM or 1 µM). After 1 hr of incubation, cells were washed and replaced with drug-free fresh media. After 24 hours, supernatants were harvested and used as conditioned media (CM). BMDM were cultured in the presence of these conditioned media for 24 hours.

c. Immunoblotting

For immunoblotting the nuclear and cytoplasm fractions, $10 \times 10^6$ cells were washed with PBS twice, then lysed cells in cytoplasm separation buffer composed of 10 mM HEPES, 60 mM KCl, 1 mM EDTA, 0.075% (v/v) NP40, 1 mM DTT and 1 mM PMSF for cytoplasm fraction, and RIPA buffer with NaF, protease inhibitor, PMSF, sodium pyrophosphate, beta glycerophosphate and sodium vanadate for nuclear fraction. Western blotting was performed using a standard protocol (Life Technologies). The following antibodies were used from Cell Signaling: anti-active caspase 3, anti-p-STAT3 (Tyr705), anti-STAT3, anti-p-NF-κB p65 (Ser536), anti-IDO, anti-LaminB, and anti-actin, and from abcam: anti-lamp2. All images were captured and analyzed using UVP BioSpectrum 500 Imaging System.

Example 1

To explore the effect of DON on cancer, an ELA mouse lymphoma model was used and it showed that DON could markedly inhibit lymphoma growth, suggesting that bone marrow derived tumors may be exquisitely susceptible to DON (FIG. 1). However, DON had a modest effect on inhibiting melanoma growth, which is a not a bone marrow derived tumor (FIG. 2).

Example 2

FIG. 3 shows that DON conditioned B16 melanoma to be killed by immunotherapy by inhibiting tumor infiltrating regulatory T cells (Foxp3$^+$).

Example 3

Summary

The glutamine antagonist 6-diazo-5-oxo-L-norleucine (DON, 1) has shown robust anti-cancer efficacy in preclinical and clinical studies, but its development was halted due to marked systemic toxicities. Herein we demonstrate that DON inhibits glutamine metabolism and provides antitumor efficacy in a murine model of gliobastoma, although toxicity was observed. To enhance DON's therapeutic index, we utilized a prodrug strategy to increase its brain delivery and limit systemic exposure. While these dual moiety prodrugs exhibited rapid metabolism in mouse plasma, several provided excellent stability in monkey and human plasma. The most stable compound (5c, methyl-POM_DON-isopropyl-ester) was evaluated in monkeys, where it achieved 10-fold enhanced brain:plasma ratio versus DON. This strategy may provide a path to DON utilization in GBM patients.

Introduction

Glioblastoma multiforme (GBM) is the most common and lethal form of glioma (Ostrom, et al., 2015). Current therapeutic options that extend survival rates in GBM patients after tumor resection are limited to radiotherapy with concomitant administration of the DNA-alkylating agent Temodar™ and/or the carmustine releasing polymer Gliadel™ (Weller, et al., 2014). But even under this standard of care, postoperative median survival rates approximate 14.6 months, (Stupp, et al., 20015) and average five-year survival is less than 10% (Stupp, et al., 2009). There is, therefore, a significant unmet medical need for more effective GBM treatments.

The ability of GBMs and other cancers rapidly and persistently proliferate often outgrowing vascular supplies necessitates that they develop a specialized metabolism (Schulze, et al., 2012; Hensley, et al., 2013). Glutamine metabolism plays an essential role in this specialized metabolism by entering the TCA cycle and then contributing to the biosynthetic pathways (nucleotide, protein and lipid synthesis) necessary for unchecked cell growth, (Hensley, et al., 2013) rendering cancer cells dependent on glutamine. This so called "glutamine addiction" has been well characterized in GBMs (Dranoff, et al., 1985; Fogal, et al., 2015; Ru. et al., 2013; Tanaka, et al., 2015) and other cancers including leukemia/lymphomas, lung, triple-negative breast cancer and pancreatic cancer (Wise, et al., 2010; Hu, et al., 2009). To combat this glutamine addiction, several groups have explored the utility of selective glutaminase inhibitors (Erickson, et al., 2010; Lee, et al., 2014). Recently compounds that selectively target glutaminase (GLS1) have been developed (McDermott, et al., 2016; Shukla, et al., 2012) and one such compound is in clinical trials (Konopleva, et al., 2015). However, the brain penetration of this GLS1 inhibitor is poor (Gross, et al., 2014) and so far the clinical efficacy of this approach has been modest (Harding, et al., 2015).

Accumulating evidence shows that, as opposed to selective inhibition of one glutamine utilizing enzyme, broadly antagonizing glutamine utilization is a highly effective means of inhibiting tumor cell growth in vitro and in vivo (Hensley. et al., 2013; Ahluwalia, et al., 1990; Dranoff. et al., Cancer Res, 1985). 6-Diazo-5-oxo-L-norleucine (DON), non-natural amino acid with structural similarity to glutamine, was first isolated from *Streptomyces* bacteria in the early 1950's. Because of its reactive diazo group, DON has demonstrated the ability to alkylate several glutamine-utilizing enzymes such as glutaminase, (Thangavelu, et al., 2014) NAD synthase, (Barclay, et al., 1966) and CTP synthetase (Hofer, et al., 2001) and FGAR aminotransferase (Grayzel, et al., 1960) in the purine and pyrimidine biosynthetic pathways, respectively. In preclinical models, DON robustly inhibited the growth of glutamine-dependent human cancer cells in vitro, and reduced tumor size and improved survival rates in vivw (Ahluwalia, et al., 1990; Cervantes-Madrid, et al., 2015). Because of the robust preclinical data, DON was evaluated in several clinical studies where it demonstrated promising results (Eagan, et al., 1982; Earhart, et al., 1982; Lynch, et al., 1982; Magill, et al., 1957; Rahman, et al., 1985; Sklaroff, et al., 1980; Sullivan, et al., 1962). For example, DON administration caused >50% regression or stable disease in late stage adult patients (Magill, et al., 1957) and in children with hematological malignancies or solid tumors (Sullivan, et al., 1988). Unfortunately, its development was hampered by dose limiting toxicities, many of which were GI-related (Magill, et al., 1957; Rahman, et al., 1985; Earhart, et al., 1990) as the GI system is highly dependent on glutamine utilization.

One strategy to improve the therapeutic index of DON for GBM therapy would be to increase its brain exposure while limiting its systemic exposure and thus toxicity (Upadhyay, et al., 2014). The prodrug approach is a well-established strategy to alter the pharmacokinetic and tissue distribution of drug molecules, however synthetically this approach is challenging with DON. Applicant has found that compounds having formula (I), formula (IIA), formula (IIB), and formula (III) exhibit unexpected enhanced CSF to plasma partitioning after administration, making them uniquely useful for the treatment of CNS cancers such as glioblastoma.

Herein we describe the efficacy of DON in a murine model of GBM, although overt toxicities were observed. Several DON prodrugs were synthesized using three types of amine promoieties including (oxodioxolenyl)methyl carbamate esters (dipeptides, and pivaloyl-oxy-methyl (POM)-based esters. The dual promoiety-containing prodrugs resulted in sufficient chemical stability permitting further evaluation in in vitro metabolic stability assays. While all of the prodrugs exhibited rapid metabolism in mouse plasma, some provided surprising plasma stability in monkeys and humans. When evaluated in vivo, the most stable DON prodrug (5c, methyl-POM-DON-isopropyl-ester) achieved an unexpected 10-fold enhanced brain: plasma ratio versus DON in monkeys, thus providing a possible clinical path to DON utilization in GBM patients.

Results and Discussion

DON Showed Robust Inhibition of Glutamine Metabolism and Antitumor Efficacy in a Murine GBM Model Despite several lines of evidence indicating the potential therapeutic efficacy of targeting glutamine metabolism in GBM, the effect of DON on GBM tumor growth has not yet been reported in vivo. Using the U87 flank xenograft mouse model of GBM, (Eshleman, et al., 2002) we first confirmed that systemic administration of DON (0.8 mg/kg, i.p) inhibited glutamine metabolism as reflected by an accumulation of endogenous glutamine in the tumor (FIG. 5A; $p<0.05$) similar to other model systems. (Willis, et al., 1977; Windmueller, et al., 1974) We next evaluated its antitumor efficacy, and observed that DON not only halted tumor growth, but also effectively induced tumor regression. Specifically, vehicle-treated mice displayed significant tumor growth over the course of the experiment, while DON-treated mice (0.8 mg/kg, i.p, q.d.) exhibited >50% reduction in tumor volume (FIG. 5B; main effect of time $[F(3,48)=6.049, p=0.0014]$; treatment $[F(1,16)=33.42, p<0.0001]$; interaction $[F(3,48)=21.70, p<0.0001]$). Although DON exhibited excellent anti-tumor efficacy, all mice receiving DON displayed significant signs of toxicity including weight loss (12±4.1%), hunching, ptosis, and lethargy. These findings are consistent with other reports of DON's efficacy and toxicity both in vitro and in vivo. (Fogal et al., 2015; Cervantes-Madrid, et al., 2015; Potter, et al., 2015)

Simple DON Alkyl Ester Prodrugs Found to be Unstable. Masking Both DON's Carboxylate and Amine Functionalities Required to Obtain Stable Prodrugs.

A prodrug strategy is often employed to enhance tissue penetration and change the pharmacokinetic parameters of effective drugs. Indeed, prodrug strategies are common in drug development as 5-7% of the approved worldwide drugs are prodrugs. (Rautio, et al., 2008) Our initial prodrug strategy for DON involved masking the carboxylic acid with simple alkyl esters such as ethyl 2a and isopropyl 2b. The synthesis of these two derivatives was straightforward affording compounds 2a and 2b in good yield. It is surprising to us that these simple DON alkyl esters had not previously been reported in the chemical literature, given that DON chemistry and utility has been described by numerous groups for over 60 years. (Magill, et al., 1957; Dion, et al., 1956; Magill, et al., 1956; Coffey, et al., 1956) One potential reason is that we discovered that 2a and 2b were unstable, slowing cyclizing to form unique diazo-imines 9a and 9b. These two unique derivatives were found to be chemically stable even at acidic pH, precluding their use as DON prodrugs.

Given the instability of simple ester prodrugs, we next masked both the primary amine and the carboxylate of DON with prodrug moieties. This dual promoiety strategy was rationalized to eliminate the potential for cyclization and potentially further improve the lipophilicity. We utilized three amine promoieties including (oxodioxolenyl)methyl carbamate esters, dipeptides, and pivaloyl-oxy-methyl (POM)-based esters. These promoeities were chosen because they target distinct metabolic enzymes including paraoxonase, aminopeptidases, and carboxylesterases, respectively. To impart further metabolic stability of the POM derivative, we prepared corresponding methyl-POM analogs. All dual promoiety-containing prodrugs exhibited sufficient chemical stability to permit further evaluation.

All DON Prodrugs were Rapidly Metabolized in Mouse Plasma, However 5b and 5c Found to be Stable in Human and Monkey Plasma Table 2 outlines the plasma stability of representative DON. All prodrugs were completely metabolized in mouse plasma within the 60 min incubation time. However in monkey and human plasma, the prodrugs 5b and 5c, with methyl-POM on the amine and ethyl or isopropyl ester on the carboxylate respectively, demonstrated moderate/high stability with 60-75% of the prodrug remaining in monkey plasma, and 80-90% remaining in human plasma within the 60 min incubation time. Given that compound 5c (also referred to as compound 14b, see Table 1) had the best stability profile in human plasma, it was selected for further evaluation in pharmacokinetic studies and compared to DON for its ability to penetrate the brain and liberate DON.

TABLE 2

Plasma stability of DON prodrugs following 60 min incubation in mouse, monkey and human plasma.

| | PLASMA STABILITY | | |
|---|---|---|---|
| Compound # | Mouse | Monkey | Human |
| 36 | 0 | 0 | 0 |
| 13 | 0 | 0 | 0 |
| 25 | 0 | 1 | 1 |
| 9 | 0 | 1 | 1 |
| 34 | 0 | 4 | 12 |
| 38 | 0 | 10 | 30 |
| 42 | 0 | 0 | 9 |
| 32 | 0 | 75 | 88 |
| 5c or 14b | 0 | 61 | 91 |

Prodrug 5c Enhanced Brain Delivery of DON in Monkeys but not in Mice

As expected from a DON prodrug which is completely metabolized in mouse plasma, we found that oral administration of DON (1) (0.8 mg/kg) and 5c (0.8 mg/kg equivalent) exhibited similar DON plasma (FIG. 6) and brain (FIG. 6) concentration profiles when dosed in mice. The $AUC_{0-t}$ of DON following administration of DON and 5c in plasma were 1.25 nmol*h/mL and 1.22 nmol*h/mL respectively, suggesting rapid and complete liberation of DON from 5c in vivo. Similarly in the mouse brain, the $AUC_{0-t}$ of DON following DON or 5c administration was 0.57 nmol*h/g and 0.69 nmol*h/g, respectively, with the brain/plasma approximately 0.46 from DON vs 0.56 from prodrug 5c. These pharmacokinetic results corroborated the in vitro metabolism studies suggesting 5c was completely converted to DON in mouse plasma.

Following the mouse studies, we evaluated the pharmacokinetics of DON and 5c in monkeys, as monkeys better mimicked the human plasma stability profile. In pigtail macaques, i.v. administration of DON and 5c (1.6 mg/kg DON equivalent) demonstrated significantly different DON plasma profiles (FIG. 7). DON administration provided high plasma exposures with $AUC_{0-t}$ of 42.7 nmol*h/mL. In contrast, 5c administration delivered ~7 fold lower plasma exposure of DON with $AUC_{0-t}$ of 5.71 nmol*h/mL. The opposite observation was seen in the CSF where enhanced DON levels were observed after 5c administration. In the CSF at 30 min post dose, DON administration resulted in 0.33 nmol/g DON while 5c delivered 1.43 nmol/g DON. When comparing plasma to CSF ratio at 30 min, 5c demonstrated 10-fold enhancement of DON CSF delivery versus DON (FIG. 7A-C).

Conclusion

We demonstrate efficacy of DON in a murine model of GBM, although overt toxicity was observed. To enhance DON's therapeutic index, we utilized a prodrug strategy to increase its brain delivery and limit its systemic exposure. While our dual promoeity prodrugs exhibited rapid metabolism in mice, our lead prodrug 5c provided excellent stability in human and monkey plasma, and achieved a 10-fold enhanced brain:plasma ratio versus DON in monkeys. This strategy may provide a path to DON utilization in GBM patients.

Mice Efficacy Studies

All mouse efficacy studies were conducted according to protocol #MO13M69 approved by the Animal Care and Use Committee at Johns Hopkins University. Female athymic (RH_Foxn1nu mice) mice between 25 and 30 g were obtained (Harlan Sprague Dawley Inc, Indianapolis, Ind.), and maintained on a 12 hour light-dark cycle with ad libitum access to food and water. U87 human glioma cells were injected s.c. ($5\times10^6$ cells in 100 ml of PBS) in four separate locations on the flanks of each mouse. When tumors grew to a mean volume of around 200 $mm^3$, mice were randomized into either vehicle (HEPES-buffered saline, i.p.) or DON (1; 0.8 mg/kg, i.p.). In one cohort, mice were administered a single dose of the appropriate solution two hours after which glutamine levels were quantified in the tumor as described previously.[49] In brief, tumors were harvested, snap frozen, and homogenized in liquid $N_2$ then subjected to metabolite extraction using methanol and DI water. Quantification was performed using Agilent 6520 Quadrupole-Time-of-Flight (Q-TOF) mass spectrometer with Agilent 1290 HPLC and using Agilent Mass Hunter and Agilent Qualitative and Quantitative Analysis Software packages. Glutamine content was averaged by group for each individual tumor (n=3-4/group), depicted as relative intensity, and analyzed by one-tailed t test. In a second cohort, efficacy experiments were conducted. Mice were injected once daily for six days; tumor volumes were measured using digital calipers and calculated according to the formula: [volume=(largest tumor dimension)×(smallest tumor dimension)$^2$×0.52] at 2, 4, and 6 days after the onset of treatment. Each individual tumor (n=8-10/group) was normalized to its pretreatment volume, averaged and analyzed by repeated measures two-way analysis of variance (ANOVA). If significant, a Bonferroni post hoc test was subsequently applied. Significance was defined as $p<0.05$.

In Vitro Metabolic Stability Studies

For metabolic stability, plasma from rodent (mouse) and non-rodent species (human and monkeys) were used. For stability, prodrugs (10 μM) were spiked in each plasma matrix and incubated in an orbital shaker at 37° C. At predetermined times (0 and 60 min), 100 μL aliquots of the mixture in duplicate were removed and the reaction quenched by addition of three times the volume of ice cold acetonitrile spiked with the internal standard (losartan 5 μM). The samples were vortexed for 30 s and centrifuged at 12000 g for 10 min. 50 μL of the supernatant was diluted with 50 μL water and transferred to a 250 μL polypropylene vial sealed with a Teflon cap. Prodrug disappearance was monitored over time using a liquid chromatography and tandem mass spectrometry (LC/MS/MS) method as described below.

Pharmacokinetic Studies in Mice

All pharmacokinetic studies in mice were conducted according to protocol (#MO13M113) approved by the Animal Care and Use Committee at Johns Hopkins University. C57BL/6 mice between 25 and 30 g were obtained from Harlan, and maintained on a 12 hour light-dark cycle with ad libitum access to food and water. To evaluate the brain and plasma pharmacokinetics of DON and its prodrug 5c, 8-12 week old C57BL/6 were administered DON (1; 0.8 mg/kg, p.o. in phosphate-buffered saline) and its prodrug 5c (at 0.8 mg/kg equivalent DON (1), p.o. in phosphate-buffered saline with 5% EtOH and 5% Tween-80). The mice were sacrificed by pentobarbital injection at 10, 30 and 90 minutes post drug administration, and blood was collected via cardiac puncture and placed into iced EDTA coated BD microtainers. Blood samples were spun at 2,000 g for 15 minutes, and plasma was removed and stored at −80° C. Brain tissues were harvested following blood collection and immediately snap frozen in liquid nitrogen and stored at −80° C. until LC/MS analysis.

Pharmacokinetic Studies in Non-Human Primates

All monkey studies were conducted according to protocol (#PR15M298) approved by the Animal Care and Use Committee at Johns Hopkins University. Two female pigtail monkeys (approximately 3.5 kg, non-drug naive) were adjacently housed in stainless steel cages on a social interaction rack (contains 4 cages, each 32.5" wide×28" deep×32" high) maintaining temperature of 64-84° F., humidity of 30-70% with alternating 14-10 hour light/dark cycle as per the USDA Animal Welfare Act (9 CFR, Parts 1, 2, and 3). Food was provided daily in amounts appropriate for the size and age of the animals and RO purified water provided ad libitum through an in-cage lixit valve. Food enrichment was provided Monday through Friday. Prior to drug administration, macaques were sedated with ketamine given as an intramuscular injection prior to test article administration. Sedation was maintained through blood and cerebrospinal fluid (CSF) sample collections with ketamine at a starting rate of 15 mg/kg with additional doses of 20-30 mg during the first hour. At subsequent time points ketamine was given at 10-15 mg/kg. DON (50 mM HEPES buffered saline) and 5c (Diastereoisomer 1), (50 mM HEPES buffered saline containing 5% ethanol and 5% tween) were administered (1.6 mg/kg equivalent) to the animals at a dosing volume of 1 mL/kg intravenously. CSF sample (target of 50 μL) was obtained by percutaneous puncture of the cisterna magna at 30 min post dose. Blood samples (I mL) were collected at 15, 30, 1, 2 4 and 6 h post dose by percutaneous puncture of a peripheral vein. Samples were processed for plasma (centrifuged at a temperature of 4° C., at 3,000×g, for 10 minutes). All samples were maintained chilled on ice throughout processing. Samples were collected in microcentrifuge tubes, flash frozen, and placed in a freezer set to maintain −80° C. until LC/MS analysis.

Bioanalysis of DON

We have previously published a highly sensitive method for analysis of DON in biological matrices (Alt, et al., 2015). However due to chemical lability of DON and its prodrugs, a milder derivatization method employing dabsyl chloride was developed and validated. Briefly, DON was extracted from samples (50 mg) with 250 μL methanol containing Glutamate-d5 (10 μM ISTD) by vortexing in low retention tubes. Samples were centrifuged at 16,000×g for 5 minutes to precipitate proteins. Supernatants (200 μL) were moved to new tube and dried at 45° C. under vacuum for 1 hour. To each tube, 50 μL of 0.2 M sodium bicarbonate buffer (pH 9.0) and 100 μL of 10 mM dabsyl chloride in acetone was added. After vortexing, samples were incubated at 60° C. for 15 minutes to derivatize. Samples (2 μL) were injected and separated on an Agilent 1290 equipped with a an Agilent Eclipse plus C18 RRHD 2.1 X100 mm column over a 2.5 minute gradient from 20-95% acetonitrile+0.1% formic acid and quantified on an Agilent 6520 QTOF mass spectrometer. Calibration curves over the range of 0.005-17.1 μg/mL in plasma and CSF for DON were constructed from the peak area ratio of the analyte to the internal standard using linear regression with a weighting factor of I/(nominal concentration). Correlation coefficient of greater than 0.99 was obtained in all analytical runs. The mean predicted relative standard deviation for back calculated concentrations of the standards and QC's for all analytes were within the range of 85 to 115%, except for the lowest concentration which was within the range of 80 to 120% with an overall accuracy and precision of 6, 7% and 6.6% respectively.

Pharmacokinetic Analysis

Mean concentration-time data was used for pharmacokinetic analysis. Non-compartmental-analysis module in WinNonlin® (version 5.3) was used to assess pharmacokinetic parameters. Peak plasma concentrations ($C_{max}$) and time to $C_{max}$ ($T_{max}$) were the observed values. Area under the curve (AUC) was calculated by log-linear trapezoidal rule to the end of sample collection ($AUC_{last}$).

Example 4

In head-to-head comparisons, 25 was found to be markedly and unexpectedly more effective than a clinical stage selective glutaminase inhibitor CB-839.

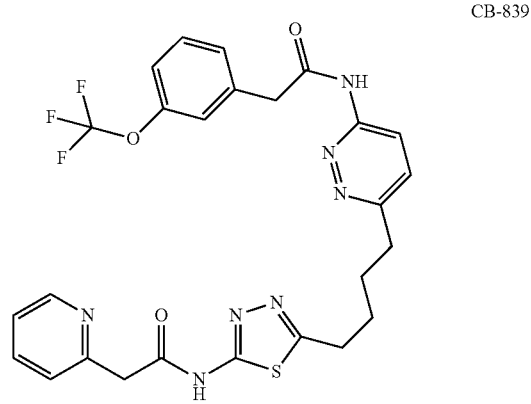 [SMILES: O=C(Cc1cccc(OC(F)(F)F)c1)Nc1ccc(CCCCc2nnc(NC(=O)Cc3ccccn3)s2)nn1]

CB-839

FIG. 8 illustrates that 25 (5 day dosing starting on day 7) is superior to CB-839 (30 day dosing starting day 1) in a CT26 tumor model.

FIG. 9 illustrates that 25 (4 days starting on day 6) is superior to CB-839 (continuous twice daily dosing starting on day 1 prior to engraftment) in a CT26 tumor model. Mice received daily 25 (1.9 mg/kg) on days 6-9 as compared to BID glutaminase inhibitor on days 1-15.

FIG. 10 illustrates that 25 (daily days 7-22) is superior to CB-839 (continuous twice daily dosing days 1-29) in a 4T1 breast cancer model. Mice received daily 25 (1.0 mg·kg/d) for days 7-22 as compared to BID glutaminase inhibitor for days 1-29.

Example 5

DON pro-drugs demonstrate efficacy in multiple tumor types, including efficacy in B & T cell lymphomas, colon cancers, breast cancer and melanoma. Daily dosing provides effective monotherapy. Every other day dosing leads to minimal resistance. FIG. 11 illustrates that 25 dosing of 1 mg/kg following by 0.3 mg/kg leads to a complete and durable response in the MC38 tumor.

FIG. 12 illustrates that 25 provides a robust response and improved overall survival in multiple tumor models, including CT26 Colon Cancer.

FIG. 13 illustrates that 25 provides a robust response and improved overall survival in multiple tumor models, including 477 Breast Cancer.

FIG. 14 illustrates that mice cured with 25 alone immunologically reject tumors upon re-challenge, demonstrating that monotherapy with certain DON prodrugs, such as 25 monotherapy, is immunotherapy.

FIG. 15 additionally illustrates that 25 is immunotherapy.

Example 6

DON/DON Prodrugs Condition Tumors to Immunotherapy and Significantly Enhance the Response to Checkpoint Inhibitors, Adoptive Cell Transfer and A2aR Inhibition Conclusions:

DON/DON prodrugs robustly enhance the immune mediated response to therapy with anti-PD1, the response to adoptive cell transfer, and the response to adenosine A2a receptor blockade. Immunotherapy fails patients with rapidly progressive disease due to the lag in response. 30-40% of patients treated with anti-PD1 therapy progress rapidly in the first few months, chemotherapy showed an early survival advantage in NSCLC likely due to it's quick effect on rapidly growing disease compared to immunotherapy, and conditioning and adjuvant therapies to immunotherapy must be able to control tumor growth to be effective in these patients.

FIG. 16 illustrates that glutamine inhibition (e.g., using DON) reduces the oxygen consumption and lactate production of tumor cells. FIG. 17 illustrates that glutamine inhibition (e.g., using DON) also improved the CD8/Treg ratio in the tumor and reduces hypoxia in the TILs.

FIG. 18 illustrates that 25 conditions tumors to be eliminated by anti-PD1 therapy in the MC38 Model, and that 25 rescues anti-PD1 failures. In addition, FIG. 19 illustrates that even in the more difficult CT26 model, 25 unexpectedly enhances the response to anti-PD1. Similarly, FIG. 20 illustrates that inhibiting glutamine metabolism unexpectedly potentiates the anti-tumor response to A2aR inhibition.

Finally, FIG. 21 illustrates that inhibiting glutamine metabolism unexpectedly enhances the efficacy of adoptive cellular therapy (ACT) in a B16-OVA model.

Example 7

Compound 14b Enhanced CSF Delivery of DON in Monkey

Figure 38A:
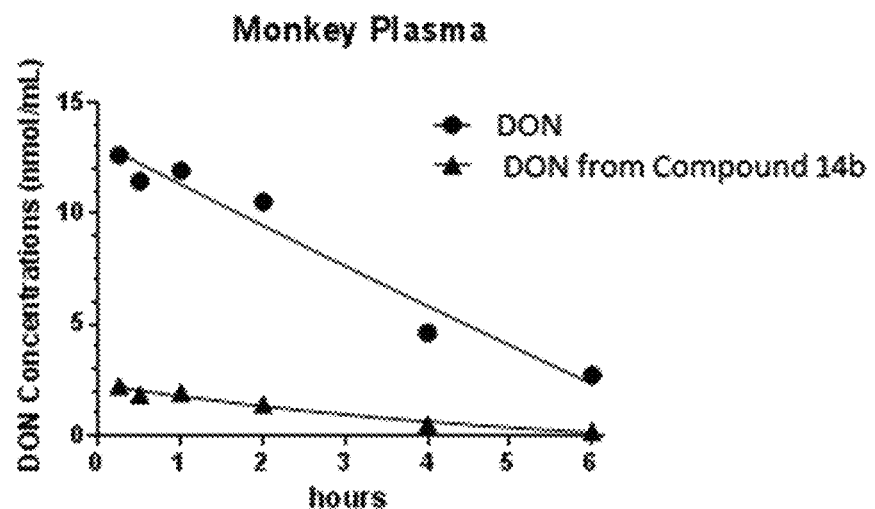
Figure 38B:
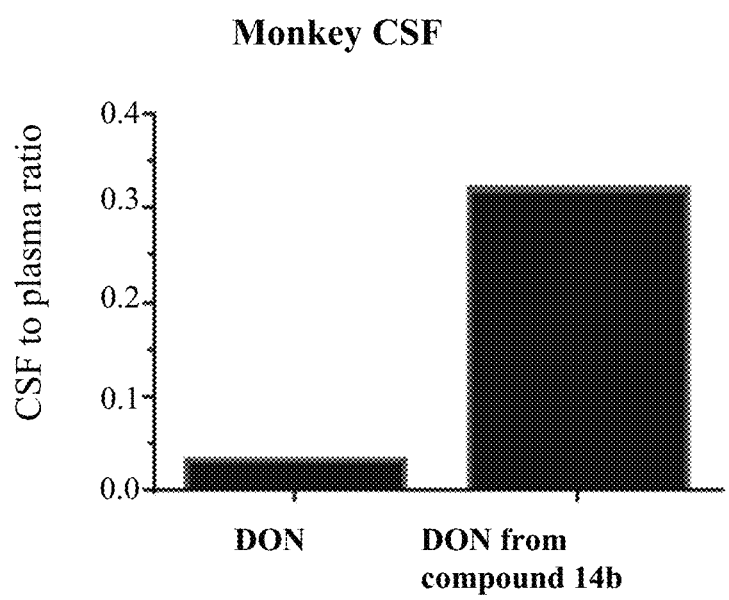

Method
  Compound:
  Compound 14b was dissolved in 50 mM HEPES buffered saline containing 5% ethanol and 5% tween on the date of administration.
  Monkey:
  Monkey studies were conducted according to protocol (#PR15M298) approved by the Animal Care and Use Committee at Johns Hopkins University. Two female pigtail monkeys (approximately 3.5 kg, non-drug naive) were adjacently housed in stainless steel cages on a social interaction rack (contains 4 cages, each 32.5" wide×28" deep×32" high) maintaining temperature of 64-84 OF, humidity of 30-70% with alternating 14-10 hour light/dark cycle as per the USDA Animal Welfare Act (9 CFR, Parts 1, 2, and 3). Food was provided daily in amounts appropriate for the size and age of the animals and RO purified water provided ad libitum through an in-cage lixit valve. Food enrichment was provided Monday through Friday.
  Treatment:
  Prior to drug administration, macaques were sedated with ketamine given as an intramuscular injection prior to test article administration. Sedation was maintained through blood and cerebrospinal fluid (CSF) sample collections with ketamine at a starting rate of 15 mg/kg with additional doses of 20-30 mg during the first hour. At subsequent time points ketamine was given at 10-15 mg/kg. DON (50 mM HEPES buffered saline) and compound 14b (50 mM HEPES buffered saline containing 5% ethanol and 5% tween) were administered (1.6 and 3.6 mg/kg equivalent dose of DON) to the animals at a dosing volume of 1 mL/kg intravenously. CSF sample (target of 50 μL) was obtained by percutaneous puncture of the cisterna magna at 30 min post dose. Blood samples (1 mL) were collected at 15 min. 30 min, 1 h, 2 h, 4 h, and 6 h post dose by percutaneous puncture of a peripheral vein. Samples were processed for plasma (centrifuged at a temperature of 4° C., at 3,000 g, for 10 minutes). All samples were maintained chilled on ice throughout processing. Samples were collected in microcentrifuge tubes, flash frozen, and placed in a freezer set to maintain −80° C. until LC/MS analysis.
  Data Analysis:
  DON was extracted from samples (50 mg) with 250 μL methanol containing glutamate-$d_5$ (10 μM ISTD) by vortexing in low retention tubes. Samples were centrifuged at 16,000 g for 5 minutes to precipitate proteins. Supernatants (200 μL) were moved to new tubes and dried at 45° C. under vacuum for 1 hour. To each tube, 50 μL of 0.2 M sodium bicarbonate buffer (pH 9.0) and 100 μL of 10 mM dabsyl chloride in acetone was added. After vortexing, samples were incubated at 60° C. for 15 minutes to derivatize. Samples (2 μL) were injected and separated on an Agilent 1290 equipped with an Agilent Eclipse plus C18 RRHD 2.1 X100 mm column over a 2.5 minute gradient from 20-95% acetonitrile+0.1% formic acid and quantified on an Agilent 6520 QTOF mass spectrometer. Calibration curves over the range of 0.005-17.1 μg/mL in plasma and CSF for DON were constructed from the peak area ratio of the analyte to the internal standard using linear regression with a weighting factor of 1/(nominal concentration). Correlation coefficient of greater than 0.99 was obtained in all analytical runs. The mean predicted relative standard deviation for back calculated concentrations of the standards and QC's for all analytes were within the range of 85 to 115%, except for the lowest concentration which was within the range of 80 to 120% with an overall accuracy and precision of 6.7% and 6.6% respectively.
  Results
  The pharmacokinetics of DON and compound 14b in monkeys were evaluated. In pigtail macaques, i.v. administration of DON (1.6 mg/kg) and compound 14b (3.6 mg/kg; 1.6 mg/kg DON equivalent) demonstrated significantly different DON plasma profiles (FIG. 38A). DON administration provided high plasma exposures with AUC0-t of 42.7 nmol*h/mL. In contrast, compound 14b administration delivered ~7 fold lower plasma exposure of DON with AUC0-t of 5.71 nmol*h/mL. The opposite observation was seen in the CSF where enhanced DON levels were observed after compound 14b administration. In the CSF at 30 min post dose, DON administration resulted in 0.33 nmol/g DON while compound 14b delivered 1.43 nmol/g DON. When comparing plasma to CSF ratio at 30 min, compound 14b demonstrated unexpected 10-fold enhancement of DON CSF delivery versus DON (FIG. 38B).

Example 8

Compounds 14b and 47 Enhanced CSF Delivery of DON in Swine

Method
  Compound:
  Compound 47 was dissolved in a sterile saline containing 5% ethanol and 5% Tween 80 on the date of administration.
  Swine:
  Swine studies were conducted under a protocol approved by the Johns Hopkins Animal Care and Use Committee. Adult, female Göttingen×Yucutan miniature swine (Massachusetts General Hospital, MA) were housed in Johns Hopkins University facilities accredited by the Association for Assessment and Accreditation of Laboratory Animal Care International in compliance with the Animal Welfare Act, Animal Welfare Regulations, and the Public Health Service Policy on the Humane Care and Use of Laboratory Animals. Animals were maintained on a 14-h light and 10-h dark schedule, provided ad libitum water and a commercial miniswine diet (Teklad, Madison, Wis.) with environmental enrichment (fruit/vegetables) twice daily.
  DON and Compounds 14b and 47 Treatment:
  Animals were individually housed while on study in order to monitor behavior and clinical health following drug administration. Whole blood for drug pharmacokinetic evaluation was collected from a dual lumen central venous catheter (CVC) implanted in the external jugular vein prior to study initiation. Animals were anesthetized with a combination of ketamine hydrochloride (20-30 mg/kg, i.m.) and xylazine (2 mg/kg, i.m.), intubated, and maintained under isoflurane (1-2%) inhalant anesthesia. A temporary peripheral saphenous vein catheter was placed in the hind limb to allow for anatomical separation of drug infusion and whole blood sampling via CVC. DON and compounds 14b and 47 were dissolved in a sterile saline solution containing 5% ethanol and 5% Tween 80 prior to i.v. infusion via saphenous vein catheter over 1 hour (1 ml/min) for a final dose of 1.6 mg/kg or molar equivalent administered at 1 ml/kg (n=1/ dose). Blood samples (1 mL) were taken from CVC at predose, 5, 15, 30, 45, and 60 min. Plasma was separated by low speed centrifugation at 3000 g for 10 min at 4° C. CSF was obtained from the cisterna magna using a 3.5 in×22 gauge spinal needle (Becton Dickinson Health Care. Franklin Lakes, N.J. USA) at 60 min post-dose. All samples were flash frozen upon harvest and stored at −80 C until bioanalysis.

Data Analysis:

Quantitation of DON in plasma, CSF, and brain homogenate by LC-MS/MS was performed. Briefly, DON was extracted from plasma, CSF, and brain samples with methanol containing glutamate-$d_5$ (10 µM ISTD) by vortexing followed by centrifugation 16000 g for 5 min. Supernatants were aliquoted and dried at 45° C. for under vacuum for 1 h. Sodium bicarbonate buffer (0.2M, pH 9.0) and dabsyl chloride (10 mM) in acetone were added to each tube, mixed, and incubated for 15 min at 60° C. to derivatize. Samples were then injected and separated on an Agilent 1290 equipped with an Agilent Eclipse plus C18 RRHD 2.1×100 mm column over a 2.5 min gradient from 20 to 95% acetonitrile+0.1% formic acid and quantified on an Agilent 6520 QTOF mass spectrometer. Peak area ratio of the analyte to the internal standard was plotted against a 14 standard curve to yield DON concentrations for each sample.

Result

Figure 39A:
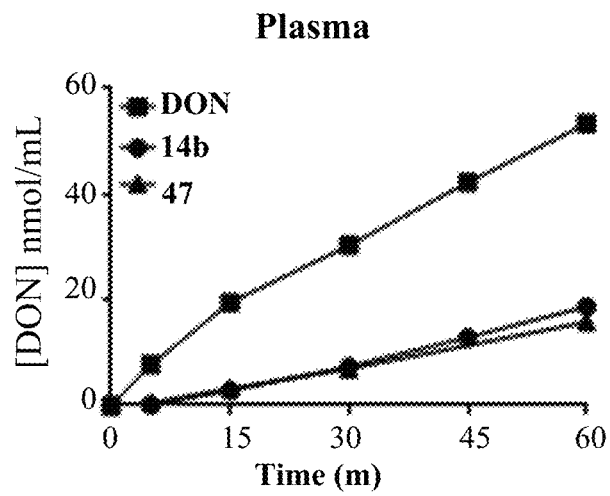
Figure 39B:
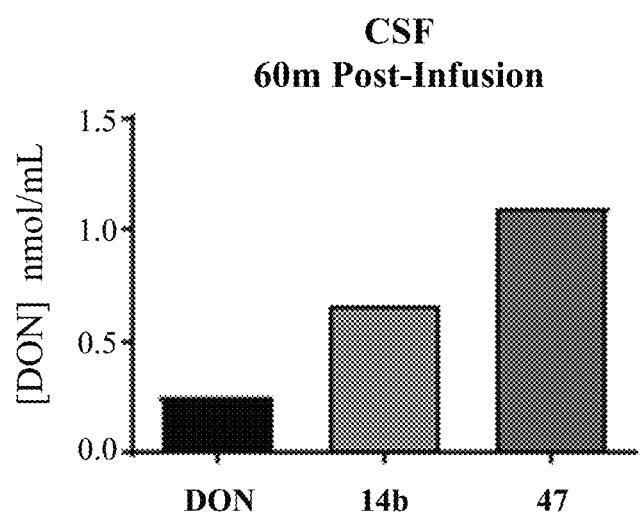
Figure 39C:
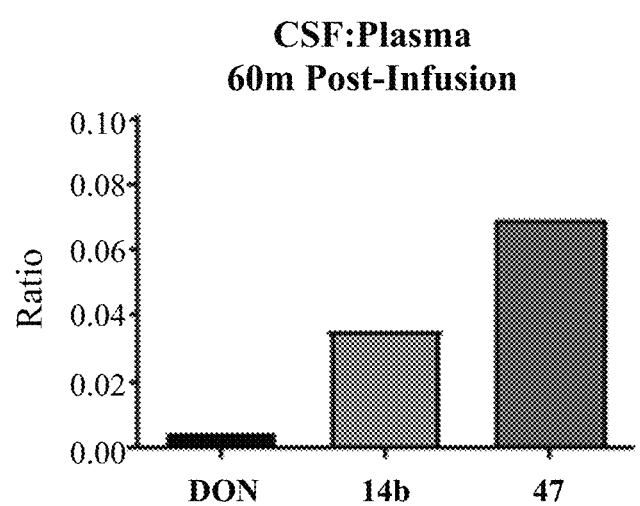

The pharmacokinetic of DON, compound 14b and compound 47 were evaluated in swine. IV administration of compounds 14b and 47 (1.6 mg/kg DON equivalent dose) resulted in 3-5-fold lower DON plasma exposures relative to an equimolar dose of DON (FIG. 39A). Plasma $AUC_{0-t}$ for DON and compounds 14b and 47 were 29.9, 8.00 and 5.70 nmol·h/mL, respectively. The opposite trend occurred in CSF, where compounds 14b and 47 delivered substantially higher amounts of DON to the CSF (FIG. 39B), resulting in unexpected increased CSF-to-plasma ratios (FIG. 39C).

Example 9

Compound 25 Enhances Immunotherapy in EO771 Tumor-Bearing Mice

Method

Mouse:

C57BL/6 (both male and female mice, 6-8 weeks of age) were purchased from Jackson Laboratories. The studies were conducted under a protocol approved by the Johns Hopkins Animal Care and Use Committee.

Cell Line:

EO771 breast cancer cell lines were purchased from CH3 BioSystems. EO771 cells were cultured in RPMI supplemented with 10% FBS, 1% penicillin/streptomycin. They were regularly tested to confirm mycoplasma free using MycoAlert mycoplasma detection kit (Lonza). Cells were never passaged more than 3 weeks before use in experiment. EO771 cells (2×10$^5$ cells in 200 µl per mouse) were subcutaneously inoculated into the mammary fat pad (C57BL/6).

Treatment with Compound 25:

EO771 tumor-bearing mice were treated with glutamine antagonist prodrug, compound 25 (1 mg/kg) starting at day 7 after tumor inoculation. After 7 days, lower dose (0.3 mg/kg) of glutamine antagonist prodrug was applied.

Treatment with Immunotherapy Alone or Combined Immunotherapy with Compound 25:

On days 9, 12, and 15, mice were injected with or without 100 µg anti-PD1 alone or 100 µg anti-PD1 in combination with 100 µg anti-CTLA4, followed by treatment with or without compound 25. Each individual mouse tumor growth and survival curves were recorded.

Result:

Treatment with compound 25 alone resulted in delayed tumor growth and increased survival (FIGS. 40A, B, and E). Anti-PD-1 therapy alone resulted in delayed tumor growth (FIGS. 40C and D). The combination of compound 25 and anti-PD-1 therapy resulted in a surprising increase in inhibition of tumor growth and survival (FIGS. 40F and G). Taken together, these data show that combining metabolic therapy with checkpoint blockade leads to a unexpected increase in susceptibility of the tumor to immunotherapy.

Example 10

Compound 25 Enhances Immunotherapy in 4T1 Tumor-Bearing Mice

Mouse:

BALB/cJ (both male and female mice, 6-8 weeks of age) were purchased from Jackson Laboratories. The studies were conducted under a protocol approved by the Johns Hopkins Animal Care and Use Committee.

Cell Line and Tumor Model:

4T1 breast cancer cell lines were purchased from the ATCC. 4T1 cells were cultured in RPMI supplemented with 10% FBS, 1% penicillin/streptomycin. They were regularly tested to confirm mycoplasma free using MycoAlert mycoplasma detection kit (Lonza). Cells were never passaged more than 3 weeks before use in experiment. 4T1 cells (1×10$^5$ cells in 200 µl per mouse) were subcutaneously inoculated into the mammary fat pad. (BALB/cJ).

Treatment with Immunotherapy Alone:

0.1×10$^6$ 4T1 cells were inoculated subcutaneously into mammary fat pad in BALB/cJ female mice. On day 7, 10, 13, 17, and 24, mice were injected IP with 250 µg anti-PD1 and/or anti-CTLA4 antibodies. Tumor size was monitored. FIGS. 41A-G show that 4T1 tumor cells are resistant to immunotherapy in the form of checkpoint blockade.

Treatment with Compound 25, Immunotherapy, or Combination of Compound 25 and Immunotherapies:

Mice were injected with 4T1 tumors as described above and treated on day 7 post injection with either no treatment (NT), compound 25 alone, anti-PD-1+anti-CTLA-4, or compound 25+anti-PD1+anti-CTLA-4. FIGS. 41H and I show that mice treated with anti-CTLA4 and anti-PD1 showed minimal therapeutic benefit compared to the vehicle treated group. FIG. 41J shows that the compound 25 treated group displayed a modest decrease in tumor growth. FIGS. 41K and L show that when mice were treated with the combination compound 25, anti-PD1, and anti-CTLA4, a substantial decrease of tumor growth and increase in survival time were observed. These findings demonstrate that altering TME glutamine inhibition unexpectedly enhances the efficacy of checkpoint blockade in tumors that are resistant to such therapy.

Example 11

Compound 25 Reduced Spontaneous Lung Metastasis in 4T1 Tumor-Bearing Mice

Treatment with Compound 25:

0.1×10$^6$ 4T1 cells were implanted subcutaneously into mammary fat pad in BALB/cJ female mice. 4T1 tumor-bearing mice were treated with compound 25 (1 mg/kg)

starting at day 7 after tumor inoculation. After 7 days, lower dose (0.3 mg/kg) of compound 25 was used. On day 30, the whole lung were harvested, and spontaneous lung metastases were analyzed by inflation with 15% india ink, to quantify tumor nodules, or by flow cytometry (FIG. 42A). FIG. 42B quantifies spontaneous lung metasteses in lungs of mice with no treatment (NT) and treatment with compound 25. These findings demonstrate that compound 25 significantly reduces lung metastasis.

Example 12

Compound 25 Inhibited Tumor Growth in Syngeneic Mouse Models

Tumor Growth and Survival Experiments:

Tumor injections were administered in the right flank. For the MC38 and MC38OVA models, C57BL/6 WT mice were injected with $5 \times 10^5$ MC38 or MC38OVA cells (s.c.) cultured in DMEM-based media. For the CT26 model, BALB/c mice were injected with $5 \times 10^5$ CT26 cells (s.c.) cultured in RPMI-based media. Compound 25 was dissolved in 2.5% ethanol in PBS (v/v) which was administered for all vehicle-treated control experiments. For MC38 and MC38OVA experiments, mice were treated with Compound 25 or vehicle by daily gavage with 1 mg/kg/day in 100 uL for days 10-14 and with 0.3 mg/kg/day for day 15-24. For CT26 experiments, mice were treated with compound 25 or vehicle by daily gavage with 1 mg/kg/day in 100 uL for days 7-11 and with 0.3 mg/kg/day for day 12-21.

Results:

Mice were injected subcutaneously with MC38 colon cancer, EL-4 lymphoma, CT26 colon cancer, and B16 melanoma. In each case treatment with compound 25 led to a marked decrease in tumor growth. FIGS. 43A-C show tumor growth and survival over time of MC38-bearing mice treated with vehicle and compound 25. In the case of MC38, monotherapy treatment with compound 25 for 14 days led to durable cures. FIGS. 44A-B show tumor growth and survival over time of CT26 tumor-bearing mice treated with vehicle and compound 25. FIGS. 45A-B show tumor growth and survival over time of B16 tumor-bearing mice treated with vehicle and compound 25. FIGS. 46A-B shows tumor growth and survival over time of EL4 tumor-bearing mice treated with vehicle and compound 25.

Example 13

Compound 25 Enhanced the Efficacy of Immunotherapy in MC38 and CT26 Bearing Mice Treating MC38 Tumor-Bearing Mice:

MC38 bearing C57BL/6 mice were treated with vehicle, anti-PD-1, compound 25, or the combination of compound 25 and anti-PD-1 beginning on day 10 after tumor inoculation. The mice treated with compound 25 and anti-PD-1 showed an unexpected increase in both tumor regression and complete responses compared with anti-PD-1 therapy alone. See FIGS. 47A-F.

Treating CT26 Tumor-Bearing Mice:

CT26 bearing BALB/c mice were treated with vehicle, anti-PD-1, compound 25, or combination of compound 25 and anti-PD-1 beginning on day 7 after tumor inoculation. Combination therapy produced significant anti-tumor responses in the CT26 model. See FIGS. 48A-F.

Example 14

Compound 25 Enhanced Endogenous Anti-Tumor Immunity

Mice that had been cured by monotherapy were rechallenged with an equal burden of tumor injected on the opposite flank. More than three-quarters of mice cured by treatment with compound 25 as a single agent unexpectedly rejected MC38 rechallenge. See FIG. 49A.

To confirm the immunologic basis of this phenomenon, MC38-bearing RAG2−/− mice and wild type mice treated with compound 25 were compared. While glutamine blockade with compound 25 had some initial effect on tumor growth in the RAG2−/− mice, tumor growth rate recovered after several days (FIG. 49C). In contrast, treatment for 14 days of WT mice (with intact adaptive immune responses) led to significant control of the tumor including complete regression in a proportion of the mice (FIGS. 49B and D). These results demonstrate that glutamine blockade with compound 25 produces a surprising enhancement in endogenous anti-tumor immunity.

Example 15

Compound 25 Enhanced the Efficacy of Adoptive Cellular Therapy

Adoptive Cellular Therapy:

OVA-expressing B16 melanoma model, C57BL/6 WT mice received a s.c. injection of $2 \times 10^5$ B16-OVA melanoma cells cultured under OVA selection media containing 400 μg/ml G418 (Life technologies). Mice were treated with compound 25 or vehicle by daily gavage with 1 mg/kg/day in 100 uL for days 7-9 post tumor inoculation. Ten days after tumor injection, mice received an adoptive transfer of $1.5 \times 10^6$ activated OT1 cells, which had been stimulated in vitro with SIINFEKL peptide for 48 h, expanded in IL-2 (1 ng/mL) for 24 h and isolated with Ficol gradient centrifugation. Mice were randomized based on tumor size before transfer of activated OT1 cells for adoptive transfer experiments. Tumor burden was assessed every 2-4 days by measuring length and width of tumor. Tumor volume was calculated using the formula $V=(L \times W \times W)/2$, where V is tumor volume, W is tumor width, and L is tumor length. Mice were sacrificed when tumor reached 2 cm in any dimension, became ulcerate or necrotic, or caused functional deficits.

Results:

Mice harboring OVA-expressing B16 melanoma that were pre-treated for 3 days with compound 25 before adoptive transfer of activated OVA-specific OT1 T cells showed an unexpected improvement in tumor control and survival. See FIGS. 50A-D.

Example 16

Compound 25 Inhibits 3LL Tumor Growth $5 \times 10^6$ 3LL cells were implanted subcutaneously into the right flank in C57BL/6J male mice. 3LL tumor-bearing mice were treated with compound 25 (1 mg/kg) starting at day 7 after tumor inoculation. After 7 days, a lower dose (0.3 mg/kg) of compound 25 was used. FIG. 51A shows that compound 25 reduced tumor growth. FIG. 51B shows that percentages of live Ly6c lo Ly6G Hi, Ly6c hi Gr1, CD8+, and CD4+ of cells from blood in 3LL tumor bearing mice, analyzed by flow cytometry at the indicated time point. FIGS. 51C-D demonstrate an increased ratio of CD8 cells to MDSCs+ and TANs from blood and tumor-infiltrating leukocytes (TIL).

REFERENCES

Ahluwalia, G. S.; Grem, J. L.; Hao, Z.; Cooney, D. A. Metabolism and action of amino acid analog anti-cancer agents. *Pharmacol Ther* 1990, 46, 243-271.

Alt, J.; Potter, M. C.; Rojas, C.; Slusher, B. S. Bioanalysis of 6-diazo-5-oxo-1-norleucine in plasma and brain by ultra-performance liquid chromatography mass spectrometry. *Anal Biochem* 2015, 474, 28-34.

Barclay, R. K.; Phillipps, M. A. Effects of 6-diazo-5-oxol-norleucine and other tumor inhibitors on the biosynthesis of nicotinamide adenine dinucleotide in mice. *Cancer Res* 1966, 26, 282-286.

Cervantes-Madrid, D.; Romero, Y.; Duenas-Gonzalez, A. Reviving Lonidamine and 6-Diazo-5-oxo-L-norleucine to Be Used in Combination for Metabolic Cancer Therapy. *Biomed Res Int* 2015, 2015, 690492.

Coffey, G. L.; Ehrlich, J.; Fisher, M. W.; Hillegas, A. B.; Kohberger, D. L.; Machamer, H. E.; Rightsel, W. A.; Roegner, F. R. 6-Diazo-5-oxo-L-norleucine, a new tumor-inhibitory substance. I. Biologic studies. *Antibiot Chemother (Northfield)* 1956, 6, 487-497.

D'Andrea, S.; Zheng, Z.; Scola, P. Inhibitors of Hepatitis C Virus. In Google Patents: 2008.

Dion, H. W.; Fusari, S. A.; Jakubowski, Z. L.; Zora, J. G.; Bartz, Q. R. 6-Diazo-5-oxo-L-norleucine, A New Tumor-inhibitory Substance. II.1 Isolation and Characterization. *J. Am. Chem. Soc.*, 1956, 78, 3075-3077.

Dolan D. E.; Gupta S. PD-1 pathway inhibitors: changing the landscape of cancer immunotherapy. *Cancer Control*, 2014, 21(3):231-7.

Dranoff. G.; Elion, G. B.; Friedman, H. S.; Bigner, D. D. Combination chemotherapy in vitro exploiting glutamine metabolism of human glioma and medulloblastoma. *Cancer Res* 1985, 45, 4082-4086.

Dranoff, G.; Elion, G. B.; Friedman, H. S.; Campbell, G. L.; Bigner, D. D. Influence of glutamine on the growth of human glioma and medulloblastoma in culture. *Cancer Res* 1985, 45, 4077-4081.

Eagan, R. T.; Frytak, S.; Nichols. W. C.; Creagan, E. T.; Ingle, J. N. Phase II study on DON in patients with previously treated advanced lung cancer. *Cancer Treat Rep* 1982, 66, 1665-1666.

Earhart, R. H.; Amato, D. J.; Chang, A. Y.; Borden, E. C.; Shiraki, M.; Dowd, M. E.; Comis, R. L.; Davis. T. E.; Smith, T. J. Phase II trial of 6-diazo-5-oxo-L-norleucine versus aclacinomycin-A in advanced sarcomas and mesotheliomas. *Invest New Drugs* 1990, 8, 113-119.

Earhart, R. H.; Koeller, J. M.; Davis, H. L. Phase I trial of 6-diazo-5-oxo-L-norleucine (DON) administered by 5-day courses. *Cancer Treat Rep* 1982, 66, 1215-1217.

Engels, E. A., et al. Spectrum of Cancer Risk among U.S. Solid Organ Transplant Recipients: The Transplant Cancer Match Study. *JAMA*, 2011.

Erickson, J. W.; Cerione, R. A. Glutaminase: a hot spot for regulation of cancer cell metabolism? *Oncotarget* 2010, 1, 734-740.

Eshleman, J. S.; Carlson, B. L.; Mladek, A. C.; Kastner, B. D.; Shide, K. L.; Sarkaria, J. N. Inhibition of the mammalian target of rapamycin sensitizes U87 xenografts to fractionated radiation therapy. *Cancer Res* 2002, 62, 7291-7297.

Fogal, V.; Babic. I.; Chao, Y.; Pastorino, S.; Mukthavaram, R.; Jiang, P.; Cho, Y. J.; Pingle, S. C.; Crawford. J. R; Piccioni, D. E.; Kesari, S. Mitochondrial p32 is upregulated in Myc expressing brain cancers and mediates glutamine addiction. *Oncotarget* 2015, 6, 1157-1170

Gallop, M. A.; Xu. F.; Phan, T.; Dilip, U.; Peng. G. Acyloxyalkyl carbamate prodrugs, methods of synthesis and use. In Google Patents: 2008.

Grayzel, A. I.; Seegmiller, J. E.; Love, E. Suppression of uric acid synthesis in the gouty human by the use of 6-diazo-5-oxo-L-norleucine. *J Clin Invest* 1960, 39, 447-454.

Gross, M. I.; Demo. S. D.; Dennison, J. B.; Chen, L.; Chemov-Rogan, T.; Goyal, B.; Janes, J. R.; Laidig, G. J.; Lewis, E. R.; Li, J.; MacKinnon, A. L.; Parlati, F.; Rodriguez, M. L. M.; Shwonek, P. J.; Sjogren, E. B.; Stanton, T. F.; Wang, T.; Yang, J.; Zhao, F. Y.; Bennett, M. K. Antitumor Activity of the Glutaminase Inhibitor CB-839 in Triple-Negative Breast Cancer. *Mol Cancer Ther* 2014.

Harding, J. J. T., M. L.; Munster, P. N.; Le, M. H.; Molineaux, C.; Bennett, M. K.; Mittra. E.; Burris, H. A.; Clark. A. S.; Dunphy, M.; Meric-Bemstam, F.; Patel, M. R; DeMichele, A.; Infante, J. R. Safety and tolerability of increasing doses of CB-839, a first-in-class, orally administered small molecule inhibitor of glutaminase, in solid tumors. *J Clin Oncol* 2015.

Hensley, C. T.; Wasti, A. T.; DeBerardinis, R. J. Glutamine and cancer: cell biology, physiology, and clinical opportunities. *J Clin Invest* 2013, 123, 3678-3684.

Hofer, A.; Steverding, D.; Chabes, A.; Brun, R.; Thelander, L. *Trypanosoma brucei* CTP synthetase: a target for the treatment of African sleeping sickness. *Proc Natl Acad Sci USA* 2001, 98, 6412-6416.

Hu, X.; Stem, H. M.; Ge, L.; O'Brien, C.; Haydu, L.; Honchell, C. D.; Haverty, P. M.; Peters, B. A.; Wu, T. D.; Amler, L. C.; Chant, J.; Stokoe, D.; Lackner, M. R.; Cavet, G. Genetic alterations and oncogenic pathways associated with breast cancer subtypes. *Mol Cancer Res* 2009, 7, 511-522.

Keicher, J. D.; Roberts, C. D.; Rajwanshi, V. K.; Griffith, R. C.; Zheng, X.; Liehr, S. J. R; Prhavc, M.; Kim, C. U.; Ray, A. S. Amino tricyclic-nucleoside compounds, compositions, and methods of use. In Google Patents: 2009.

Konopleva, M. Y.; Flinn, I. W.; Wang, E.; DiNardo, C. D.; Bennett, M.; Molineaux, C.; Le, M.; Maris, M.; Frankfurt, O. In *Phase 1 study: Safety and tolerability of increasing doses of cb-839, an orally-administered small molecule inhibitor of glutaminase, in acute leukemia*, Haematologica, 2015; Ferrata Storti Foundation Via Giuseppe Belli 4, 27100 Pavia, Italy: 2015; pp 378-379.

Le, A.; Lane, A. N.; Hamaker, M.; Bose, S.; Gouw, A.; Barbi, J.; Tsukamoto, T.; Rojas, C. J.; Slusher, B. S.; Zhang, H.; Zimmerman, L. J.; Liebler, D. C.; Slebos, R. J.; Lorkiewicz, P. K.; Higashi. R. M.; Fan, T. W.; Dang, C. V. Glucose-independent glutamine metabolism via TCA cycling for proliferation and survival in B cells. *Cell Metab* 2012, 15, 110-121.

Lee, Y. Z.; Yang, C. W.; Chang, H. Y.; Hsu, H. Y.; Chen, I. S.; Chang, H. S.; Lee, C. H.; Lee, J. C.; Kumar, C. R.; Qiu, Y. Q.; Chao, Y. S.; Lee, S. J. Discovery of selective inhibitors of Glutaminase-2, which inhibit mTORC1, activate autophagy and inhibit proliferation in cancer cells. *Oncotarget* 2014, 5, 6087-6101.

Liddy et al., *Nature Med.* 18:980-7, (2012); Grupp et al., *New England J. Med.* 368:1509-18, (2013)).

Lynch, G.; Kemeny, N.; Casper, E. Phase II evaluation of DON (6-diazo-5-oxo-L-norleucine) in patients with advanced colorectal carcinoma. *Am J Clin Oncol* 1982, 5, 541-543.

Magill, G. B.; Myers, W. P. Alterations in calcium metabolism in cancer patients treated with 6-diazo-5-oxo-L-norleucine. *Proc Soc Exp Biol Med* 1956, 93, 314-318.

Magill, G. B.; Myers, W. P.; Reilly, H. C.; Putnam. R. C.; Magill, J. W.; Sykes, M. P.; Escher, G. C.; Karnofsky, D. A.; Burchenal, J. H. Pharmacological and initial therapeutic observations on 6-diazo-5-oxo-1-norleucine (DON) in human neoplastic disease. *Cancer* 1957, 10, 1138-1150.

McDermott, L. A.; Iyer, P.; Vemetti, L. Rimer, S.; Sun, J.; Boby, M.; Yang, T.; Fioravanti, M.; O'Neill, J.; Wang, L.; Drakes, D.; Katt, W.; Huang, Q.; Cerione, R. Design and evaluation of novel glutaminase inhibitors. *Bioorg Med Chem* 2016, 24, 1819-1839.

Ngiow S. F.; Teng M. W., Smyth M. J. Prospects for TIM3-Targeted Antitumor Immunotherapy. *Cancer Res* 2011, 71(21):6567-71.

Ostrom, Q. T.; Gittleman, H.; Fulop, J.; Liu. M.; Blanda, R.; Kromer, C.; Wolinsky, Y.; Kruchko, C.; Barnholtz-Sloan. J. S. CBTRUS Statistical Report: Primary Brain and Central Nervous System Tumors Diagnosed in the United States in 2008-2012. *Neuro Oncol* 2015, 17 Suppl 4, iv1-iv62.

Potter, M. C.; Baxter, V. K.; Mathey, R. W.; Alt, J.; Rojas, C.; Griffin. D. E.; Slusher, B. S. Neurological sequelae induced by alphavirus infection of the CNS are attenuated by treatment with the glutamine antagonist 6-diazo-5-oxo-1-norleucine. *J Neurovirol* 2015, 21, 159-173.

Powell et al., "A2aR antagonists: Next generation checkpoint blockade for cancer immunotherapy," *Comput Struct Biotechnol J.* 2015; 13: 265-272.

Rahman, A.; Smith, F. P.; Luc, P. T.; Woolley, P. V. Phase I study and clinical pharmacology of 6-diazo-5-oxo-L-norleucine (DON). *Invest New Drugs* 1985, 3, 369-374.

Rautio, J.; Kumpulainen, H.; Heimbach, T.; Oliyai, R.; Oh, D.; Jarvinen, T., Savolainen, J. Prodrugs: design and clinical applications. *Nat Rev Drug Discov* 2008, 7, 255-270.

Ru, P.; Williams, T. M.; Chakravarti, A.; Guo, D. Tumor metabolism of malignant gliomas. *Cancers (Basel)* 2013, 5, 1469-1484.

Schulze, A.; Harris, A. L. How cancer metabolism is tuned for proliferation and vulnerable to disruption. *Nature* 2012, 491, 364-373.

Shukla, K.; Ferraris, D. V.; Thomas, A. G.; Stathis, M.; Duvall, B.; Delahanty, G.; Alt, J.; Rais, R.; Rojas, C.; Gao, P.; Xiang, Y.; Dang, C. V.; Slusher, B. S.; Tsukamoto, T. Design, synthesis, and pharmacological evaluation of bis-2-(5-phenylacetamido-1,2,4-thiadiazol-2-yl)ethyl sulfide 3 (BPTES) analogs as glutaminase inhibitors. *J Med Chem* 2012, 55, 10551-10563.

Sklaroff, R. B.; Casper, E. S.; Magill, G. B.; Young. C. W. Phase I study of 6-diazo-5-oxo-L-norleucine (DON). *Cancer Treat Rep* 1980, 64, 1247-1251.

Stupp, R.; Hegi, M. E.; Mason, W. P.; van den Bent, M. J.; Taphoom, M. J.; Janzer, R. C.; Ludwin, S. K.; Allgeier, A.; Fisher, B.; Belanger, K.; Hau, P.; Brandes, A. A.; Gijtenbeek, J.; Marosi, C.; Vecht, C. J.; Mokhtari, K.; Wesseling, P.; Villa. S.; Eisenhauer, E.; Gorlia. T.; Weller, M.; Lacombe, D.; Caimcross. J. G.; Mirimanoff, R. O. Effects of radiotherapy with concomitant and adjuvant temozolomide versus radiotherapy alone on survival in glioblastoma in a randomised phase III study: 5-year analysis of the EORTC-NCIC trial. *Lancet Oncol* 2009, 10, 459-466.

Stupp, R.; Mason, W. P.; van den Bent, M. J.; Weller, M.; Fisher, B.; Taphoom, M. J.; Belanger, K.; Brandes, A. A.; Marosi, C.; Bogdahn, U.; Curschmann, J.; Janzer, R. C.; Ludwin, S. K.; Gorlia. T.; Allgeier, A.; Lacombe, D.; Caimcross, J. G.; Eisenhauer, E.; Mirimanoff. R. O. Radiotherapy plus concomitant and adjuvant temozolomide for glioblastoma. *N Engl J Med* 2005, 352, 987-996.

Sullivan, M. P.; Beatty, E. C., Jr.; Hyman, C. B.; Murphy, M. L.; Pierce, M. I.; Severo, N.C. A comparison of the effectiveness of standard dose 6-mercaptopurine, combination 6-mercaptopurine and DON, and high-loading 6-mercaptopurine therapies in treatment of the acute leukemias of childhood: results of a coperative study. *Cancer Chemother Rep* 1962, 18, 83-95.

Sullivan, M. P.; Nelson, J. A.; Feldman, S.; Van Nguyen, B. Pharmacokinetic and phase I study of intravenous DON (6-diazo-5-oxo-L-norleucine) in children. *Cancer Chemother Pharmacol* 1988, 21, 78-84.

Tanaka, K.; Sasayama, T.; Irino, Y.; Takata. K.; Nagashima, H.; Satoh, N.; Kyotani, K.; Mizowaki, T.; Imahori, T.; Ejima, Y.; Masui, K.; Gini, B.; Yang, H.; Hosoda. K.; Sasaki, R.; Mischel, P. S.; Kohmura, E. Compensatory glutamine metabolism promotes glioblastoma resistance to mTOR inhibitor treatment. *J Clin Invest* 2015, 125, 1591-1602.

Thangavelu, K.; Chong, Q. Y.; Low, B. C.; Sivaraman, J. Structural basis for the active site inhibition mechanism of human kidney-type glutaminase (KGA). *Sci Rep* 2014, 4, 3827.

Upadhyay, R. K. Drug delivery systems, CNS protection, and the blood brain barrier. *Biomed Res Int* 2014, 2014, 869269.

Weller, M.; van den Bent, M.; Hopkins, K.; Tonn, J. C.; Stupp, R.; Falini, A.; Cohen-Jonathan-Moyal, E.; Frappaz. D.; Henriksson, R; Balana, C.; Chinot. O.; Ram. Z.; Reifenberger, G.; Soffietti, R.; Wick, W. EANO guideline for the diagnosis and treatment of anaplastic gliomas and glioblastoma. *Lancet Oncol* 2014, 15, e395-403.

Willis, R. C.; Seegmiller, J. E. The inhibition by 6-diazo-5-oxo-1-norleucine of glutamine catabolism of the cultured human lymphoblast. *J Cell Physiol* 1977, 93, 375-382.

Windmueller, H. G.; Spaeth, A. E. Uptake and metabolism of plasma glutamine by the small intestine. *J Biol Chem* 1974, 249, 5070-5079.

Wise, D. R.; Thompson, C. B. Glutamine addiction: a new therapeutic target in cancer. *Trends Biochem Sci* 2010, 35, 427-433.

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method of treating cancer in a subject, the method comprising simultaneously or sequentially administering to the subject in need thereof:
   (a) a therapeutically effective amount of an immunotherapeutic agent; and
   (b) a therapeutically effective amount of:

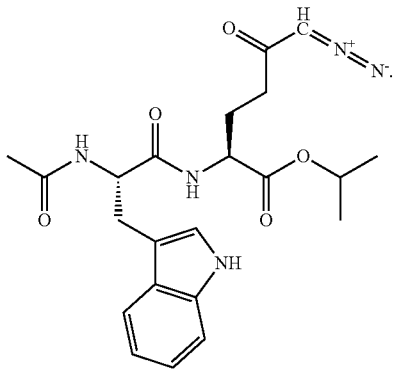

2. The method of claim 1, wherein the immunotherapeutic agent is an immune checkpoint blockade therapy.

3. The method of claim 2, wherein the immune checkpoint blockade therapy is selected from the group consisting of PD-1 antagonists, PD-L1 antagonists, CTLA-4 antagonists, LAG3 antagonists, and B7-H3 antagonists, and combinations thereof.

4. The method of claim 1, wherein the immunotherapeutic agent is an adoptive cellular therapy.

5. The method of claim 1, wherein the immunotherapeutic agent is marrow-infiltrating lymphocytes (MILs).

6. The method of claim 1, wherein the immunotherapeutic agent is an adenosine A2aR inhibitor.

7. The method of claim 1, wherein the immunotherapeutic agent is a tumor vaccine.

8. The method of claim 1, wherein the immunotherapeutic agent is a passive immunotherapy antibody.

9. The method of claim 8, wherein the passive immunotherapy antibody is selected from the group consisting of bevacizumab, cetuximab, rituximab, trastuzumab, alemtuzumab, ibritumomab tiuxetan, and panitumumab, and combinations thereof.

10. The method of claim 1, wherein the cancer is a newly diagnosed, recurrent, relapsed, and/or refractory cancer selected from the group consisting of celnasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, oligodendroglioma, neuroblastoma, meningioma, spinal cord tumor, bone cancer, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, colorectal cancer, rectal cancer, esophagus cancer, gall bladder cancer, head cancer, eye cancer, neck cancer, kidney cancer, Wilms' tumor, liver cancer, Kaposi's sarcoma, prostate cancer, lung cancer, testicular cancer, Hodgkin's disease, non-Hodgkin's lymphoma, oral cancer, skin cancer, mesothelioma, multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer and tonsil cancer.

11. The method of claim 1, wherein the cancer is refractory to monotherapy with the immunotherapeutic agent.

12. The method of claim 1, wherein the cancer is glioma, astrocytoma, oligodendroglioma, ependymoas, meningioma, medulloblastoma, ganglioglioma, schwannoma, craniopharyngioma, chordoma, non-Hodgkin lymphoma, or glioblastoma multiform.

13. The method of claim 1, wherein the cancer is colorectal cancer, gastric cancer, melanoma, non-small cell lung cancer, ovarian cancer, pancreatic cancer, or renal cell carcinoma.

14. The method of claim 1, where the immunotherapeutic agent is an anti-PD-1 antibody.

15. The method of claim 14, wherein the anti-PD-1 antibody is atezolizumab, nivolumab, pembrolizumab, or pidilizumab.

16. A method of preventing a relapse or reducing the incidence of relapse of a cancer subject in remission, the method comprising administering to the subject in need thereof a compound which is:

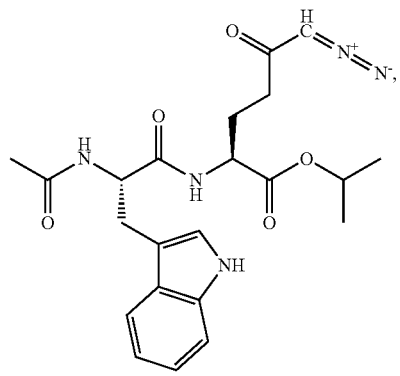

or a pharmaceutically acceptable salt thereof.

* * * * *